(12) United States Patent
Hamilton

(10) Patent No.: US 8,999,671 B2
(45) Date of Patent: *Apr. 7, 2015

(54) PRODUCTION OF SIALYLATED N-GLYCANS IN LOWER EUKARYOTES

(75) Inventor: Stephen R. Hamilton, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 226 days.

This patent is subject to a terminal disclaimer.

(21) Appl. No.: 13/554,126

(22) Filed: Jul. 20, 2012

(65) Prior Publication Data

US 2013/0018177 A1    Jan. 17, 2013

Related U.S. Application Data

(63) Continuation of application No. 12/819,305, filed on Jun. 21, 2010, now Pat. No. 8,268,609, which is a continuation of application No. 11/429,672, filed on May 5, 2006, now Pat. No. 7,863,020, which is a continuation-in-part of application No. 11/084,624, filed on Mar. 17, 2005, now abandoned, application No. 11/429,672, which is a continuation-in-part of application No. 11/108,088, filed on Apr. 15, 2005, now Pat. No. 7,795,002, which is a continuation-in-part of application No. 10/371,877, filed on Feb. 20, 2003, now Pat. No. 7,449,308.

(60) Provisional application No. 60/554,139, filed on Mar. 17, 2004.

(51) Int. Cl.
| C12P 19/26 | (2006.01) |
| C12P 21/00 | (2006.01) |
| C12N 15/00 | (2006.01) |
| C12N 9/10  | (2006.01) |
| C12N 9/24  | (2006.01) |

(52) U.S. Cl.
CPC ............ *C12N 9/1081* (2013.01); *C12N 9/2402* (2013.01); *C12P 21/005* (2013.01); *C12Y 302/01018* (2013.01); *C07K 2319/036* (2013.01); *C07K 2319/05* (2013.01); *C07K 2319/055* (2013.01)

(58) Field of Classification Search
None
See application file for complete search history.

(56) References Cited

U.S. PATENT DOCUMENTS

| 4,414,329 A | 11/1983 | Wegner |
| 4,617,274 A | 10/1986 | Wegner |
| 4,683,293 A | 7/1987  | Craig |
| 4,775,622 A | 10/1988 | Hitzeman et al. |
| 4,808,537 A | 2/1989  | Stroman et al. |
| 4,812,405 A | 3/1989  | Lair et al. |
| 4,818,700 A | 4/1989  | Cregg et al. |
| 4,837,148 A | 6/1989  | Cregg |
| 4,855,231 A | 8/1989  | Stroman et al. |
| 4,857,467 A | 8/1989  | Sreekrishna et al. |
| 4,879,231 A | 11/1989 | Stroman et al. |
| 4,882,279 A | 11/1989 | Cregg |
| 4,885,242 A | 12/1989 | Cregg |
| 4,925,796 A | 5/1990  | Bergh et al. |
| 4,929,555 A | 5/1990  | Cregg et al. |
| 4,935,349 A | 6/1990  | McKnight et al. |
| 5,002,876 A | 3/1991  | Sreekrishna et al. |
| 5,004,688 A | 4/1991  | Craig et al. |
| 5,032,516 A | 7/1991  | Cregg |
| 5,032,519 A | 7/1991  | Paulson et al. |
| 5,037,743 A | 8/1991  | Welch et al. |
| 5,047,335 A | 9/1991  | Paulson et al. |
| 5,122,465 A | 6/1992  | Cregg et al. |
| 5,135,854 A | 8/1992  | MacKay et al. |
| 5,143,830 A | 9/1992  | Holland et al. |
| 5,166,329 A | 11/1992 | Cregg |
| 5,324,663 A | 6/1994  | Lowe |
| 5,595,900 A | 1/1997  | Lowe |
| 5,602,003 A | 2/1997  | Pierce et al. |
| 5,696,088 A | 12/1997 | Innis et al. |
| 5,707,828 A | 1/1998  | Sreekrishna et al. |
| 5,766,910 A | 6/1998  | Fukuda et al. |

(Continued)

FOREIGN PATENT DOCUMENTS

| CA | 2505784 | 6/2004 |
| EP | 0905232 | 3/1999 |

(Continued)

OTHER PUBLICATIONS

"sialyltransferase" under "Protein" of MEDLINE, Retrieved from the Internet sites/entrez>, [Retrieved on Mar. 26, 2008]), the glycosylation.*

(Continued)

*Primary Examiner* — Suzanne M Noakes
*Assistant Examiner* — Jae W Lee
(74) *Attorney, Agent, or Firm* — Gloria Fuentes; Immac Thampoe

(57) ABSTRACT

The present invention relates to eukaryotic host cells which have been modified to produce sialylated glycoproteins by the heterologous expression of a set of glycosyltransferases, including sialyltransferase and/or trans-sialidase, to become host-strains for the production of mammalian, e.g., human therapeutic glycoproteins. Novel eukaryotic host cells expressing a CMP-sialic acid biosynthetic pathway for the production of sialylated glycoproteins are also provided. The invention provides nucleic acid molecules and combinatorial libraries which can be used to successfully target and express mammalian enzymatic activities (such as those involved in sialylation) to intracellular compartments in a eukaryotic host cell. The process provides an engineered host cell which can be used to express and target any desirable gene(s) involved in glycosylation.

5 Claims, 69 Drawing Sheets

(56) References Cited

U.S. PATENT DOCUMENTS

| | | |
|---|---|---|
| 5,834,251 A | 11/1998 | Maras et al. |
| 5,849,904 A | 12/1998 | Gerardy-Schahn et al. |
| 5,854,018 A | 12/1998 | Hitzeman et al. |
| 5,861,293 A | 1/1999 | Kojiri et al. |
| 5,910,570 A | 6/1999 | Elhammer et al. |
| 5,945,314 A | 8/1999 | Prieto et al. |
| 5,945,322 A | 8/1999 | Gotschlich |
| 5,955,347 A | 9/1999 | Lowe |
| 5,955,422 A | 9/1999 | Lin |
| 5,962,294 A | 10/1999 | Paulson et al. |
| 6,017,743 A | 1/2000 | Tsuji et al. |
| 6,040,498 A | 3/2000 | Stomp et al. |
| 6,096,512 A | 8/2000 | Elhammer et al. |
| 6,204,431 B1 | 3/2001 | Prieto et al. |
| 6,300,113 B1 | 10/2001 | Landry |
| 6,333,182 B1 | 12/2001 | Coleman et al. |
| 6,410,246 B1 | 6/2002 | Zhu et al. |
| 6,783,971 B2 | 8/2004 | Coleman et al. |
| 6,858,415 B2 | 2/2005 | Coleman et al. |
| 6,949,372 B2 | 9/2005 | Betenbaugh et al. |
| 7,029,872 B2 | 4/2006 | Gerngross |
| 7,064,191 B2 | 6/2006 | Shinkawa et al. |
| 7,214,775 B2 | 5/2007 | Hanai et al. |
| 2002/0137134 A1 | 9/2002 | Gerngross |
| 2003/0013173 A1 | 1/2003 | Clausen et al. |
| 2004/0018590 A1 | 1/2004 | Gerngross et al. |
| 2004/0171826 A1 | 9/2004 | Hamilton |
| 2004/0230042 A1 | 11/2004 | Hamilton |
| 2005/0170452 A1 | 8/2005 | Wildt et al. |
| 2005/0208617 A1 | 9/2005 | Bobrowicz et al. |
| 2005/0260729 A1 | 11/2005 | Hamilton |
| 2006/0024292 A1 | 2/2006 | Gerngross et al. |
| 2006/0024304 A1 | 2/2006 | Gerngross et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0040353 A1 | 2/2006 | Davidson et al. |
| 2006/0078963 A1 | 4/2006 | Gerngross |
| 2006/0148035 A1 | 7/2006 | Gerngross |
| 2006/0160179 A1 | 7/2006 | Bobrowicz et al. |
| 2006/0177898 A1 | 8/2006 | Gerngross |
| 2006/0211085 A1 | 9/2006 | Bobrowicz |
| 2006/0286637 A1 | 12/2006 | Hamilton |
| 2007/0105127 A1 | 5/2007 | Gerngross |

FOREIGN PATENT DOCUMENTS

| | | |
|---|---|---|
| EP | 1054062 | 11/2000 |
| EP | 1211310 | 6/2002 |
| EP | 1522590 | 4/2005 |
| EP | 1297172 | 11/2005 |
| JP | 8-336387 | 12/1998 |
| JP | 11137247 | 5/1999 |
| WO | 96/21038 | 7/1996 |
| WO | 97/30087 | 8/1997 |
| WO | 98/05768 | 2/1998 |
| WO | 99/31224 | 6/1999 |
| WO | 99/54342 | 10/1999 |
| WO | 00/52135 | 9/2000 |
| WO | 00/61739 | 10/2000 |
| WO | 01/14522 | 3/2001 |
| WO | 01/19960 | 3/2001 |
| WO | 01/25406 | 4/2001 |
| WO | 02/00856 | 1/2002 |
| WO | 02/00879 | 1/2002 |
| WO | 03/031464 | 4/2003 |
| WO | 03/056914 | 7/2003 |
| WO | 2004/003194 | 1/2004 |
| WO | 2004/063370 | 7/2004 |
| WO | 2004/074458 | 9/2004 |
| WO | 2004/074461 | 9/2004 |
| WO | 2004/074497 | 9/2004 |
| WO | 2004/074498 | 9/2004 |
| WO | 2004/074499 | 9/2004 |
| WO | 2007/028144 | 3/2007 |

OTHER PUBLICATIONS

Fukuta et al., Glycoconjugate Journal, vol. 17 (2000) pp. 895-904.
Office Action issued by Canadian Intellectual Property Office Action in Canadian Application No. 2,562,772, dated Jan. 4, 2013.
English Abstract of JP11137247, published May 25, 1999.
Lawrence, "Cloning and expression of human sialic acid . . . ", Glycoconjugate Journal (2001), vol. 18, pp. 205-213.
Davidson, "A PCR-based strategy to generate integrative . . . ", Microbiology (2002), vol. 148, pp. 2607-2615.
Liao, "Cloning, expression, purification, and characterization . . . ", J. Biol. Chem. (1996), vol. 271, pp. 28348-28358.
Ren, "Purification and properties of a Golgl-derived (alpha 1, 2)- . . . ", Biochemistry (1995), vol. 34, pp. 2489-2495.
Svetina, "Expression of catalytic subunit of bovine . . . ", J. Biotechnology (2000), vol. 76, pp. 245-251.
Yamashita, "An alpha-mannosidase purified from *Aspergillus Saitol* . . . ", Biochem. & Biophys. Research Comm. (1980), vol. 96, pp. 1336-1342.
EP1297172B1—Glycode Opposition Brief (French text), dated Jul. 26, 2006, pp. 1-26.
EP1297172B1—Glycode Opposition Brief (English translation), dated Aug. 25, 2006, pp. 1-26.
EP1297172B1—Novozyme Opposition Brief, dated Mar. 22, 2007, pp. 1-38.
EP1297172B1—Patentee's Rep;y to Notice of Opinion, dated Aug. 4, 2006, pp. 1-34.
EP1297172B1—EPO Non-Binding Opinion, dated Jun. 29, 2007, pp. 1-9.
Roberts, "*Drosophila melanogaster* GMII gene, exons 1-5", XP002293614, Database accession No. AJ132715, abstract, Database EMBL (1999).
Satou, "*Ciona intestinalis* cDNA, clone:cieg014e11 . . . ", XP002293811, Database accession No. AK116684, the whole document, Database EMBL (2002).
Shinn, "*Arabidopsis thaliana* AT5g14950/F2G14_70 mRNA . . . ," XP002293612, Database accession No. AY052707, Abstract, Database EMBL (2001).
SWISS-PROT Entry P11655 (Sec12_Yeast), "Membrane glycoprotein SEC12", Oct. 1989.
SWISS-PROT Entry P32906 (MNS1_Yeast), "Endoplasmic reticulum mannosyl-oligosaccharide 1,2-alpha-mannosidase", Oct. 1993.
SWISS-PROT Entry P39107 (MNN9_Yeast), "Mannan polymerase complexes MNN9 subunit", Feb. 1995.
SWISS-PROT Entry P50108 (MNN10_Yeast), "Probable alpha-1,6-mannosyltransferase MNN10", Oct. 1996.
SWISS-PROT Entry P53008 (CWH41_Yeast), "Mannosyl-oligosaccharide glucosidase", Oct. 1996.
Accession No. AF005034, *Spodoptera frugiperda* alpha-mannosidase II mRNA . . . , Jul. 10, 1997.
Accession No. CAA98114, "Hypothetical protein D2030.1 (*Caenorhabditis elegans*)", Aug. 9, 2005.
Accession No. X77652, "*D. melanogaster* putative golgi/mannosidase II mRNA", Apr. 24, 1995.
Accession No. X61172, "Mouse mRNA for alpha-mannosidase II", Apr. 18, 2005.
Accession No. XM_218816, "Predicted: *Rattus norvegicus* mannosidase 2, alpha 2 (predicted) . . . ", Apr. 15, 2005.
Accession No. U31520, "Human alpha mannosidase II mRNA . . . ", Dec. 13, 1995.
Accession No. NM_008715, "*Homo sapiens* mannosidase, alpha, class 2C, member 1 (MAN2C1) . . . ", Oct. 18, 2006.
Accession No. AF106080, "*Kluyveromyces lactis* alpha N-acetylglucosamine transferase . . . ", Apr. 17, 1999.
Accession No. D55649, "*Homo sapiens* mRNA for alpha mannosidase II isozyme . . . ", Feb. 7, 2003.
Accession No. NM_002406, "*Homo sapiens* mannosyl (alpha-1, 3-)-glycoprotein . . . ", Sep. 23, 2005.

(56) References Cited

OTHER PUBLICATIONS

Accession No. NM_073594, "*Caenorhabditis elegans* F58H1.1 (alpha-mannosidase) . . . ", Aug. 19, 2005.
Accession No. NM_008548, "*Mus musculus* mannosidase 1, alpha . . . ", Apr. 7, 2003.
Accession No. NM_000528, "*Homo sapiens* mannosidase, alpha, class 2B . . . ", Sep. 24, 2005.
Accession No. AK116684, "Clona intestinalis cDNA, clone:cleig014e11 . . . ", Nov. 30, 2002.
Accession No. NM_121499, "*Arabidopsis thaliana* alpha-mannosidase AT5G14950 mRNA . . . ", Nov. 4, 2005.
Abeijon, "Molecular cloning of the Golgi apparatus uridine . . . ", PNAS (1996), vol. 93, pp. 5963-5988.
Adachi, "*Mus musculus* adult male testis cDNA . . . ", XP002293645, Database accession No. AK029913, abstract Database EMBL (2002).
Alani, "A method for gene disruption that allows repeated use . . . ", Genetics (1987). vol. 116, pp. 541-545.
Altman, "Insect cells as hosts for the expression of recombinant glycoproteins", Glycoconjugate Journal (1999), vol. 16, pp. 109-123.
Altman, "Processing of asparagine-linked oligosaccharides in insect cells: . . . ", Glycoconjugate Journal (1995), vol. 12, pp. 150-155.
Alvaino, "Sialic acids in fungi: . . . ", Glycoconiugate Journal (1999), vol. 16, pp. 545-554.
Andersen, "The effect of cell-culture conditions on the oligosaccharide . . . ", Curr. Opin. Biotech. (1994), vol. 5, pp. 546-549.
Annunziato, "Nucleotide sequence and genetic analysis of the neuD . . . ", J. Bacteriol. (1995), vol. 177, pp. 312-319.
Aoki, "Expression and activity of chimeric molecules between human . . . ", J. BioChem. (Tokyo) (1999), vol. 126, pp. 940-950.
Aumiller, "A transgenic insect cell line engineered to produce CMP-sialic . . . ", Glycobiology (2003), vol. 13, pp. 497-507.
Bakker, "Galactose-extended glycans of antibodies produced by transgenic . . . ", PNAS (2001), vol. 98, pp. 2899-2904.
Ballou, "Isolation, characterization, and properties of *Saccharomyces cerevisiae* . . . ", Methods Enzymology (1990), vol. 185, pp. 440-470.
Barak Briles, "Isolation of wheat germ agglutinin-resistant clones . . . ", J. Biol. Chem. (1977), vol. 252, pp. 1107-1116.
Bardor, "Analysis of the N-glycosylation of recombinant glycoproteins ..", Trends in Plant Science (1999), vol. 4, pp. 376-380.
Beaudet, "High-level expression of mouse Mdr3 P-glycoprotein in yeast . . . ", Methods Enzymol. (1998). vol. 292, pp. 397-413.
Berka, "The filamentous fungus *Aspergillus-niger* var awamori as host . . . ", Abstr. Papers (203rd ACS National Meeting, San Francisco, CA, Amer. Chem. Soc. (1992), vol. 203, pp. 121-BIOT.
Accession No. NP010872, "Gdalp (*Saccharomyces cerevisiae* )", submitted Nov. 17, 1999.
Accession No. NP010920, "Apyrase with wide substrate specificity, involved in preventing . . . ", submitted Nov. 10, 1999.
Jacobs, "Engineering complex-type N-glycosylation in *Pichia pastoris* . . . ", Nature Protocols (2009), vol. 4, pp. 58-70.
Velardo, "The presence of UDP-N-acetyiglucosamine:alpha-3-D-mannoside . . . ", J. Biol. Chem. (1993), vol. 268, pp. 17902-17907.
Ren, "Purification and properties of alpha-mannosidase II from Goigi-like membranes . . . ", Biochem. J., (1997), vol. 324, pp. 951-956.
Wu, "The methylotrophic yeast *Pichia pastoris* synthesizes a functionally active chromophore . . . ", PNAS (1996), vol. 93, pp. 8989-8994.
Voet, "Antifreeze glycoproteins prevent antarctic fish from freezing", Biochemistry (1990), Section 10-3, Glycoproteins, pp. 266-267.
Tatara, "Identification of catalytic residues of Ca2+-independent 1 ,2-α-d-mannosidase . . . ", J. Biol. Chem. (2003), vol. 278, pp. 25289-25294.
Fujita, "Five crucial carboxyl residues of 1,2-α-mannosidase . . . ", Biochem. & Biophys. Res. Comm. (1997), vol. 238, pp. 779-783.
Merriam-Webster, on-line definition of the word "Domain" (2007), Item No. 9, "any of three-dimensional subunits of a protein that are formed by the folding of its linear peptide chain . . . ".

Lee, "Sequential-integration for the regulated insertion of cloned genes in *Saccharomyces cerevisiae* . . . ", Biotech. Prog. (1997), vol. 13, pp. 368-373.
Weng, "Evaluation of the early processing routes of N-linked oligosaccharides . . . ", Glycobiology (1996), vol. 6, pp. 861-888.
Schlegel, "Human prostate expression marker cDNA 29377" Database GSN Derwent (2002), Abstract No. ABV29386, XP002293375.
Zhu, "Structural studies of α-N-acetylgalactosaminidase: . . . ", Arch. Biochem. Biophys. (1998), vol. 352, pp. 1-8.
Vervecken, "In vivo synthesis of marnmalian-like, hybrid-type N-glycans in *Pichia pastoris*", Appl. Environ. Microbiol. (2004), vol. 70, pp. 2639-2646.
Minowa, "cDNA cloning and expression of bovine UDP-N-acetylglucosamine: . . . ", J. Biol. Chem. (1998), vol. 273, pp. 11556-11562.
Fukuta, "Remodeling of sugar chain structures of human Interferon-gamma", Glycobiology (2000), vol. 10, pp. 421-430.
Duman, "O-Mannasylation of *Pichia pastoris* cellular and recombinant proteins", Biotech. Appl. Biochem. (1998), vol. 26, pp. 39-45.
Li, "Optimization of humanized IgGs in glycoengineered *Pichia pastoris*", Nature Biotech. (2006), vol. 24, pp. 210-215.
Lifely, "Glycosylation and biological activity of CAMPATH-1H . . . ", Glycobiology (1995), vol. 5, pp. 813-822.
Yamane-Ohnuki, "Establishment of FUT8 knockout Chinese hamster . . . ", Biotech. Bioengin. (2004), vol. 87, pp. 614-622.
Weikert, "Engineering Chinese hamster ovary cells to maximize . . . ", Nature Biotech. (1999), vol. 17, pp. 1116-1121.
Maras, "Filamentous fungi as production organisms for glycoproteins . . . ", Glycoconjugate Journal (1999), vol. 16, pp. 99-107.
Seffernick, "Melamine deaminase and atrazine chlorohydroiase: . . . ", J. of Bacteriol. (2001), vol. 183, p. 2405-2410.
Witkowski, "Conversion of a beta-ketoacyl synthase to a malonyl decarboxylase . . . ", Biochemistry (1999), vol. 38, pp. 11643-11650.
Broun, "Catalytic plasticity of fatty acid modification enzymes . . . ", Science (1998), vol. 282, pp. 1315-1317.
Berninsone, "Functional expression of the murine Golgi CMP-sialic acid . . . ", J. Biol. Chem. (1997), vol. 272, p. 12616-12619.
Berninsone, "Regulation of yeast Golgi glycosylation . . . ", J. Biol. Chem. (1995), vol. 270, pp. 14564-14567.
Berninsone, "The Golgi guanosine diphosphatase is required . . . ", J. Biol. Chem. (1994), vol. 269, pp. 207-211.
Bianchi, "Transformation of the yeast Kluyweromycas lactis by new vectors . . . ", Curr. Genetics (1987), vol. 12, pp. 185-192.
Boehm, "Disruption of the KEX1 gene in *Pichia pastoris* allows expression . . . ", Yeast (1999), vol. 16, pp. 563-572.
Boevink, "Stacks on tracks: the plant Golgi apparatus traffics on an actin/ER network," Plant Journal (1998), vol. 15, pp. 441-447.
Bonneaud, "A family of low and high copy replicative, integrative, . . . ", Yeast (1991), vol. 7, pp. 809-615.
Bretthauer, "Genetic engineering of *Pichia pastoris* to humanize . . . ", Trends in Biochem. (2003), vol. 21, pp. 459-462.
Bretthauer, "Glycosylation of *Pichia pastoris*-derived proteins", Biotech. Appl. Biochem. (1999), vol. 30, pp. 193-200.
Brockhausen, "Control of glycoprotein synthesis. The use of oligosaccharide substrates . . . ", Biochem. Cell Biol. (1988), vol. 66, pp. 1134-1151.
Callewaert, "Use of HDEL-tagged *Trichoderma reesei* mannosyl oligosaccharide . . . ", FEBS Letters (2001), vol. 503, pp. 173-178.
Lin Cereghino, "Heterologous protein expression in the methylotrophic yeast . . . ", FEMS Microbiol. Rev. (2000), vol. 24, pp. 45-66.
Lin Cereghino, "New selectable marker/auxotrophic host strain . . . ", Gene (2001), vol. 263, pp. 159-169.
Chadrasekaran, "Purification and properties of alpha-D-mannose-beta-1,2- . . . ", Cancer Res. (1984), vol. 44, pp. 4059-4068.
Chen, "Purification and characterization of N-acetylneuraminic acid . . . ", Glycobiology (2002), vol. 12, pp. 65-71.
Chiba, "Production of human compatible high mannose-type . . . ", J Biol. Chem. (1998), vol. 273, pp. 26298-26304.
Choi, "Use of combinatorial generic libraries to humanize N-linked glycosylation . . . ", PNAS (2003), vol. 100, pp. 5022-5027.

(56) References Cited

OTHER PUBLICATIONS

Chui, "Alpha-mannosidase-II deficiency results in Dyserythropoiesis and . . . ", Cell (1997), vol. 90, pp. 157-167.
Chui, "Genetic remodeling of protein glycosylation in vivo . . . ", PNAS (2001), vol. 98, pp. 1142-1147.
Colli, "Trans-slalidase: a unique enzyme activity discovered in the protozoan . . . ", FASEB J., (1993), vol. 7, pp. 1257-1264.
Cregg, "Recombinant protein expression in *Pichia pastoris*", Mol. Technol. (2000), vol. 16, pp. 23-52.
Daniel, "Mammalian alpha-mannosidases—multiple forms . . . ", Glycobiology (1994), vol. 4, pp. 551-586.
Dente, "Human alpha-1-acid glycoprotein genes", Prog. Clin. Biol. Res. (1989), vol. 300, pp. 85-98.
Dirnberger, "The Golgi locaRzation of *Arabidopsis thaliana* beta 1,2- . . . ", Plant Mol. Biol. (2002), vol. 50, pp. 273-281.
Duvet, "Cytosolic deglycosylation process of newly synthesized . . . ", Biochem J. (1998) vol. 335, pp. 389-396.
Eades, "Characterization of the Class I alpha-mannosidase gene family . . . ", Gene (2000), vol. 255, pp. 25-34.
Eckhardt, "Molecular cloning of the hamster CMP-sialic acid . . . ", Eur. J. Biochem. (1997), vol. 248, pp. 187-192.
Essl, "The N-terminal 77 amino acids from tobacco . . . ", FEBS Letters (1999), vol. 18, pp. 169-173.
Foster, "Cloning and sequence analysis of Gmil, a drosophila . . . ", Gene (1995), vol. 154, pp. 183-186.
Fritsch, "Determination of cytidine 5'-monophospho-N-acetylneuraminic . . . ". J Chromatogr. A. (1996), vol. 727, pp. 223-230.
Fujiyama, "In vivo conversion of a glycan to human compatible type . . . ", Biochem. Blophys. Res. Comm. (2001), vol. 289, pp. 553-557.
Gleeson, "Targeting of proteins to the Golgi apparatus", Histochem. Cell Biol. (1998), vol. 109, pp. 517-532.
Gonzalez, "The alpha-mannosidases: Phylogeny and adaptive . . . ", Molecular Biology and Evolution (2000), vol. 17, pp. 292-300.
Graham, "Compartmental organization of Goigi-specific protein modification . . . ", J. Cell Biol. (1991), vol. 114, pp. 207-218.
Grard, "Oligomannosides or oligosaccharide-lipids as potential substrates . . . ", Biochem. J. (1998), vol. 316, pp. 787-792.
Gu, "Improvement of interferon-gamma sialylation in Chinese hamster . . . ", Biotech. and Bioeng. (1998), vol. 58, pp. 642-648.
Guillen, "Mammalian Golgi apparatus UDP-N-acetylglucosamine . . . ", PNAS (1998), vol. 95, pp. 7888-7892.
Hamilton, "Production of complex human glycoproteins in yeast", Science (2003), vol. 301, pp. 1244-1246.
Hansen, "Further development of the cassette-based pYC plasmid . . . ", FEMS Yeast Res. (2003), vol. 4, pp. 323-337.
Harkki, "A novel fungal express system—secretion of active . . . ", Bio-Tech (1989), vol. 7 (1989), pp. 596-603.
Harms, "Biosynthesis of N-acetylneuraminic acid in Morris . . . ", Eur. J. Biochem. (1973), vol. 32, pp. 254-262.
Harris, "*Caenorhabditis elegans* cosmid F58H1" XP002293610, Protein F58H1.1, abstract, Database EMBL (1996).
Hinderlich, "A bifunctional enzyme catalyzes the first two steps . . . ", J. Biol. Chem. (1997), vol. 272, pp. 24313-24316.
Hollister, "Stable expression of mammalian beta 1,4-galactosyltransferase . . . ", Glycobiology (1998), vol. 8, pp. 473-480.
Hollister, "Engineering lepidopteran Insect cells for siaioglycoprotein production . . . ", Glycobiology (2001), vol. 11, pp. 1-9.
Ichishima, "Molecular and enzymic properties of recombinant . . . ", Biochem. J. (1999), vol. 339, pp. 589-297.
Inoue, "Molecular cloning and sequence analysis of a cDNA encoding . . . ", J. Biol. Chem. (1990), vol. 265, pp. 6556-6561.
Ishida, "Molecular cloning and functional expression of the human Golgi . . . ", J. Biochem. (1999), vol. 126, pp. 68-77.
Jarvis, "Engineering N-glycosylation pathways in the baculovirus-insect . . . ", Curr. Opin. Biotech. (1998), vol. 9, p. 528-533.
Jarvis, "Isolation and characterization of a Class II alpha-mannosidase . . . ", Glycobiology (1997), vol. 7, pp. 113-127.
Kainuma, "Coexpression of alpha1,2-galactosyltransferase . . . ", Glycobiology (1999), vol. 9, p. 133-141.
Kalsner, "Insertion into *Aspergillus nidulans* of functional UDP-GlcNAc: . . . ", Glycoconjugate J. (1995), vol. 12, pp. 360-370.
Kawar, Insect cells encode a Class II . . . :, J. Biol. Chem. (2001), vol. 276, pp. 16335-16340.
Kelm, "Sialic acids in molecular and cellular interactions", Int. Rev. Cytol. (1997), vol. 175, pp. 137-240.
Keppler, "UDP-GicNAo 2-epimerase: A regulator of cell . . . ", Science (1999), vol. 284, pp. 1372-1376.
Khatra, "Some kinetic properties of human milk . . . ", Eur. J Biochem. (1974), vol. 44, pp. 537-560.
Krezdorn, "Human beta1,4 galactosyltransferase and alpha2,6 sialytransferase . . . ", Eur. J Biochem. (1994), vol. 220, p. 809-817.
Lal, "Substrate specificities of recombinant murine Golgi . . . ", Glycoblology (1998), vol. 8, pp. 981-995.
Lal, "Isolation and expression of murine and rabbit cDNAs encoding . . . ", J. Biol. Chem. (1994), vol. 269, pp. 9872-9881.
Laroy, "Characterization of sielyltransferase mutants using surface . . . ", Glycobiology (2000), vol. 11, pp. 175-182.
Lawrence, "Cloning and expression of the human N-acetylneuraminic acid phosphate . . . ", J. Biol. Chem. (2000), vol. 275, pp. 17869-17877.
Lehle, "Membrane-bound mannosyl transferase in yeast . . . ", Biochem. Biophys. Acta (1974), vol. 350, pp. 225-235.
Lerouge, "N-glycoprotein biosynthesis in plants: . . . ", Plant Mol. Biol. (1998), vol. 38, pp. 31-48.
Lu, "Cloning and disruption of the b-isopropylmalate dehydrogenase . . . ", Appl. Microbiol. Biotech. (1998), vol. 49, pp. 141-146.
Lussier, "The KTR and MNNI mannosyltransferase families . . . ", Biochimica et Biophys. Acta (1999), vol. 1426, pp. 323-334.
Maliekal, "Identification of the sequence encoding N-acetylneuraminate- . . . ", Glycobiology (2006), vol. 16, pp. 165-172.
Malissard, "Expression of functional soluble forms of human beta- . . . ", Biochem. Biophys. Res. Comm. (2000), vol. 267, pp. 169-173.
Wishart, "A single mutation converts a novel phosphotyrosine . . . ", J. Biol. Chem. (1995), vol. 270, pp. 26782-26785.
Maras, "In vitro conversion of the carbohydrate moiety of fungal . . . ", Eur. J. Biochem. (1997), vol. 249, pp. 701-707.
Maras, "Molecular cloning and enzymatic characterization of a Trichoderma reeisi . . . ", J. Biotech. (2000), vol. 77, pp. 255-263.
Marchal, "Expression of a membrane-bound form of *Trypanosoma cruzi* trans-sialidase . . . ", Glycobiology (2001), vol. 1, pp. 693-603.
Martinet, "Modification of the protein glycosylation pathway . . . ", Biotech. Letters (1998), vol. 20, pp. 1171-1177.
Maru, "Molecular cloning and identification of N-acyl-D-glucosamine- . . . ", J. Biol. Chem. (1996), vol. 271, pp. 16294-16299.
Maruyama, "A 1,2-alpha-D-mannosidase from a *Bacillus* sp.: . . . ", Carbohydrate Res. (1994), vol. 251, pp. 89-98.
Mattila, "Targeting of active rat alpha 2,3-sialyltransferase . . . ", Glycobiology (1996), vol. 6, pp. 851-859.
McClure, "Modeling the growth, survival and death of microorganisms . . . ", Int. J. Food Microbiol. (1994), vol. 23, pp. 285-275.
McGarvey, "Expression of the rabies virus glycoprotein in transgenic tomatoes," Bio-Technology (1995), vol. 13, pp. 1484-1487.
McKerrell, "Construction and characerization of an acapsular mutant Mannhelmla haemolytica A1," Infect. Immun. (2002), vol. 20, pp. 2622-2629.
Mercker, "Biosynthesis of the polysialic acid capsule in *Escherichia coli* . . . ", Glycobiology (1990), vol. 1, pp. 93-100.
Merkle, "Cloning, expression, purification, and characterization of the murine . . . ", Biochim. Biophys. Acta (1997), vol. 1336, pp. 132-146.
Miele, "Glycosylation properties of the *Pichla pastoris*-expressed recombinant . . . ", Biotech. Appl. Biochem. (1997), vol. 25, pp. 151-157.
Misaki, "Plant cultured cells expressing human beta1,4-galactosyltransferase . . . ", Glycobiology (2003), vol. 13, pp. 199-205.
Moremen, "Biosynthesis and modffication of Golgi mannosidase II in HeLa . . . ", J. Biol. Chem. (1965), vol. 260, pp. 6654-6662.

(56) References Cited

OTHER PUBLICATIONS

Moremen, "Glycosidases of the asparagine-linked oilgosaccharide . . . ", Glycobiology (1994), vol. 4, pp. 113-125.
Moremen, Isolation, characterization, and expression of cDNAs encoding murine . . . , J. Cell Biology (1991), vol. 116, pp. 1521-1534.
Moremen, "Topology of mannosidase II in rat liver Golgi membranes . . . ", J. Biol. Chem. (1986), vol. 261, pp. 10945-10951.
Moremen, "Golgi alpha-mannosidase II deficiency in vertebrate systems: . . . ", Biochimica Biophysica Acta. (2002), vol. 1573, pp. 225-235.
Moremen, Isolation of a rat liver Golgi mannosidase II clone . . . :, PNAS (1989), vol. 86, pp. 5276-5280.
Morin-Ganet, "Morphogenesis and dynamics of the yeast Golgi . . . ", Traffic (2000), vol. 1, pp. 56-58.
Munster, "Mammalian cytidine 5'-monophosphate conserved . . . ", PNAS (1998), vol. 95, pp. 9140-9145.
Nakanishi-Shindo, "Structure of the N-linked oligosaccharides . . . ", J. Biol. Chem (1993), vol. 288, pp. 26338-26345.
Nakata, "Molecular cloning and expression of the mouse . . . ", Biochem. Biophys. Res. Comm. (2000), vol. 273, pp. 642-648.
Nakayama, "Substrate specificity of . . . ", FEBS Lett. (1997), vol. 412, pp. 547-550.
Nakayama, "OCHI1 encodes a novel membrane bound . . . ", Embo Journal (1992), vol. 11, pp. 2511-2519.
Neiman, "*Saccharomyces cerevisiae* HOC1, . . . ", Genetics (1997), vol. 145, pp. 637-646.
Nett, "Cloning and disruption of the *Pichia pastoris* . . .", Yeast (2006), vol. 22, pp. 295-304.
Nikawa "Structural and functional conservation of human . . .", Gene (1998), vol. 171, pp. 107-111.
Ogawa, "Structure and transcriptional regulation of human . . . ", Eur. J. Biochem. (1996), vol. 242, pp. 446-453.
Oh-Neda, "Overexpression of the Golgi-localized enzyme . . . ", Eur. J. Biochem. (2001), vol. 268, pp. 1280-1288.
Ohta, "Complete nucleotide sequence of the *E. coli* N-acetylneuraminate . . . ", Nucleic Acids Res. (1985), vol. 13, pp. 8843-8852.
Palacpac, "Stable expression of human beta1,4-galactosyltransferase . . . ", PNAS (1999), vol. 96, pp. 4692-4697.
Papac, "A high-throughput microscale method to release N-linked . . . ", Glycobiology (1998), vol. 8, pp. 445-454.
Parodi, "N-glycoslation in trypanosomatid protozoa", Glycobiology (1993), vol. 3, pp. 193-199.
Pereira, "The *Trypanosoma cruzi* neuraminidase contains sequences . . . ", J. Exp. Med. (1991), vol. 174, pp. 179-191.
Perez, "Transport of sugar nucleotides into the lumen of vesicles . . . ", Methods in Enzymology (1987), vol. 138, pp. 709-715.
Puglielli, "Reconstitution, identfication, and purification of the rat liver Golgi ,..", J. Biol. Chem. (1999), vol. 274, pp. 35596-35600.
Rabouille, "The Drosophila GMII gene encodes Golgi alpha-mannosidase II", J. Cell Sci. (1999), vol. 112, pp. 3319-3330.
Raju, "Analysis of glycoconjugates", Anal. Biochem. (2000), vol. 283, p. 123-124.
Raju, "Glycoengineering of therapeutic glycoproteins: in vitro galactosylation . . . ", Biochem. (2001), vol. 40, pp. 8868-8876.
Raschke, "Genetic control of yeast mannan structure. Isolation and . . . ", J. Biol. Chem. (1973), vol. 248, pp. 4660-4686.
Ringenberg, "The first committed step in the biosynthesis of sialic acid by *Escherichia coli* K1 . . . ", Mol. Microbiol. (2003), vol. 50, pp. 961-975.
Ringenberg, "Redirection of sialic acid metabolism in genetically . . . ", Glycobiology (2001), vol. 11, pp. 533-539.
Rodrigues, "Sialylglycoconjugates and sialyltransferase activity . . . ", Glycoconjugate Journal (2002), vol. 19, pp. 165-173.
Romero, "Ktr1P is an . . . ", Biochem. Journal (1997), vol. 321, pp. 289-295.
Romero, "Mutation of Arg273 to Leu alters the specificity of the yeast . . . ", J. Biol. Chem. (2000), vol. 275, pp. 11071-11074.
Rump, "Biosynthesis of ganliosides in primary cultures of rat . . . ", Biol. Chem. Hoppe Sayler (1986), vol. 367, pp. 425-432.
Ruther, "o-fos expression interferes with thymus development . . . " Cell (1988), vol. 53, pp. 847-856.
Sato, "*Arabidopsis thaliana* DNA chromosome 5, BAC clone . . . ", Database accession No. AL391146, Abstract, Database EMBL Aug. 7, 2000.
Schacter, "The 'Yellow Brick Road' to branched complex N-glycans", Glycobiology (1991), vol. 1, pp. 453-461.
Schenkman, "Structural and functional properties of Trypanosoma . . . ", Ann. Rev. Microbiol. (1994), vol. 48, pp. 499-523.
Schneikert, "Characterization of a novem mouse recombinant . . . ", Glycobiology (1994), vol. 4, pp. 445-450.
Schwientek, "Golgi localization in yeast is mediated by the membrane . . . ", J. Biol. Chem. (1995), vol. 270, pp. 5483-5489.
Segawa, "*Schizosaccharomyces pombe* UDP-galactose transporter: . . . ", FEBS Letters (1999), vol. 451, pp. 295-296.
Sikorski, "A system of shuttle vectors and yeast host strains . . . ", Genetics (1989), vol. 122, pp. 19-27.
Soderholm, "Vector for pop-in/pop-out gene replacement . . . ", Biotechniques (2001), vol. 31, pp. 308-310.
Sommers, "Transport of sugar nucleotides into rat liver Golgi", J. Cell Biol. (1981), vol. 91, pp. A406-A406.
Sommers, "Transport of sugar nucleotides into rat liver Golgi . . . ", J. Biol. Chem. (1982), vol. 257, pp. 10811-10817.
Stasche, "A bifunctional enzyme catalyzes the first two steps in N-acetylneuraminic acid . . . ", J. Biol. Chem. (1997), vol. 272, pp. 24319-24324.
Staub, "High-yield production of a human therapeutic protein . . . ", Nature Biotech. (2000), vol. 18, pp. 333-336.
Stix, "Supercharging protein manufacture," Scientific American (2004), vol. 290, pp. 32-33.
Strasser, "Molecular cloning of cDNA encoding N-acetylglucosaminyl-transferase . . . ", Glycoconjugate Journal (1999), vol. 16, pp. 787-791.
Takeuchi, "Trial for molecular breeding of yeast for the production . . . ", Trends in Glycoscience and Glycotech. (1997), vol. 9, pp. S29-S35.
Umana, "Engineered glycoforms of antineuroblastoma IgG1 with . . . ", Nature Biotech. (1999), vol. 17, pp. 176-180.
Ware, "Expression of human platelet glycoprotein Ib-alpha . . . ", Thrombosis end Haemostasis (1993), vol. 69, pp. 1194, Abstract No. 2328.
Wee, "Targeting of active sialyltransferase to the plant Golgi . . . ", Plant Cell (1998), vol. 10, pp. 1759-1768.
Weig, "Systematic Identification in silico of covalently bound cell wall . . . ", Microbiology (2004), vol. 150, pp. 3129-3144.
Sigmund, "Viewpoint: Are studies in genetically altered . . . ", Arterioscler. Throm. Vasc. Biol. (2000), vol. 20, pp. 1425-1429.
Werner, "Appropriate mammalian expression systems . . . ", Arzneimittelforschung (1998), vol. 48, pp. 870-880.
Wiggins, "Activity of the yeast MNN1 alpha-1,3-mannosyltransferase . . . ", PNAS (1998), vol. 95, pp. 7945-7950.
Yang, "Effects of ammonia on CHO cell growth, erythropoietin . . . ", Biotech. Bioeng. (2000), vol. 68, pp. 370-380.
Yang, "Glycosylation and proteolytic processing of 70 kDa . . . ", Glycobiology (1999), vol. 9, pp. 1347-1355.
Yip, "Cloning and analysis of the *Saccharomyces cerevisiae* MNN9 . . . ", PNAS (1994), vol. 91, pp. 2723-2727.
Yoko-O, "*Schizosaccharomyces pombe* och1(+) encodes . . . ", FEBS Letters (2001), vol. 489, pp. 75-80.
Yoshida, "1,2-alpha-D-mannosidase from Penicillum citriunum: . . . ", Biochem. Journal (1993), vol. 290, pp. 349-354.
Yoshida, "Expression and characterization of rat UDP-N- . . . ", Glycobiology (1999), vol. 9, pp. 53-58.
Zapata, "Sequence and expression of the *Escherichia coli* . . . ", J. Bacteriol. (1992), vol. 174, pp. 315-319.
Zapata, "Sequence of the cloned *Escherichia coli* . . .", J. Biol. Chem. (1989), vol. 264, pp. 14769-14774.
Zerangue, "Analsysis of endoplasmic reticulum trafficking signals . . . ", PNAS (2001), vol. 98, pp. 2431-2436.
Yamamoto, "alpha 2,6-sialyltransferase gene transfection . . . ", Neurochem. (1997), vol. 68, pp. 2566-2576.

(56) References Cited

OTHER PUBLICATIONS

Kappel, "Regulating gene expression in transgenic animals", Curr. Opin. in Biotech. (1992). vol. 3, pp. 558-583.
Taft, "Know thy mouse" Trends in Genetics (2005), vol. 22, pp. 649-653.
Linder, "The influence or genetic background on spontaneous and . . . ", Lab. Animal (2001), vol. 30, pp. 34-39.
Bilbo, "Behavioral phenotyping of transgenic and knockout animals: . . . ", Lab. Animal (2001), vol. 30, pp. 24-29.
Holschneider, "Genotype to phenotype: challenges and opportunities" Int. J. Dev. Neurosci. (2000), vol. 18, pp. 815-818.
Wood, "Phenotype assessment: Are you missing something?", Comp. Med. (2000), vol. 50, pp. 12-15.
Schwientek "Golgi localization in vivo activity of a mammalian . . . ", J. Biol. Chem. (1996), vol. 271, pp. 3398-3405.
Malissard, "Expression of functional soluble forms of human . . . ", Biochem. & Biophys. Res. Comm. (2000), vol. 267, pp. 169-173.
Schwientek "Cloning of a novel member of the UDP-galactose: . . . ", J. Biol. Chem. (1998), vol. 273, pp. 29331-29340.
Wildt, "The humanization of N-glycosylation pathways in yeast", Nat. Rev. Microbiol. (2005), vol. 3, pp. 119-128.
Orlean, "Dolichol phosphate mannose synthase is required in vivo . . . ", Mol. Cell. Biol. (1990), vol. 10, pp. 5796-5805.
Bobrowicz, "Engineering of an artificial glycosylation pathway blocked in core . . . ", Glycobiology (2004), vol. 14, pp. 757-766.
Fisher, "Towards molecular farming in the future: *Pichia pastoris*-based production . . . ", Biotech. Appl. Biochem., (1999), vol. 30, pp. 117-120.
Ramasamy, "Oligosaccharide preferences of beta1,4-galactosyltranserese-1: . . . ," J. Mol. Biol. (2005), vol. 353, p. 53-67.
Waters, "Prepro-alpha-factor has a cleavable signal sequence" J. Biol. Chem. (1988), vol. 263, pp. 6209-6213.
Van Die, "Glycosylation in Lepidopteran Insect cells: identification of a beta 14-N-acetylgalactosaminyltransferase", Glycobiology (1996), vol. 6, pp. 157-164.
Davidson, "Functional analysis of the ALG3 gene encoding the Dol-P-Man: . . . ", Glycobiology (2004), vol. 14, pp. 399-407.
Kawar, "N-Glycan processing by a lepidopteran insect alpha1,2-mannosidase", Glycobiology (2000), vol. 10, pp. 347-355.
Stanley, "Complementation between mutants of CHO cells resistant . . . ", Somatic Cell Genetics (1977), vol. 3, pp. 391-405.
Umana, "Tetracycline-regulated overexpression of glycosyltransferases . . . ", Biotech. Bioeng. (1999), vol. 65, pp. 542-549.
Stockert, "The Asialoglycoprotein receptor: relationships beween . . . ", Physiol. Rev. (1995), vol. 75, pp. 591-609.
Thoden, "Human UDP-galactose 4-epimerase", J. Biol. Chem. (2001), vol. 275, pp. 15131-15138.
Schwientek, "Golgi localization and in vivo activity of a mammalian . . . ", J. Biol. Chem. (1996), vol. 271, pp. 245-251.
Harris, "Irreversible inhibition of bovine lung angiotensin . . . ", J. Biol. Chem. (1982), vol. 257, pp. 811-815.
Majumdar, "UDPgalactose 4-epimerase from *Saccharomyces cerevisiae*", Eur. J. Biochem. (2004), vol. 271, pp. 753-759.
Lopez-Avalos, "The UDPase activity of the *Kluyveromyces lactis* Golgi . . . ", Glycobiology (2001), vol. 11, pp. 413-422.
Huffaker, "Yeast mutants deficient in protein glycosylation", PNAS (1983), vol. 80, pp. 7466-7470.
Abeijon, "Guanosine diphosphatase is required for protein and Sphingolipid . . . ", J. Cell Biol. (1993), vol. 122, pp. 307-323.
Fukuta, "The widespread effect of beta1,4-galactosyltransferase . . . ", Arch. Bloohem. & Biophys. (2001), vol. 392, pp. 79-86.
Gao, "YND1, a homologue of GDA1, encodes membrane-bound apyrase . . . ", J. Biol. Chem. (1999), vol. 274, pp. 21450-21456.
D'Alessio, "Nucleoside diphosphatase and glycosyltransferase . . . ", J. Biol. Chem. (2003), vol. 278, pp. 22379-22387.
Nett, "Cloning and disruption of the PpURA5 gene and construction . . . ", Yeast (2003), vol. 20, pp. 1279-1290.
Goldstein, "Three new dominant drug resistant cassettes for gene disruption . . . ", Yeast (1999), vol. 15, pp. 1541-1553.
Accession No. X65415, "Human mRNA for UDP_galactose: . . . ", submitted Nov. 1, 1990.
Accession No. AF616032, *Homo sapiens* guanosine-diphospatas like protein mRNA, . . . , submitted Jul. 24, 1997.
Accession No. AF038651, "*Homo sapiens* chromosome 1a21-1q23 . . . ", submitted Dec. 16, 1997.
Accession No. AF038860, "*Homo sapiens* chromosome 1p33-p34 . . . ", submitted Dec. 15, 1997.
Accession No. BAAP96814. "UDP-galactose transportter 2 (Homo sapients)", submitted May 8, 2000.
Accession No. BAA95815, "UDP-galactose transportter 1 (Homo sapients)", submitted May 8, 2000.
Accession No. NP 593447, Hypothetical protein SPAC824.08 (*Schizosaccaromyces pombe* 972h-). submitted Jun. 3, 2005.
Accession No. AL022598, "*S. pombe* chromosome III cosmid c1795", submitted Apr. 22, 1998.
Accession No. AH003575, "Genomic structure and expression of human . . . ", Biochem. Biophys. Res. Comm. (1991), vol. 176, pp. 1269-1276.
Accession No. CAC21576, Guanosine diphosphatase (*Kluyveromyces lactis*), submitted Jul. 11, 2000.

* cited by examiner

M. musculus alpha-1,2-mannosidase IA open reading frame. The transmembrane and catalytic domains are highlighted in bold respectively. The sequence of the primers used to generate the N-terminal truncations are highlighted by underlining and the start of each respective protein fragment indicated by an arrow.

```
  1  atgcccgtgggggggcctgctgttgcctgctcttcagtagccctggggggcggcctgggcagtggcctgggcctgggcggggaggaaggggg
  1▲ M  P  V  G  G  L  L  P  L  F  S  S  P  G  G  G  L  G  S  G  L  G  G  L  G  G  G  R  K  G
 97  tctggccccgctgccttccgcctccaccgagaagttcgtgctgctgtgttcagcgctttcatcacgctctgcttcggggcaatc
 33▲ S  G  P  A  A  F  R  L  T  E  K  F  V  L  L  V  F  S  A  F  I  T  L  C  F  G  A  I
184  ttcttcctgcctgactcctccaagctgctcagcggggtcctgttccactccaacccagccctgcagccgccagcacaagcccgggctcg
 62▲ F  F  L  P  D  S  S  K  L  L  S  G  V  L  F  H  S  N  P  A  L  Q  P  P  A  E  H  K  P  G  L
      d65 primer
278  gggcgcgtgcgggagatgccgccgagggggagagtccgcaccgaccgcgaggaaggcgcgcctgggactgaagacaacttagcca
 93▲ G  A  R  A  E  D  A  A  E  G  R  V  R  H  R  E  E  G  A  P  G  D  P  G  A  G  L  E  D  N  L  A
                                    d105 primer
374  ggatccgcgaaaccacgagcgggctctcaggagacccctcaggagaccctgcagaagctgccgagagatcaaagagacattctgctgagaagg
125▲ R  I  R  E  N  H  E  R  A  L  R  E  A  K  E  T  L  Q  K  L  P  E  E  I  Q  R  D  I  L  L  E  K
470  aaaaggtggcccaggaccagctgcgtgacaaggatctgttagggggcttgccaaggtggacttcctgcccccgtcggggtagagaaccgggagg
157▲ E  K  V  A  Q  D  Q  L  R  D  K  D  L  F  R  G  L  P  K  V  D  F  L  P  P  V  G  V  E  N  R  E
                                                                                      d187 primer
566  ccgctgacgaccaccatccgtgagaagggcaaagatcaaagagatgatgaccatgcttgaataattataaccgctatgcgtgggc
189▲ P  A  D  A  T  I  R  E  K  R  A  K  I  K  E  M  M  T  H  A  W  N  N  Y  K  R  Y  A  W  G
```

FIG.3

```
 655       ttgaacgaactgaaactatatcaaagaaggccattcaagcagtttgtttggcaacatcaaggagctacaatagtagatg
 219►            L  N  E  L  K  P  I  S  K  E  G  H  S  S  S  L  F  G  N  I  K  G  A  T  I  V  D
 737       ccctggatacccttttcattatgggcatgaagactgaattcaagaagctaaatcgtggattaaaaatatttagattttaa
 246►       A  L  D  T  L  F  I  M  G  M  K  T  E  F  Q  E  A  K  S  W  I  K  K  Y  L  D  F  N
 819       tgtgaatgctgaagtttctgttttttgaagtcaacatacgcttcgtgtgactgctgtcagcctactatttgtccggagag
 273►       V  N  A  E  V  S  V  F  E  V  N  I  R  F  V  G  G  L  L  S  A  Y  Y  L  S  G  E
 901       gagatatttcgaaagaaagcagtggaacttggggtaaattggtacttgcattcatcctctgaataccttggcat
 301►       E  I  F  R  K  K  A  V  E  L  G  V  K  L  L  P  A  F  H  T  P  S  G  I  P  W  A
 983       tcgtgaatatgaaagtgggatcgggcgaactgccctggaacgcagtatcctgccgcagtttggaactct
 328►       L  L  N  M  K  S  G  I  G  R  N  W  P  W  A  S  S  G  S  S  I  L  A  E  F  G  T  L
1065       gcatttagagtttatgcacttgtcccacttatcaggagaccagtctttgccgaaaagtttatgaaaattcgaacagtgttg
 355►       H  L  E  F  M  H  L  S  H  L  S  G  D  P  V  F  A  E  K  V  M  K  I  R  T  V  L
1147       aacaaactggacaaaccagaaggcctttatctgaacccagtagtggacagtgggtcaacatcatgtgtcgg
 383►       N  K  L  D  K  P  E  G  L  Y  P  N  Y  L  N  P  S  S  G  Q  W  G  Q  H  H  V  S
1229       ttggagacttggagacagctttatgaatattgctaaggcgtggttaatgtctgacaagacagatctcgaagccaagaa
 410►       V  G  G  L  G  D  S  F  Y  E  Y  L  L  K  A  W  L  M  S  D  K  T  D  L  E  A  K  K
1311       gatgtatttgatgctgttcaggccatcgagactcacttgatccgcaagtcaaggggactaacgtacatcgcagagtgg
 437►       M  Y  F  D  A  V  Q  A  I  E  T  H  L  I  R  K  S  S  G  G  L  T  Y  I  A  E  W
1393       aaggggggcctctgttgcacttgcttttgcaggaggacatgtttttgcacttgggcagatgggagctc
 465►       K  G  L  L  E  H  K  M  G  H  L  T  C  F  A  G  G  M  F  A  L  G  A  D  G  A
1475       cggaagcccggccaacactacctgaactggaagctgaaattgccccgcacttgtcatgaatcttatatcgtacatatgt
 492►       P  E  A  R  A  Q  H  Y  L  E  L  G  A  E  I  A  R  T  C  H  E  S  Y  N  R  T  Y  V
1557       gaagttgggaccggaagcgtttcgatttgatggcgcgtgtgaagctatttgccacgaggcaaaatgaaaagtattacatctta
 519►       K  L  G  P  E  A  F  R  F  D  G  G  V  E  A  I  A  T  R  Q  N  E  K  Y  Y  I  L
1639       cggcccgaggtcatcgagagtcatcgagacatatgtggcgaactgactcacgacccaagtacgaccctgggcctgggaagccg
 547►       R  P  E  V  I  E  T  Y  M  Y  M  W  R  L  T  H  D  P  K  Y  R  T  W  A  W  E  A
1721       tggaggtctagaaagtcactgcagagtgaacggaggctactcaggcttacggatgtttacattgcccgtgagagtttatga
 574►       V  E  A  L  E  S  H  C  R  V  N  G  G  Y  S  G  L  R  D  V  Y  I  A  R  E  S  Y  D
1803       cgatgtccagcaaagtttcttcctggcagagacactgaagtattgtacttgatatttccgatgatgaccttcttccacta
 601►       D  V  Q  Q  S  F  L  A  E  T  L  K  Y  L  Y  L  I  F  S  D  D  L  L  P  L
1885       gaacactggatctttcaacaccgaggctcatcctttccctatactccgtgaacagaagaaattgatgcaaagaaatga
 629►       E  H  W  I  F  N  T  E  A  H  P  F  P  I  L  R  E  Q  K  K  E  I  D  G  K  E  K
```

FIG.3 cont.

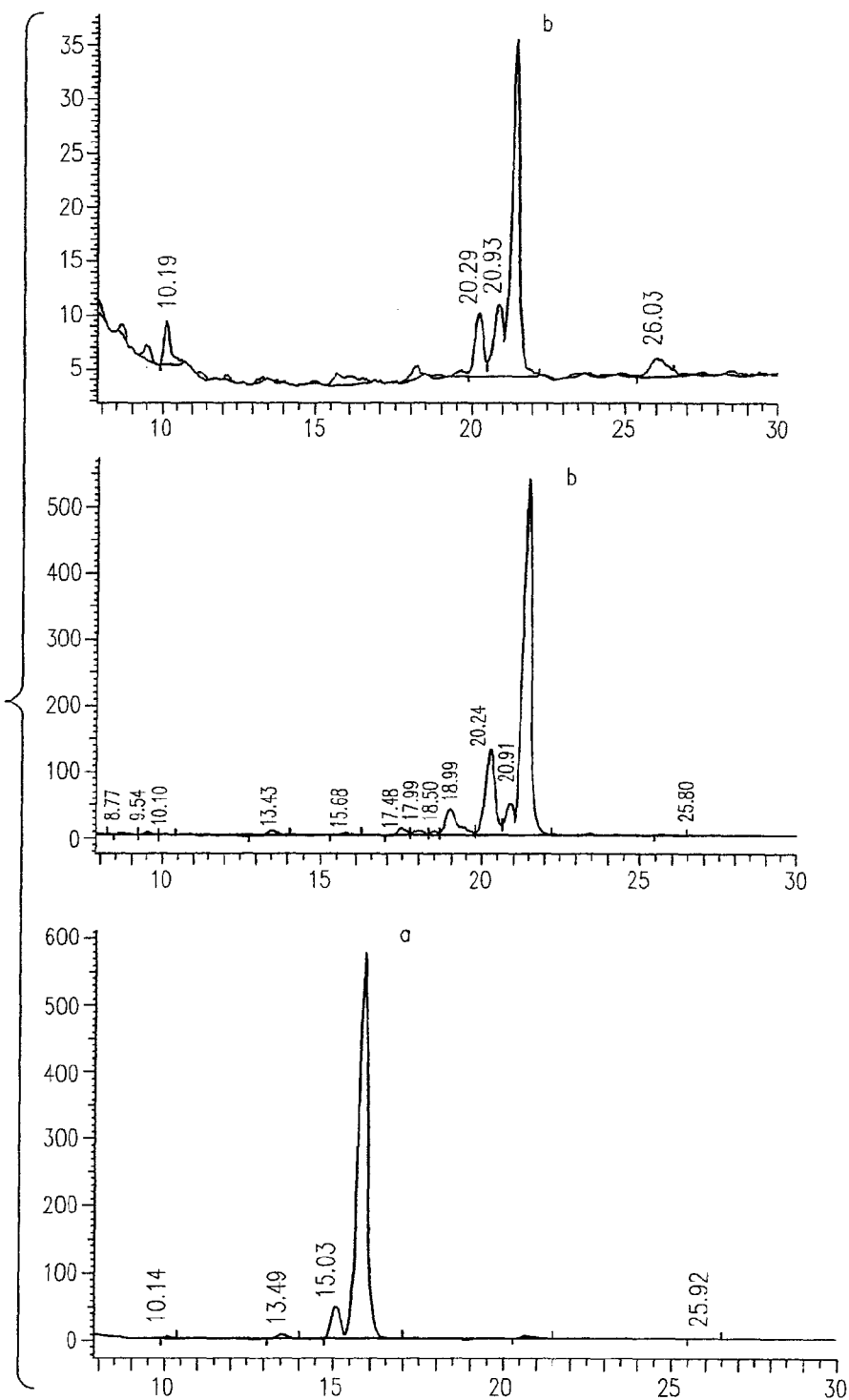

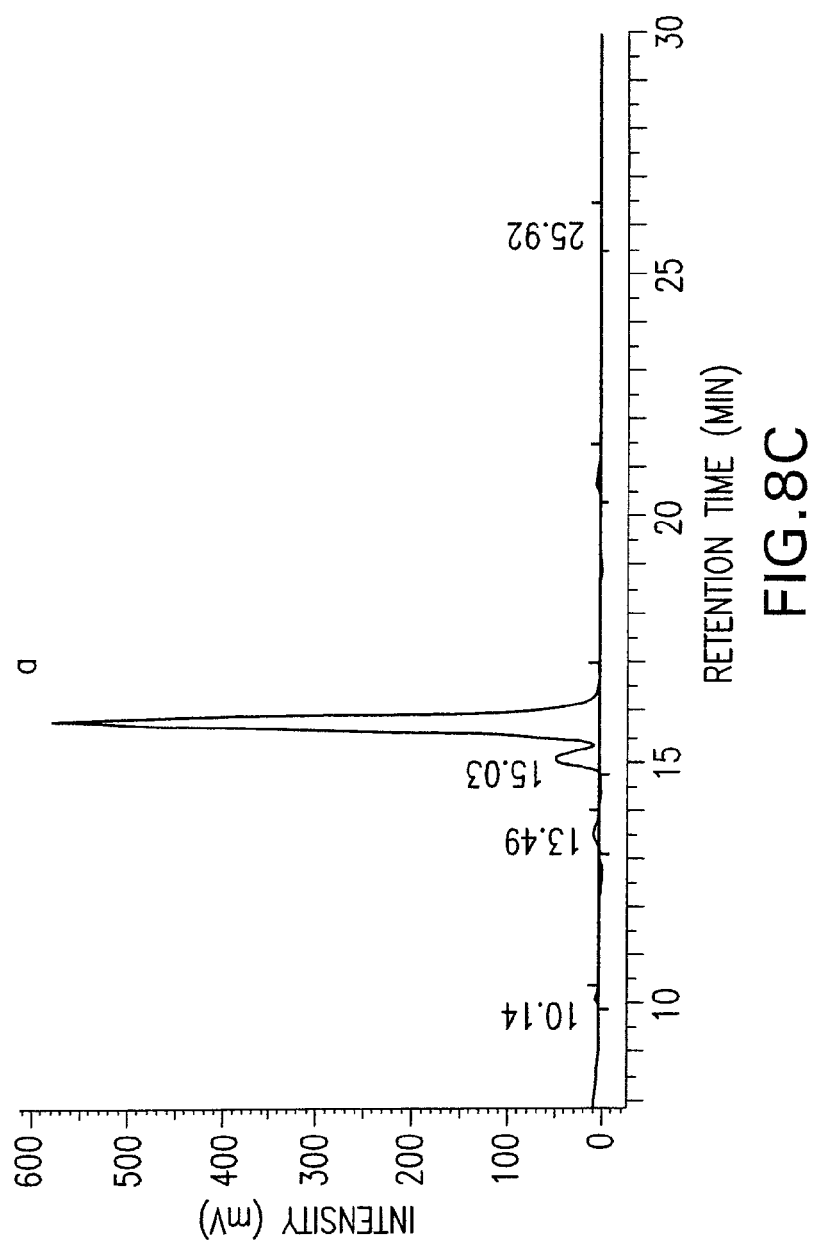

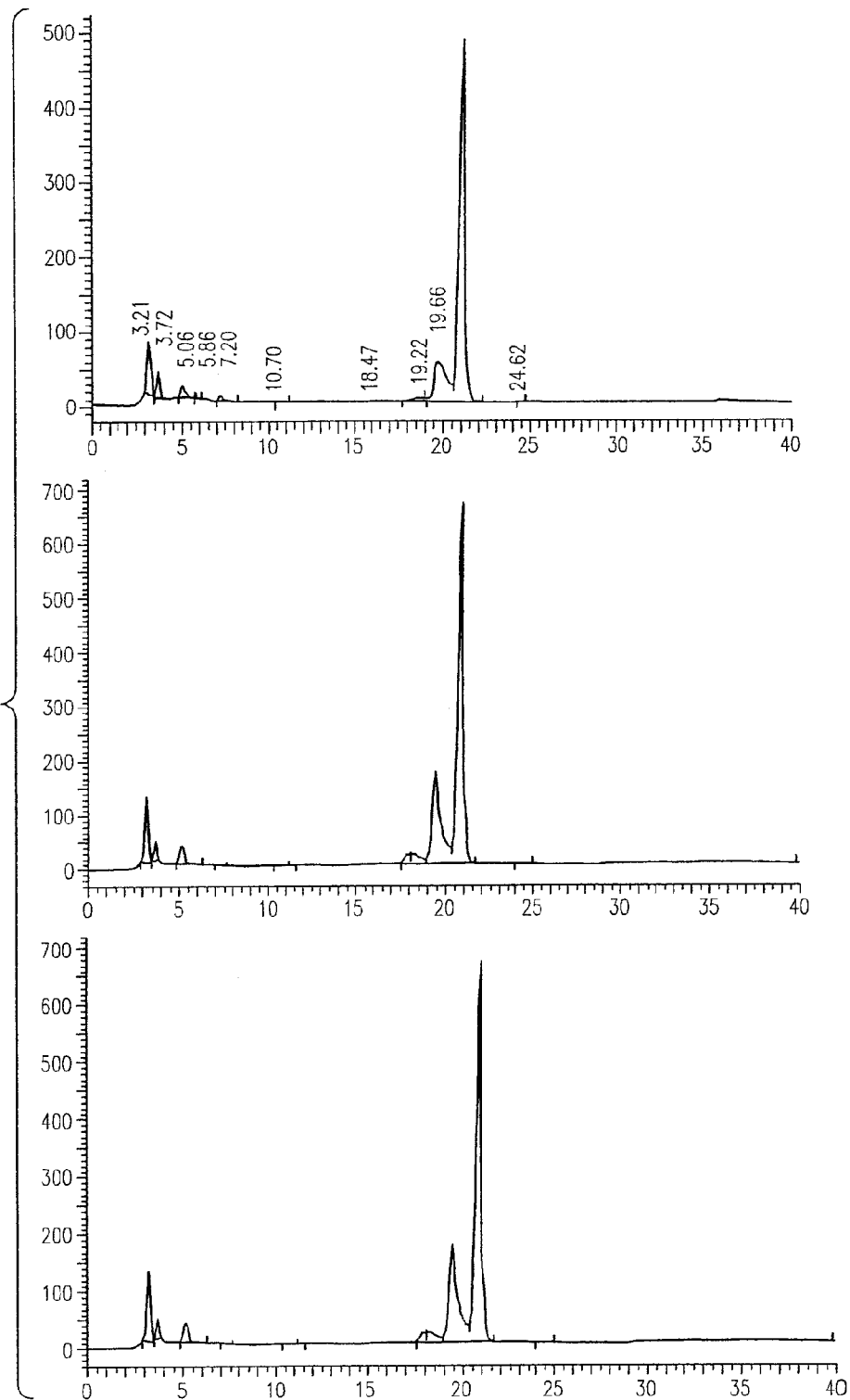

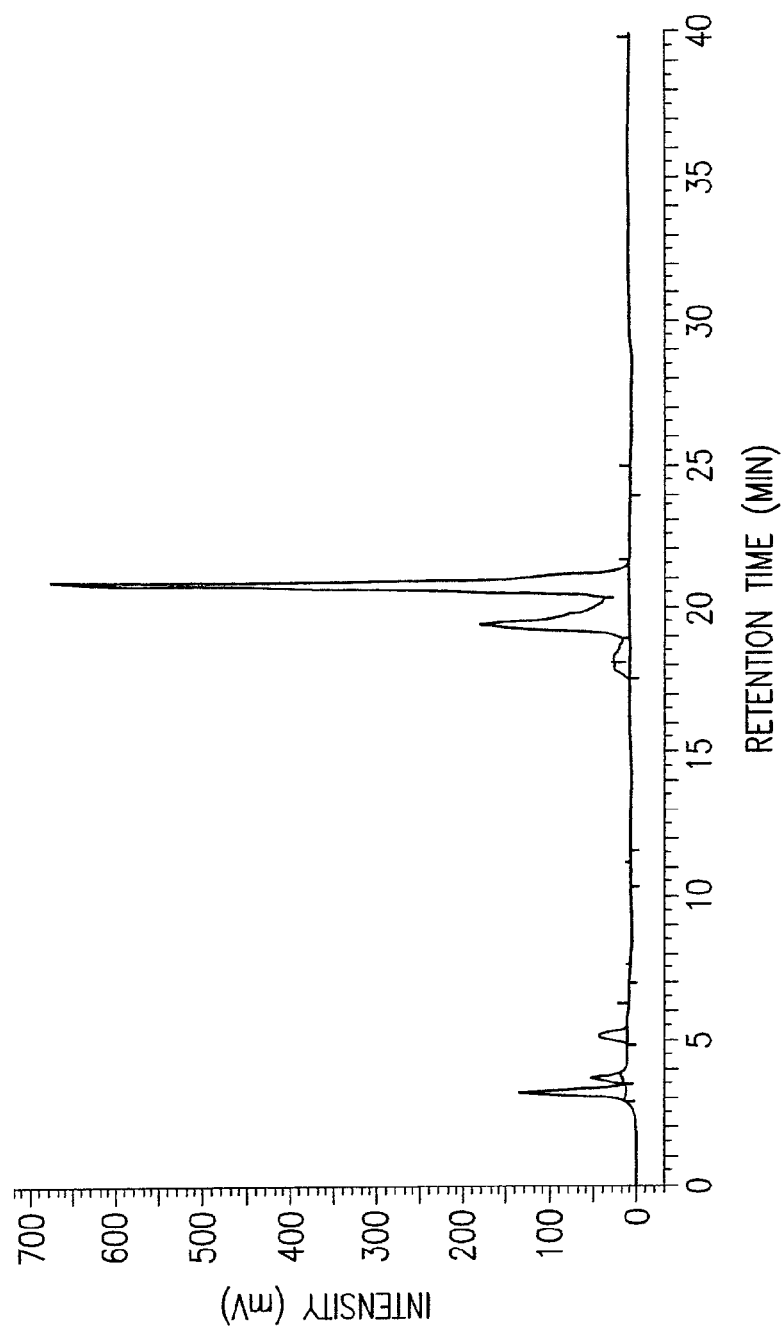

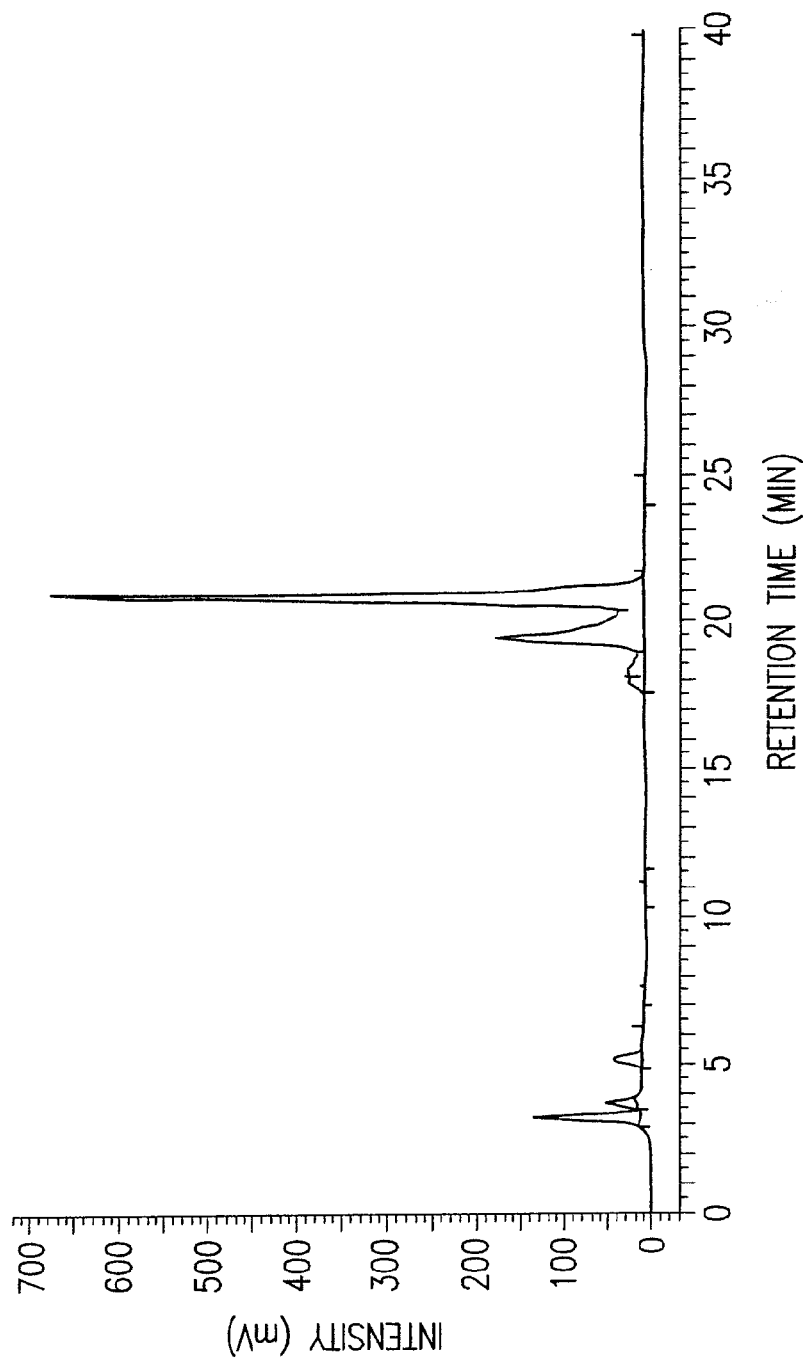

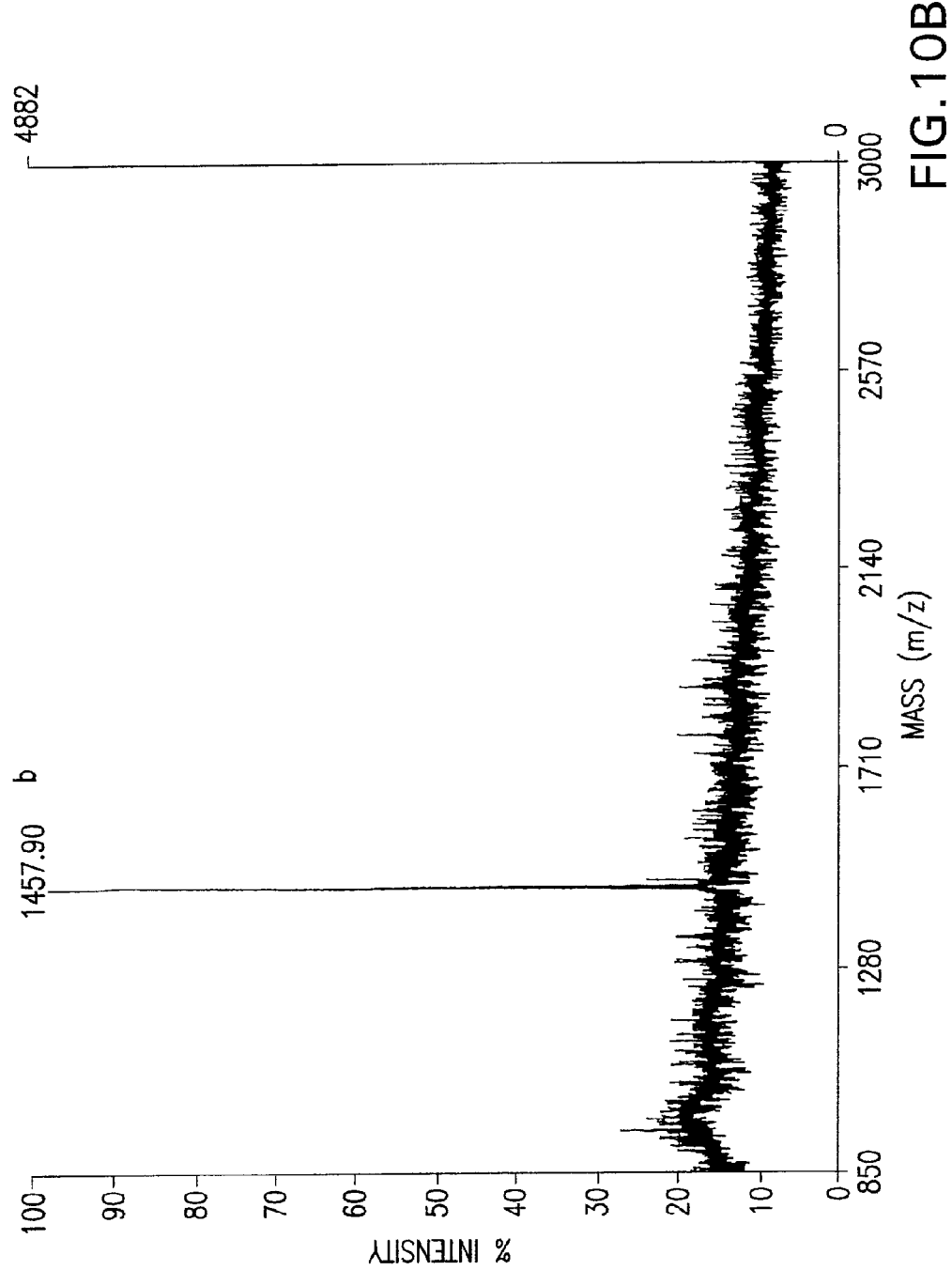

FIG. 15

NeuB

```
  1 ATGAGTAATATATCGTTGCTGAAATTGGTTGCAACCATAATGGTAGTGTTGATATTGCAAGAGAAATGATATTAAAAGCCAAAGAGGCCGGTGTT
  1▸  M  S  N  I  Y  I  V  A  E  I  G  C  N  H  N  G  S  V  D  I  A  R  E  M  I  L  K  A  K  E  A  G  V
100 AATGCAGTAAAATTCCAAACATTTAAAGCTGATAAATTCAGCTGTATTGCACCTAAGGCAGAGTATCAAATAAAAAACACAGGAGAATTAGAATCT
 34▸  N  A  V  K  F  Q  T  F  K  A  D  K  L  I  S  A  I  A  P  K  A  E  Y  Q  I  K  N  T  G  E  L  E  S
199 CAGTTAGAAATGACAAAAAAGCTTGAAATGAAGTATGACGATTATCTCCATCTAATGGAATATGCAGTCAGTTAAATTTAGATGTTTTTCTACCCCT
 67▸  Q  L  E  M  T  K  K  L  E  M  K  Y  D  D  Y  L  H  L  M  E  Y  A  V  S  L  N  L  D  V  F  S  T  P
298 TTTGACGAAGACTCTATTGATTTTTTAGCATCTTTGAAACAAAAAATATGGAAAATCCCTTCAGGTGAGTTATTGAATTTACCGTATCTTGAAAAAATA
100▸  F  E  D  S  I  D  F  L  A  S  L  K  Q  K  I  W  K  I  P  S  G  E  L  L  N  L  P  Y  L  E  K  I
397 GCCAAGCTTCCGATCCCTGATAAGAAGAATAATCATATTCAACAGTGTACTATTGATGAGATAAAACAGTCTGTTTCTATTTTTAATAATAAA
133▸  A  K  L  P  I  P  D  K  K  I  I  I  S  T  G  M  A  T  I  D  E  I  K  Q  S  V  S  I  F  N  N  K
496 GTTCCGGTTGGTAATATTACAATATTACATTGCAATACTGAATATCCAACCTTAATGATGTAAACCTTAATGCTATTAATGATTTGAAAAAACAC
166▸  V  P  V  G  N  I  T  I  L  H  C  N  T  E  Y  P  T  P  F  E  D  V  N  L  N  A  I  N  D  L  K  K  H
595 TTCCCTAAGAATAACATAGGCTTCTCTGATCATTCTAGCGGGTTTATGCAGCTATTGCGGCGGTCAGCATCTTTGTATTGGGGTCAGGTGTGTTGAAAAATCT
199▸  F  P  K  N  I  G  F  S  D  H  S  S  G  F  Y  A  A  I  A  A  V  P  Y  G  I  T  F  I  E  K  H  F
694 ACTTTAGATAAATCTATGTCTGGCCCAGATCATTTGGCCTCAATAGAACCTGATGAACTGAAACATCTTGTATTGGGGTCAGGTGTGTTGAAAAATCT
232▸  T  L  D  K  S  M  S  G  P  D  H  L  A  S  I  E  P  D  E  L  K  H  L  C  I  G  V  R  C  V  E  K  S
793 TTAGGTTCAAATAGTAAAGTTGTTACAGCTTCAGAAAGGAAGAATAAAATCGTAGCAAGAAAGTCTATTATTGCTAAAACAGAGATAAAAAAGGTGAG
265▸  L  G  S  N  S  K  V  V  T  A  S  E  R  K  N  K  I  V  A  R  K  S  I  I  A  K  T  E  I  K  K  G  E
892 GTTTTTTCAGAAAATATAACAAAAAGACCTGGTAATGGTATCAGTCCGATGGAGTGGTATAATTTATTGGGTAAAATTGCAGAGCAAGACTTT
298▸  V  F  S  E  K  N  I  T  T  K  R  P  G  N  G  I  S  P  M  E  W  Y  N  L  L  G  K  I  A  E  Q  D  F
991 ATTCCAGATGAATTAATAATTCATAGCGAATTCAAAAATCAGGGGAATAA
331▸  I  P  D  E  L  I  I  H  S  E  F  K  N  Q  G  E
```

FIG. 16

NeuA

```
   1 ATGAGAACAAAAATTATTGCGATAATTCCAGCCCGTAGTGGATCTAAAGGGTTGAGAAATAAAAATGCTTTGATGCTGATAGATAAACCTCTTCTTGCT
   1▶ M  R  T  K  I  I  I  P  A  R  S  G  S  K  G  L  R  N  K  N  A  L  M  L  I  D  K  P  L  L  A
 100 TATACAATTGAAGCTGCCTTGCAGTCAGAATGTTTGAGAAGTAATTGTGACAACTGACTCCGAACAGTATGGAGCAATAGCAGAGTCATATGGTGCT
  34▶ Y  T  I  E  A  A  L  Q  S  E  M  F  E  K  V  I  V  T  T  D  S  E  Q  Y  G  A  I  A  E  S  Y  G  A
 199 GATTTTTTGCTGAGACCGGAAGAACTAGCAACTGATAAAGCATCAATCATTGAATTTATAAAACATGCGTTAAGTATATATCGATTATGAGAGCTTT
  67▶ D  F  L  L  R  P  E  E  L  A  T  D  K  A  S  S  F  E  F  I  K  H  A  L  S  I  Y  T  D  Y  E  S  F
 298 GCTTTATTACAACCAACTTCACCCTTTAGAGATTCGACCCATATTATTGAGGCTGTAAAGTTATATCAAACTTAGACCTTGATTATAGTAATAATCGAAAC
 100▶ A  L  L  Q  P  T  S  P  F  R  D  S  T  H  I  E  A  V  K  L  Y  Q  T  L  D  L  D  Y  S  K  Y  N  R  N
 397 GTTACTAGAAGCAATAAGCCATCATCACAAATAATTAGACCATTAGATGATTACTGACACTGTCTCTTTTTGACCAATACAAAGCATTTTTGGTCGCTATTCACTAGCTTAT
 133▶ V  T  R  S  N  K  P  S  Q  I  I  R  P  L  D  D  Y  S  T  L  S  F  F  D  L  D  Y  S  K  Y  N  R  N
 496 TCAATAGTAGAATATCATCCGAATGGAGCTCTTTTAGATATAGAGAAAATGGAGTCAATTGCAATTCGAACTTCAGCAGAAATAGAACAAAAATTGACCTT
 166▶ S  I  V  E  Y  H  P  N  G  A  I  F  I  A  N  K  Q  H  Y  L  H  T  K  H  F  F  G  R  Y  S  L  A  Y
 595 ATTATGGATAAGGAAAGCTCTTTAGATATAGATGATGATCGAATGGATTTCGAACTTGCAATTACCATTCAGCAAAAAAATAGACAAAAATTGACCTT
 199▶ I  M  D  K  E  S  S  L  D  I  D  D  D  R  M  D  F  E  L  A  I  T  I  Q  Q  K  N  R  Q  K  I  D  L
 694 TATCAAACATACATAAGAATCAATGAGAAACGAAATGAATTTGATAGTGAAGTTAACTTAATTGGACACTCGCTGTTTGATTATTGGGAC
 232▶ Y  Q  N  I  H  R  I  N  E  K  R  N  E  F  D  S  V  S  D  I  T  L  I  G  H  S  L  F  D  Y  W  D
 793 GTAAAAAAAATGATATAGAAGTTAATAACTTAGGTATCGCTGGTATAAACTGGTATAGTGTTGATGATTGGAACTAGTGTTGAAGAAACATGC
 265▶ V  K  K  I  N  D  I  E  V  N  N  L  G  I  A  G  I  N  S  K  E  Y  Y  E  Y  I  I  E  K  E  L  I  V
 892 AATTTCGGAGAGTTTGTTTCATCTTTTGGGACTAATGATATAGTGTAGTGATTGTTGGGAACTATTGTGGTATTGAAGAAACATGC
 298▶ N  F  G  E  F  V  F  I  F  F  G  T  N  D  I  V  S  D  W  K  K  E  D  T  L  W  Y  L  K  K  T  C
 991 CAGTATATAAAAGAAGCTGCATCAAAAATTTATTTATTGTCGGTTCCTCCTGTTTTGGGCGTATTGATCGAGATAATAGAATAATAGAATTAATGAT
 331▶ Q  Y  I  K  K  N  A  A  S  K  I  Y  L  L  S  V  P  P  V  F  G  R  I  D  R  D  N  R  I  I  N  D
1090 TTAAATTCTTATCTTCGAGAATGTGATTTTGCGAAGTTTATTAGCTTGGATCACGTTTTAAAGACTCTTAAATAATAAATGATACT
 364▶ L  N  S  Y  L  R  E  N  V  D  F  A  K  F  I  S  L  D  H  V  L  K  D  S  Y  G  N  L  N  K  M  Y  T
1189 TATGATGGCTTACATTTTAATAGTAATGGGTATACAGTATTAGAAAACGAAATAGCGGAGATTGTTAAATGA
 397▶ Y  D  G  L  H  F  N  S  N  G  Y  T  V  L  E  N  E  I  A  E  I  V  K
```

FIG. 17 mCMP-Sia synthase

```
   1 ATGGACGCGCTGGAGAAGGGGGCCGTCACGTCGGGGCCCGCCCCCGGGGCCGGCCGTGGAACGGCTGCAGCCGGGCGCG
   1▶ M  D  A  L  E  K  G  A  V  T  S  G  P  A  P  R  G  R  P  S  R  G  R  P  P  K  L  Q  R  S  R  G  A
 100 GGGCGCGGCCTAGAGAAGCCGCCGCACCTGGCAGCGCTGGTGCTGGCCCGCGCGGCAGCAGACATCCGAAGAACATCAAGCGCCTGGCGGGG
  34▶ G  R  G  L  E  K  P  P  H  L  A  A  L  V  L  A  R  G  G  S  K  G  I  P  L  K  N  I  K  R  L  A  G
 199 GTTCCGCTCATTGGCTGGGTCTTCTGCGCGCCCTGGATGCGGAAGGTCTTCAAGACAGTGTGGGTTTCAACAGACCATGATGAAATTGAGAATGTGGCC
  67▶ V  P  L  I  G  W  V  L  R  A  A  L  D  A  G  V  F  Q  S  V  W  V  S  T  D  H  D  E  I  E  N  V  A
 298 AAACAGTTTGGTGCACAGGTTCCATGCGAAGAAGTTCTGAACACAGCTCTACCTGTCTACTAGACGCCATTGTAGAATTCCTGAATTATCACAAT
 100▶ K  Q  F  G  A  Q  V  H  R  R  S  S  E  T  S  K  D  S  S  T  S  L  D  A  I  V  E  F  L  N  Y  H  N
 397 GAGGTTGACATTGTGGGAATATCCAAGCGCTCCATGTTTACATCTCCACTGACCTGCAGAAAGTTGCAGAAATGATCCGAGAAGGATATGAC
 133▶ E  V  D  I  V  G  N  I  Q  A  T  S  P  C  L  H  P  T  D  L  Q  K  V  A  E  M  I  R  E  E  G  Y  D
 496 TCTGTCTTCTCCGTTGTGAGGCGCCATCAGTTCGATGGAGTGAAATTCAGAAGGAGTTCGTGAACTGACTGAGCCTCTGAACTTGAATCCAGCGAAA
 166▶ S  V  F  S  V  V  R  R  H  Q  F  R  W  S  E  I  Q  K  G  V  R  E  V  T  E  P  L  N  L  N  P  A  K
 595 CGGGCCTCGTCGTCGACAAGACTGGGATGATATGAGAACGGCTCATTTATTTTGCTAAAAAGACATTTATAGACATTTGAGAGCAGAGCAAAGAGTTCTGAGATTGGCTAT
 199▶ R  P  R  R  Q  D  W  D  G  E  L  Y  E  N  G  S  F  Y  F  A  K  F  H  L  I  E  M  G  Y  L  Q  G  G
 694 AAAATGGCATATTATGAAATGCGAGCTGAAAGGAGATAAAAGCTTTTGGTTTGTAATATTGATGGATGTCTCACCAATGGCCGATTGGCCAGATCGACGTGGATATCAGGAGACCAAAAGAA
 232▶ K  M  A  Y  Y  E  M  R  A  E  H  S  V  D  I  D  V  D  I  D  W  P  I  A  E  Q  R  V  L  R  F  G  Y
 793 TTTGGAAAGAGAAGCTTGAACGACTTATCTCGGCAATGAAAAGACGCCATTGGAGGTGAGGCTCATCTCAGAATGGGCCTGCTCCAAGCAG
 265▶ F  G  K  E  K  L  K  E  I  K  L  L  V  C  N  I  D  G  C  L  T  N  G  H  I  Y  V  S  G  D  Q  K  E
 892 ATAATATCTTATGATGTAAAAGACGGCTGTAAGCTTATTAAAGAAAGCGGTATTGAGGTGAGGCTCATCTCAGAACGGGCCTGCTCCAAGCAG
 298▶ I  I  S  Y  D  V  K  D  A  I  G  I  S  L  L  K  K  S  G  I  E  V  R  L  I  S  E  R  A  C  S  K  Q
 991 ACGCTCTCTCTGCCCTAAAGCTGGACTGTAAAACGAAGTCAGTGTCTCCGATAAGCTGGCCACCGTGGATGAGTGGAGGAAGGAGATGGGCCTGTGCTGG
 331▶ T  L  S  A  L  K  L  D  C  K  T  E  V  S  V  S  D  K  L  A  T  V  D  E  W  R  K  E  M  G  L  C  W
1090 AAAGAAGTGGCCTATCTCGGCAATGTCTGATGAAGAATGCCTCAAGAGAGTGGGCTGCTGTTCCTGCGACGCCATTGCAGTGCCTGCAGACTGTAGCGGAGCAC
 364▶ K  E  V  A  Y  L  G  N  E  V  S  D  E  E  C  L  K  R  V  G  L  S  A  V  P  A  D  A  C  S  G  A  Q
1189 AAGGCTGTGGGGTACATCTGCAAATGCAGCGGGTGCCGGAGTTGCAGAGACACATCCGCTACTGATGAAAAAGTTAATAACTCA
 397▶ K  A  V  G  Y  I  C  K  C  S  G  G  R  G  A  I  R  E  F  A  E  H  I  F  L  L  I  E  K  V  N  N  S
1288 TGCCAAAAATAC
 430▶ C  Q  K
```

FIG.18

Pig GlcNAc epimerase

```
   1    ATGGAAGGAGGCGAAACTCTGCAGGCCTGGAAGGAGCGTGTGGGCCAAGAGCTGGACCGCGTGATGGCTTTCTGGCTGGAGCACTCCCACGATCGG
   1  ► M  E  G  G  E  T  L  Q  A  W  K  E  R  V  G  Q  E  L  D  R  V  M  A  F  W  L  E  H  S  H  D  R
 100    GAGCACGGGGCTTCTTCACGTGCCTGGGCCGCGACGGCCGGGTGTATGACGACCTCAAGTACGTCTGGCTGCAGGGAGGCAGGTGTGGATGTACTGT
  34  ► E  H  G  G  F  F  T  C  L  E  R  D  G  R  V  Y  D  D  L  K  Y  V  W  L  Q  G  R  Q  V  W  M  Y  C
 199    CGCCTGTACCGCAAGCTTGAGCGCTTCCACCGCCCTGAGCTCTTGGATGCGGCTAAAGCAGGGGAGTTTTTGCTGCGCCATGCCCGAGTGGCACCT
  67  ► R  L  Y  R  K  L  E  R  F  H  R  P  E  L  L  D  A  A  K  A  G  G  E  F  L  L  R  H  A  R  V  A  P
 298    CCTGAAAAAGAAGTGTGCGCCTTTGTGCTTGACGGGAGACGGCCCGGTCAAGGTGCAGGAGCATCTTCAGTGAGTGCTTCTACACCATGGCCATGAAC
 100  ► P  E  K  K  C  A  F  V  L  T  R  D  G  R  P  V  K  V  Q  R  S  I  F  S  E  C  F  Y  T  M  A  M  N
 397    GAGCTGTGGAGGGTGACGGCGGAGCACGGTACCAGAGGCAAGCGGTGGACATGATGGACCAGATCGTGCACTGGGTGCGAGAGGACCCCTCTGGGCTG
 133  ► E  L  W  R  V  T  A  E  R  Y  Q  S  E  A  V  D  M  M  D  Q  I  V  H  W  V  R  E  D  P  S  G  L
 496    GGCCGGCCCCAGCTCCCCGGAGCCGTGGCCTCAGCGAGTCCATGGCCGTGCCCATGATGCTCCTGGTGGAGCAGCTCGGGGAGGAGGACGAGGAG
 166  ► G  R  P  Q  L  P  G  A  V  A  S  E  S  M  A  V  P  M  M  L  L  C  L  V  E  Q  L  G  E  E  D  E  E
 595    CTGGCCAGGCCGCTACGCCAGTTTCGGGGAGAACTTCAGGCCACCAGAACCAGGCCAAGCTTCCTGCTCCGCCACAGCCGGAGCGGT
 199  ► L  A  G  R  Y  A  Q  L  G  H  W  C  A  R  R  I  L  Q  H  V  Q  R  D  G  Q  A  V  L  E  N  V  S  E
 694    GATGGCGAGGAACTTTCTGAGGCCCAGCTGCATCGAGACACGTTCCTGCTGCCCTTCCGGCTGCTGATCAGGACGGAGGCCTCTTCTACTTCCAGGAT
 232  ► D  G  E  E  L  S  G  C  L  G  R  H  Q  N  P  G  H  A  L  E  A  G  W  F  L  L  R  H  S  S  R  S  G
 793    GACGCCAAACTTGAGCGGGCCCAGTCATCGAGACACGTTCCTGCTGCCCTTCCGGCTGCTGATCAGGACGGAGGCCTTTCTACTTCCAGGAT
 265  ► D  A  K  L  R  A  H  V  I  D  T  F  L  L  L  P  F  R  S  G  W  D  A  D  H  G  G  L  F  Y  F  Q  D
 892    GCCGATGGCCTGCCCCACCTGCTTGGGGAGTGGCCATGAAGCTCTGGGCCATGAAGCTCTGGGCCATGAAGGCCTGGGCCATG
 298  ► A  D  G  L  C  P  T  Q  L  E  W  A  M  K  L  W  P  H  S  E  A  M  I  A  F  L  M  G  Y  S  E  S
 991    GGGGACCCTGCCTTACTGCTCCGTCTTCTTCTACCAGGTGGCCGAGTACACGTTTCGCCAGTTTCGTGATCCCGAGTACGGGGAATGGTTTGGCTACTTGAAC
 331  ► G  D  P  A  L  L  R  L  F  Y  Q  V  A  E  Y  T  F  R  Q  F  R  D  P  E  Y  G  E  W  F  G  Y  L  N
1090    CGAGAGGGGAAGTTGCCCTCACTATCAAGGGGGTCCCTTTAAAGGCTGCTTCCACGTGCCGCGGTGCCTTGCCATGTGCGAAGATGCTGAGCGCC
 364  ► R  E  G  K  V  A  L  T  I  K  G  G  P  F  K  G  C  F  H  V  P  R  C  L  A  M  C  E  E  M  L  S  A
1189    CTGCTGAGCCGCCTCGCCTAG
 397  ► L  L  S  R  L  A
```

Codon-optimized hST6Gal leader 53 fusion:

```
        NotI
   1  GCGGCCGCCACCATGTTGTTGACTAAGAGATTCTCCAAGTTGTTCAAGTTGACTTTCATCGTTTTGATCTTGTGTGGTTTGTTCGTTATCACTAACAAGTA
   1▶  M  L  L  T  K  R  F  S  K  L  F  K  L  T  F  I  V  L  I  L  C  G  L  F  V  I  T  N  K  Y
 102  CATGGACGAGAATACTTCAGGGCGCCGCCGAATTCAAGTTTGAAGTCCTTGGGAAAGTTGGCTATGGGTTCTGACTTTGAAGTCCTCAATCTGTTCCTCCTCTA
  30▶  M  D  E  N  T  S  G  R  A▲ E  F  Q  V  L  K  S  L  G  K  L  A  M  G  S  D  S  Q  S  S  S
                                 AscI
 203  CTCAAGATCCACACAGAGGGTAGACAAACTTTGGGATCTTTGAGAGGATTGGCTAAGGCTAAGCCAGAAGCTTCTTTCCAAGTTTGGAACAAGGACTCCTCC
  64▶  S  Q  D  P  H  R  G  R  Q  T  L  G  S  L  R  G  L  A  K  A  K  P  E  A  S  F  Q  V  W  N  K  D  S  S
 304  TCCAAGAACTTGATCCCAAGATTGCAGAAATCTGGAAGAATCTGTCATGCAGAACAAGTACTGTTCCATGAACAAGTACAAGGTTCCTACAAGGGTCCAGGTATTAAGTT
  98▶  S  K  N  L  I  P  R  L  Q  K  I  W  K  N  Y  L  S  M  N  K  Y  K  V  S  Y  K  G  P  G  I  K  F
 405  CTCCGCTGAGGCTTTGAGATGTCACTTGAGAGACCACGTTAACGTTTCCATGGTTGAAGTTACTGACTTCCCGGTTCTTTGAAGTCCTCCAGTTGGGTAGAGAAATT
 131▶  S  A  E  A  L  R  C  H  L  R  D  H  V  N  V  S  M  V  E  V  T  D  F  P  F  N  T  S  E  W  E  G  Y
 506  TGCCAAAGGAGTCCATCAGAACTGGTCCATGGGAACTGGTCATTGGGAACTGGTGGTCATTGGGGTACCTCCAACAGATGTTGGTACTACAAGATTGATGAACTCCCAGTT
 165▶  L  P  K  E  S  I  R  T  K  A  G  P  W  G  R  C  A  V  V  S  S  A  G  S  L  K  S  S  Q  L  G  R  E  I
 607  GATGACCACGACGCTGTTTTGAGATTCAACGGTGCTCCAACTGCTAACTTCCAACAAGATGTTGGTACTAAGACTACTATCAGATTGATGAACTCCCAGTT
 199▶  D  D  H  D  A  V  L  R  F  N  G  A  P  T  A  N  F  Q  Q  D  V  G  T  K  T  T  I  R  L  M  N  S  Q  L
 708  GGTTACTACTGAGAAGAGATTCTTGAAGGACTCCTTGTACAACGAGGGAATCTTGATCGTTGTTGGACCATCTGTTTACCACTCCGACATCCCAAAGTGGT
 232▶  V  T  T  E  K  R  F  L  K  D  S  L  Y  N  E  G  I  L  I  V  V  D  P  S  V  Y  H  S  D  I  P  K  W
 809  ATCAGAAACCCAGACTACAACTTCTTCAACAACTACAAGACTTACAGAAAAGTTGCACCACCATCTTCTGGAATGTTGGGTATCATCATGATGACTTTGTGTGACCA
 266▶  I  R  N  P  D  Y  N  F  F  N  N  Y  K  T  Y  R  K  L  H  P  N  Q  P  F  Y  I  L  K  P  Q  M  P  W  E
 910  TTGTGGGACATCTTGCAAGAAATTCCCAGAGGAGATTCAACCAAGAAGACTGATGTTTGTTACTACCAGAAGTTCTTCGACTCCGCTTGTACTATGGGAGCTTACCACC
 300▶  L  W  D  I  L  Q  E  I  S  P  E  E  I  Q  P  N  P  S  S  G  M  L  G  I  I  I  M  T  L  C  D  Q
1011  GGTTGACATCTACGAGAAGAATCTGGTTAAGCACTTGAACCAAGGTACTGACGAGGACATCTACTTGTTGGGAAAGGCTACTTTGCCAGGTTTCAGAACTATC
 333▶  V  D  I  Y  E  F  L  P  S  K  R  K  T  D  V  C  Y  Y  Q  K  F  F  D  S  A  C  T  M  G  A  Y  H
1112  CATTGTTGTACGAGAAGAACTTGGTTAAGCACTTGAACCAAGGTACTGACGAGGACATCTACTTGTTGGGAAAGGCTACTTTGCCAGGTTTCAGAACTATC
 367▶  P  L  L  Y  E  K  N  L  V  K  H  L  N  Q  G  T  D  E  D  I  Y  L  L  G  K  A  T  L  P  G  F  R  T  I
        PacI
1213  CACTGTTAATTAA
 401▶  H  C
```

FIG.33

PRODUCTION OF SIALYLATED N-GLYCANS IN LOWER EUKARYOTES

CROSS-REFERENCE TO RELATED APPLICATIONS

This application is a continuation of U.S. application Ser. No. 12/819,305, filed Jun. 21, 2010, which is a continuation of U.S. application Ser. No. 11/429,672, filed May 5, 2006, now U.S. Pat. No. 7,863,020, which is a continuation-in-part of: (1) U.S. application Ser. No. 11/084,624, filed Mar. 17, 2005, which claims the benefit of U.S. Provisional Application No. 60/554,139, filed Mar. 17, 2004, and (2) U.S. application Ser. No. 11/108,088, filed Apr. 15, 2005, now U.S. Pat. No. 7,795,002, which is a continuation-in-part of U.S. application Ser. No. 10/371,877, filed Mar. 20, 2003, now U.S. Pat. No. 7,449,308. Each of the above cited references is incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "GFIBIO0025USCNT4SEQUENCE.TXT", creation date of Jul. 19, 2012 and a size of 188 KB. This sequence listing submitted via EFS-Web is part of the specification and is herein incorporated by reference in its entirely.

FIELD OF THE INVENTION

The present invention is directed to methods and compositions by which non-human eukaryotic host cells, such as fungi or other eukaryotic cells, can be genetically modified to produce glycosylated proteins (glycoproteins) having patterns of glycosylation similar to those of glycoproteins produced by animal cells, especially human cells, which are useful as human or animal therapeutic agents. In particular this application relates to methods and compositions for the production of sialylated glycoproteins in non-human eukaryotic host cells that do not normally produce sialylated glycoproteins.

BACKGROUND OF THE INVENTION

Glycosylation Pathways in Humans and Lower Eukaryotes

After DNA is transcribed and translated into a protein, further post-translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of the same protein, will be different depending on the host system in which the particular protein is being expressed. Bacteria typically do not glycosylate proteins, and if so only in a very unspecific manner (Moens, 1997). (Throughout the specification, scientific publications will be cited by reference to the senior author and publication year; complete citations are found at the end of the specification.) Lower eukaryotes such as filamentous fungi and yeast add primarily mannose and mannosylphosphate sugars. The resulting glycan is known as a "high-mannose" type glycan or a mannan. Plant cells and insect cells (such as Sf9 cells) glycosylate proteins in yet another way. By contrast, in higher eukaryotes such as humans, the nascent oligosaccharide side chain may be trimmed to remove several mannose residues and elongated with additional sugar residues that typically are not found in the N-glycans of lower eukaryotes. See, e.g., Bretthauer, 1999; Martinet, 1998; Weikert, 1999; Malissard, 2000; Jarvis 1998; and Takeuchi, 1997.

Synthesis of a mammalian-type oligosaccharide structure begins with a set of sequential reactions in the course of which sugar residues are added and removed while the protein moves along the secretory pathway in the host organism. The enzymes which reside along the glycosylation pathway of the host organism or cell determine the resulting glycosylation patterns of secreted proteins. Thus, the resulting glycosylation pattern of proteins expressed in lower eukaryotic host cells differs substantially from the glycosylation pattern of proteins expressed in higher eukaryotes such as humans and other mammals (Bretthauer, 1999). The structure of a typical fungal N-glycan is shown in FIG. 1A.

The early steps of human glycosylation can be divided into at least two different phases: (i) lipid-linked $Glc_3Man_9GlcNAc_2$ oligosaccharides are assembled by a sequential set of reactions at the membrane of the endoplasmic reticulum (ER) and (ii) the transfer of this oligosaccharide from the lipid anchor dolichyl pyrophosphate onto de novo synthesized protein. The site of the specific transfer is defined by an asparagine (Asn) residue in the sequence Asn-Xaa-Ser/Thr where Xaa can be any amino acid except proline (Gavel, 1990). Further processing by glucosidases and mannosidases occurs in the ER before the nascent glycoprotein is transferred to the early Golgi apparatus, where additional mannose residues are removed by Golgi specific alpha ($\alpha$)-1,2-mannosidases. Processing continues as the protein proceeds through the Golgi. In the medial Golgi, a number of modifying enzymes, including N-acetylglucosaminyl Transferases (GnTI, GnTII, GnTIII, GnTIV and GnTV), mannosidase II and fucosyltransferases, add and remove specific sugar residues. Finally, in the trans-Golgi, galactosyltransferases (GalT) and sialyltransferases (ST) produce a glycoprotein structure that is released from the Golgi. It is this structure, characterized by bi-, tri- and tetra-antennary structures, containing galactose, fucose, N-acetylglucosamine and a high degree of terminal sialic acid, that gives glycoproteins their human characteristics. The structure of a typical human N-glycan is shown in FIG. 1B.

In nearly all eukaryotes, glycoproteins are derived from a common lipid-linked oligosaccharide precursor $Glc_3Man_9GlcNAc_2$-dolichol-pyrophosphate. Within the endoplasmic reticulum, synthesis and processing of dolichol pyrophosphate bound oligosaccharides are identical between all known eukaryotes. However, further processing of the core oligosaccharide by fungal cells, e.g., yeast, once it has been transferred to a peptide leaving the ER and entering the Golgi, differs significantly from humans as it moves along the secretory pathway and involves the addition of several mannose sugars.

In yeast, these steps are catalyzed by Golgi residing mannosyltransferases, like Och1p, Mnt1p and Mnn1p, which sequentially add mannose sugars to the core oligosaccharide. The resulting structure is undesirable for the production of human-like proteins and it is thus desirable to reduce or eliminate mannosyltransferase activity. Mutants of *Saccharomyces cerevisiae* (*S. cerevisiae*), deficient in mannosyltransferase activity (for example och1 or mnn9 mutants) have been shown to be non-lethal and display reduced mannose content in the oligosaccharide of yeast glycoproteins. Other oligosaccharide processing enzymes, such as mannosylphosphate transferase, may also have to be eliminated depending on the host's particular endogenous glycosylation pattern.

Sugar Nucleotide Precursors

The N-glycans of animal glycoproteins typically include galactose, fucose, and terminal sialic acid. These sugars are not found on glycoproteins produced in yeast and filamentous fungi. In humans and other non-human eukaryotic cells, the full range of sugar nucleotide precursors (e.g. UDP-N-acetylglucosamine, UDP-N-acetylgalactosamine, CMP-N-acetylneuraminic acid, UDP-galactose, GDP-fucose, etc.) are synthesized in the cytosol and transported into the Golgi, where they are attached to the core oligosaccharide by glycosyltransferases. (Sommers, 1981; Sommers, 1982; Perez, 1987).

Glycosyl transfer reactions typically yield a side product which is a nucleoside diphosphate or monophosphate. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction is important for efficient glycosylation; for example, GDPase from Saccharomyces cerevisiae (S. cerevisiae) has been found to be necessary for mannosylation. However that GDPase has 90% reduced activity toward UDP (Berninsone, 1994). Lower eukaryotes typically lack UDP-specific diphosphatase activity in the Golgi since they do not utilize UDP-sugar precursors for Golgi-based glycoprotein synthesis. Schizosaccharomyces pombe, a yeast found to add galactose residues to cell wall polysaccharides (from UDP-galactose) has been found to have specific UDPase activity, indicating the potential requirement for such an enzyme (Berninsone, 1994). UDP is known to be a potent inhibitor of glycosyltransferases and the removal of this glycosylation side product may be important to prevent glycosyl-transferase inhibition in the lumen of the Golgi (Khatara, 1974). See Berninsone, 1995; Beaudet, 1998.

Sequential Processing of N-Glycans by Compartmentalized Enzyme Activities

Sugar transferases and glycosidases (e.g., mannosidases) line the inner (luminal) surface of the ER and Golgi apparatus and thereby provide a "catalytic" surface that allows for the sequential processing of glycoproteins as they proceed through the ER and Golgi network. The multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may be synthesized. Much work has been dedicated to revealing the exact mechanism by which these enzymes are retained and anchored to their respective organelle. The evolving picture is complex but evidence suggests that stem region, membrane spanning region and cytoplasmic tail, individually or in concert, direct enzymes to the membrane of individual organelles and thereby localize the associated catalytic domain to that locus (see, e.g., Gleeson, 1998).

In some cases, these specific interactions were found to function across species. For example, the membrane spanning domain of α2,6-ST from rats, an enzyme known to localize in the trans-Golgi of the animal, was shown to also localize a reporter gene (invertase) in the yeast Golgi (Schwientek, 1995). However, the very same membrane spanning domain as part of a full-length α2,6-ST was retained in the ER and not further transported to the Golgi of yeast (Krezdorn, 1994). A full length GalT from humans was not even synthesized in yeast, despite demonstrably high transcription levels. In contrast, the transmembrane region of the same human GalT fused to an invertase reporter was able to direct localization to the yeast Golgi, albeit it at low production levels. Schwientek and co-workers have shown that fusing 28 amino acids of a yeast mannosyltransferase (MNT1), a region containing a cytoplasmic tail, a transmembrane region and eight amino acids of the stem region, to the catalytic domain of human GalT are sufficient for Golgi localization of an active GalT. Other galactosyltransferases appear to rely on interactions with enzymes resident in particular organelles because, after removal of their transmembrane region, they are still able to localize properly.

Improper localization of a glycosylation enzyme may prevent proper functioning of the enzyme in the pathway. For example, Aspergillus nidulans, which has numerous α-1,2-mannosidases (Eades, 2000), does not add GlcNAc to $Man_5GlcNAc_2$ when transformed with the rabbit GnTI gene, despite a high overall level of GnTI activity (Kalsner et al., 1995). GnTI, although actively expressed, may be incorrectly localized such that the enzyme is not in contact with both of its substrates: UDP-GlcNAc and a productive $Man_5GlcNAc_2$ substrate (not all $Man_5GlcNAc_2$ structures are productive; see below). Alternatively, the host organism may not provide an adequate level of UDP-GlcNAc in the Golgi or the enzyme may be properly localized but nevertheless inactive in its new environment. In addition, $Man_5GlcNAc_2$ structures present in the host cell may differ in structure from $Man_5GlcNAc_2$ found in mammals. Maras and coworkers found that about one third of the N-glycans from cellobiohydrolase I (CBHI) obtained from T. reesei can be trimmed to $Man_5GlcNAc_2$ by A. saitoi 1,2 mannosidase in vitro. Fewer than 1% of those N-glycans, however, could serve as a productive substrate for GnTI. The mere presence of $Man_5GlcNAc_2$, therefore, does not assure that further processing to $Man_5GlcNAc_2$ can be achieved. It is formation of a productive, GnTI-reactive $Man_5GlcNAc_2$ structure that is required. Although $Man_5GlcNAc_2$ could be produced in the cell (about 27 mol %), only a small fraction could be converted to $Man_5GlcNAc_2$ (less than about 5%, see WO 01/14522).

To date, there is no reliable way of predicting whether a particular heterologously expressed glycosyltransferase or mannosidase in a lower eukaryote will be (1), sufficiently translated (2), catalytically active or (3) located to the proper organelle within the secretory pathway. Because all three of these are necessary to affect glycosylation patterns in lower eukaryotes, a systematic scheme to achieve the desired catalytic function and proper retention of enzymes in the absence of predictive tools, which are currently not available, would be desirable.

Production of Therapeutic Glycoproteins

A significant number of proteins isolated from humans or animals are post-translationally modified, with glycosylation being one of the most significant modifications. An estimated 70% of all therapeutic proteins are glycosylated and thus currently rely on a production system (i.e., host cell) that is able to glycosylate in a manner similar to humans. Several studies have shown that glycosylation plays an important role in determining the (1) immunogenicity, (2) pharmacokinetic properties, (3) trafficking, and (4) efficacy of therapeutic proteins. It is thus not surprising that substantial efforts by the pharmaceutical industry have been directed at developing processes to obtain glycoproteins that are as "humanoid" or "human-like" as possible. To date, most glycoproteins are made in a mammalian host system. This may involve the genetic engineering of such mammalian cells to enhance the degree of sialylation (i.e., terminal addition of sialic acid) of proteins expressed by the cells, which is known to improve pharmacokinetic properties of such proteins. Alternatively, one may improve the degree of sialylation by in vitro addition of such sugars using known glycosyltransferases and their respective nucleotide sugars (e.g., 2,3-sialyltransferase and CMP-sialic acid).

While most higher eukaryotes carry out glycosylation reactions that are similar to those found in humans, recombinant human proteins expressed in the above mentioned host systems invariably differ from their "natural" human counterpart (Raju, 2000). Extensive development work has thus been directed at finding ways to improve the "human character" of proteins made in these expression systems. This includes the optimization of fermentation conditions and the genetic modification of protein expression hosts by introducing genes encoding enzymes involved in the formation of human-like glycoforms (Werner, 1998; Weikert, 1999; Andersen, 1994; Yang, 2000). Inherent problems associated with all mammalian expression systems have not been solved.

Most, if not all, currently produced therapeutic glycoproteins are therefore expressed in mammalian cells and much effort has been directed at improving (i.e., "humanizing") the glycosylation pattern of these recombinant proteins. Changes in medium composition as well as the co-expression of genes encoding enzymes involved in human glycosylation have been successfully employed (see, for example, Weikert, 1999).

Glycoprotein Production Using Eukaryotic Microorganisms

The lack of a suitable mammalian expression system is a significant obstacle to the low-cost and safe production of recombinant human glycoproteins for therapeutic applications. It would be desirable to produce recombinant proteins similar to their mammalian, e.g., human, counterparts in lower eukaryotes (fungi and yeast). Production of glycoproteins via the fermentation of microorganisms would offer numerous advantages over existing systems. Although the core oligosaccharide structure transferred to a protein in the endoplasmic reticulum is basically identical in mammals and lower eukaryotes, substantial differences have been found in the subsequent processing reactions which occur in the Golgi apparatus of fungi and mammals. In fact, even amongst different lower eukaryotes there exist a great variety of glycosylation structures. This has historically prevented the use of lower eukaryotes as hosts for the production of recombinant human glycoproteins despite otherwise notable advantages over mammalian expression systems.

Therapeutic glycoproteins produced in a microorganism host such as yeast utilizing the endogenous host glycosylation pathway differ structurally from those produced in mammalian cells and typically show greatly reduced therapeutic efficacy. Such glycoproteins are typically immunogenic in humans and show a reduced half-life (and thus bioactivity) in vivo after administration (Takeuchi, 1997). Specific receptors in humans and animals (i.e., macrophage mannose receptors) can recognize terminal mannose residues and promote the rapid clearance of the foreign glycoprotein from the bloodstream. Additional adverse effects may include changes in protein folding, solubility, susceptibility to proteases, trafficking, transport, compartmentalization, secretion, recognition by other proteins or factors, antigenicity, or allergenicity.

Yeast and filamentous fungi have both been successfully used for the production of recombinant proteins, both intracellular and secreted (Cereghino, 2000; Harkki, 1989; Berka, 1992; Svetina, 2000). Various yeasts, such as *K. lactis, Pichia pastoris, Pichia methanolica*, and *Hansenula polymorpha*, have played particularly important roles as eukaryotic expression systems because they are able to grow to high cell densities and secrete large quantities of recombinant protein. Likewise, filamentous fungi, such as *Aspergillus niger*, *Fusarium* sp., *Neurospora crassa* and others, have been used to efficiently produce glycoproteins at the industrial scale. However, as noted above, glycoproteins expressed in any of these eukaryotic microorganisms differ substantially in N-glycan structure from those in animals. This has prevented the use of yeast or filamentous fungi as hosts for the production of many therapeutic glycoproteins.

Although glycosylation in yeast and fungi is very different than in humans, some common elements are shared. The first step, the transfer of the core oligosaccharide structure to the nascent protein, is highly conserved in all eukaryotes including yeast, fungi, plants and humans (compare FIGS. 1A and 1B). Subsequent processing of the core oligosaccharide, however, differs significantly in yeast and involves the addition of several mannose sugars. This step is catalyzed by mannosyltransferases residing in the Golgi (e.g. OCH1, MNT1, MNN1, etc.), which sequentially add mannose sugars to the core oligosaccharide. The resulting structure is undesirable for the production of humanoid proteins and it is thus desirable to reduce or eliminate mannosyltransferase activity. Mutants of *S. cerevisiae* deficient in mannosyltransferase activity (e.g. och1 or mnn9 mutants) have shown to be non-lethal and display a reduced mannose content in the oligosaccharide of yeast glycoproteins. Other oligosaccharide processing enzymes, such as mannosylphosphate transferase, may also have to be eliminated depending on the host's particular endogenous glycosylation pattern. After reducing undesired endogenous glycosylation reactions, the formation of complex N-glycans has to be engineered into the host system. This requires the stable expression of several enzymes and sugar-nucleotide transporters. Moreover, one has to localize these enzymes so that a sequential processing of the maturing glycosylation structure is ensured.

Several efforts have been made to modify the glycosylation pathways of eukaryotic microorganisms to provide glycoproteins more suitable for use as mammalian therapeutic agents. However, N-glycans resembling those made in human cells (e.g., with complex or hybrid glycan structures) were not obtained.

Yeasts produce a variety of mannosyltransferases (e.g., 1,3-mannosyltransferases such as MNN1 in *S. cerevisiae*; Graham, 1991, 1,2-mannosyltransferases (e.g. KTR/KRE family from *S. cerevisiae*), 1,6-mannosyltransferases (e.g., OCH1 from *S. cerevisiae*), mannosylphosphate transferases and their regulators (e.g., MNN4 and MNN6 from *S. cerevisiae*) and additional enzymes that are involved in endogenous glycosylation reactions. Many of these genes have been deleted individually giving rise to viable organisms having altered glycosylation profiles.

While it is useful to engineer strains that are able to produce $Man_5GlcNAc_2$ as the primary N-glycan structure, any attempt to further modify these high mannose precursor structures to more closely resemble human glycans requires additional in vivo or in vitro steps. Methods to further humanize glycans from fungal and yeast sources in vitro are described in U.S. Pat. No. 5,834,251. As discussed above, however, if $Man_5GlcNAc_2$ is to be further humanized in vivo, one has to ensure that the generated $Man_5GlcNAc_2$ structures are, in fact, generated intracellularly and not the product of mannosidase activity in the medium. Complex N-glycan formation in yeast or fungi will require high levels of $Man_5GlcNAc_2$ to be generated within the cell because only intracellular $Man_5GlcNAc_2$ glycans can be further processed to hybrid and complex N-glycans in vivo. In addition, one has to demonstrate that the majority of $Man_5GlcNAc_2$ structures generated are in fact a substrate for GnTI and thus allow the formation of hybrid and complex N-glycans.

Accordingly, the need exists for methods to produce glycoproteins characterized by a high intracellular Man$_5$GlcNAc$_2$ content which can be further processed into human-like glycoprotein structures in non-human eukaryotic host cells, and particularly in yeast and filamentous fungi.

Addition of Sialic Acid to N-Glycans

Sialic acids (Sia) are a unique group of N- or O-substituted derivatives of N-acetylneuraminic acid (Neu5Ac) which are ubiquitous in animals of the deuterostome lineage, from starfish to humans. In other organisms, including most plants, protists, Archaea, and eubacteria, these compounds are thought to be absent (Warren, 1994). Exceptions have been identified, all of which are in pathogenic organisms, including certain bacteria, protozoa and fungi (Kelm, 1997; Parodi, 1993; Alviano, 1999). The mechanism by which pathogenic fungi, including *Cryptococcus neoformans* and *Candida albicans*, acquire sialic acid on cell surface glycoproteins and glycolipids remains undetermined (Alviano, 1999). When these organisms are grown in sialic acid-free media, sialic acid residues are found on cellular glycans, suggesting de novo synthesis of sialic acid. To date, no enzymes have been identified in fungi that are involved in the biosynthesis of sialic acid. The mechanism by which protozoa sialylate cell surface glycans has been well-characterized. Protozoa, such as *Trypanosoma cruzi*, possess an external trans-sialidase that adds sialic acid to cell surface glycoproteins and glycolipids in a CMP-Sia independent mechanism (Parodi, 1993). The identification of a similar trans-sialidase in fungi would help to elucidate the mechanism of sialic acid transfer on cellular glycans, but such a protein has not yet been identified or isolated.

Despite the absence and/or ambiguity of sialic acid biosynthesis in fungi, sialic acid biosynthesis in pathogenic bacteria and mammalian cells is well understood. A group of pathogenic bacteria have been identified that synthesize sialic acids de novo to generate sialylated glycolipids that occur on the cell surface (Vimr, 1995). Although sialic acids on the surface of these pathogenic organisms are predominantly thought to be a means of evading the host immune system, these same sialic acid molecules are also involved in many processes in higher organisms, including protein targeting, cell-cell interaction, cell-substrate recognition and adhesion (Schauer, 2000).

The presence of sialic acids can affect biological activity and half-life of glycoproteins in vivo (MacDougall, 1999). For example, the importance of sialic acids has been demonstrated in studies of human erythropoietin (hEPO). The terminal sialic acid residues on the carbohydrate chains of the N-linked glycan of this glycoprotein prevent rapid clearance of hEPO from the blood and improve in vivo activity. Asialylated-hEPO (asialo-hEPO), which terminates in a galactose residue, has dramatically decreased erythropoietic activity in vivo. This decrease is caused by the increased clearance of the asialo-hEPO by the hepatic asialoglycoprotein receptor (Fukuda, 1989; Spivak, 1989; Spivak, 1989). Similarly, the absence of terminal sialic acid on many therapeutic glycoproteins can reduce efficacy in vivo, and thus require more frequent patient dosing regimes.

SUMMARY OF THE INVENTION

Host cells and cell lines having genetically modified glycosylation pathways that allow them to carry out a specified sequence of enzymatic reactions which mimic the processing of glycoproteins in mammals, especially in humans, have been developed. Recombinant proteins expressed in these engineered hosts yield glycoproteins more similar, if not substantially identical, to their mammalian, e.g., human counterparts. Moreover, substantially homogeneous glycoprotein populations having particular desired glycan structures may be produced. Host cells of the invention, e.g., lower eukaryotic micro-organisms and other non-human, eukaryotic host cells grown in culture, are modified to produce N-glycans produced along human glycosylation pathways. This is achieved using a combination of engineering and/or selection of strains that: (1) do not express certain enzymes which create the undesirable structures characteristic of the fungal glycoproteins; (2) express heterologous enzymes selected either to have optimal activity under the conditions present in the host cell where activity is to be achieved; or (3) combinations thereof; wherein the genetically engineered host cell expresses at least one heterologous enzyme activity required to produce a "human-like" glycoprotein. Host cells of the invention may be modified further by heterologous expression of one or more activities such as glycosyltransferases, glycosidase (such as mannosidases), sugar nucleotide transporters, and the like, to become strains for the production of mammalian, e.g., human therapeutic glycoproteins.

The present invention thus provides a glycoprotein production method using (1) a lower eukaryotic host such as a unicellular or filamentous fungus, or (2) any eukaryotic organism, e.g., a non-human eukaryotic cell or organism that has a different glycosylation pattern from humans, to modify the glycosylation composition and structures of the proteins made in a host organism ("host cell") so that they resemble more closely carbohydrate structures found in mammalian, e.g., human proteins. The process allows one to obtain an engineered host cell in which desirable gene(s), e.g., one(s) involved in glycosylation, is(are) expressed and its (their) product(s) targeted to a subcellular location in the host cell by methods that are well-established in the scientific literature and generally known to the artisans in the field of protein expression. For the production of therapeutic proteins, this method may be adapted to engineer cell lines in which any desired glycosylation structure may be obtained on proteins expressed in the engineered cells.

In one embodiment, N-glycans made in the host cells have a Man$_5$GlcNAc$_2$ core structure which may then be modified further by heterologous expression of one or more enzymes, e.g., glycosyltransferases, glycosidases such as mannosidases, sugar transporters and the like, to yield modified glycoproteins, e.g., having human-like complex or hybrid N-glycan structures. In certain embodiments, N-glycans made in the host cells have a complex Gal$_{(1-4)}$GlcNAc$_{(1-4)}$Man$_3$GlcNAc$_2$ structure which may then be modified further by heterologous expression of one or more enzymes, e.g., glycosyltransferases, glycosidases such as mannosidases, sugar transporters and the like, to yield modified glycoproteins, e.g., having human-like complex or hybrid N-glycan structures. In other embodiments, N-glycans made in the host cells have a hybrid GalGlcNAcMan$_5$GlcNAc$_2$ structure which may then be modified further by heterologous expression of one or more enzymes, e.g., glycosyltransferases, glycosidases such as mannosidases, sugar transporters and the like, to yield modified glycoproteins, e.g., having human-like complex or hybrid N-glycan structures.

In one embodiment, glycoproteins made in the engineered host cells have a complex NANA$_{(1-4)}$Gal$_{(1-4)}$GlcNAc$_{(1-4)}$Man$_3$GlcNA$_2$ glycoform of N-glycan. In other embodiments, glycoproteins made in the engineered host cells have a hybrid NANAGalGlcNAcMan$_5$GlcNA$_2$ glycoform of N-glycan. Thus, in one embodiment, glycoprotein compositions of the present invention may comprise predominantly complex NANA$_{(1-4)}$Gal$_{(1-4)}$GlcNAc$_{(1-4)}$Man$_3$GlcNA$_2$ glycoforms. In other embodiments, glycoprotein compositions of the present invention will comprise predominantly hybrid NANAGalGlcNAcMan$_5$GlcNA$_2$ glycoforms. Methods for producing the Man$_5$GlcNAc$_2$ core structure and its modification to form either complex and hybrid glycoforms are provided in Gerngross, WO02/00879 and U.S. Pat. No. 7,029,872, the specification of which are hereby incorporated herein by reference for its disclosure cited herein.

Accordingly, in one embodiment, the invention provides a method for producing a human-like glycoprotein in a non-human eukaryotic host cell. The host cell of the invention is selected or engineered to be depleted in 1,6-mannosyltransferase activities which would otherwise add mannose residues onto the N-glycan on a glycoprotein. One or more enzymes (enzymatic activities) are introduced into the host cell which enable the production of a Man$_5$GlcNAc$_2$ carbohydrate structure at a high yield, e.g., at least 30 mole percent. In a preferred embodiment, at least 10% of the Man$_5$GlcNAc$_2$ produced within the host cell is a productive substrate for GnTI and thus for further glycosylation reactions in vivo and/or in vitro that produce a finished N-glycan that is similar or identical to that formed in mammals, especially humans.

In another embodiment, a nucleic acid molecule encoding one or more enzymes for production of a Man$_5$GlcNAc$_2$ carbohydrate structure is introduced into a host cell selected or engineered to be depleted in 1,6-mannosyltransferase activities. In one preferred embodiment, at least one enzyme introduced into the host cell is selected to have optimal activity at the pH of the subcellular location where the carbohydrate structure is produced. In another preferred embodiment, at least one enzyme is targeted to a host subcellular organelle where the enzyme will have optimal activity, e.g., by means of a chimeric protein comprising a cellular targeting signal peptide not normally associated with the enzyme.

The invention further provides isolated nucleic acid molecules and vectors comprising such molecules which encode an initiating α1,6-mannosyltransferase activity isolated from *P. pastoris* or from *K. lactis*. These nucleic acid molecules comprise sequences that are homologous to the OCH1 gene in *S. cerevisiae*. These and homologous sequences are useful for constructing host cells which will not hypermannosylate the N-glycan of a glycoprotein.

In another embodiment, the host cell is engineered to express a heterologous glycosidase, e.g., by introducing into the host one or more nucleic acid molecules encoding the glycosidase. In one embodiment, a nucleic acid molecule encodes one or more mannosidase activities involved in the production of Man$_5$GlcNAc$_2$ from Man$_5$GlcNAc$_2$ or Man$_9$GlcNAc$_2$. In a preferred embodiment, at least one of the encoded mannosidase activities has a pH optimum within 1.4 pH units of the average pH optimum of other representative enzymes in the organelle in which the mannosidase activity is localized, or has optimal activity at a pH of between about 5.1 and about 8.0, preferably between about 5.5 and about 7.5. Preferably, the heterologous enzyme is targeted to the endoplasmic reticulum, the Golgi apparatus or the transport vesicles between ER and Golgi of the host organism, where it trims N-glycans such as Man$_8$GlcNAc$_2$ to yield high levels of Man$_5$GlcNAc$_2$.

In another embodiment, the host cell is engineered to express a heterologous galactosyltransferase. In yet another embodiment, the host cell is engineered to express a heterologous sialyltransferase or a trans-sialidase.

In certain embodiments, the glycosylation enzyme is targeted to a subcellular location by forming a fusion protein between a catalytic domain of the enzyme and a cellular targeting signal peptide, e.g., by the in-frame ligation of a DNA, fragment encoding a cellular targeting signal peptide with a DNA fragment encoding a glycosylation enzyme or catalytically active fragment thereof.

In certain embodiments, the glycosylation pathway of a host is modified to express a sugar nucleotide transporter. In a preferred embodiment, a nucleotide diphosphatase enzyme is also expressed. The transporter and diphosphatase improve the efficiency of engineered glycosylation steps, by providing the appropriate substrates for the glycosylation enzymes in the appropriate compartments, reducing competitive product inhibition, and promoting the removal of nucleoside diphosphates.

In another embodiment, the host cell is engineered to express a functional CMP-sialic acid (CMP-Sia) biosynthetic pathway.

In another embodiment, a method of engineering a CMP-Sia biosynthetic pathway into a non-human eukaryotic cell is provided. The method involves the cloning and expression of several enzymes of mammalian origin, bacterial origin or both, in a host cell, particularly a fungal host cell or other host cell that lacks endogenous sialylation or that can benefit from increased levels of CMP-Sia. The engineered CMP-Sia biosynthetic pathway is useful for producing sialylated glycolipids, O-glycans and N-glycans in vivo. The present invention is thus useful for facilitating the generation of sialylated therapeutic glycoproteins in non-human host cells lacking endogenous sialylation or in non-human host cells lacking adequate levels of endogenous sialylation. Examples of non-human host cells lacking adequate levels of endogenous sialylation include lower eukaryotic host cells, insect cells and plant cells. Thus, in certain embodiments of the invention, the host cells are engineered to produce sialylated glycoproteins where none would otherwise be produced endogenously. In other embodiments, of the invention, the host cells are engineered to increase the level of sialylated glycoproteins above native endogenous levels.

The present invention also provides a combinatorial nucleic acid library useful for making fusion constructs which can target a desired protein or polypeptide fragment, e.g., an enzyme involved in glycosylation or a catalytic domain thereof, to a selected subcellular region of a host cell. In one preferred embodiment, the combinatorial nucleic acid library comprises (a) nucleic acid sequences encoding different cellular targeting signal peptides and (b) nucleic acid sequences encoding different polypeptides to be targeted. Nucleic acid sequences of or derived from (a) and (b) are ligated together to produce fusion constructs, at least one of which encodes a functional protein domain (e.g., a catalytic domain of an enzyme) ligated in-frame to a heterologous cellular targeting signal peptide, i.e., one which it normally does not associate with.

The invention also provides a method for modifying the glycosylation pathway of a host cell (e.g., any eukaryotic host cell, including a human host cell) using enzymes involved in modifying N-glycans including glycosidases and glycosyltransferases; by transforming the host cell with a nucleic acid (e.g., a combinatorial) library of the invention to produce a genetically mixed cell population expressing at least one and preferably two or more distinct chimeric glycosylation enzymes having a catalytic domain ligated in-frame to a cellular targeting signal peptide which it normally does not associate with. A host cell having a desired glycosylation phenotype may optionally be selected from the population. Host cells modified using the library and associated methods of the invention are useful, e.g., for producing glycoproteins having a glycosylation pattern similar or identical to those produced in mammals, especially humans.

In another aspect, the combinatorial library of the present invention enables production of one or a combination of catalytically active glycosylation enzymes, which successfully localize to intracellular compartments in which they function efficiently in the glycosylation/secretory pathway. Preferred enzymes convert ($\alpha$-1,2-Man)$_{3-9}$ Man$_5$GlcNAc$_2$ to Man$_5$GlcNAc$_2$ at high efficiency in vivo. In addition, the invention provides eukaryotic host strains, and in particular, yeasts, fungal, insect, plant, plant cells, algae and insect cell hosts, capable of producing glycoprotein intermediates or products with Man$_5$GlcNAc$_2$ and/or GlcNAcMan$_5$GlcNAc$_2$ as the predominant N-glycan.

The present invention also provides methods using the combinatorial library for producing, in vivo, glycoprotein intermediates or products with predominantly Man$_5$GlcNAc$_2$ or GlcNAcMan$_5$GlcNAc$_2$ N-glycans covalently attached to proteins, e.g., recombinant proteins expressed in host cells of the invention. The present invention also provides methods for producing, in vivo, complex glycoprotein products bearing a terminal galactose, preferably having the structure Gal$_{(1-4)}$GlcNAc$_{(1-4)}$Man$_3$GlcNAc$_2$ as well as hybrid glycoprotein products bearing a terminal galactose, preferably having the structure GalGlcNAcMan$_5$GlcNAc$_2$. The present invention also provides methods for producing, in vivo, glycoprotein products bearing a terminal sialic acid, preferably having the structure NANA$_{(1-4)}$Gal$_{(1-4)}$GlcNAc$_{(1-4)}$Man$_3$GlcNAc$_2$ as well as hybrid glycoprotein products bearing a terminal sialic acid, preferably having the structure NANAGalGlcNAcMan$_5$GlcNAc$_2$.

The present invention also provides recombinant molecules derived from a combinatorial nucleic acid library; vectors, including expression vectors, comprising such recombinant molecules; proteins encoded by the recombinant molecules and vectors; host cells transformed with the recombinant molecules or vectors; and glycoproteins produced from such transformed hosts.

Further aspects of this invention include methods, compositions and kits for diagnostic and therapeutic uses in which the presence or absence on a glycoprotein of Man$_5$GlcNAc$_2$, GlcNAcMan$_5$GlcNAc$_2$, Gal$_{(1-4)}$GlcNAc$_{(1-4)}$Man$_3$GlcNAc$_2$, GalGlcNAcMan$_5$GlcNAc$_2$, NANAGalGlcNAcMan$_5$GlcNAc$_2$ and/or NANA$_{(1-4)}$Gal$_{(1-4)}$GlcNAc$_{(1-4)}$Man$_3$GlcNAc$_2$ may be detected.

In one embodiment, the invention comprises a method for producing a recombinant glycoprotein comprising sialic acid in a non-human eukaryotic host cell comprising introducing into the host cell a nucleic acid encoding a sialyltransferase enzyme. In certain embodiments, said host cell lacks an endogenous sialyltransferase activity. The sialyltransferase enzyme may be a fusion protein comprising a sialyltransferase catalytic domain and a cellular targeting signal peptide to target the sialyltransferase catalytic domain to the secretory pathway of the host cell. The cellular targeting signal peptide may be derived from Mnn2 and may comprise amino acids 1 to 108 of GenBank Accession No. ("GenBank AN") NP_009571.

The invention also comprises a method for producing a recombinant glycoprotein comprising sialic acid in a non-human eukaryotic host cell, comprising introducing into the host cell a nucleic acid encoding a trans-sialidase enzyme. In other embodiments, said nucleic acid encodes a fusion protein comprising a trans-sialidase catalytic domain with a cellular targeting signal peptide to target the trans-sialidase catalytic domain to the secretory pathway, cell wall or plasma membrane of the host cell. In one embodiment, said method further comprises supplementing the medium for growing the host cell with a sialic acid donor, such as CMP-Sia. In other embodiments, said method may comprise supplementing the medium with one or more precursors to a sialic acid donor. Such precursors may include, for example, one or more of glucosamine [GlcN], GlcNAc, UDP-GlcNAc, and ManNAc, respectively. In one embodiment, the method further comprises the step of introducing into the host cell one or more nucleic acids encoding one or more enzymes involved in the biosynthesis or transport of CMP-Sialic acid.

In one embodiment, the invention provides a method for producing a recombinant sialylated glycoprotein in a host cell, the host cell selected or engineered to produce glycoproteins comprising a Gal$_{(1-4)}$GlcNAc$_{(1-4)}$Man$_3$GlcNAc$_2$ glycoform, the method comprising the step of introducing into the host cell a nucleic acid encoding an enzyme having sialyltransferase activity, the enzyme comprising a sialyltransferase catalytic domain and a cellular targeting signal peptide to target the sialyltransferase catalytic domain to the secretory pathway of the host cell; wherein, upon passage of the recombinant glycoprotein through the secretory pathway of the host cell, a recombinant glycoprotein comprising a NANA$_{(1-4)}$Gal$_{(1-4)}$GlcNAc$_{(1-4)}$Man$_3$GlcNA$_2$ glycoform is produced. In one embodiment, the cellular targeting signal peptide targets the sialyltransferase catalytic domain to a location in the secretory pathway selected from the group consisting of the endoplasmic reticulum, the Golgi apparatus, the trans-Golgi network and secretory vesicles. In one embodiment, the method further comprises the step of introducing into the host cell a nucleic acid encoding one or more enzymes involved in the biosynthesis or transport of CMP-Sia.

In another embodiment, the invention provides a method for producing a recombinant sialylated glycoprotein in a host cell, the host cell selected or engineered to produce glycoproteins comprising a Gal$_{(1-4)}$GlcNAc$_{(1-4)}$Man$_3$GlcNAc$_2$ glycoform, the method comprising the step of introducing into the host cell: (a) a nucleic acid encoding an enzyme having sialyltransferase activity; and (b) a nucleic acid encoding one or more enzymes involved in the biosynthesis or transport of CMP-Sia; wherein upon passage of the recombinant glycoprotein through the secretory pathway of the host cell, a recombinant glycoprotein comprising a NANA$_{(1-4)}$Gal$_{(1-4)}$GlcNAc$_{(1-4)}$Man$_3$GlcNA$_2$ glycoform is produced. In one embodiment, wherein the enzyme having sialyltransferase activity comprises a sialyltransferase catalytic domain and a cellular targeting signal peptide to target the sialyltransferase catalytic domain to the secretory pathway of the host cell.

In another embodiment, the invention comprises a method for producing a recombinant sialylated glycoprotein in a host cell, the host cell selected or engineered to produce glycoproteins comprising a GalGlcNAcMan$_5$GlcNAc$_2$ glycoform, the method comprising the step of introducing into the host cell a nucleic acid encoding an enzyme having sialyltransferase activity, the enzyme comprising a sialyltransferase catalytic domain and a cellular targeting signal peptide to target the sialyltransferase catalytic domain to the secretory pathway of the host cell; wherein, upon passage of the recombinant glycoprotein through the secretory pathway of the host cell, a recombinant glycoprotein comprising a NANAGalGlcNAcMan$_5$GlcNA$_2$ glycoform is produced.

In another embodiment, the invention comprises a method for producing a recombinant sialylated glycoprotein in a host cell, the host cell selected or engineered to produce glycoproteins comprising a GalGlcNAcMan$_5$GlcNAc$_2$ glycoform, the method comprising the step of introducing into the host cell: (a) a nucleic acid encoding an enzyme having sialyltransferase activity; and (b) a nucleic acid encoding one or more enzymes involved in the biosynthesis or transport of CMP- Sia; wherein upon passage of the recombinant glycoprotein through the Golgi apparatus of the host cell, a recombinant glycoprotein comprising a NANAGalGlcNAcMan$_5$GlcNA$_2$ glycoform is produced.

The invention also comprises a method for producing a recombinant glycoprotein comprising sialic acid in a recombinant non-human eukaryotic host cell comprising introducing into medium used for growing the host cell a trans-sialidase enzyme and a sialic acid donor.

In other embodiments, the above described methods may further comprise the step of introducing into the host cell one or more additional nucleic acids encoding one or more enzymes selected from the group consisting of glycosyltransferases, glycosidases and sugar transporters.

In one embodiment, said method produces a recombinant glycoprotein comprising a NANA$_{(1-4)}$Gal$_{(1-4)}$GlcNAc$_{(1-4)}$Man$_3$GlcNAc$_2$ glycoform. In another embodiment, said method produces a recombinant glycoprotein comprising a NANAGalGlcNAcMan$_5$GlcNA$_2$ glycoform.

In certain embodiments, the host cell to be used in the claimed methods may be selected or engineered to comprise a cellular pool of CMP-sialic acid, or may be cultured in the presence of a sialic acid donor, such as CMP-sialic acid, or in the presence of a precursor of a sialic acid donor. In certain embodiments, the host cell may be selected or engineered to produce CMP-sialic acid. In other embodiments, the host cell may be modified to express one or more enzyme activities involved in the CMP-Sia pathway.

In yet other embodiments, the host cell to be used in the claimed methods may be modified to express one or more glycosylation enzymes selected from the group consisting of glycosyltransferases, glycosidases and sugar transporters. In a preferred embodiment, the host cell of the claimed methods has bee modified (selected or engineered) to express a CMP-sialic acid transporter. The glycosylation enzymes may also be fusion proteins comprising a catalytic domain and a cellular targeting signal peptide to target the catalytic domain to a subcellular location in the host cell.

The host cell to be used in the above described method may be any host cell. In some embodiments, the host cell lacks endogenous sialyltransferase activity. In some embodiments, the host cell lacks endogenous CMP-Sia. In other embodiments, the host cell is selected from the group consisting of a lower eukaryotic host cell, an insect cell or a plant cell. In other embodiments, the host cell is selected from the group consisting of any *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp. and *Neurospora crassa*.

In other embodiments, the host cell to be used in the above described methods produces a glycoprotein comprising a terminal galactose.

In some embodiments, the host cells to be used in the claimed methods may produce glycoproteins comprise a terminal galactose. In some embodiments, the host cell may produce complex glycoproteins comprising a Gal$_{(1-4)}$GlcNAc$_{(1-4)}$Man$_3$GlcNAc$_2$ glycoform. In other embodiments, the host cell may produce hybrid glycoproteins comprising a GalGlcNAcMan$_5$GlcNAc$_2$ glycoform.

In certain embodiments, the above described method may further comprise the step of introducing into the host cell which lacks endogenous CMP-Sia one or more additional nucleic acids encoding one or more enzymes involved in the biosynthesis or transport of CMP-Sialic acid. In one embodiment, the above described method comprises the step of introducing into the host cell one or more additional nucleic acids encoding one or more mammalian enzymes selected from the group consisting of: UDP-N-acetylglucosamine-2-epimerase/N-acetylmannosamine kinase, N-acetylneuraminate-9-phosphate synthase, N-acetylneuraminate-9-phosphatase, CMP-sialic acid phosphatase and CMP-sialic acid synthase. In another embodiment, the above described method comprises the step of introducing into the host cell one or more additional nucleic acids encoding one or more bacterial enzymes selected from the group consisting of: UDP-GlcNAc epimerase, sialate synthase and CMP-Sia synthase. In another embodiment, the above described method comprises the step of introducing into the host cell one or more additional nucleic acids encoding one or more bacterial enzymes selected from the group consisting of: bacterial UDP-GlcNAc epimerase (NeuC), sialate synthase (NeuB) and a mammalian CMP-Sia synthase.

The invention also comprises a nucleic acid encoding a fusion protein comprising a sialyltransferase catalytic domain and a cellular targeting signal peptide to target the sialyltransferase catalytic domain to the secretory pathway of the host cell. For example, suitable cellular targeting signal peptides may target the sialyltransferase catalytic domain to the endoplasmic reticulum, the Golgi apparatus, the trans-Golgi network, or secretory vesicles. In one embodiment, the cellular targeting signal peptide targets the sialyltransferase catalytic domain to the Golgi apparatus. In one embodiment, said cellular targeting signal comprises amino acids 1 to 108 of GenBank AN: NP_00971.

The invention also comprises a nucleic acid encoding a fusion protein comprising a trans-sialidase catalytic domain and a cellular targeting signal peptide to target the trans-sialidase catalytic domain to the secretory pathway, the cell wall or cell membrane of the host cell.

The invention also comprises the host cells to be used in the methods of the invention, having the characteristics disclosed above in connection to the claimed methods. In one embodiment, a host cell of the invention comprises a non-human eukaryotic host cell that has been genetically engineered to express a nucleic acid encoding an enzyme having sialyltransferase activity or a trans-sialidase activity. In one embodiment, the host cell of the invention is a non-human eukaryotic host cell that has been genetically engineered to produce CMP-sialic acid. In one embodiment, a host cell of the invention comprises a non-human eukaryotic host cell that has been genetically engineered to express a nucleic acid encoding an enzyme having sialyltransferase activity or a trans-sialidase activity, and to produce CMP-sialic acid.

In another embodiment, the invention comprises a lower eukaryotic host cell capable of producing a recombinant glycoprotein comprising a complex NANA$_{(1-4)}$Gal$_{(1-4)}$GlcNAc$_{(1-4)}$Man$_3$GlcNAc$_2$ glycoform, or a hybrid NANAGalGlcNAcMan$_5$GlcNAc$_2$, or a NANAGalGlcNAcMan$_5$GlcNAc$_2$ glycoform.

The invention also comprises glycoprotein compositions produced according to the methods of the invention. In certain embodiments, said glycoprotein composition may predominantly comprise a complex NANA$_{(1-4)}$Gal$_{(1-4)}$GlcNAc$_{(1-4)}$Man$_3$GlcNAc$_2$ glycoform. In other embodiments, said glycoprotein composition may comprise a hybrid NANAGalGlcNAcMan$_5$GlcNAc$_2$.

The invention also comprises glycoprotein compositions produced according to the methods of the invention. In certain embodiments, said glycoprotein compositions predominantly comprise complex NANA$_{(1-4)}$Gal$_{(1-4)}$GlcNAc$_{(1-4)}$Man$_3$GlcNAc$_2$ glycoforms. In other embodiments, said glycoprotein compositions comprise predominantly hybrid NANAGalGlcNAcMan$_5$GlcNAc$_2$.

The invention also provides a method for producing a sialylated glycoprotein in a recombinant non-human eukaryotic host cell comprising introducing into medium used for growing the host a trans-sialidase enzyme and a sialic acid donor.

The invention also provides a method of enhancing the production of CMP-sialic acid in a host cell comprising the step of introducing into the host cell a nucleic acid encoding an enzyme having GlcNAc epimerase activity.

The invention also provides a method of enhancing the production of CMP-sialic acid in a host cell comprising the step of introducing into the host cell a nucleic acid encoding an enzyme having sialate aldolase activity.

BRIEF DESCRIPTION OF THE DRAWINGS

FIG. 2A diagrams the insertion of a targeting peptide fragment into pCR2.1-TOPO (Invitrogen, Carlsbad, Calif.). FIG. 2B shows the generated targeting peptide sub-library having restriction sites NotI-AscI. FIG. 2C diagrams the insertion of a catalytic domain region into pJN347, a modified pUC19 vector. FIG. 2D shows the generated catalytic domain sub-library having restriction sites NotI, AscI and PacI. FIG. 2E depicts one particular fusion construct generated from the targeting peptide sub-library and the catalytic domain sub-library.

FIG. 3 (SEQ ID NOS: 45-46 respectively, in order of appearance) illustrates the *M. musculus* α-1,2-mannosidase IA open reading frame. The sequences of the PCR primers used to generate N-terminal truncations are underlined.

FIG. 5A depicts the standard $Man_5GlcNAc_2$ [a] glycan (Glyko, Novato, Calif.) and $Man_5GlcNAc_2+Na^+$ [b]. FIG. 5B shows PNGase-released glycans from K3 wild type. The N-glycans shown are as follows: $Man_9GlcNAc_2$ [d]; $Man_{10}GlcNAc_2$ [e]; $Man_{11}GlcNAc_2$ [f]; $Man_{12}GlcNAc_2$ [g]. FIG. 5C depicts the och1 deletion resulting in the production of $Man_8GlcNAc_2$ [c] as the predominant N-glycan. FIGS. 5D and 5E show the production of $Man_5GlcNAc_2$ [b] after in vivo trimming of $Man_8GlcNAc_2$ with a chimeric α-1,2-mannosidase. The predominant N-glycan is indicated by a peak with a mass (m/z) of 1253 consistent with its identification as $Man_5GlcNAc_2$ [b].

FIG. 6A shows the standard $Man_5GlcNAc_2$ [a] and $Man_5GlcNAc_2+Na^+$ [b] as the standard (Glyko, Novato, Calif.). FIG. 6B shows PNGase-released glycans from IFN-β wildtype. FIG. 6C depicts the och1 knock-out producing $Man_8GlcNAc_2$ [c]; $Man_9GlcNAc_2$ [d]; $Man_{10}GlcNAc_2$ [e]; $Man_{11}GlcNAc_2$ [f]; $Man_{12}GlcNAc_2$ [g]; and no production of $Man_5GlcNAc_2$ [b]. FIG. 6D shows relatively small amount of $Man_5GlcNAc_2$ [b] among other intermediate N-glycans $Man_8GlcNAc_2$ [c] to $Man_{12}GlcNAc_2$ [g]. FIG. 6E shows a significant amount of $Man_5GlcNAc_2$ [b] relative to the other glycans $Man_8GlcNAc_2$ [c] and $Man_9GlcNAc_2$ [d] produced by pGC5 (*Saccharomyces* MNS1(m)/mouse mannosidase IB Δ99). FIG. 6F shows predominant production of $Man_5GlcNAc_2$ [b] on the secreted glycoprotein IFN-β by pFB8 (*Saccharomyces* SEC12 (m)/mouse mannosidase IA Δ187). The N-glycan is indicated by a peak with a mass (m/z) of 1254 consistent with its identification as $Man_5GlcNAc_2$ [b].

FIGS. 10 and 10A-10B demonstrate the activity of an UDP-GlcNAc transporter in the production of $GlcNAcMan_5GlcNAc_2$ in *P. pastoris*. FIG. 10A depicts a *P. pastoris* strain (YSH-3) with a human GnTI but without the UDP-GlcNAc transporter resulting in some production of $GlcNAcMan_5GlcNAc_2$ [b] but a predominant production of $Man_5GlcNAc_2$ [a]. FIG. 10B depicts the addition of UDP-GlcNAc transporter from *K. lactis* in a strain (PBP-3) with the human GnTI, which resulted in the predominant production of $GlcNAcMan_5GlcNAc_2$ [b]. The single prominent peak of mass (m/z) at 1457 is consistent with its identification as $GlcNAcMan_5GlcNAc_2$ [b] as shown in FIG. 10B.

FIG. 12A shows the N-glycans released from wild-type cells, which includes high-mannose type N-glycans. FIG. 12B shows the N-glycans released from och1 mnn1 deleted cells, revealing a distinct peak of mass (m/z) at 1908 consistent with its identification as $Man_9GlcNAc_2$ [d]. FIG. 12C shows the N-glycans released from och1 mnn1 deleted cells after in vitro α-1,2-mannosidase digest corresponding to a peak consistent with $Man_5GlcNAc_2$.

FIG. 15 shows the open reading frame (ORF) of *E. coli* protein NeuC (GenbankAN: M84026.1; SEQ ID NO: 57) and the predicted amino acid sequence (SEQ ID NO:58). The underlined DNA sequences are regions to which primers have been designed to amplify the ORF.

FIG. 16 shows the ORF of *E. coli* protein NeuB (Genbank AN: U05248.1; SEQ ID NO:59) and the predicted amino acid sequence (SEQ ID NO:60). The underlined DNA sequences are regions to which primers have been designed to amplify the ORF.

FIG. 17 shows the ORF of *E. coli* protein NeuA (Genbank AN: J05023.1; SEQ ID NO:61) and the predicted amino acid sequence (SEQ ID NO:62). The underlined DNA sequences are regions to which primers have been designed to amplify the ORF.

FIG. 18 shows the ORF of *Mus musculus* CMP-Sia synthase (Genbank AN: AJ006215; SEQ ID NO:63) and the amino acid sequence (SEQ ID NO:64). The underlined DNA sequences are regions to which primers have been designed to amplify the ORF.

FIG. 20 shows the ORF of *Sus scrota* GlcNAc epimerase (Genbank AN: D83766; SEQ ID NO:65) and the amino acid sequence (SEQ ID NO:66). The underlined DNA sequences are regions to which primers have been designed to amplify the ORF.

FIG. 22 shows the ORF of *E. coli* sialate aldolase (Genbank AN: X03345; SEQ ID NO:67) and the amino acid sequence (SEQ ID NO:68). The underlined DNA sequences are regions to which primers have been designed to amplify the ORF.

FIG. 33 shows the nucleic acid (SEQ ID NO:101) and amino acid sequence (SEQ ID NO:102) of the codon-optimized hST6Gal leader 53 fusion described in Example 17.

DETAILED DESCRIPTION OF THE INVENTION

Figure 1A:
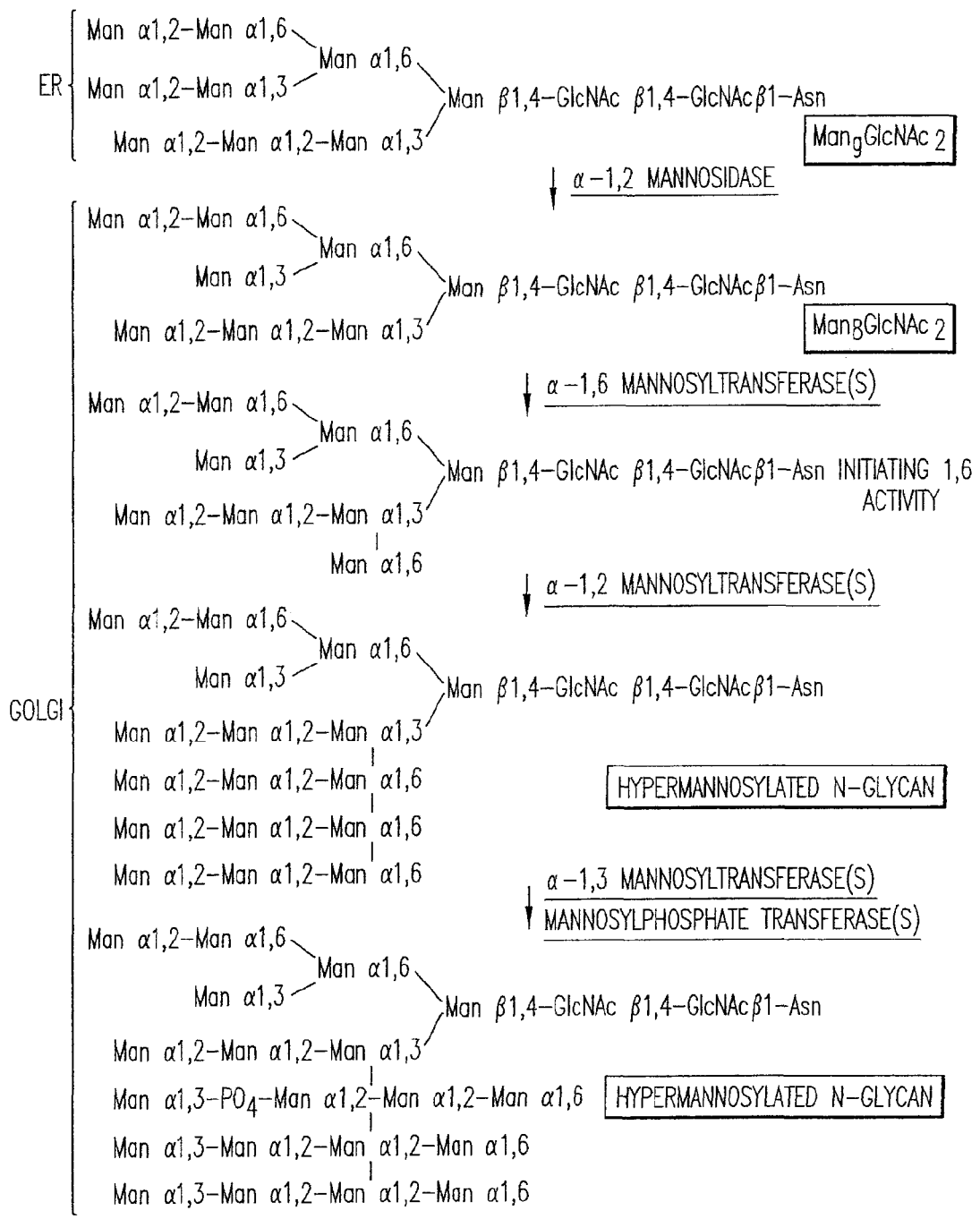
FIG. 1A is a schematic diagram of a typical fungal N-glycosylation pathway.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, molecular and cellular biology, protein biochemistry, enzymology and medicinal and pharmaceutical chemistry described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure $Man_3GlcNAc_2$ ("$Man_3$"). N-glycans differ with respect to the number of branches (antennae) comprising peripheral sugars (e.g., fucose and sialic acid) that are added to the $Man_3$ core structure. N-glycans are classified according to their branched constituents (e.g., high mannose, complex or hybrid).

A "high mannose" type N-glycan has five or more mannose residues. A "complex" type N-glycan typically has at least one GlcNAc attached to the 1,3 mannose arm and at least one GlcNAc attached to the 1,6 mannose arm of the trimannose core. Complex N-glycans may also have galactose ("Gal") residues that are optionally modified with sialic acid or derivatives ("NeuAc", where "Neu" refers to neuraminic acid and "Ac" refers to acetyl). A complex N-glycan typically has at least one branch that terminates in an oligosaccharide such as, for example: NeuNAc-; NeuAca2-6GalNAca1-; NeuAca2-3Galb1-3GalNAca1-; NeuAca2-3/6Galb1-4GlcNAcb1-; GlcNAca1-4Galb1-(mucins only); Fuca1-2Galb1-(blood group H). Sulfate esters can occur on galactose, GalNAc, and GlcNAc residues, and phosphate esters can occur on mannose residues. NeuAc (Neu: neuraminic acid; Ac:acetyl) can be O-acetylated or replaced by NeuGl (N-glycolylneuraminic acid). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

The term "predominant" or "predominantly" used with respect to the production of N-glycans refers to a structure which represents the major peak detected by matrix assisted laser desorption ionization time of flight mass spectrometry (MALDI-TOF) analysis.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr" or "GnT," which refers to N-acetylglucosaminyl Transferase enzymes; "NANA" refers to N-acetylneuraminic acid.

As used herein, a "humanized glycoprotein" or a "human-like glycoprotein" refers alternatively to a protein having attached thereto N-glycans having less than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50-100 mole % of the $Man_5GlcNAc_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "enzyme", when used herein in connection with altering host cell glycosylation, refers to a molecule having at least one enzymatic activity, and includes full-length enzymes, catalytically active fragments, chimerics, complexes, and the like. A "catalytically active fragment" of an enzyme refers to a polypeptide having a detectable level of functional (enzymatic) activity.

A "lower eukaryotic host cell," when used herein in connection with glycosylation profiles, refers to any eukaryotic cell which ordinarily produces high mannose containing N-glycans, and thus is meant to include, in a functional sense, some animal or plant cells whose glycosylation profiles are like those of lower eukaryotic cells, and most typical lower eukaryotic cells, including uni- and multicellular fungal and algal cells.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. The term "secretory pathway" thus refers to organelles and components within the cell where glycoproteins are modified in preparation for secretion. The secretory pathway includes the endoplasmic reticulum or ER, the Golgi apparatus, the trans-Golgi network and the secretory vesicles. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

The term "targeting peptide" a "targeting signal peptide" as used herein refers to nucleotide or amino acid sequences encoding a cellular targeting signal peptide which mediates the localization (or retention) of an associated sequence to sub-cellular locations, e.g., organelles.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA. A nucleic acid molecule of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, hereby incorporated herein by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, hereby incorporated herein by reference.

The terms "significant alignment", "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, significant alignment, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated herein by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled artisan that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, 1989; Caldwell, 1992; and "oligonucleotide-directed mutagenesis" (a process which enables the generation of site-specific mutations in any cloned DNA segment of interest. See, e.g., Reidhaar-Olson 1988).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell that has been genetically engineered. A recombinant host cell includes a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. The term "host" refers to any organism, animal or plant, comprising one or more "host cells", or to the source of the "host cells".

Moreover, as used herein a "host cell which lacks endogenous CMP-Sia" refers to a cell that does not endogeneously produce CMP-Sia, including cells which lack a CMP-Sia pathway. As used herein, a "fungal host cell" refers to a fungal host cell that lacks CMP-Sia.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" as used herein encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well-known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel et al., 1992, hereby incorporated by reference.

A "polypeptide mutant" or "mutein" or "variant" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in-frame with a nucleic acid sequence encoding a different protein or peptide and then expressing the fusion protein. Alternatively, a fusion protein can be produced chemically by crosslinking the polypeptide or a fragment thereof to another protein.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

"Specific binding" refers to the ability of two molecules to bind to each other in preference to binding to other molecules in the environment. Typically, "specific binding" discriminates over adventitious binding in a reaction by at least twofold, more typically by at least 10-fold, often at least 100-fold. Typically, the affinity or avidity of a specific binding reaction is at least about $10^{-7}$ M (e.g., at least about $10^{-8}$ M or $10^{-9}$ M).

As used herein, a "CMP-Sialic acid biosynthetic pathway" or a "CMP-Sia biosynthetic pathway" refers to one or more glycosylation enzymes which results in the formation of CMP-Sia in a host.

As used herein, a "CMP-Sia pool" refers to a detectable level of cellular CMP-Sia. The CMP-Sia pool may be the result of the production of CMP-Sia by the host cell, or of the uptake of CMP-Sia from the culture media.

The substrate UDP-GlcNAc is the abbreviation for UDP-N-acetylglucosamine. The intermediate ManNAc is the abbreviation for N-acetylmannosamine. The intermediate ManNAc-6-P is the abbreviation for N-acetylmannosamine-6-phosphate. The intermediate Sia-9-P is the abbreviation for sialate-9-phosphate. The intermediate Cytidine monophosphate-sialic acid is abbreviated as "CMP-Sia." Sialic acid is abbreviated as "Sia," "Neu5Ac," "NeuAc" or "NANA" herein.

As used herein, the term "sialic acid" refers to a group of molecules where the common molecule includes N-acetyl-5-neuraminic acid (Neu5Ac) having the basic 9-carbon neuraminic acid core modified at the 5-carbon position with an attached acetyl group. Common derivatives of Neu5Ac at the 5-carbon position include: 2-keto-3-deoxy-d-glycero-d-galactononoic acid (KDN) which possesses a hydroxyl group in place of the acetyl group; de-N-acetylation of the 5-N-acetyl group produces neuraminic (Neu); hydroxylation of the 5-N-acetyl group produces N-glycolylneuraminic acid (Neu5Gc). The hydroxyl groups at positions 4-, 7-, 8- and 9- of these four molecules (Neu5Ac, KDN, Neu and Neu5Gc) can be further substituted with O-acetyl, O-methyl, O-sulfate and phosphate groups to enlarge this group of compounds. Furthermore, unsaturated and dehydro forms of sialic acids are known to exist.

The gene encoding for the UDP-GlcNAc epimerase is abbreviated as "NeuC." The gene encoding for the sialate synthase is abbreviated as "NeuB." The gene encoding for the CMP-Sialate synthase is abbreviated as "NeuA."

Sialate aldolase is also commonly referred to as sialate lyase and sialate pyruvate-lyase. More specifically in *E. coli*, sialate aldolase is referred to as NanA. See Ringerberg et al. (2001).

As used herein, the term "sialic acid donor" refers to a molecule or entity that is capable of providing a sialic acid residue for transfer to a substrate by enzymatic or synthetic means. A sialic acid donor can be a sugar nucleotide precursor such as CMP-Sia. In certain embodiments of the invention, a precursor to a sialic acid donor may be used, in conjunction with adapted host cells which are competent for conversion of the precursor molecule to the sialic acid donor. Such adapted host cells may, for example have be capable of producing one or more sugar nucleotide precursors of CMP-Sia such as UDP-GlcNAc [glucosamine] and ManNAc. Thus the "sialic acid donor" may be provided by providing an adapted host cell which contains one or more sugar nucleotide precursors, such as UDP-GlcNAc or ManNAc, and which has functional enzyme activity for the conversion of these molecules to CMP-Sialic acid. The host cell may have such enzyme activity endogenously, or may be engineered to express enzymes which are able to convert UDP-GlcNAc or ManNAc to CMP-Sia. In other embodiments, the host cell may be cultured in media containing the necessary enzymes for the conversion of the precursor molecule to the sialic acid donor.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise" or variations such as "comprises" or "comprising", will be understood to imply the inclusion of a stated integer or group of integers but not the exclusion of any other integer or group of integers.

Methods for Producing Host Cells Having $Man_5GlcNAc_2$ Modified Oligosaccharides for the Generation of Human-Like N-Glycans The invention provides a method for producing a glycoprotein having human-like glycosylation in a non-human eukaryotic host cell. As described in more detail below, a eukaryotic host cell that does not naturally express, or which is engineered not to express, one or more enzymes involved in production of high mannose structures is selected as a starting host cell. Such a selected host cell is engineered to express one or more enzymes or other factors required to produce human-like glycoproteins. A desired host strain can be engineered one enzyme or more than one enzyme at a time. In addition, a nucleic acid molecule encoding one or more enzymes or activities may be used to engineer a host strain of the invention. Preferably, a library of nucleic acid molecules encoding potentially useful enzymes (e.g., chimeric enzymes comprising a catalytically active enzyme fragment ligated in-frame to a heterologous subcellular targeting sequence) is created (e.g., by ligation of sub-libraries comprising enzymatic fragments and subcellular targeting sequences), and a strain having one or more enzymes with optimal activities or producing the most "human-like" or otherwise desirable glycoproteins may be selected by transforming target host cells with one or more members of the library.

In particular, the methods described herein enable one to obtain, in vivo, $Man_5GlcNAc_2$ structures in high yield, at least transiently, for the purpose of further modifying it to yield complex N-glycans. A successful scheme to obtain suitable $Man_5GlcNAc_2$ structures in appropriate yields in a host cell, such as a lower eukaryotic organism, generally involves two parallel approaches: (1) reducing high mannose structures made by endogenous mannosyltransferase activities, if any, and (2) removing 1,2-α-mannose by mannosidases to yield high levels of suitable $Man_5GlcNAc_2$ structures which may be further reacted inside the host cell to form complex, human-like glycoforms.

Accordingly, a first step involves the selection or creation of a eukaryotic host cell, e.g., a lower eukaryote, capable of producing a specific precursor structure of $Man_5GlcNAc_2$ that is able to accept in vivo GlcNAc by the action of a GlcNAc transferase I ("GnTI"). In one embodiment, the method involves making or using a non-human eukaryotic host cell depleted in a 1,6 mannosyltransferase activity with respect to the N-glycan on a glycoprotein. Preferably, the host cell is depleted in an initiating 1,6 mannosyltransferase activity such as an alpha 1,6 mannosyltransferase activity (see below). Such a host cell will lack one or more enzymes involved in the production of high mannose structures which are undesirable for producing human-like glycoproteins.

One or more enzyme activities are then introduced into such a host cell to produce N-glycans within the host cell characterized by having at least 30 mol % of $Man_5GlcNAc_2$ ("$Man_5$") carbohydrate structures. $Man_5GlcNAc_2$ structures are necessary for complex N-glycan formation: $Man_5GlcNAc_2$ must be formed in vivo in a high yield (e.g., in excess of 30%), at least transiently, as subsequent mammalian- and human-like glycosylation reactions require $Man_5GlcNAc_2$ or a derivative thereof.

This step also requires the formation of a particular isomeric structure of $Man_5GlcNAc_2$ within the cell at a high yield. While $Man_5GlcNAc_2$ structures are necessary for complex N-glycan formation, their presence is by no means sufficient. That is because $Man_5GlcNAc_2$ may occur in different isomeric forms, which may or may not serve as a substrate for GlcNAc transferase I. As most glycosylation reactions are not complete, a particular glycosylated protein generally contains a range of different carbohydrate structures (i.e. glycoforms) on its surface. Thus, the mere presence of trace amounts (i.e., less than 5%) of a particular structure like $Man_5GlcNAc_2$ is of little practical relevance for producing mammalian- or human-like glycoproteins. It is the formation of a GlcNAc transferase I-accepting $Man_5GlcNAc_2$ intermediate (FIG. 1B) in high yield (i.e., above 30%), which is required. The formation of this intermediate is necessary to enable subsequent in vivo synthesis of complex N-glycans on glycosylated proteins of interest (target proteins).

Accordingly, some or all of the $Man_5GlcNAc_2$ produced by the selected host cell must be a productive substrate for enzyme activities along a mammalian glycosylation pathway, e.g., can serve as a substrate for a GlcNAc transferase I activity in vivo, thereby forming the human-like N-glycan intermediate $GlcNAcMan_5GlcNAc_2$ in the host cell. In a preferred embodiment, at least 10%, more preferably at least 30% and most preferably 50% or more of the $Man_5GlcNAc_2$ intermediate produced in the host cell of the invention is a productive substrate for GnTI in vivo. It is understood that if, for example, $GlcNAcMan_5GlcNAc_2$ is produced at 10% and $Man_5GlcNAc_2$ is produced at 25% on a target protein, the total amount of transiently produced $Man_5GlcNAc_2$ is 35% because $GlcNAcMan_5GlcNAc_2$ is a product of $Man_5GlcNAc_2$.

As described later herein, N-glycans having a terminal GlcNAc residue, such as $GlcNAcMan_5GlcNAc_2$ can serve as a substrate for sequential addition of galactose [e.g., UDP-galactosyltransferase] and sialic acid [e.g., sialyltransferase, CMP-Sia] to produce the hybrid N-glycans of the present invention.

One of ordinary skill in the art can select host cells from nature, e.g., existing fungi or other lower eukaryotes that produce significant levels of $Man_5GlcNAc_2$ in vivo. As yet, however, no lower eukaryote has been shown to provide such structures in vivo in excess of 1.8% of the total N-glycans (see e.g. Maras, 1997). Alternatively, such host cells may be genetically engineered to produce the $Man_5GlcNAc_2$ structure in vivo. Methods such as those described in U.S. Pat. No. 5,595,900 may be used to identify the absence or presence of particular glycosyltransferases, mannosidases and sugar nucleotide transporters in a target host cell or organism of interest.

Inactivation of Undesirable Host Cell Glycosylation Enzymes

The methods of the invention are directed to making host cells that produce glycoproteins having altered, and preferably human-like, N-glycan structures. In a preferred embodiment, the methods are directed to making host cells in which oligosaccharide precursors are enriched in $Man_5GlcNAc_2$. Preferably, a eukaryotic host cell is used that does not express one or more enzymes involved in the production of high mannose structures. Such a host cell may be found in nature or may be engineered, e.g., starting with or derived from one of many such mutants already described in yeasts. Thus, depending on the selected host cell, one or a number of genes that encode enzymes known to be characteristic of non-human glycosylation reactions may have to be deleted. Such genes and their corresponding proteins have been extensively characterized in a number of lower eukaryotes (e.g., *S. cerevisiae, T. reesei, A. nidulans* etc.), thereby providing a list of known glycosyltransferases in lower eukaryotes, their activities and their respective genetic sequence. These genes are likely to be selected from the group of mannosyltransferases e.g. 1,3 mannosyltransferases (e.g. MNN1 in *S. cerevisiae*) (Graham, 1991), 1,2 mannosyltransferases (e.g. KTR/KRE family from *S. cerevisiae*), 1,6 mannosyltransferases (OCH1 from *S. cerevisiae*), mannosylphosphate transferases and their regulators (MNN4 and MNN6 from *S. cerevisiae*) and additional enzymes that are involved in aberrant, i.e. non human, glycosylation reactions. Many of these genes have in fact been deleted individually giving rise to viable phenotypes with altered glycosylation profiles. Examples are shown in Table 1.

Preferred lower eukaryotic host cells of the invention, as described herein to exemplify the required manipulation steps, are hypermannosylation-minus (och1) mutants of *Pichia pastoris* or *K. lactis*. Like other lower eukaryotes, *P. pastoris* processes $Man_9GlcNAc_2$ structures in the ER with an α-1,2-mannosidase to yield $Man_8GlcNAc_2$ (FIG. 1A). Through the action of several mannosyltransferases, this structure is then converted to hypermannosylated structures ($Man_{>9}GlcNAc_2$), also known as mannans. In addition, it has been found that *P. pastoris* is able to add non-terminal phosphate groups, through the action of mannosylphosphate transferases, to the carbohydrate structure. This differs from the reactions performed in mammalian cells, which involve the removal rather than addition of mannose sugars. It is of particular importance to eliminate the ability of the eukaryotic host cell, e.g., fungus, to hypermannosylate an existing $Man_8GlcNAc_2$ structure. This can be achieved by either selecting for a host cell that does not hypermannosylate or by genetically engineering such a cell.

Genes that are involved in the hypermannosylation process have been identified, e.g., in *Pichia pastoris*, and by creating mutations in these genes, one can reduce the production of "undesirable" glycoforms. Such genes can be identified by homology to existing mannosyltransferases or their regulators (e.g., OCH1, MNN4, MNN6, MNN1) found in other lower eukaryotes such as *C. albicans, Pichia angusta* or *S. cerevisiae* or by mutagenizing the host strain and selecting for a glycosylation phenotype with reduced mannosylation. Based on homologies amongst known mannosyltransferases and mannosylphosphate transferases, one may either design PCR primers (SEQ ID NOS: 7, 8, 47 and 4 left to right, respectively, in order of appearance) (examples of which are shown in Table 2), or use genes or gene fragments encoding such enzymes as probes to identify homologs in DNA libraries of the target or a related organism. Alternatively, one may identify a functional homolog having mannosyltransferase activity by its ability to complement particular glycosylation phenotypes in related organisms.

TABLE 2

PCR Primers

| PCR primer A | PCR primer B | Target Gene(s) in P. pastoris | Homologs |
| --- | --- | --- | --- |
| ATGGCGAAGGCAG ATGGCAGT (SEQ ID NO: 1) | TTAGTCCTTCCAAC TTCCTTC (SEQ ID NO: 2) | 1,6-mannosyltransferase | OCH1 S. cerevisiae, Pichia albicans |
| TAYTGGMGNGTNG ARCYNGAYATHAA (SEQ ID NO: 3) | GCRTCNCCCCANCK YTCRTA (SEQ ID NO: 4) | 1,2 mannosyltransferases | KTR/KRE family, S. cerevisiae |

Legend: M = A or C, R = A or G, W = A or T, S = C or G, Y = C or T, K = G or T, V = A or C or G, H = A or C or T, D = A or G or T, B = C or G or T, N = G or A or T or C.

To obtain the gene or genes encoding 1,6-mannosyltransferase activity in *P. pastoris*, for example, one would carry out the following steps: OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. Mutants of *S. cerevisiae* are available, e.g., from Stanford University and are commercially available from ResGen, an Invitrogen Corp. (Carlsbad, Calif.). Mutants that display a normal growth phenotype at elevated temperature, after having been transformed with a *P. pastoris* DNA library, are likely to carry an OCH1 homolog of *P. pastoris*. Such a library can be created by partially digesting chromosomal DNA of *P. pastoris* with a suitable restriction enzyme and, after inactivating the restriction enzyme, ligating the digested DNA into a suitable vector, which has been digested with a compatible restriction enzyme.

Suitable vectors include, e.g., pRS314, a low copy (CEN6/ARS4) plasmid based on pBluescript containing the Trp1 marker (Sikorski, 1989) and pFL44S, a high copy (2µ) plasmid based on a modified pUC19 containing the URA3 marker (Bonneaud, 1991). Such vectors are commonly used by academic researchers and similar vectors are available from a number of different vendors (e.g., Invitrogen (Carlsbad, Calif.); Pharmacia (Piscataway, N.J.); New England Biolabs (Beverly, Mass.)). Further examples include pYES/GS, 2µ origin of replication based yeast expression plasmid from Invitrogen, or Yep24 cloning vehicle from New England Biolabs.

After ligation of the chromosomal DNA and the vector, one may transform the DNA library into a strain of *S. cerevisiae* with a specific mutation and select for the correction of the corresponding phenotype. After sub-cloning and sequencing the DNA fragment that is able to restore the wild-type phenotype, one may use this fragment to eliminate the activity of the gene product encoded by OCH1 in *P. pastoris* using in vivo mutagenesis and/or recombination techniques well-known to those skilled in the art.

Alternatively, if the entire genomic sequence of a particular host cell, e.g., fungus, of interest is known, one may identify such genes simply by searching publicly available DNA databases, which are available from several sources, such as NCBI, Swissprot. For example, by searching a given genomic sequence or database with sequences from a known 1,6 mannosyltransferase gene (e.g., OCH1 from *S. cerevisiae*), one can identify genes of high homology in such a host cell genome which may (but do not necessarily) encode proteins that have 1,6-mannosyltransferase activity. Nucleic acid sequence homology alone is not enough to prove, however, that one has identified and isolated a homolog encoding an enzyme having the same activity. To date, for example, no data exist to show that an OCH1 deletion in *P. pastoris* eliminates the crucial initiating 1,6-mannosyltransferase activity. (Martinet, 1998; WO 02/00856 A2). Thus, no data prove that the *P. pastoris* OCH1 gene homolog actually encodes that function. That demonstration is provided for the first time herein.

Homologs to several *S. cerevisiae* mannosyltransferases have been identified in *P. pastoris* using these approaches. Homologous genes often have similar functions to genes involved in the mannosylation of proteins in *S. cerevisiae* and thus their deletion may be used to manipulate the glycosylation pattern in *P. pastoris* or, by analogy, in any other host cell, e.g., fungus, plant, insect or animal cells, with similar glycosylation pathways.

The creation of gene knock-outs, once a given target gene sequence has been determined, is a well-established technique in the art and can be carried out by one of ordinary skill in the art (see, e.g., Rothstein, 1991). The choice of a host organism may be influenced by the availability of good transformation and gene disruption techniques.

If several mannosyltransferases are to be knocked out, the method developed by Alani, 1987, for example, enables the repeated use of a selectable marker, e.g., the URA3 marker in yeast, to sequentially eliminate all undesirable endogenous mannosyltransferase activity. This technique has been refined by others but basically involves the use of two repeated DNA sequences, flanking a counter selectable marker. For example: URA3 may be used as a marker to ensure the selection of a transformants that have integrated a construct. By flanking the URA3 marker with direct repeats one may first select for transformants that have integrated the construct and have thus disrupted the target gene. After isolation of the transformants, and their characterization, one may counter select in a second round for those that are resistant to 5-fluoroorotic acid (5-FOA). Colonies that are able to survive on plates containing 5-FOA have lost the URA3 marker again through a crossover event involving the repeats mentioned earlier. This approach thus allows for the repeated use of the same marker and facilitates the disruption of multiple genes without requiring additional markers. Similar techniques for sequential elimination of genes adapted for use in another eukaryotic host cells with other selectable and counter-selectable markers may also be used.

Eliminating specific mannosyltransferases, such as 1,6 mannosyltransferase (OCH1) or mannosylphosphate transferases (MNN6, or genes complementing lbd mutants) or regulators (MNN4) in *P. pastoris* enables one to create engineered strains of this organism which synthesize primarily $Man_8GlcNAc_2$ and which can be used to further modify the glycosylation pattern to resemble more complex glycoform structures, e.g., those produced in mammalian, e.g., human cells. A preferred embodiment of this method utilizes DNA sequences encoding biochemical glycosylation activities to eliminate similar or identical biochemical functions in *P. pastoris* to modify the glycosylation structure of glycoproteins produced in the genetically altered *P. pastoris* strain.

Methods used to engineer the glycosylation pathway in yeasts as exemplified herein can be used in filamentous fungi to produce a preferred substrate for subsequent modification. Strategies for modifying glycosylation pathways in *A. niger* and other filamentous fungi, for example, can be developed using protocols analogous to those described herein for engineering strains to produce human-like glycoproteins in yeast. Undesired gene activities involved in 1,2 mannosyltransferase activity, e.g., KTR/KRE homologs, are modified or eliminated. A filamentous fungus, such as *Aspergillus*, is a preferred host because it lacks the 1,6 mannosyltransferase activity and as such, one would not expect a hypermannosylating gene activity, e.g. OCH1, in this host. By contrast, other desired activities (e.g., α-1,2-mannosidase, UDP-GlcNAc transporter, glycosyltransferase (GnT), galactosyltransferase (GalT) and sialyltransferase (ST)) involved in glycosylation are introduced into the host using the targeting methods of the invention.

Engineering or Selecting Hosts Having Diminished Initiating α-1.6 Mannosyltransferase Activity In a preferred embodiment, the method of the invention involves making or using a host cell which is diminished or depleted in the activity of an initiating α-1,6-mannosyltransferase, i.e., an initiation specific enzyme that initiates outer chain mannosylation on the α-1,3 arm of the $Man_3GlcNAc_2$ core structure. In *S. cerevisiae*, this enzyme is encoded by the OCH1 gene. Disruption of the OCH1 gene in *S. cerevisiae* results in a phenotype in which N-linked sugars completely lack the poly-mannose outer chain. Previous approaches for obtaining mammalian-type glycosylation in fungal strains have required inactivation of OCH1 (see, e.g., Chiba, 1998). Disruption of the initiating α-1,6-mannosyltransferase activity in a host cell of the invention may be optional, however (depending on the selected host cell), as the Och1p enzyme requires an intact $Man_8GlcNAc_2$ for efficient mannose outer chain initiation. Thus, host cells selected or produced according to this invention which accumulate oligosaccharides having seven or fewer mannose residues may produce hypoglycosylated N-glycans that will likely be poor substrates for Och1p (see, e.g., Nakayama, 1997).

The OCH1 gene was cloned from *P. pastoris* (Example 1) and *K. lactis* (Example 18), as described. The nucleic acid and amino acid sequences of the OCH1 gene from *K. lactis* are set forth in SEQ ID NOS: 41 and 42. Using gene-specific primers, a construct was made from each clone to delete the OCH1 gene from the genome of *P. pastoris* and *K. lactis* (Examples 1 and 18, respectively). Host cells depleted in initiating α-1, 6-mannosyltransferase activity and engineered to produce N-glycans having a $Man_5GlcNAc_2$ carbohydrate structure were thereby obtained (see, e.g., FIGS. 5 and 6; Examples 11 and 18).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* OCH1 gene (SEQ ID NO: 41), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. Also provided are vectors, including expression vectors, which comprise the above nucleic acid molecules of the invention, as described further herein. Similarly, host cells transformed with the nucleic acid molecules or vectors of the invention are provided.

Host Cells Enriched in $Man_5GlcNAc_2$

A preferred host cell of the invention is a lower eukaryotic cell, e.g., yeast, a unicellular and multicellular or filamentous fungus. However, a wide variety of host cells are envisioned as being useful in the methods of the invention. Plant cells or insect cells, for instance, may be engineered to express a human-like glycoprotein according to the invention (Examples 19 and 20). Likewise, a variety of non-human, mammalian host cells may be altered to express more human-like or otherwise altered glycoproteins using the methods of the invention. As one of skill in the art will appreciate, any eukaryotic host cell (including a human cell) may be used in conjunction with a library of the invention to express one or more chimeric proteins which is targeted to a subcellular location, e.g., organelle, in the host cell where the activity of the protein is modified, and preferably is enhanced. Such a protein is preferably—but need not necessarily be—an enzyme involved in protein glycosylation, as exemplified herein. It is envisioned that any protein coding sequence may be targeted and selected for modified activity in a eukaryotic host cell using the methods described herein.

Figure 1B:
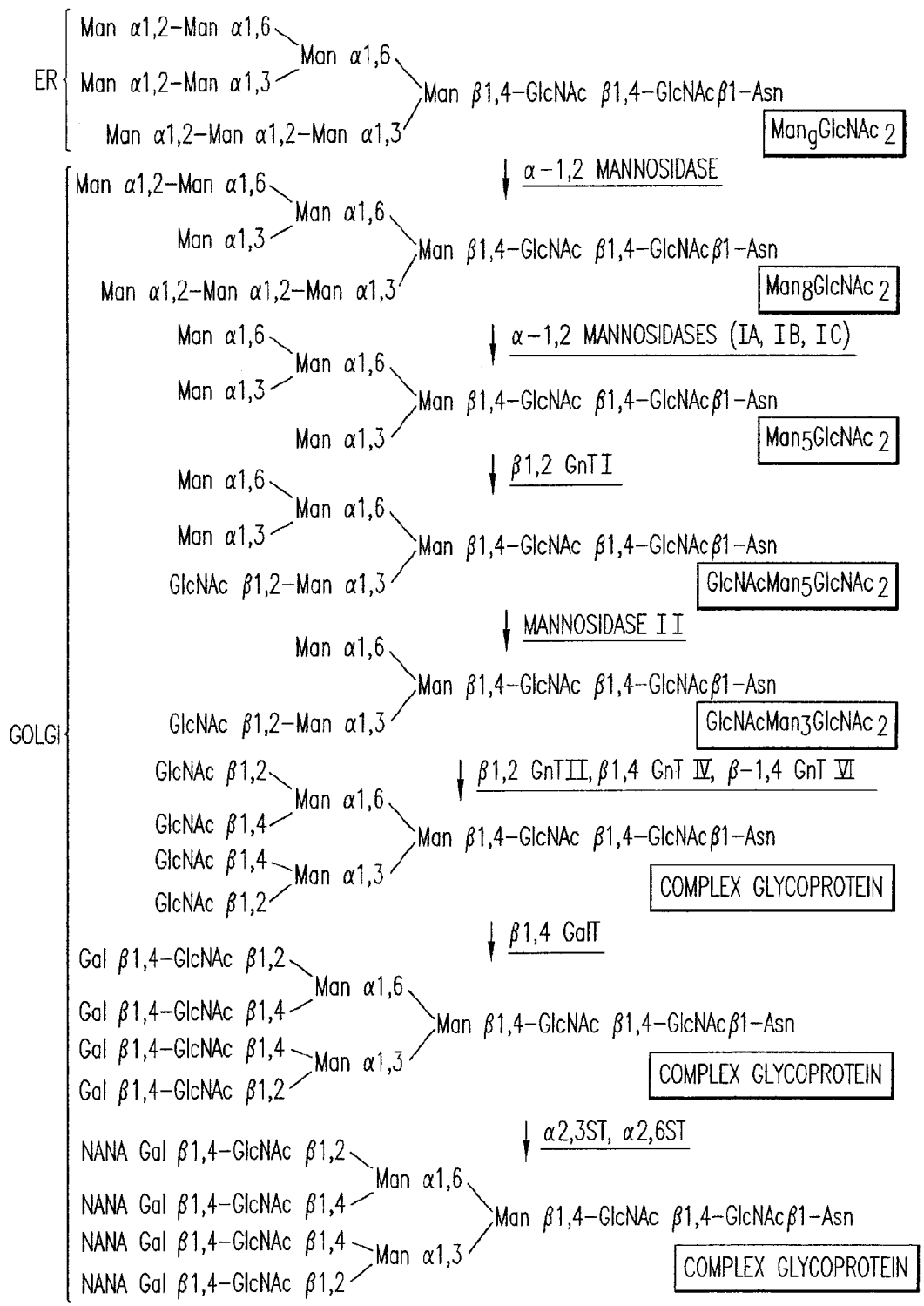
FIG. 1B is a schematic diagram of a typical human N-glycosylation pathway.

Lower eukaryotes that are able to produce glycoproteins having the attached N-glycan $Man_5GlcNAc_2$ are particularly useful because (a) lacking a high degree of mannosylation (e.g. greater than 8 mannoses per N-glycan, or especially 30-40 mannoses), they show reduced immunogenicity in humans; and (b) the N-glycan is a substrate for further glycosylation reactions to form an even more human-like glycoform, e.g., by the action of GlcNAc transferase I (FIG. 1B; $\beta1,2$ GnTI) to form $GlcNAcMan_5GlcNAc_2$. A yield is obtained of greater than 30 mole %, more preferably a yield of 50-100 mole %, glycoproteins with N-glycans having a $Man_5GlcNAc_2$ structure. In a preferred embodiment, more than 50% of the $Man_5GlcNAc_2$ structure is shown to be a substrate for a GnTI activity and can serve as such a substrate in vivo. Lower eukaryotes may also be useful host cells of the invention because they typically lack (unless otherwise engineered to add) galactose, fucose and N-acetylglycosamine. Thus, recombinant proteins lacking, e.g., fucose, may be made in these host cells.

Preferred lower eukaryotes of the invention include but are not limited to: any *Pichia* sp., including but limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis* and *Pichia methanolica*; any *Saccharomyces* sp including but not limited to: *Saccharomyces cerevisiae, Hansenula polymorpha*; any *Kluyveromyces* sp. including but not limited to: *Kluyveromyces lactis; Candida albicans; Aspergillus nidulans; Aspergillus niger; Aspergillus oryzae; Trichoderma reseei; Chrysosporium lucknowense*; any *Fusarium* sp. including but not limited to: *Fusarium gramineum* and *Fusarium venenatum*; and *Neurospora crassa*.

In each above embodiment, the method is directed to making a host cell in which the oligosaccharide precursors are enriched in $Man_5GlcNAc_2$. These structures are desirable because they may then be processed by treatment in vitro, for example, using the method of U.S. Pat. No. 5,834,251. In a preferred embodiment, however, precursors enriched in $Man_5GlcNAc_2$ are processed by at least one further glycosylation reaction in vivo—with glycosidases (e.g., $\alpha$-mannosidases) and glycosyltransferases (e.g., GnTI)—to produce human-like N-glycans. Oligosaccharide precursors enriched in $Man_5GlcNAc_2$, for example, are preferably processed to those having $GlcNAcMan_XGlcNAc_2$ core structures, wherein X is 3, 4 or 5, and is preferably 3. N-glycans having a $GlcNAcMan_XGlcNAc_2$ core structure where X is greater than 3 may be converted to $GlcNAcMan_3GlcNAc_2$, e.g., by treatment with an $\alpha$-1,3 and/or $\alpha$-1,6 mannosidase activity, where applicable. Additional processing of $GlcNAcMan_3GlcNAc_2$ by treatment with glycosyltransferases (e.g., GnTII) produces $GlcNAc_2Man_3GlcNAc_2$ core structures which may then be modified, as desired, e.g., by ex vivo treatment or by heterologous expression in the host cell of additional glycosylation enzymes, including glycosyltransferases, sugar transporters and mannosidases (see below), to comprise specific human-like N-glycans, as desired.

Preferred human-like glycoproteins which may be produced according to the invention include those that comprise N-glycans having seven or fewer, or three or fewer, mannose residues; and that comprise one or more sugars selected from the group consisting of galactose, GlcNAc, sialic acid, and fucose. Other preferred human-like glycoproteins which may be produced according to the invention lack fucose.

Formation of Complex N-Glycans

Formation of complex N-glycan synthesis is a sequential process by which specific sugar residues are removed and attached to the core oligosaccharide structure. In higher eukaryotes, this is achieved by having the substrate sequentially exposed to various processing enzymes. These enzymes carry out specific reactions depending on their particular location within the entire processing cascade. This "assembly line" consists of ER, early, medial and late Golgi, and the trans Golgi network all with their specific processing environment. To re-create the processing of human glycoproteins in the Golgi and ER of lower eukaryotes, numerous enzymes (e.g. glycosyltransferases, glycosidases, phosphatases and transporters) have to be expressed and specifically targeted to these organelles, and preferably, in a location so that they function most efficiently in relation to their environment as well as to other enzymes in the pathway.

Because one goal of the methods described herein is to achieve a robust protein production strain that is able to perform well in an industrial fermentation process, the integration of multiple genes into the host cell chromosome involves careful planning. As described above, one or more genes which encode enzymes known to be characteristic of non-human glycosylation reactions are preferably deleted. The engineered cell strain is transformed with a range of different genes encoding desired activities, and these genes are transformed in a stable fashion, thereby ensuring that the desired activity is maintained throughout the fermentation process.

Any combination of the following enzyme activities may be engineered singly or multiply into the host using methods of the invention: sialyltransferases, mannosidases, fucosyltransferases, galactosyltransferases, GlcNAc transferases, ER and Golgi specific transporters (e.g. syn- and antiport transporters for UDP-galactose and other precursors), other enzymes involved in the processing of oligosaccharides, and enzymes involved in the synthesis of activated oligosaccharide precursors such as UDP-galactose and CMP-N-acetylneuraminic acid. Preferably, enzyme activities are introduced on one or more nucleic acid molecules (see also below). Nucleic acid molecules may be introduced singly or multiply, e.g., in the context of a nucleic acid library such as a combinatorial library of the invention. It is to be understood, however, that single or multiple enzymatic activities may be introduced into a host cell in any fashion, including but not limited to protein delivery methods and/or by use of one or more nucleic acid molecules without necessarily using a nucleic acid library or combinatorial library of the invention.

Expression of Glycosyltransferases to Produce Complex N-Glycans

With DNA sequence information, the skilled artisan can clone DNA molecules encoding one or more GnT activities such as GnTI, II, III, IV or IV (e.g., Examples 3 and 4); galactosyltransferase activities (Example 4); and/or sialyltransferase activities (Examples 6 and 17). Using standard techniques well-known to those of skill in the art, nucleic acid molecules encoding one or more of the above described enzymes (or encoding catalytically active fragments thereof) may be inserted into appropriate expression vectors under the transcriptional control of promoters and other expression control sequences capable of driving transcription in a selected host cell of the invention, e.g., a fungal host such as *Pichia* sp., *Kluyveromyces* sp. and *Aspergillus* sp., as described herein, such that one or more of these mammalian enzymes may be actively expressed in a host cell of choice for production of a human-like complex glycoprotein (e.g., Examples 15, 16, 17, 19 and 20).

Several individual glycosyltransferases have been cloned and expressed in *S. cerevisiae* (GalT, GnTI), *Aspergillus nidulans* (GnTI) and other fungi, without however demonstrating the desired outcome of "humanization" on the glycosylation pattern of the organisms (Yoshida, 1995; Schwientek, 1995; Kalsner, 1995). It was speculated that the carbohydrate structure required to accept sugars by the action of such glycosyltransferases was not present in sufficient amounts, which most likely contributed to the lack of complex N-glycan formation.

A preferred method of the invention provides the functional expression of a GnT, such as GnTI, in the early or medial Golgi apparatus as well as ensuring a sufficient supply of UDP-GlcNAc (e.g., by expression of a UDP-GlcNAc transporter; see below).

Another preferred method of the invention provides functional expression of a sialyltransferase, such as ST6Gal or ST3Gal, in the Golgi as well as ensuring a sufficient supply of CMP-Sialic acid (e.g., by expression of a CMP-Sialic acid biosynthetic pathway in the host as illustrated in Example 16). Sialyltransferases from many species are known and may be useful in the present invention. Sialyltransferases are described for example, in Harduin-Lepers, 2001; Hardeuin-Lepers, 2005; and Tsji, 1996. The disclosures of all of these references are hereby incorporated herein by reference.

Methods for Providing Sugar Nucleotide Precursors to the Golgi Apparatus

For a glycosyltransferase to function satisfactorily in the Golgi, the enzyme requires a sufficient concentration of an appropriate nucleotide sugar, which is the high-energy donor of the sugar moiety added to a nascent glycoprotein. In humans and other non-human eurkayotic cells, the full range of nucleotide sugar precursors (e.g. UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases.

To replicate this process in host cells that do not comprise these nucleotide precursors in the Golgi (e.g., in non-human host cells such as lower eukaryotes), sugar nucleoside specific transporters have to be expressed in the Golgi to ensure adequate levels of nucleoside sugar precursors (Sommers, 1981; Sommers, 1982; Perez, 1987). Nucleotide sugars may be provided to the appropriate compartments, e.g., by expressing in the host cell an exogenous gene encoding a sugar nucleotide transporter. The choice of transporter enzyme is influenced by the nature of the exogenous glycosyltransferase being used. For example, a GlcNAc transferase may require a UDP-GlcNAc transporter, a fucosyltransferase may require a GDP-fucose transporter, a galactosyltransferase may require a UDP-galactose transporter, and a sialyltransferase may require a CMP-sialic acid transporter.

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, e.g. UDP, GDP, or CMP. Nucleoside monophosphates can be directly exported from the Golgi in exchange for nucleoside triphosphate sugars by an antiport mechanism. Accumulation of a nucleoside diphosphate, however, inhibits the further activity of a glycosyltransferase. As this reaction appears to be important for efficient glycosylation, it is frequently desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate.

Suitable transporter enzymes, which are typically of mammalian origin, are described below. Such enzymes may be engineered into a selected host cell using the methods of the invention (see also Examples 7-10).

In another example, α 2,3- or α 2,6-sialyltransferase caps galactose residues with sialic acid in the trans-Golgi and TGN of humans leading to a mature form of the glycoprotein (FIG. 1B). To reengineer this processing step into a lower eukaryotic host cell and other host cells which naturally lack sialyltransferase activity will require (1) α 2,3- or α 2,6-sialyltransferase activity and (2) a sufficient supply of CMP-N-acetyl neuraminic acid, in the late Golgi (Examples 6, 16 and 17). To obtain sufficient α 2,3-sialyltransferase activity in the secretory pathway (e.g. late Golgi), for example, the catalytic domain of a known sialyltransferase (e.g. from humans) has to be directed to the secretory pathway in lower eukaryotic host cells (see above). Likewise, transporters have to be engineered to allow the transport of CMP-N-acetyl neuraminic acid into the same location of the secretory pathway (e.g. late Golgi). There is currently no indication that host cells such as lower eukaryotic host cells synthesize or can even transport sufficient amounts of CMP-N-acetyl neuraminic acid into the Golgi. Consequently, to ensure the adequate supply of substrate for the corresponding glycosyltransferases, one has to metabolically engineer the production of CMP-sialic acid into these host cells.

UDP-N-Acetylglucosamine Transporter

The cDNA of human UDP-N-acetylglucosamine transporter, which was recognized through a homology search in the expressed sequence tags database (dbEST), has been cloned (Ishida, 1999). The mammalian Golgi membrane transporter for UDP-N-acetylglucosamine was cloned by phenotypic correction with cDNA from canine kidney cells (MDCK) of a recently characterized *Kluyveromyces lactis* mutant deficient in Golgi transport of the above nucleotide sugar (Guillen, 1998). Results demonstrate that the mammalian Golgi UDP-GlcNAc transporter gene has all of the necessary information for the protein to be expressed and targeted functionally to the Golgi apparatus of yeast and that two proteins with very different amino acid sequences may transport the same solute within the same Golgi membrane (Guillen, 1998).

Accordingly, one may incorporate the expression of a UDP-GlcNAc transporter in a host cell by means of a nucleic acid construct which may contain, for example: (1) a region by which the transformed construct is maintained in the cell (e.g. origin of replication or a region that mediates chromosomal integration), (2) a marker gene that allows for the selection of cells that have been transformed, including counterselectable and recyclable markers such as ura3 or T-urf13 (Soderholm, 2001) or other well characterized selection-markers (e.g., his4, bla, Sh ble etc.), (3) a gene or fragment thereof encoding a functional UDP-GlcNAc transporter, e.g. from *K. lactis* (Abeijon, 1996), or from *H. sapiens* (Ishida, 1996), and (4) a promoter activating the expression of the above mentioned localization/catalytic domain fusion construct library.

GDP-Fucose Transporter

The rat liver Golgi membrane GDP-fucose transporter has been identified and purified by Puglielli, L. and C. B. Hirschberg (Puglielli, 1999). The corresponding gene has not been identified; however, N-terminal sequencing can be used for the design of oligonucleotide probes specific for the corresponding gene. These oligonucleotides can be used as probes to clone the gene encoding for GDP-fucose transporter.

UDP-Galactose Transporter

Two heterologous genes, gma12(+) encoding alpha 1,2-galactosyltransferase (alpha 1,2 GalT) from *Schizosaccharomyces pombe* and (hUGT2) encoding human UDP-galactose (UDP-Gal) transporter, have been functionally expressed in *S. cerevisiae* to examine the intracellular conditions required for galactosylation. Correlation between protein galactosylation and UDP-galactose transport activity indicated that an exogenous supply of UDP-Gal transporter, rather than alpha 1,2 GalT played a key role for efficient galactosylation in *S. cerevisiae* (Kainuma, 1999). Likewise, an UDP-galactose transporter from *S. pombe* was cloned (Aoki, 1999; Segawa, 1999).

CMP-N-Acetylneuraminic Acid (CMP-Sialic Acid) Transporter

Human CMP-sialic acid transporter (hCST) has been cloned and expressed in Lec 8 CHO cells (Aoki, 1999; Eckhardt, 1997). The functional expression of the murine CMP-sialic acid transporter was achieved in *Saccharomyces cerevisiae* (Berninsone, 1997). Sialic acid has been found in some fungi, however it is not clear whether the chosen host system will be able to supply sufficient levels of CMP-Sialic acid. Sialic acid can be either supplied in the medium or alternatively fungal pathways involved in sialic acid synthesis can also be integrated into the host genome as described below.

Expression of Diphosphatases

When sugars are transferred onto a glycoprotein, either a nucleoside diphosphate or monophosphate is released from the sugar nucleotide precursors. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from *S. cerevisiae* has been found to be necessary for mannosylation. However, the enzyme only has 10% of the activity towards UDP (Berninsone, 1994). Lower eukaryotes often do not have UDP-specific diphosphatase activity in the Golgi as they do not utilize UDP-sugar precursors for glycoprotein synthesis in the Golgi. *Schizosaccharomyces pombe*, a yeast which adds galactose residues to cell wall polysaccharides (from UDP-galactose), was found to have specific UDPase activity, further suggesting the requirement for such an enzyme (Berninsone, 1994). UDP is known to be a potent inhibitor of glycosyltransferases and the removal of this glycosylation side product is important to prevent glycosyltransferase inhibition in the lumen of the Golgi (Khatara, 1974).

Formation of Hybrid Glycoproteins

With minor modifications, the same "assembly line" of enzymes and glycosylation pathway may be utilized to accomplish the formation of complex N-glycans. The primary difference is that after action of GNT I on the Man5GlcNAc2 core to produce GlcNAcMan5GlcNAc2, it is not necessary that the GlcNAcMan5GlcNAc2 be exposed to the action mannosidase II to form GlcNAcMan3GlcNAc2. See, e.g., Gerngross, WO02/00879 and U.S. Pat. No. 7,029,872.

Methods for Altering N-Glycans in a Host by Expressing a Targeted Enzymatic Activity from a Nucleic Acid Molecule In one preferred embodiment, the invention provides a method for producing a glycoprotein comprising $Man_5GlcNAc_2$. In one preferred embodiment, a nucleic acid molecule encoding one or more mannosidase activities involved in the production of $Man_5GlcNAc_2$ from $Man_8GlcNAc_2$ or $Man_9GlcNAc_2$ is introduced into the host.

In another embodiment, the invention provides a method for producing a human-like glycoprotein in a non-human eukaryotic host cell comprising the step of introducing into the host cell one or more nucleic acid molecules that encode an enzyme or enzymes for production of $NANA_{(1-4)}Gal_{(1-4)}GlcNAc_{(1-4)}Man_3GlcNAc_2$ carbohydrate structure.

The invention additionally relates to methods for making altered glycoproteins in a host cell comprising the step of introducing into the host cell a nucleic acid molecule which encodes one or more glycosylation enzymes or activities. Preferred enzyme activities are selected from the group consisting of UDP-GlcNAc transferase, UDP-galactosyltransferase, GDP-fucosyltransferase, CMP-sialyltransferase, UDP-GlcNAc transporter, UDP-galactose transporter, GDP-fucose transporter, CMP-sialic acid transporter, and nucleotide diphosphatases. In a particularly preferred embodiment, the host is selected or engineered to express two or more enzymatic activities in which the product of one activity increases substrate levels of another activity, e.g., a glycosyltransferase and a corresponding sugar transporter, e.g., GnTI and UDP-GlcNAc transporter activities. In another preferred embodiment, the host is selected or engineered to expresses an activity to remove products which may inhibit subsequent glycosylation reactions, e.g. a UDP- or GDP-specific diphosphatase activity.

Preferred methods of the invention involve expressing one or more enzymatic activities from a nucleic acid molecule in a host cell and comprise the step of targeting at least one enzymatic activity to a desired subcellular location (e.g., an organelle) by forming a fusion protein comprising a catalytic domain of the enzyme and a cellular targeting signal peptide, e.g., a heterologous signal peptide which is not normally ligated to or associated with the catalytic domain. The fusion protein is encoded by at least one genetic construct ("fusion construct") comprising a nucleic acid fragment encoding a cellular targeting signal peptide ligated in the same translational reading frame ("in-frame") to a nucleic acid fragment encoding an enzyme (e.g., glycosylation enzyme), or catalytically active fragment thereof.

The targeting signal peptide component of the fusion construct or protein is preferably derived from a member of the group consisting of: membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases and phosphomannosyltransferases.

The catalytic domain component of the fusion construct or protein is preferably derived from a glycosidase, mannosidase or a glycosyltransferase activity derived from a member of the group consisting of GnTI, GnTII, GnTIII, GnTIV, GnTV, GnTVI, GalT, Fucosyltransferase and Sialyltransferase. The catalytic domain preferably has a pH optimum within 1.4 pH units of the average pH optimum of other representative enzymes in the organelle in which the enzyme is localized, or has optimal activity at a pH between 5.1 and 8.0.

Selecting a Glycosylation Enzyme: pH Optima and Subcellular Localization

In one embodiment of the invention, a human-like glycoprotein is made efficiently in a non-human eukaryotic host cell by introducing into a subcellular compartment of the cell a glycosylation enzyme selected to have a pH optimum similar to the pH optima of other enzymes in the targeted subcellular compartment. For example, most enzymes that are active in the ER and Golgi apparatus of *S. cerevisiae* have pH optima that are between about 6.5 and 7.5 (see Table 3). Because the glycosylation of proteins is a highly evolved and efficient process, the internal pH of the ER and the Golgi is likely also in the range of about 6-8. All previous approaches to reduce mannosylation by the action of recombinant mannosidases in fungal hosts, however, have introduced enzymes that have a pH optimum of around pH 5.0 (Martinet, 1998 and Chiba, 1998). At pH 7.0, the in vitro determined activity of those mannosidases is reduced to less than 10%, which is likely insufficient activity at their point of use, namely, the ER and early Golgi, for the efficient in vivo production of $Man_5GlcNAc_2$ on N-glycans.

Accordingly, a preferred embodiment of this invention targets a selected glycosylation enzyme (or catalytic domain thereof), e.g., an α-mannosidase, to a subcellular location in the host cell (e.g., an organelle) where the pH optimum of the enzyme or domain is within 1.4 pH units of the average pH optimum of other representative marker enzymes localized in the same organelle(s). The pH optimum of the enzyme to be targeted to a specific organelle should be matched with the pH optimum of other enzymes found in the same organelle to maximize the activity per unit enzyme obtained. Table 3 summarizes the activity of mannosidases from various sources and their respective pH optima. Table 4 summarizes their typical subcellular locations.

TABLE 3

Mannosidases And Their pH Optimum.

Figure 11:
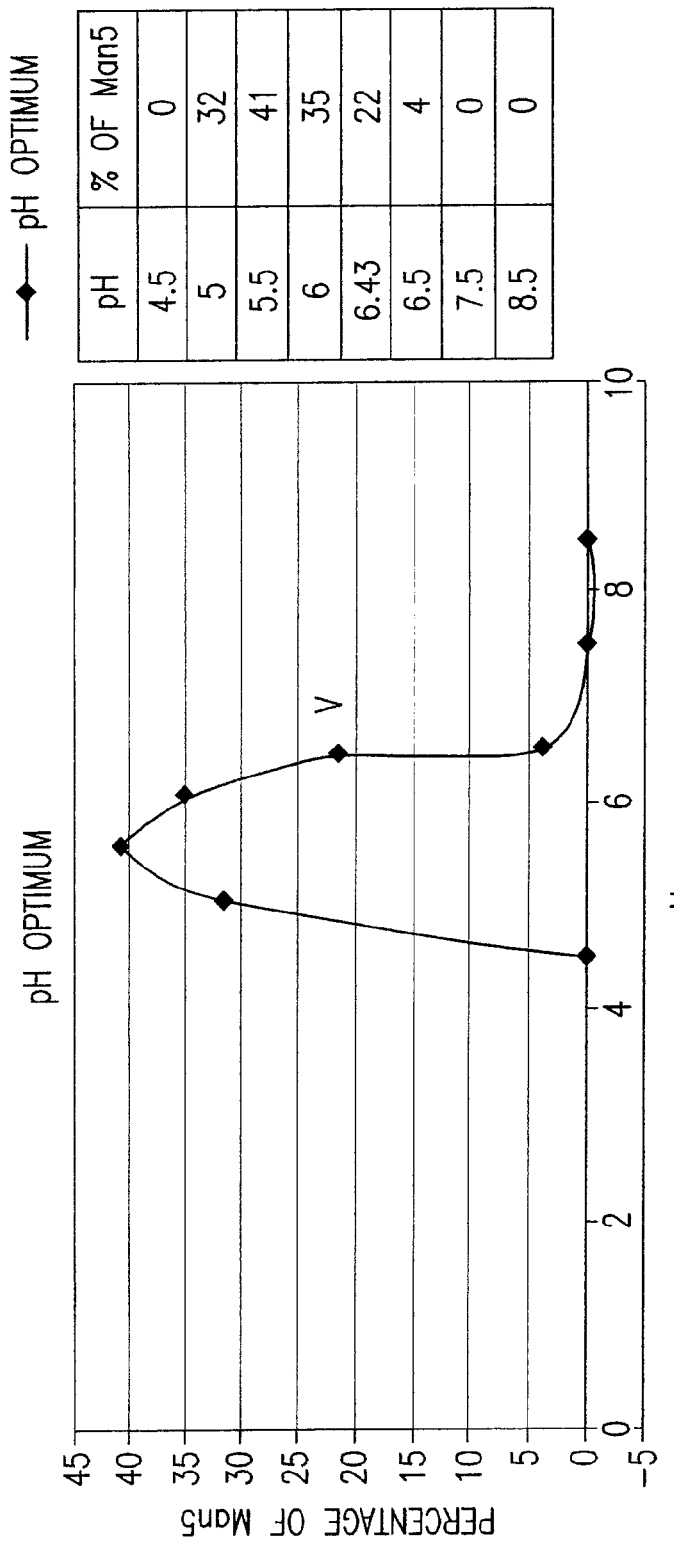
FIG. 11 shows a pH optimum of a heterologous mannosidase enzyme encoded by pBB27-2 (*Saccharomyces* MNN10 (s)/*C. elegans* mannosidase IB Δ31) expressed in *P. pastoris*.

| Source | Enzyme | pH optimum | Reference |
|---|---|---|---|
| *Aspergillus saitoi* | α-1,2-mannosidase | 5.0 | Ichishima, 1999 |
| *Trichoderma reesei* | α-1,2-mannosidase | 5.0 | Maras, 2000 |
| *Penicillium citrinum* | α-D-1,2-mannosidase | 5.0 | Yoshida, 1993 |
| *C. elegans* | α-1,2-mannosidase | 5.5 | see FIG. 11 |
| *Aspergillus nidulans* | α-1,2-mannosidase | 6.0 | Eades and Hintz, 2000 |
| *Homo sapiens* IA(Golgi) | α-1,2-mannosidase | 6.0 | |
| *Homo sapiens* IB (Golgi) | α-1,2-mannosidase | 6.0 | |
| *Lepidopteran* insect cells | Type I α-1,2-Man₆-mannosidase | 6.0 | Ren, 1995 |
| *Homo sapiens* | α-D-mannosidase | 6.0 | Chandrasekaran, 1984 |
| *Xanthomonas manihotis* | α-1,2,3-mannosidase | 6.0 | U.S. Pat. No. 6,300,113 |
| Mouse IB (Golgi) | α-1,2-mannosidase | 6.5 | Schneikert, 1994 |
| *Bacillus* sp. (secreted) | α-D-1,2-mannosidase | 7.0 | Maruyama, 1994 |

In a preferred embodiment, a particular enzyme or catalytic domain is targeted to a subcellular location in the host cell by means of a chimeric fusion construct encoding a protein comprising a cellular targeting signal peptide not normally associated with the enzymatic domain. Preferably, an enzyme or domain is targeted to the ER, the early, medial or late Golgi of the trans Golgi apparatus of the host cell.

In a more preferred embodiment, the targeted glycosylation enzyme is a glycosyltransferase or a glycosidase (such as a mannosidase). In an especially preferred embodiment, an enzyme having sialyltransferase activity is targeted to the late Golgi, where the early reactions of glycosylation occur. While the methods disclosed herein are useful for producing a human-like glycoprotein in a non-human host cell, it will be appreciated that the methods discussed herein are also useful more generally for modifying carbohydrate profiles of a glycoprotein in any eukaryotic host cell, including human host cells. See Gerngross, WO02/00879.

Targeting sequences which mediate retention of proteins in certain organelles of the host cell secretory pathway are well-known and described in the scientific literature and public databases, as discussed in more detail below with respect to libraries for selection of targeting sequences and targeted enzymes. Such subcellular targeting sequences may be used alone or in combination to target a selected glycosylation enzyme (or catalytic domain thereof) to a particular subcellular location in a host cell, i.e., especially to one where the enzyme will have enhanced or optimal activity based on pH optima or the presence of other stimulatory factors.

When one attempts to trim high mannose structures to yield $Man_5GlcNAc_2$ in the ER or the Golgi apparatus of a host cell such as *S. cerevisiae*, for example, one may choose any enzyme or combination of enzymes that (1) has a sufficiently close pH optimum (i.e. between pH 5.2 and pH 7.8), and (2) is known to generate, alone or in concert, the specific isomeric $Man_5GlcNAc_2$ structure required to accept subsequent addition of GlcNAc by GnTI. Any enzyme or combination of enzymes that is shown to generate a structure that can be converted to $GlcNAcMan_5GlcNAc_2$ by GnTI in vitro would constitute an appropriate choice. This knowledge may be obtained from the scientific literature or experimentally.

For example, one may determine whether a potential mannosidase can convert $Man_8GlcNAc_2$-2AB (2-aminobenzamide) to $Man_5GlcNAc_2$-AB and then verify that the obtained $Man_5GlcNAc_2$-2AB structure can serve a substrate for GnTI and UDP-GlcNAc to give $GlcNAcMan_5GlcNAc_2$ in vitro. Mannosidase IA from a human or murine source, for example, would be an appropriate choice (see, e.g., Example 11). Examples described herein utilize 2-aminobenzamide labeled N-linked oligomannose followed by HPLC analysis to make this determination.

TABLE 4

Cellular Location And pH Optima Of Various Glycosylation-Related Enzymes Of *S. cerevisiae*.

| Gene | Activity | Location | pH optimum | Reference(s) |
|---|---|---|---|---|
| KTR1 | α-1,2 mannosyltransferase | Golgi | 7.0 | Romero, 1997 |
| MNS1 | α-1,2-mannosidase | ER | 6.5 | |
| CWH41 | glucosidase I | ER | 6.8 | |
| — | mannosyltransferase | Golgi | 7-8 | Lehele, 1974 |
| KRE2 | α-1,2 mannosyltransferase | Golgi | 6.5-9.0 | Romero, 1997 |

Accordingly, a glycosylation enzyme such as an α-1,2-mannosidase enzyme used according to the invention has an optimal activity at a pH of between 5.1 and 8.0. In a preferred embodiment, the enzyme has an optimal activity at a pH of between 5.5 and 7.5. The *C. elegans* mannosidase enzyme, for example, works well in the methods of the invention and has an apparent pH optimum of about 5.5).

The experiment which illustrates the pH optimum for an α-1,2-mannosidase enzyme is described in Example 14. A chimeric fusion protein BB27-2 (*Saccharomyces* MNN10 (s)/*C. elegans* mannosidase IB Δ31), which leaks into the medium was subjected to various pH ranges to determine the optimal activity of the enzyme. The results of the experiment show that the α-1,2-mannosidase has an optimal pH of about 5.5 for its function (FIG. 11).

In a preferred embodiment, a single cloned mannosidase gene is expressed in the host organism. However, in some cases it may be desirable to express several different mannosidase genes, or several copies of one particular gene, in order to achieve adequate production of $Man_5GlcNAc_2$. In cases where multiple genes are used, the encoded mannosidases preferably all have pH optima within the preferred range of about 5.1 to about 8.0, or especially between about 5.5 and about 7.5. Preferred mannosidase activities include α-1,2-mannosidases derived from mouse, human, *Lepidoptera, Aspergillus nidulans*, or *Bacillus* sp., *C. elegans, D. melanogaster, P. citrinum, X. laevis* or *A. nidulans*.

In Vivo Alteration of Host Cell Glycosylation Using a Combinatorial DNA Library Certain methods of the invention are preferably (but need not necessarily be) carried out using one or more nucleic acid libraries. An exemplary feature of a combinatorial nucleic acid library of the invention is that it comprises sequences encoding cellular targeting signal peptides and sequences encoding proteins to be targeted (e.g., enzymes or catalytic domains thereof, including but not limited to those which mediate glycosylation).

In one embodiment, a combinatorial nucleic acid library comprises: (a) at least two nucleic acid sequences encoding different cellular targeting signal peptides; and (b) at least one nucleic acid sequence encoding a polypeptide to be targeted. In another embodiment, a combinatorial nucleic acid library comprises: (a) at least one nucleic acid sequence encoding a cellular targeting signal peptide; and (b) at least two nucleic acid sequences encoding a polypeptide to be targeted into a host cell. As described further below, a nucleic acid sequence derived from (a) and a nucleic acid sequence derived from (b) are ligated to produce one or more fusion constructs encoding a cellular targeting signal peptide functionally linked to a polypeptide domain of interest. One example of a functional linkage is when the cellular targeting signal peptide is ligated to the polypeptide domain of interest in the same translational reading frame ("in-frame").

In a preferred embodiment, a combinatorial DNA library expresses one or more fusion proteins comprising cellular targeting signal peptides ligated in-frame to catalytic enzyme domains. The encoded fusion protein preferably comprises a catalytic domain of an enzyme involved in mammalian- or human-like modification of N-glycans. In a more preferred embodiment, the catalytic domain is derived from an enzyme selected from the group consisting of mannosidases, glycosyltransferases and other glycosidases which is ligated in-frame to one or more targeting signal peptides. The enzyme domain may be exogenous and/or endogenous to the host cell. A particularly preferred signal peptide is one normally associated with a protein that undergoes ER to Golgi transport.

The combinatorial DNA library of the present invention may be used for producing and localizing in vivo enzymes involved in mammalian- or human-like N-glycan modification. The fusion constructs of the combinatorial DNA library are engineered so that the encoded enzymes are localized in the ER, Golgi or the trans-Golgi network of the host cell where they are involved in producing particular N-glycans on a glycoprotein of interest. Localization of N-glycan modifying enzymes of the present invention is achieved through an anchoring mechanism or through protein-protein interaction where the localization peptide constructed from the combinatorial DNA library localizes to a desired organelle of the secretory pathway such as the ER, Golgi or the trans Golgi network.

An example of a useful N-glycan, which is produced efficiently and in sufficient quantities for further modification by human-like (complex) glycosylation reactions is $Man_5GlcNAc_2$. A sufficient amount of $Man_5GlcNAc_2$ is needed on a glycoprotein of interest for further human-like processing in vivo (e.g., more than 30 mole %). The $Man_5GlcNAc_2$ intermediate may be used as a substrate for further N-glycan modification to produce $GlcNAcMan_5GlcNAc_2$ (FIG. 1B; see above). Accordingly, the combinatorial DNA library of the present invention may be used to produce enzymes which subsequently produce $GlcNAcMan_5GlcNAc_2$, or other desired complex N-glycans, in a useful quantity.

A further aspect of the fusion constructs produced using the combinatorial DNA library of the present invention is that they enable sufficient and often near complete intracellular N-glycan trimming activity in the engineered host cell. Preferred fusion constructs produced by the combinatorial DNA library of the invention encode a glycosylation enzyme, e.g., a mannosidase, which is effectively localized to an intracellular host cell compartment and thereby exhibits very little and preferably no extracellular activity. The preferred fusion constructs of the present invention that encode a mannosidase enzyme are shown to localize where the N-glycans are modified, namely, the ER and the Golgi. The fusion enzymes of the present invention are targeted to such particular organelles in the secretory pathway where they localize and act upon N-glycans such as $Man_8GlcNAc_2$ to produce $Man_5GlcNAc_2$ on a glycoprotein of interest.

Figure 5:
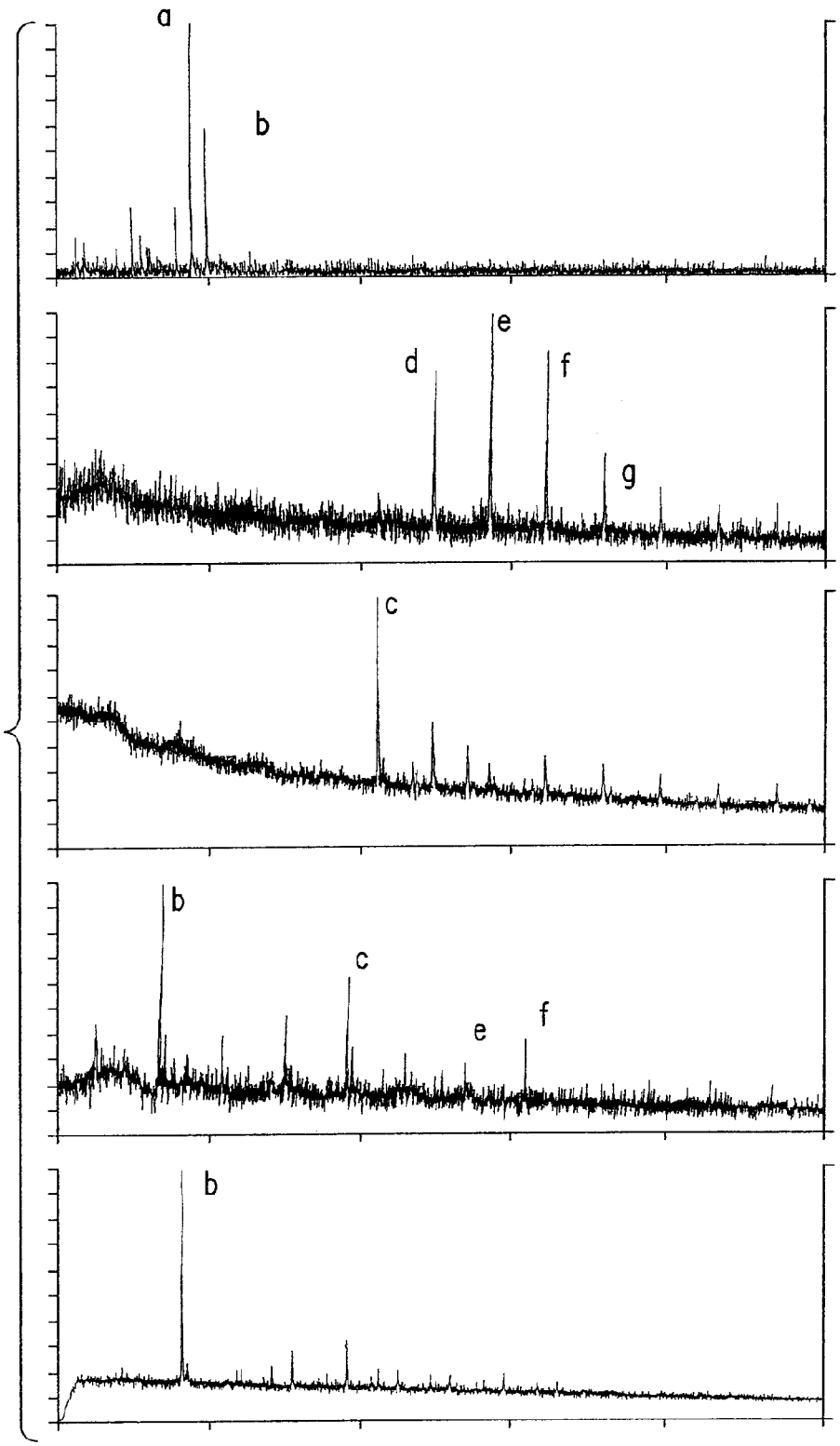
FIGS. 5 and 5A-5E show MALDI-TOF analysis demonstrating production of kringle 3 domain of human plasminogen (K3) glycoproteins having $Man_5GlcNAc_2$ as the predominant N-glycan structure in *P. pastoris*.
Figure 5A:
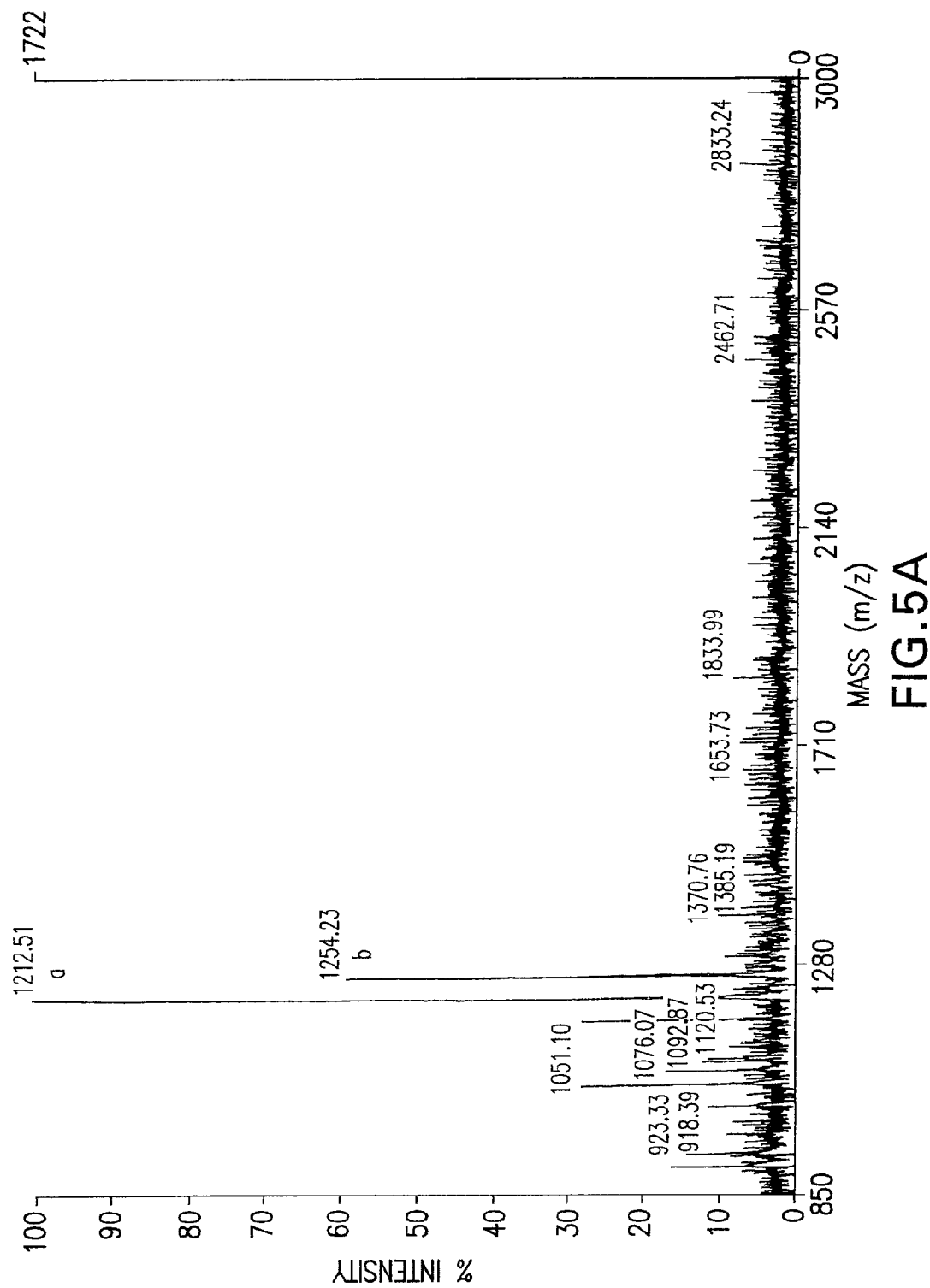
Figure 6:
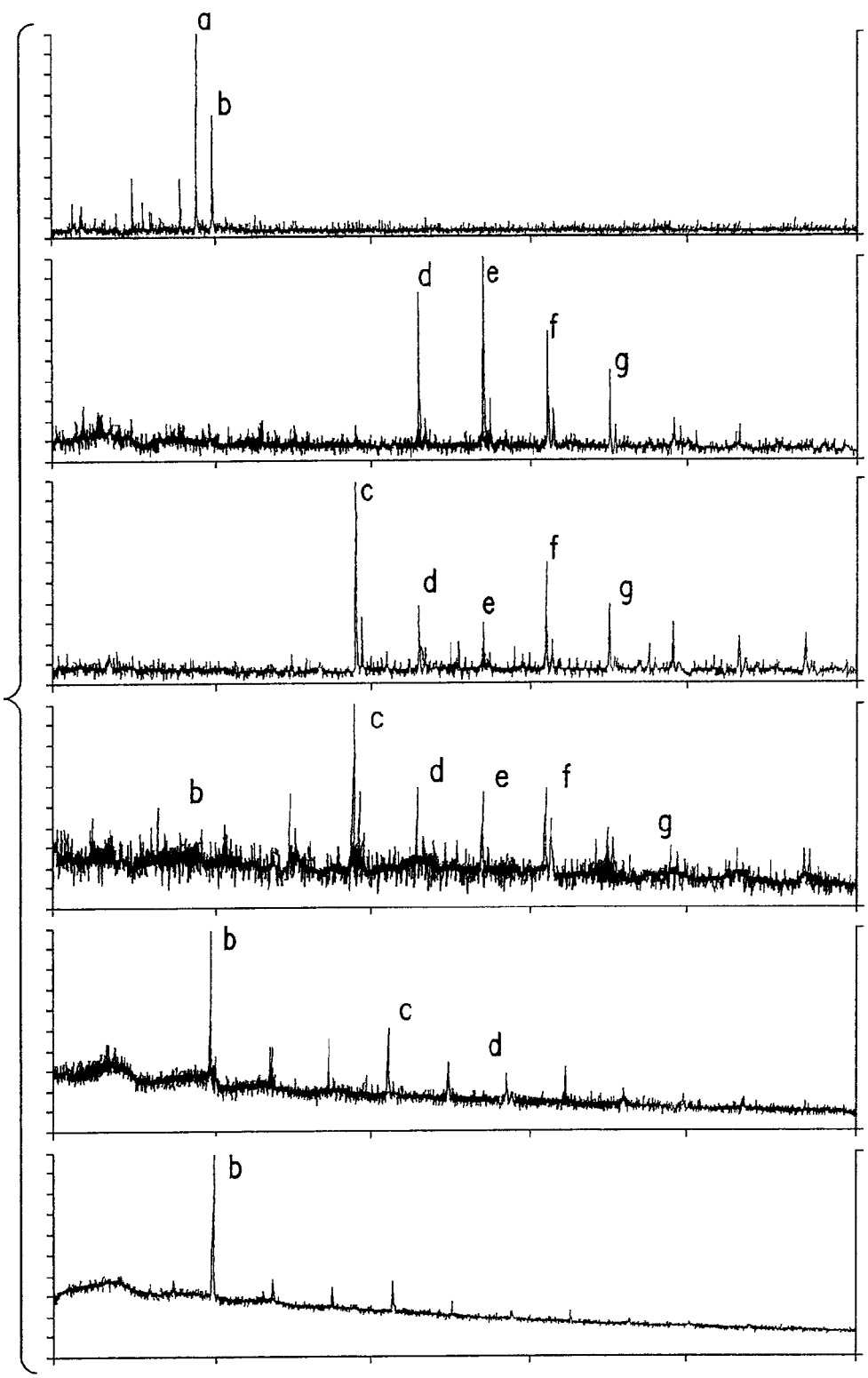
FIGS. 6 and 6A-6F show MALDI-TOF analysis demonstrating production of IFN-β glycoproteins having $Man_5GlcNAc_2$ as the predominant N-glycan structure in *P. pastoris*.
Figure 6A:
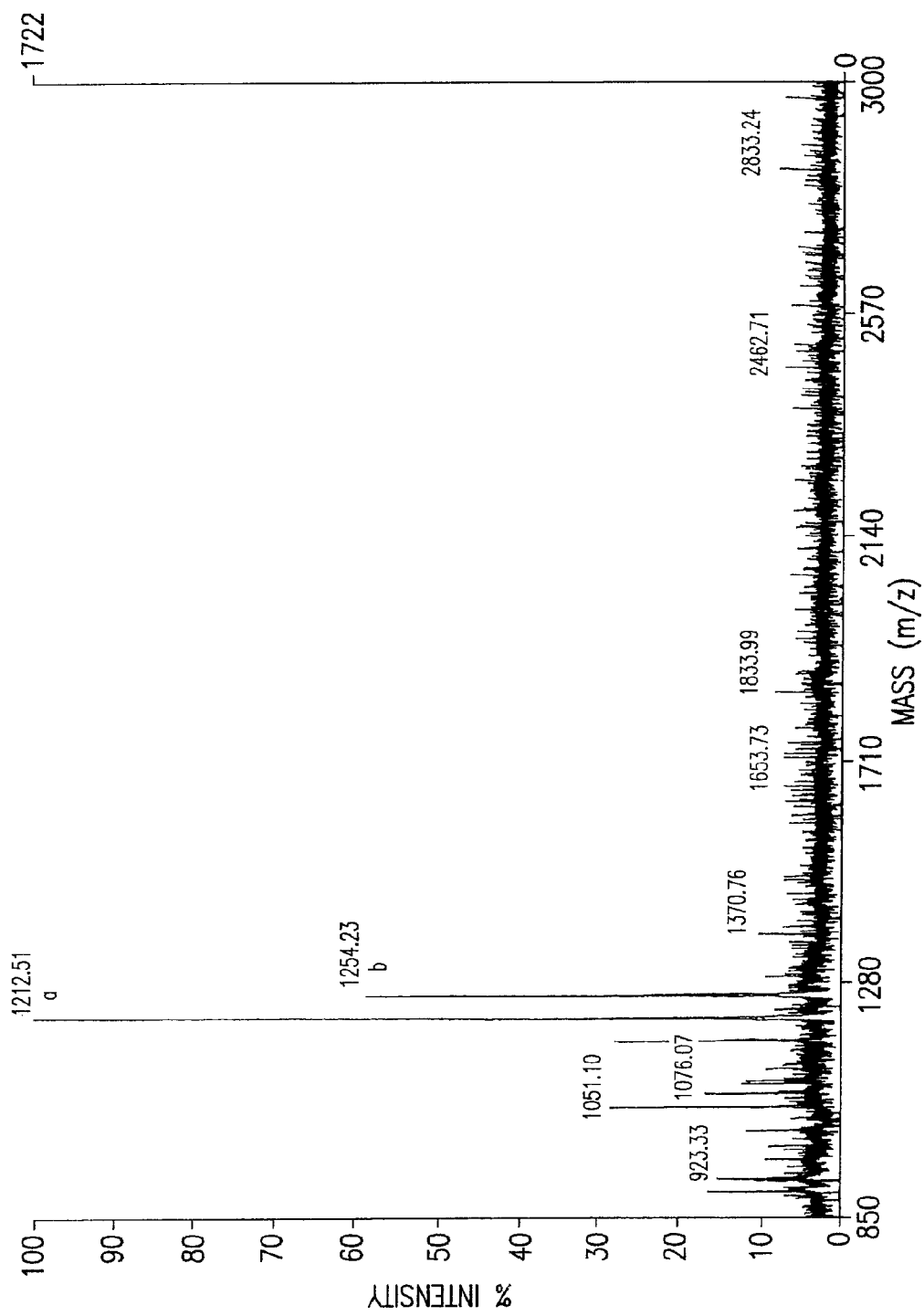
Figure 6B:
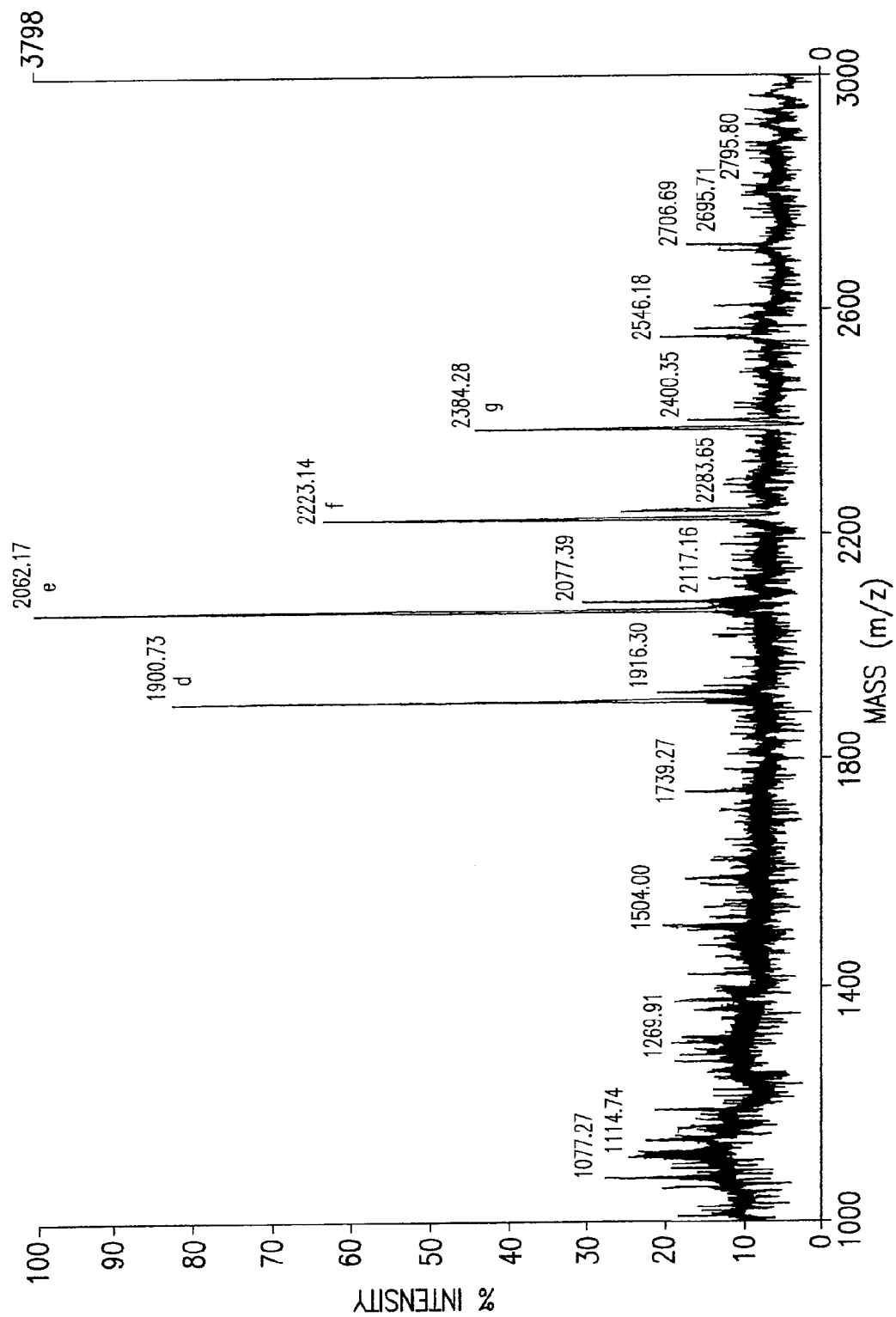
Figure 6C:
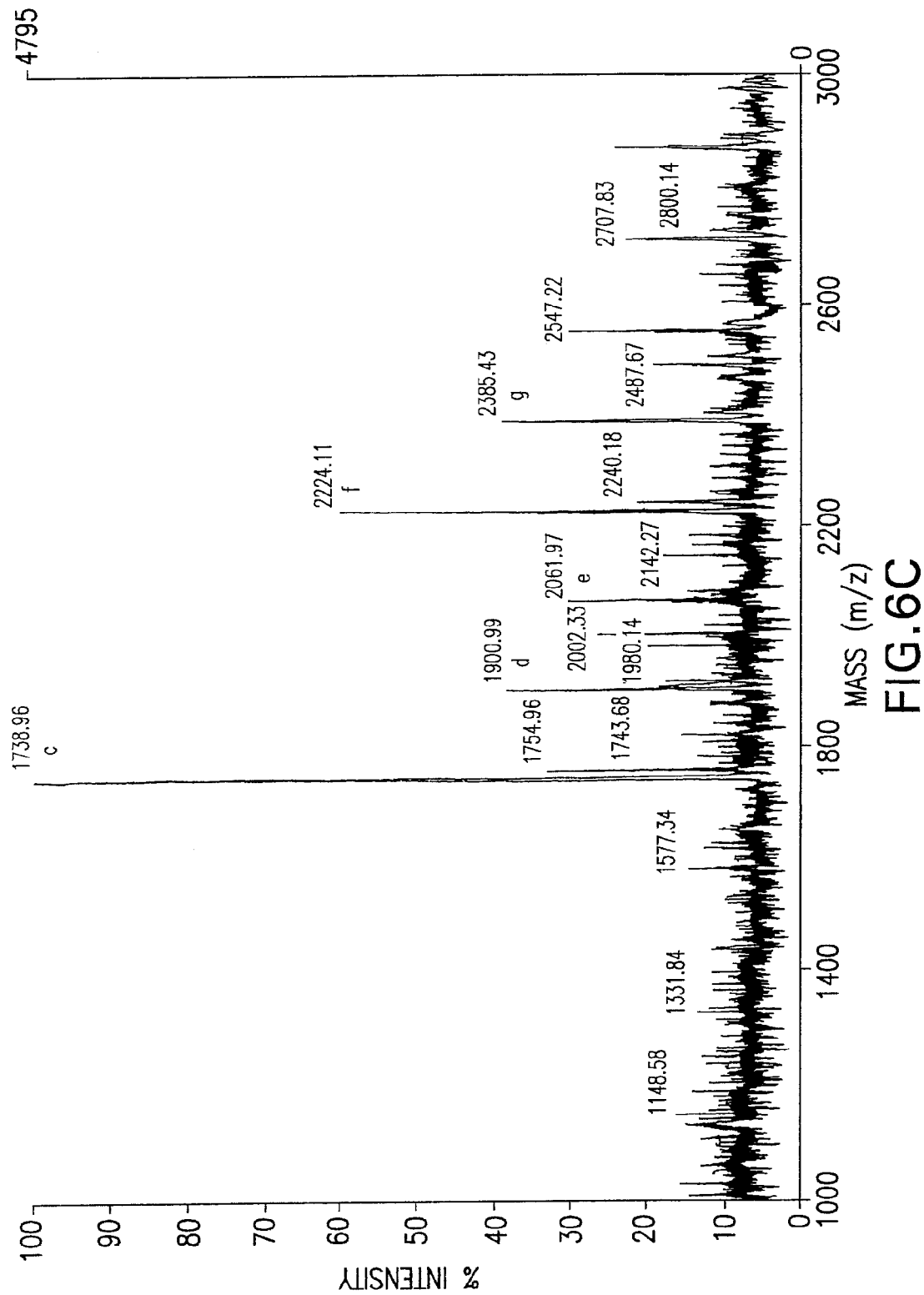
Figure 6D:
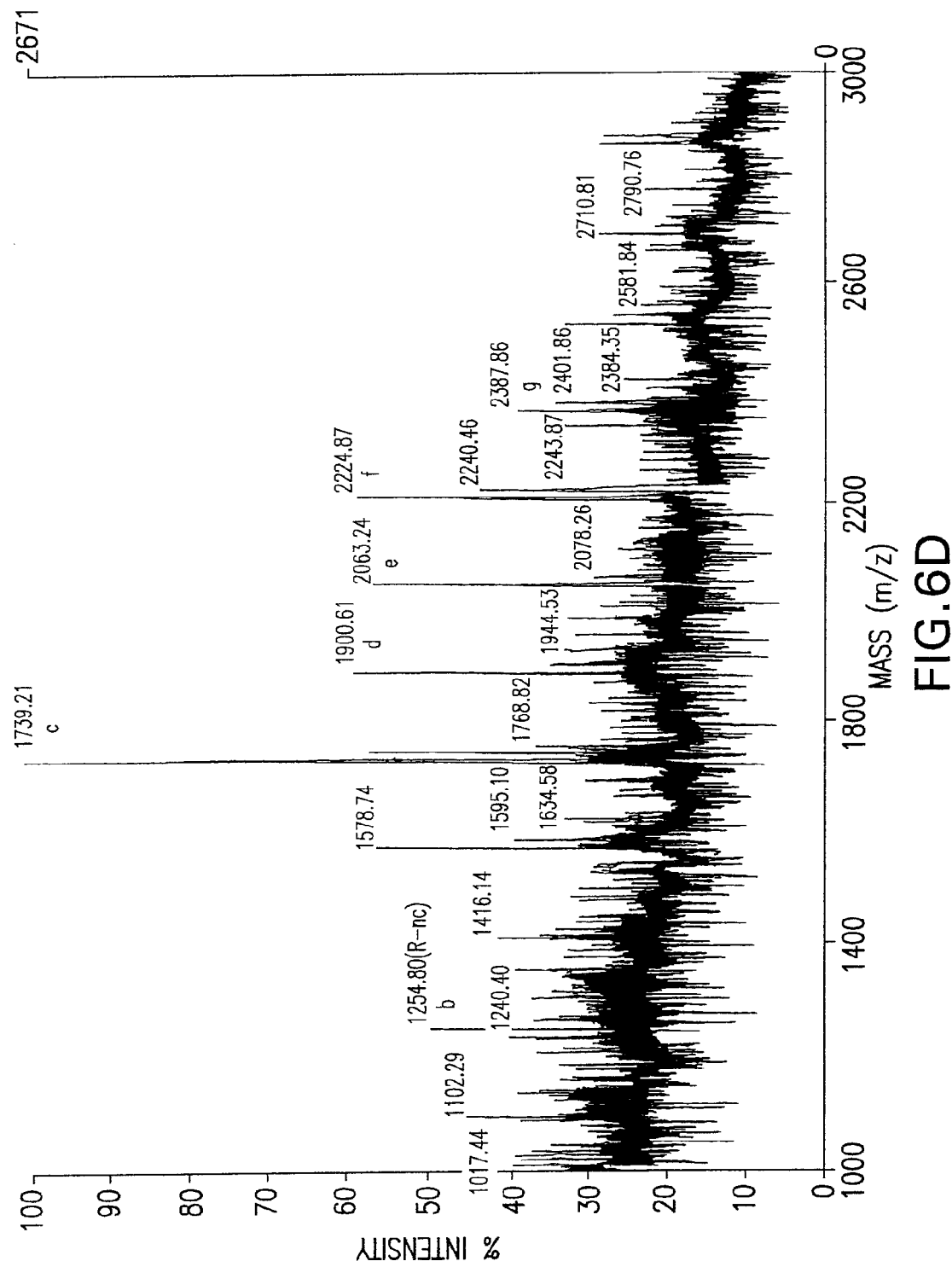
Figure 6E:
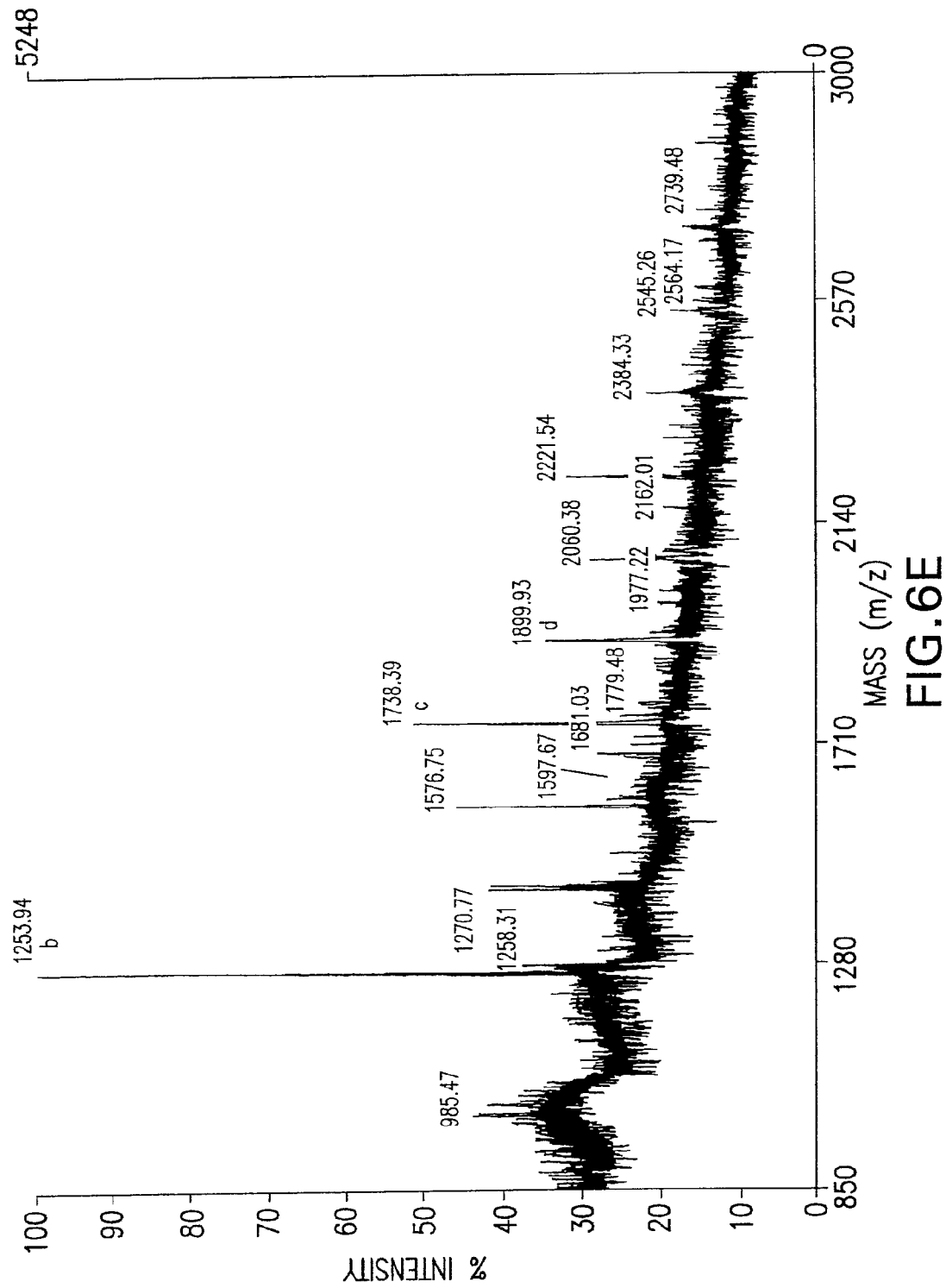

Enzymes produced by the combinatorial DNA library of the present invention can modify N-glycans on a glycoprotein of interest as shown for K3 or IFN-β proteins expressed in *P. pastoris*, as shown in FIG. 5 and FIG. 6, respectively (see also Examples 2 and 11). It is, however, appreciated that other types of glycoproteins, without limitation, including erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-feto proteins, AAT, rhTBP-1 (onercept, aka TNF Binding protein 1), TACI-Ig (transmembrane activator and calcium modulator and cyclophilin ligand interactor), FSH (follicle stimulating hormone), GM-CSF, GLP-1 w/ and w/o FC (glucagon like protein 1) IL-1 receptor agonist, sTNFr (enbrel, aka soluble TNF receptor Fc fusion) ATIII, rhThrombin, glucocerebrosidase and CTLA4-Ig (Cytotoxic T Lymphocyte associated Antigen 4-Ig) may be glycosylated in this way.

Constructing a Combinatorial DNA Library of Fusion Constructs

A combinatorial DNA library of fusion constructs features one or more cellular targeting signal peptides ("targeting peptides") generally derived from N-terminal domains of native proteins (e.g., by making C-terminal deletions). Some targeting peptides, however, are derived from the C-terminus of native proteins (e.g. SEC12). Membrane-bound proteins of the ER or the Golgi are preferably used as a source for targeting peptide sequences. These proteins have sequences encoding a cytosolic tail (et), a transmembrane domain (tmd) and a stem region (sr) which are varied in length. These regions are recognizable by protein sequence alignments and comparisons with known homologs and/or other localized proteins (e.g., comparing hydrophobicity plots).

The targeting peptides are indicated herein as short (s), medium (m) and long (l) relative to the parts of a type II membrane. The targeting peptide sequence indicated as short (s) corresponds to the transmembrane domain (tmd) of the membrane-bound protein. The targeting peptide sequence indicated as long (l) corresponds to the length of the transmembrane domain (tmd) and the stem region (sr). The targeting peptide sequence indicated as medium (m) corresponds to the transmembrane domain (tmd) and approximately half the length of the stem region (sr). The catalytic domain regions are indicated herein by the number of nucleotide deletion with respect to its wild-type glycosylation enzyme.

Sub-Libraries

In some cases a combinatorial nucleic acid library of the invention may be assembled directly from existing or wild-type genes. In a preferred embodiment, the DNA library is assembled from the fusion of two or more sub-libraries. By the in-frame ligation of the sub-libraries, it is possible to create a large number of novel genetic constructs encoding useful targeted protein domains such as those which have glycosylation activities.

Catalytic Domain Sub-Libraries Encoding Glycosylation Activities

One useful sub-library includes DNA sequences encoding enzymes such as glycosidases (e.g., mannosidases), glycosyltransferases (e.g., fucosyltransferases, galactosyltransferases, glucosyltransferases), GlcNAc transferases and sialyltransferases. Catalytic domains may be selected from the host to be engineered, as well as from other related or unrelated organisms. Mammalian, plant, insect, reptile, algal or fungal enzymes are all useful and should be chosen to represent a broad spectrum of biochemical properties with respect to temperature and pH optima. In a preferred embodiment, genes are truncated to give fragments some of which encode the catalytic domains of the enzymes. By removing endogenous targeting sequences, the enzymes may then be redirected and expressed in other cellular loci.

The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, or the late Golgi is known to have a particular pH, then a catalytic domain is chosen which exhibits adequate, and preferably maximum, activity at that pH, as discussed above.

Targeting Peptide Sequence Sub-Libraries

Another useful sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL (SEQ ID NO: 5) or KDEL (SEQ ID NO: 6) tetrapeptide; and (3) membrane spanning regions from various proteins, e.g., nucleotide sugar transporters, which are known to localize in the Golgi.

In the first case, where the targeting peptide consists of various elements (ct, tmd and sr), the library is designed such that the ct, the tmd and various parts of the stem region are represented. Accordingly, a preferred embodiment of the sub-library of targeting peptide sequences includes ct, tmd, and/or sr sequences from membrane-bound proteins of the ER or Golgi. In some cases it may be desirable to provide the sub-library with varying lengths of sr sequence. This may be accomplished by PCR using primers that bind to the 5' end of the DNA encoding the cytosolic region and employing a series of opposing primers that bind to various parts of the stem region.

Still other useful sources of targeting peptide sequences include retrieval signal peptides, e.g. the tetrapeptides HDEL (SEQ ID NO: 5) or KDEL (SEQ ID NO: 6), which are typically found at the C-terminus of proteins that are transported retrograde into the ER or Golgi. Still other sources of targeting peptide sequences include (a) type II membrane proteins, (b) the enzymes listed in Table 3, (c) membrane spanning nucleotide sugar transporters that are localized in the Golgi, and (d) sequences referenced in Table 5. (The HDEL signal in column 1, cell 8 is shown in SEQ ID NO: 5).

TABLE 5

Sources Of Useful Compartmental Targeting Sequences

| Gene or Sequence | Organism | Function | Location of Gene Product |
|---|---|---|---|
| MNSI | A. nidulans | α-1,2-mannosidase | ER |
| MNSI | A. niger | α-1,2-mannosidase | ER |
| MNSI | S. cerevisiae | α-1,2-mannosidase | ER |
| GLSI | S. cerevisiae | glucosidase | ER |
| GLSI | A. niger | glucosidase | ER |
| GLSI | A. nidulans | glucosidase | ER |
| HDEL at C-terminus | Universal in fungi | retrieval signal | ER |
| SEC12 | S. cerevisiae | COPII vesicle protein | ER/Golgi |
| SEC12 | A. niger | COPII vesicle protein | ER/Golgi |
| OCH1 | S. cerevisiae | 1,6-mannosyltransferase | Golgi (cis) |
| OCH1 | P. pastoris | 1,6-mannosyltransferase | Golgi (cis) |
| MNN9 | S. cerevisiae | 1,6-mannosyltransferase complex | Golgi |
| MNN9 | A. niger | undetermined | Golgi |
| VAN1 | S. cerevisiae | undetermined | Golgi |
| VAN1 | A. niger | undetermined | Golgi |
| ANP1 | S. cerevisiae | undetermined | Golgi |

TABLE 5-continued

Sources Of Useful Compartmental Targeting Sequences

| Gene or Sequence | Organism | Function | Location of Gene Product |
|---|---|---|---|
| HOCI | S. cerevisiae | undetermined | Golgi |
| MNN10 | S. cerevisiae | undetermined | Golgi |
| MNN10 | A. niger | undetermined | Golgi |
| MNN11 | S. cerevisiae | undetermined | Golgi (cis) |
| MNN11 | A. niger | undetermined | Golgi (cis) |
| MNT1 | S. cerevisiae | 1,2-mannosyltransferase | Golgi (cis, medial |
| KTR1 | P. pastoris | undetermined | Golgi (medial) |
| KRE2 | P. pastoris | Undetermined | Golgi (medial) |
| KTR3 | P. pastoris | Undetermined | Golgi (medial) |
| MNN2 | S. cerevisiae | 1,2-mannosyltransferase | Golgi (medial) |
| KTR1 | S. cerevisiae | Undetermined | Golgi (medial) |
| KTR2 | S. cerevisiae | Undetermined | Golgi (medial) |
| MNN1 | S. cerevisiae | 1,3-mannosyltransferase | Golgi (trans) |
| MNN6 | S. cerevisiae | Phosphomannosyl-transferase | Golgi (trans) |
| 2,6 ST | H. sapiens | 2,6-sialyltransferase | trans Golgi network |
| UDP-Gal T | S. pombe | UDP-Gal transporter | Golgi |

In any case, it is highly preferred that targeting peptide sequences are selected which are appropriate for the particular enzymatic activity or activities to function optimally within the sequence of desired glycosylation reactions. For example, in developing a modified microorganism capable of terminal sialylation of nascent N-glycans, a process which occurs in the late Golgi in humans, it is desirable to utilize a sub-library of targeting peptide sequences derived from late Golgi proteins. Similarly, the trimming of $Man_8GlcNAc_2$ by an α-1,2-mannosidase to give $Man_5GlcNAc_2$ is an early step in complex N-glycan formation in humans (FIG. 1B). It is therefore desirable to have this reaction occur in the ER or early Golgi of an engineered host microorganism. A sub-library encoding ER and early Golgi retention signals is used.

A series of fusion protein constructs (i.e., a combinatorial DNA library) is then constructed by functionally linking one or a series of targeting peptide sequences to one or a series of sequences encoding catalytic domains. In a preferred embodiment, this is accomplished by the in-frame ligation of a sub-library comprising DNA encoding targeting peptide sequences (above) with a sub-library comprising DNA encoding glycosylation enzymes or catalytically active fragments thereof (see below).

The resulting library comprises synthetic genes encoding targeting peptide sequence-containing fusion proteins. In some cases it is desirable to provide a targeting peptide sequence at the N-terminus of a fusion protein, or in other cases at the C-terminus. In some cases, targeting peptide sequences may be inserted within the open reading frame of an enzyme, provided the protein structure of individual folded domains is not disrupted. Each type of fusion protein is constructed (in a step-wise directed or semi-random fashion) and optimal constructs may be selected upon transformation of host cells and characterization of glycosylation patterns in transformed cells using methods of the invention. Using such methods, lower eukaryotic host cells may be engineered to produce recombinant glycoprotein having desirable N-glucan properties, e.g., tailored to the particular protein of interest.

Generating Additional Sequence Diversity

The method of this embodiment is most effective when a nucleic acid, e.g., a DNA library transformed into the host contains a large diversity of sequences, thereby increasing the probability that at least one transformant will exhibit the desired phenotype. Single amino acid mutations, for example, may drastically alter the activity of glycoprotein processing enzymes (Romero et al., 2000). Accordingly, prior to transformation, a DNA library or a constituent sub-library may be subjected to one or more techniques to generate additional sequence diversity. For example, one or more rounds of gene shuffling, error prone PCR, in vitro mutagenesis or other methods for generating sequence diversity, may be performed to obtain a larger diversity of sequences within the pool of fusion constructs.

Expression Control Sequences

In addition to the open reading frame sequences described above, it is generally preferable to provide each library construct with expression control sequences, such as promoters, transcription terminators, enhancers, ribosome binding sites, and other functional sequences as may be necessary to ensure effective transcription and translation of the fusion proteins upon transformation of fusion constructs into the host organism.

Suitable vector components, e.g., selectable markers, expression control sequences (e.g., promoter, enhancers, terminators and the like) and, optionally, sequences required for autonomous replication in a host cell, are selected as a function of which particular host cell is chosen. Selection criteria for suitable vector components for use in a particular mammalian or a lower eukaryotic host cell are routine. Preferred lower eukaryotic host cells of the invention include but are not limited to: any *Pichia* sp., including but limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis* and *Pichia methanolica*; any *Saccharomyces* sp including but not limited to *Saccharomyces cerevisiae; Hansenula polymorpha*; any *Kluyveromyces* sp. including but not limited to *Kluyveromyces lactis; Candida albicans; Aspergillus nidulans; Aspergillus niger; Aspergillus oryzae; Trichoderma reseei; Chrysosporium lucknowense*; any *Fusarium* sp. including but not limited to: *Fusarium gramineum* and *Fusarium venenatum*; and *Neurospora crassa*. Where the host is *Pichia pastoris*, suitable promoters include, for example, the AOX1, AOX2, GAPDH and P40 promoters.

Selectable Markers

It is also preferable to provide each construct with at least one selectable marker, such as a gene to impart drug resistance or to complement a host metabolic lesion. The presence of the marker is useful in the subsequent selection of transformants; for example, in yeast the URA3, HIS4, SUC2, G418, BLA, or SH BLE genes may be used. A multitude of selectable markers are known and available for use in yeast, fungi, plant, insect, mammalian and other eukaryotic host cells. A method for transforming yeast cells by inactivating alternately at least two biosynthetic pathways in methylotrophic yeast is described in US2004/0229306, US2005/0170452, and Nett, 2005, which are hereby incorporated herein by reference. The method involves (a) inactivating a first yeast gene in a pathway involved in synthesizing an amino acid or a nucleotide selected from the group consisting of adenine, arginine, histidine, lysine, methionine, proline and uracil with a first selectable marker thereby rendering the host auxotrophic for the amino acid or nucleotide; and then (b) inactivating a second yeast gene not from the same pathway that was inactivated in (a) involved in synthesizing an amino acid or a nucleotide selected from the group consisting of adenine, arginine, histidine, lysine, methionine, proline and uracil using the yeast gene that was inactivated in (a) as a second selectable marker.

Transformation

The nucleic acid library is then transformed into the host organism. In yeast, any convenient method of DNA transfer may be used, such as electroporation, the lithium chloride method, or the spheroplast method. In filamentous fungi and plant cells, conventional methods include particle bombardment, electroporation and *agrobacterium* mediated transformation. To produce a stable strain suitable for high-density culture (e.g., fermentation in yeast), it is desirable to integrate the DNA library constructs into the host chromosome. In a preferred embodiment, integration occurs via homologous recombination, using techniques well-known in the art. For example, DNA library elements are provided with flanking sequences homologous to sequences of the host organism. In this manner, integration occurs at a defined site in the host genome, without disruption of desirable or essential genes.

In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a nucleic acid molecule, plasmid, vector (e.g., viral or retroviral vector), chromosome, and may be introduced as an autonomous nucleic acid molecule or by homologous or random integration into the host genome. In any case, it is generally desirable to include with each library DNA construct at least one selectable marker gene to allow ready selection of host organisms that have been stably transformed. Recyclable marker genes such as ura3, which can be selected for or against, are especially suitable.

Screening and Selection Processes

After transformation of the host strain with the DNA library, transformants displaying a desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly, a host microorganism displays protein N-glycans on the cell surface, where various glycoproteins are localized.

One may screen for those cells that have the highest concentration of terminal GlcNAc on the cell surface, for example, or for those cells which secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen, 1998).

Accordingly, intact cells may be screened for a desired glycosylation phenotype by exposing the cells to a lectin or antibody that binds specifically to the desired N-glycan. A wide variety of oligosaccharide-specific lectins are available commercially (e.g., from EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen, 1998).

Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In a preferred embodiment, a reporter protein is secreted into the medium and purified by affinity chromatography (e.g. Ni-affinity or glutathione-S-transferase affinity chromatography). In cases where an isolated N-glycan is preferred, an enzyme such as endo-β-N-acetylglucosaminidase (Genzyme Co., Boston, Mass.; New England Biolabs, Beverly, Mass.) may be used to cleave the N-glycans from glycoproteins. Isolated proteins or N-glycans may then be analyzed by liquid chromatography (e.g. HPLC), mass spectroscopy, or other suitable means. U.S. Pat. No. 5,595,900 teaches several methods by which cells with desired extracellular carbohydrate structures may be identified. In a preferred embodiment, MALDI-TOF mass spectrometry is used to analyze the cleaved N-glycans.

Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e. high levels of incorporated mannose (Huffaker, 1983). Alternatively, a cytotoxic lectin or antibody, directed against an undesirable N-glycan, may be used to deplete a transformed population of undesired phenotypes (e.g., Stanley, 1977). U.S. Pat. No. 5,595,900 teaches several methods by which cells with a desired extracellular carbohydrate structures may be identified. Repeatedly carrying out this strategy allows for the sequential engineering of more and more complex glycans in lower eukaryotes.

To detect host cells having on their surface a high degree of the human-like N-glycan intermediate GlcNAcMan$_3$GlcNAc$_2$, for example, one may select for transformants that allow for the most efficient transfer of GlcNAc by GlcNAc Transferase from UDP-GlcNAc in an in vitro cell assay. This screen may be carried out by growing cells harboring the transformed library under selective pressure on an agar plate and transferring individual colonies into a 96-well microliter plate. After growing the cells, the cells are centrifuged, the cells resuspended in buffer, and after addition of UDP-GlcNAc and GnT II, the release of UDP is determined either by HPLC or an enzyme linked assay for UDP. Alternatively, one may use radioactively labeled UDP-GlcNAc and GnT II, wash the cells and then look for the release of radioactive GlcNAc by N-actylglucosaminidase. All this may be carried manually or automated through the use of high throughput screening equipment. Transformants that release more UDP, in the first assay, or more radioactively labeled GlcNAc in the second assay, are expected to have a higher degree of GlcNAcMan$_3$GlcNAc$_2$ on their surface and thus constitute the desired phenotype. Similar assays may be adapted to look at the N-glycans on secreted proteins as well.

Alternatively, one may use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal α-1,3 mannose, which is expected to be reduced if sufficient mannosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g., *Galantus nivalis* lectin bound to agarose, Sigma, St. Louis, Mo.) over those that have a low terminal mannose content.

In addition, one may directly create such fusion protein constructs, as additional information on the localization of active carbohydrate modifying enzymes in different lower eukaryotic hosts becomes available in the scientific literature. For example, it is known that human β1,4-GalTr can be fused to the membrane domain of MNT, a mannosyltransferase from *S. cerevisiae*, and localized to the Golgi apparatus while retaining its catalytic activity (Schwientek et al., J. Biol. Chem. 270:5483-9 1995). If *S. cerevisiae* or a related organism is the host to be engineered one may directly incorporate such findings into the overall strategy to obtain complex N-glycans from such a host. Several such gene fragments in *P. pastoris* have been identified that are related to glycosyltransferases in *S. cerevisiae* and thus could be used for that purpose.

Figure 2:
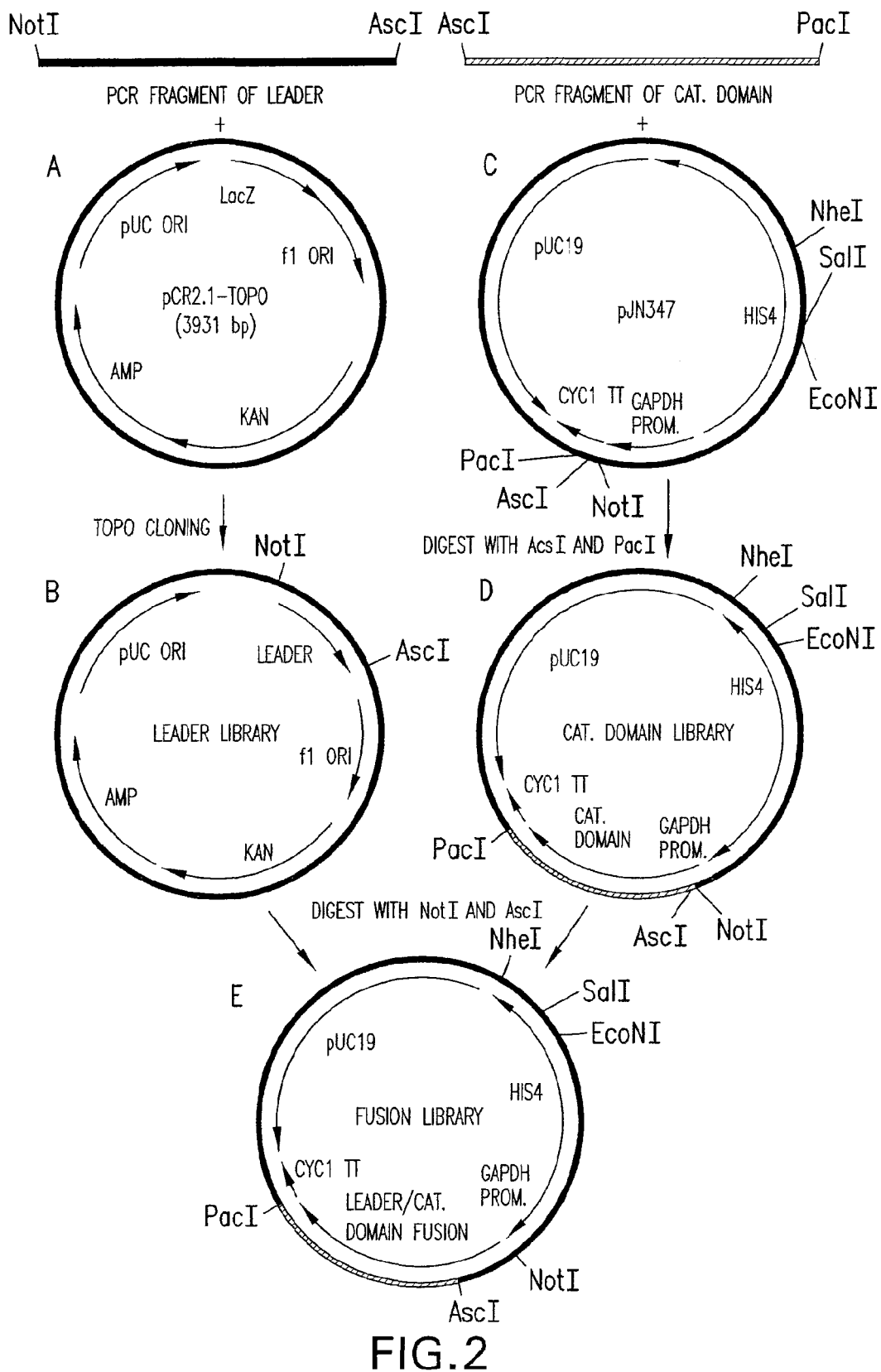
FIG. 2 depicts construction of a combinatorial DNA library of fusion constructs.

Alteration of Host Cell Glycosylation Using Fusion Constructs from Combinatorial Libraries The construction of a preferred combinatorial DNA library is illustrated schematically in FIG. 2 and described in Example 11. The fusion construct may be operably linked to a multitude of vectors, such as expression vectors well-known in the art. A wide variety of such fusion constructs were assembled using representative activities as shown in Table 6. Combinations of targeting peptide/catalytic domains may be assembled for use in targeting glycosyltransferase and glycosidase (such as mannosidase) activities in the ER, Golgi and the trans Golgi network according to the invention. Surprisingly, the same catalytic domain may have no effect to a very profound effect on N-glycosylation patterns, depending on the type of targeting peptide used (see, e.g., Table 7, Example 11).

The present invention also provides for the nucleic acid encoding the fusion constructs described herein, vectors comprising such fusion constructs, and host cells transformed with such fusion constructs.

Mannosidase Fusion Constructs

Figure 6F:
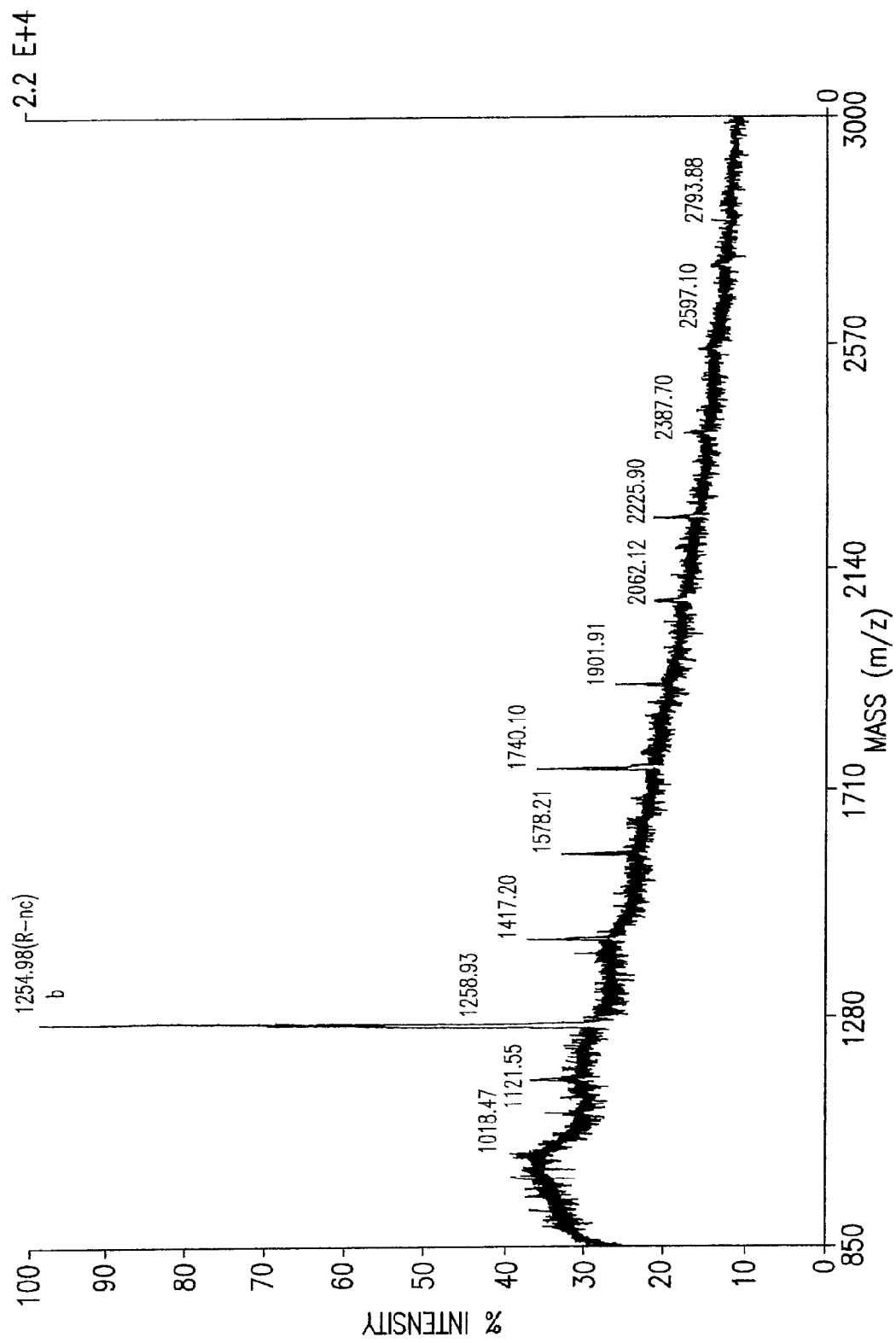
Figure 7:
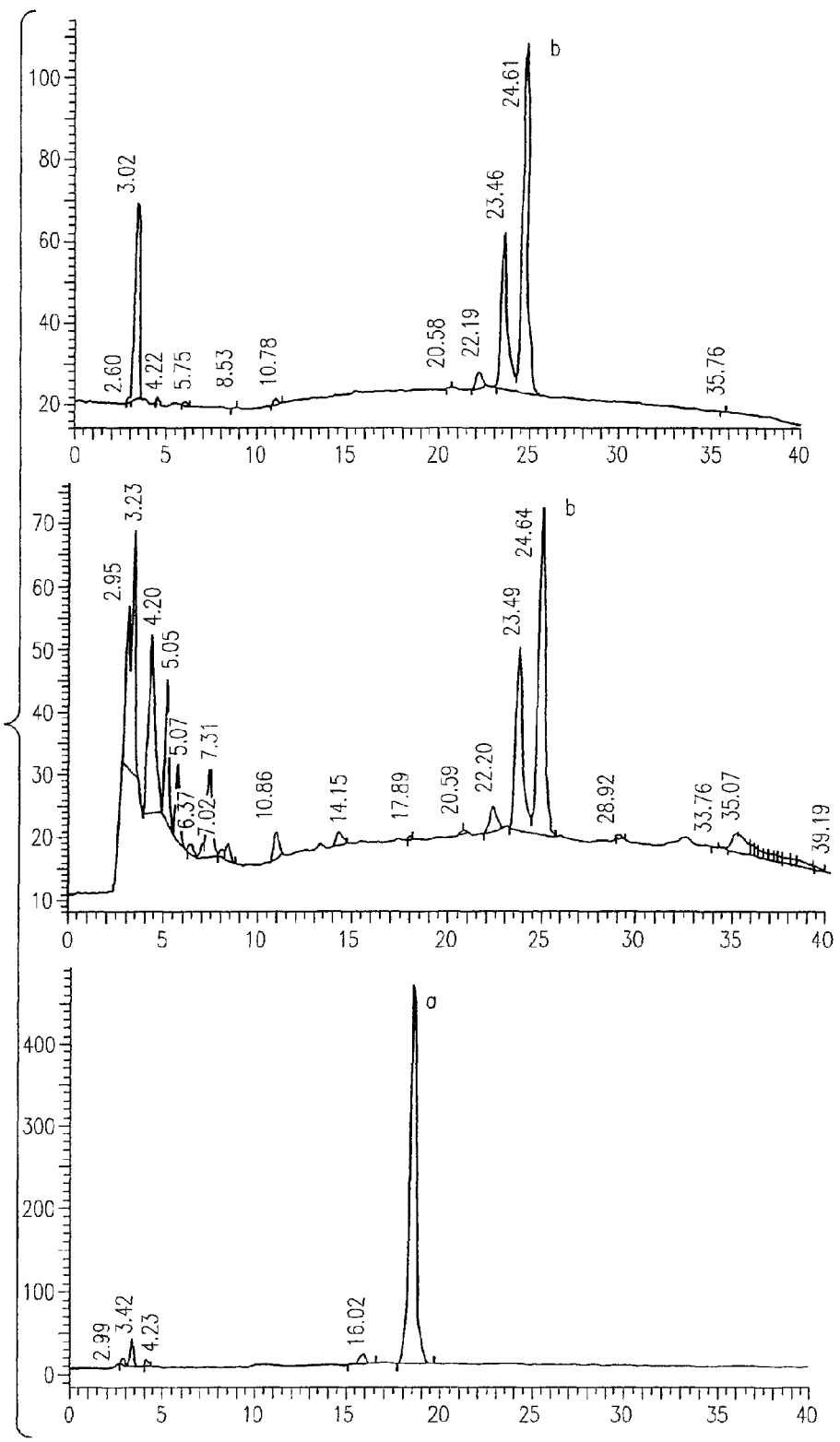
FIG. 7 shows a high performance liquid chromatogram for: (A) $Man_9GlcNAc_2$ standard labeled with 2-AB (negative control); (B) supernatant of medium *P. pastoris*, Δoch1 transformed with pFB8 mannosidase, which demonstrates a lack of extracellular mannosidase activity in the supernatant; and (C) $Man_9GlcNAc_2$ standard labeled with 2-AB after exposure to *T. reesei* mannosidase (positive control).
Figure 7A:
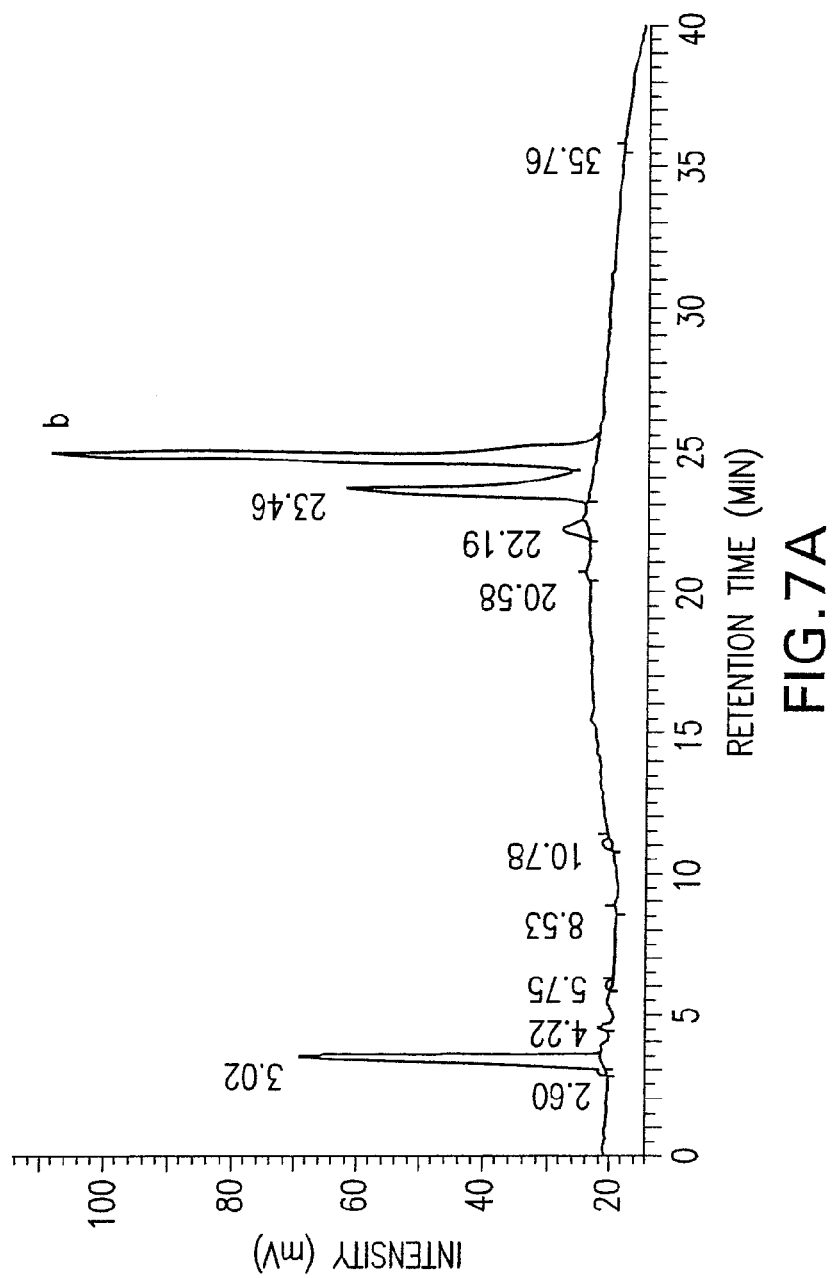
Figure 7B:
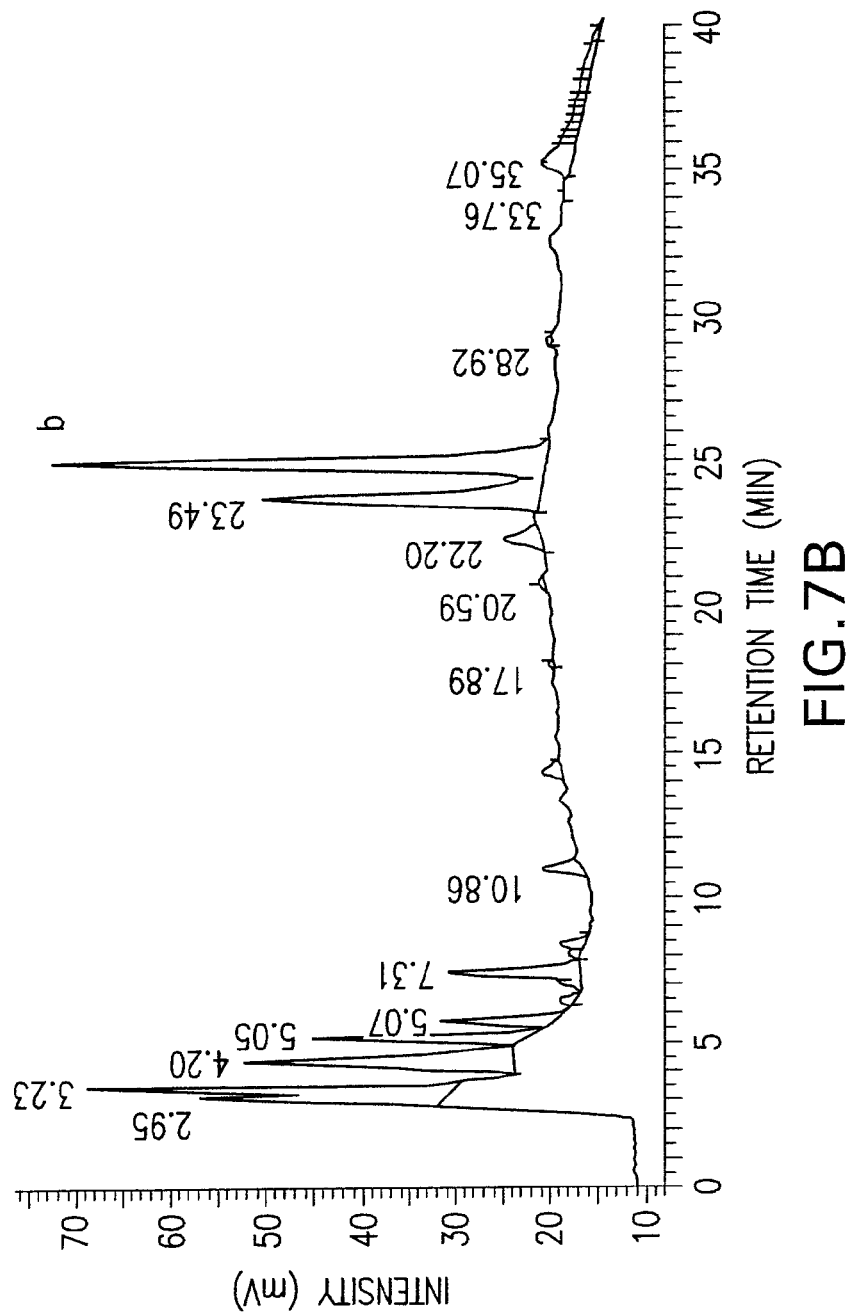

A representative example of a mannosidase fusion construct derived from a combinatorial DNA library of the invention is pFB8, which a truncated *Saccharomyces* SEC12(m) targeting peptide (988-1296 nucleotides of SEC12 from SwissProt P11655) ligated in-frame to a 187 N-terminal amino acid deletion of a mouse α-mannosidase IA (Genbank AN: 6678787). The nomenclature used herein, thus, refers to the targeting peptide/catalytic domain region of a glycosylation enzyme as *Saccharomyces* SEC12 (m)/mouse mannosidase IA Δ187. The encoded fusion protein localizes in the ER by means of the SEC12 targeting peptide sequence while retaining its mannosidase catalytic domain activity and is capable of producing in vivo N-glycans having a $Man_5GlcNAc_2$ structure (Example 11; FIG. 6F, FIG. 7B).

Figure 5B:
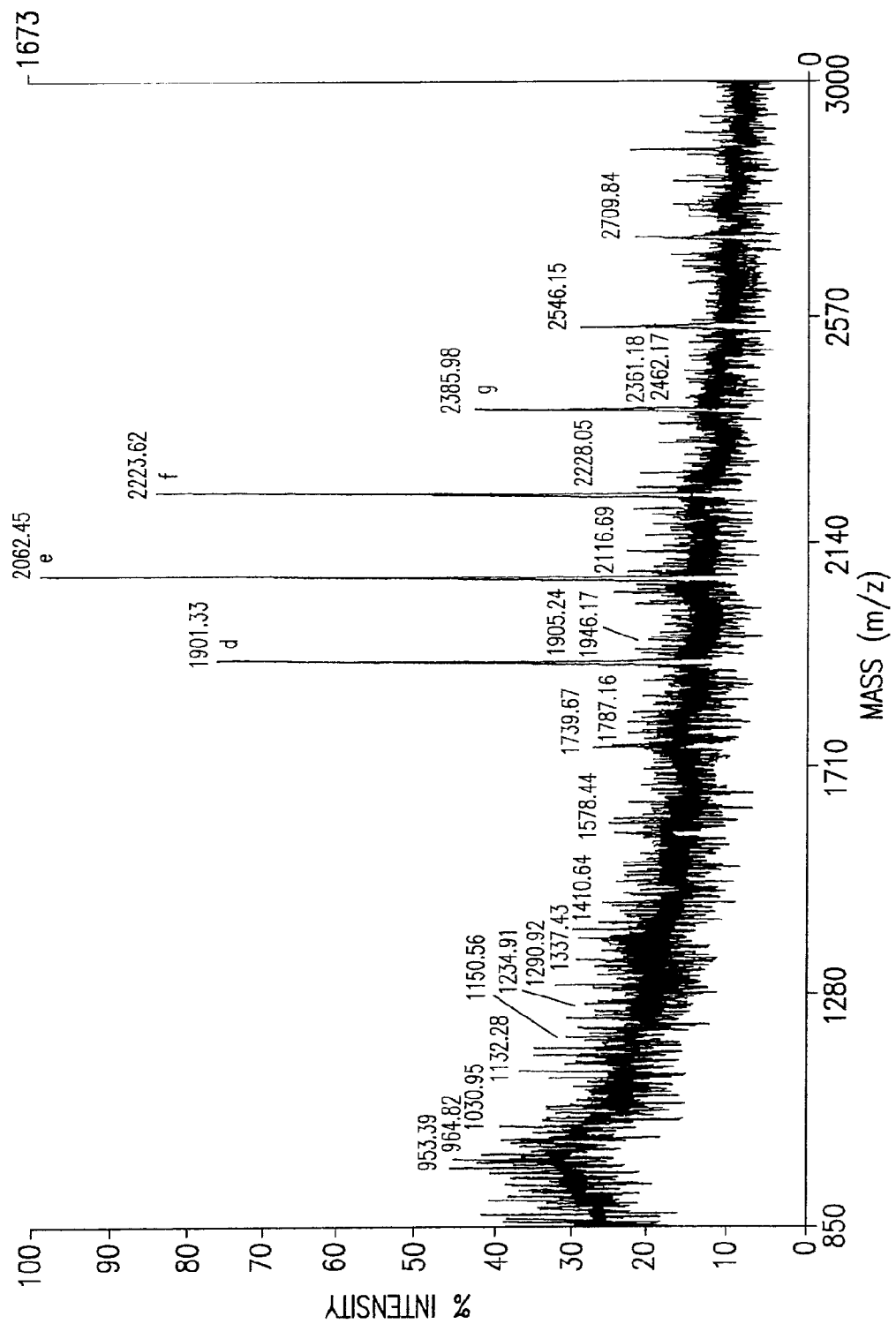
Figure 5C:
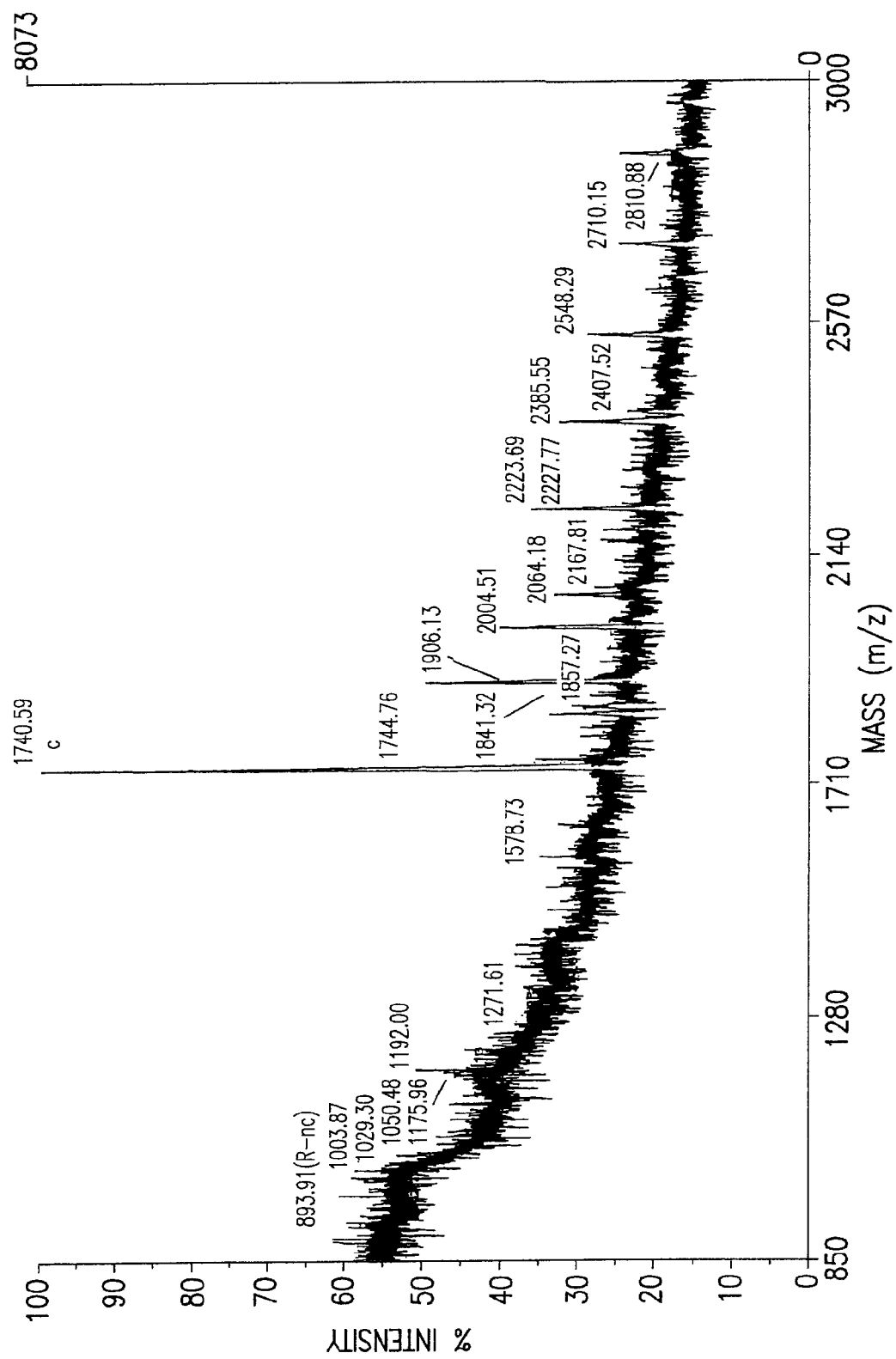
Figure 5D:
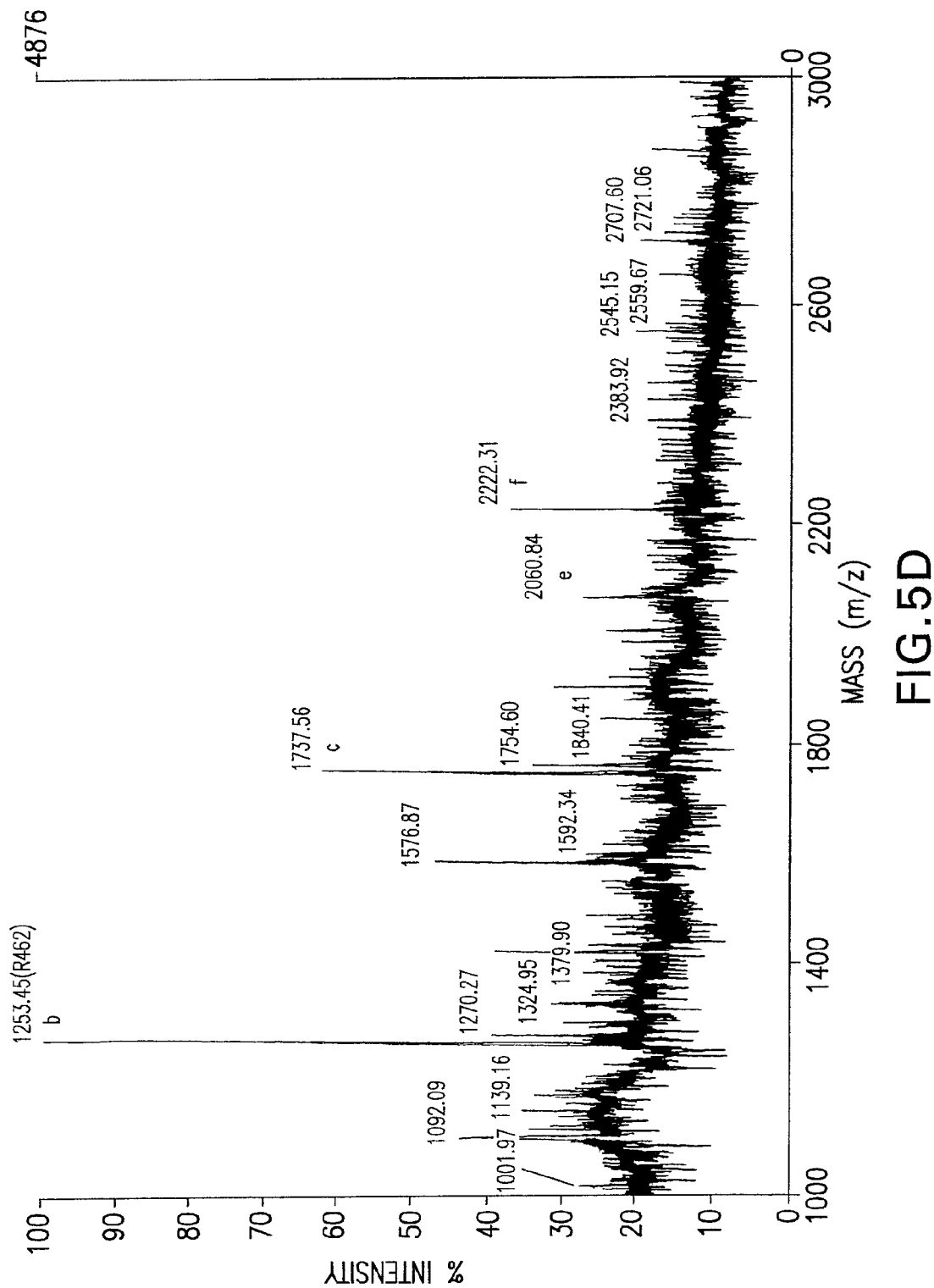
Figure 8A:
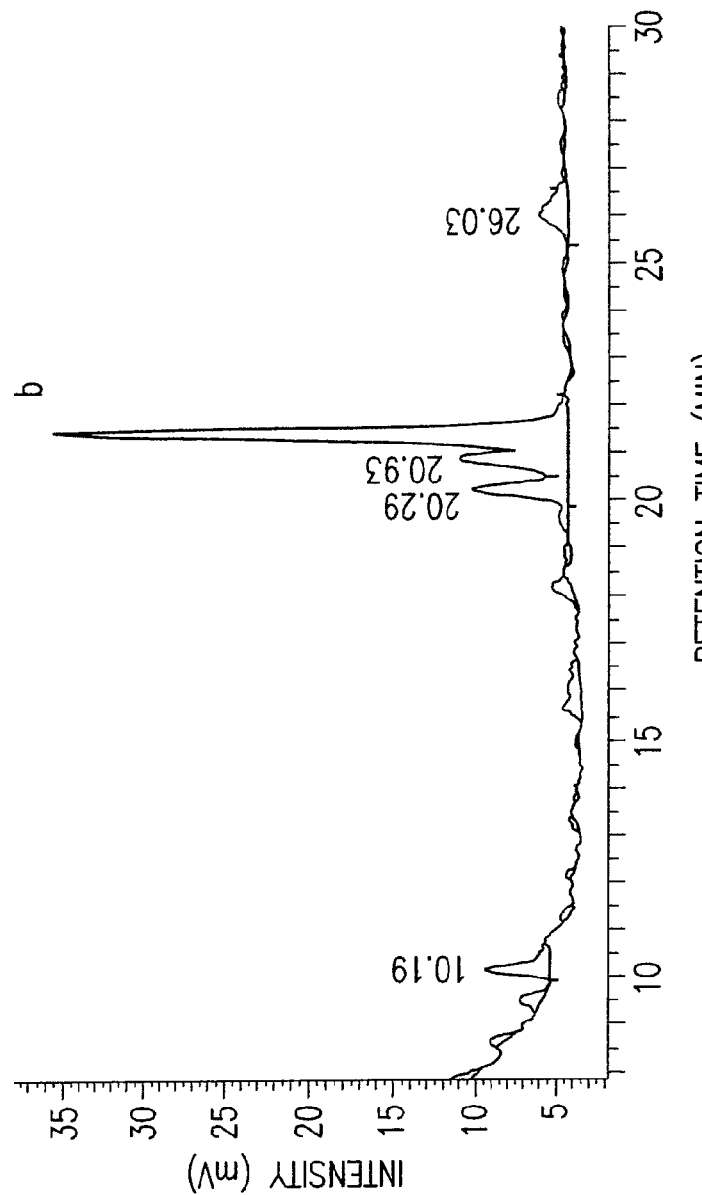
FIG. 8 shows a high performance liquid chromatogram for: (A) $Man_9GlcNAc_2$ standard labeled with 2-AB (negative control); (B) supernatant of medium *P. pastoris*, Δoch1 transformed with pGC5 mannosidase, which demonstrates a lack of extracellular mannosidase activity in the supernatant; and (C) $Man_9GlcNAc_2$ standard labeled with 2-AB after exposure to *T. reesei* mannosidase (positive control).
Figure 8B:
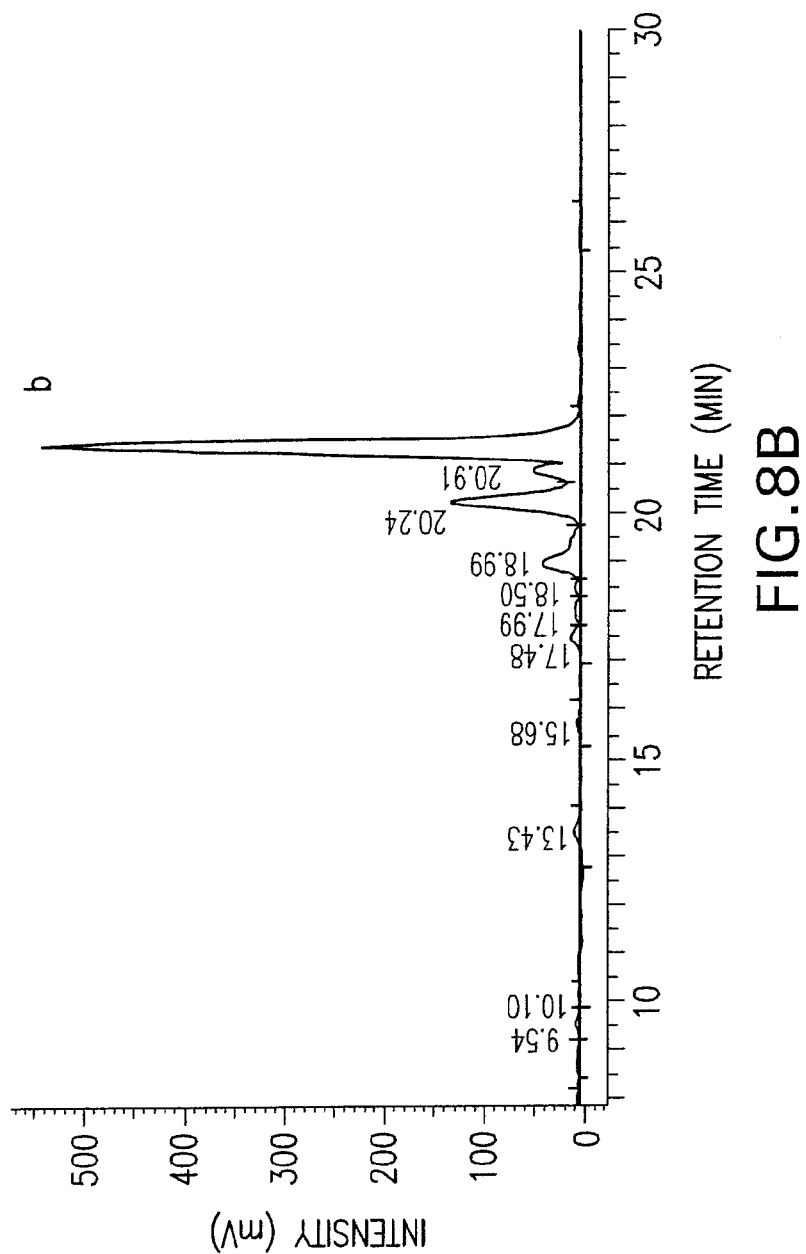

The fusion construct pGC5, *Saccharomyces* MNS1(m)/mouse mannosidase IB Δ99, is another example of a fusion construct having intracellular mannosidase trimming activity (Example 11; FIG. 5D, FIG. 8B). Fusion construct pBC18-5 (*Saccharomyces* VAN1(s)/*C. elegans* mannosidase IB Δ80) is yet another example of an efficient fusion construct capable of producing N-glycans having a $Man_5GlcNAc_2$ structure in vivo. By creating a combinatorial DNA library of these and other such mannosidase fusion constructs according to the invention, a skilled artisan may distinguish and select those constructs having optimal intracellular trimming activity from those having relatively low or no activity. Methods using combinatorial DNA libraries of the invention are advantageous because only a select few mannosidase fusion constructs may produce a particularly desired N-glycan in vivo.

In addition, mannosidase trimming activity may be specific to a particular protein of interest. Thus, it is to be further understood that not all targeting peptide/mannosidase catalytic domain fusion constructs may function equally well to produce the proper glycosylation on a glycoprotein of interest. Accordingly, a protein of interest may be introduced into a host cell transfected with a combinatorial DNA library to identify one or more fusion constructs which express a mannosidase activity optimal for the protein of interest. One skilled in the art will be able to produce and select optimal fusion construct(s) using the combinatorial DNA library approach described herein.

It is apparent, moreover, that other such fusion constructs exhibiting localized active mannosidase catalytic domains (or more generally, domains of any enzyme) may be made using techniques such as those exemplified in Example 11 and described herein. It will be a matter of routine experimentation for one skilled in the art to make and use the combinatorial DNA library of the present invention to optimize, for example, $Man_5GlcNAc_2$ production from a library of fusion constructs in a particular expression vector introduced into a particular host cell.

Glycosyltransferase Fusion Constructs

Similarly, a glycosyltransferase combinatorial DNA library was made using the methods of the invention. A combinatorial DNA library of sequences derived from glycosyltransferase I (GnTI) activities were assembled with targeting peptides and screened for efficient production in a lower eukaryotic host cell of a $GlcNAcMan_5GlcNAc_2$ N-glycan structure on a marker glycoprotein. A fusion construct shown to produce $GlcNAcMan_5GlcNAc_2$ (pPB104), *Saccharomyces* MNN9(s)/human GnTI Δ38 was identified (Example 15). A wide variety of such GnTI fusion constructs were assembled (Example 15, Table 10). Other combinations of targeting peptide/GnTI catalytic domains can readily be assembled by making a combinatorial DNA library. It is also apparent to one skilled in the art that other such fusion constructs exhibiting glycosyltransferase activity may be made as demonstrated in Example 15. It will be a matter of routine experimentation for one skilled in the art to use the combinatorial DNA library method described herein to optimize $GlcNAcMan_5GlcNAc_2$ production using a selected fusion construct in a particular expression vector and host cell line.

As stated above for mannosidase fusion constructs, not all targeting peptide/GnTI catalytic domain fusion constructs will function equally well to produce the proper glycosylation on a glycoprotein of interest as described herein. However, one skilled in the art will be able to produce and select optimal fusion construct(s) using a DNA library approach as described herein. Example 15 illustrates a preferred embodiment of a combinatorial DNA library comprising targeting peptides and GnTI catalytic domain fusion constructs involved in producing glycoproteins with predominantly $GlcNAcMan_5GlcNAc_2$ structure. Example 17 discloses the use of a sialyltransferase fusion construct and two different GnTII and MannII fusion constructs.

Using Multiple Fusion Constructs to Alter Host Cell Glycosylation

In another example of using the methods and libraries of the invention to alter host cell glycosylation, a *P. pastoris* strain with an OCH1 deletion that expresses a reporter protein (K3) was transformed with multiple fusion constructs isolated from combinatorial libraries of the invention to convert high mannose N-glycans to human-like N-glycans (Example 15). First, the mannosidase fusion construct pFB8 (*Saccharomyces* SEC12 (m)/mouse mannosidase IA Δ187) was transformed into a *P. pastoris* strain lacking 1,6 initiating mannosyltransferases activity (i.e. och1 deletion; Example 1). Second, pPB103 comprising a *K. lactis* MNN2-2 gene (Genbank AN: AF106080) encoding an UDP-GlcNAc transporter was constructed to increase further production of GlcNAcMan$_5$GlcNAc$_2$. The addition of the UDP-GlcNAc transporter increased production of GlcNAcMan$_5$GlcNAc$_2$ significantly in the *P. pastoris* strain as illustrated in FIG. 10B. Third, pPB104 comprising *Saccharomyces* MNN9 (s)/human GnTI Δ38 was introduced into the strain. This *P. pastoris* strain is referred to as "PBP-3."

It is understood by one skilled in the art that host cells such as the above-described yeast strains can be sequentially transformed and/or co-transformed with one or more expression vectors. It is also understood that the order of transformation is not particularly relevant in producing the glycoprotein of interest. The skilled artisan recognizes the routine modifications of the procedures disclosed herein may provide improved results in the production of the glycoprotein of interest.

Figure 5E:
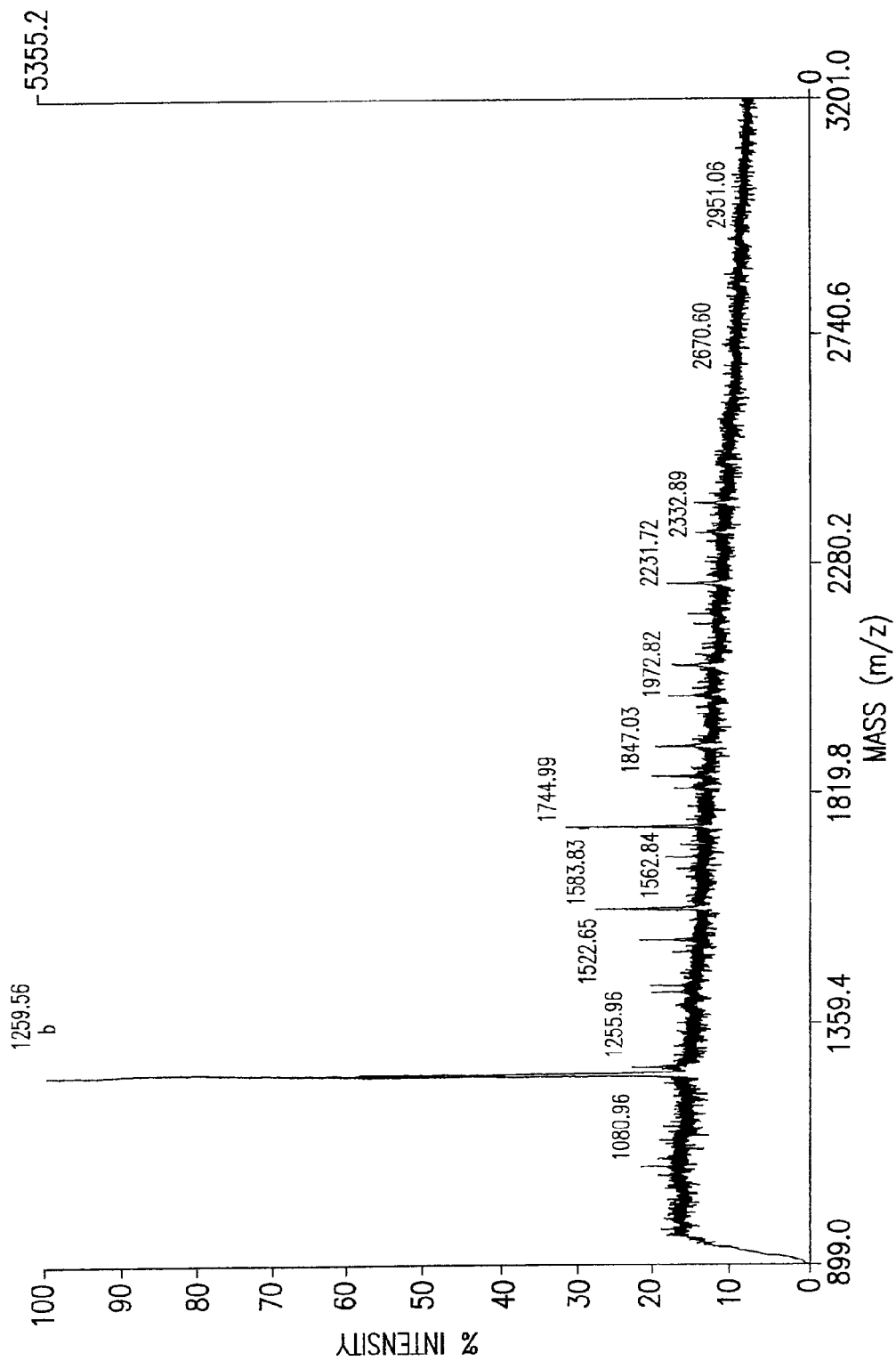

The importance of using a particular targeting peptide sequence with a particular catalytic domain sequence becomes readily apparent from the experiments described herein. The combinatorial DNA library provides a tool for constructing enzyme fusions that are involved in modifying N-glycans on a glycoprotein of interest, which is especially useful in producing human-like glycoproteins. (Any enzyme fusion, however, may be selected using libraries and methods of the invention.) Desired transformants expressing appropriately targeted, active α-1,2-mannosidase produce K3 with N-glycans of the structure Man$_5$GlcNAc$_2$ as shown in FIGS. 5D and 5E. This confers a reduced molecular mass to the cleaved glycan compared to the K3 of the parent OCH1 deletion strain, as was detected by MALDI-TOF mass spectrometry in FIG. 5C.

Figure 10:
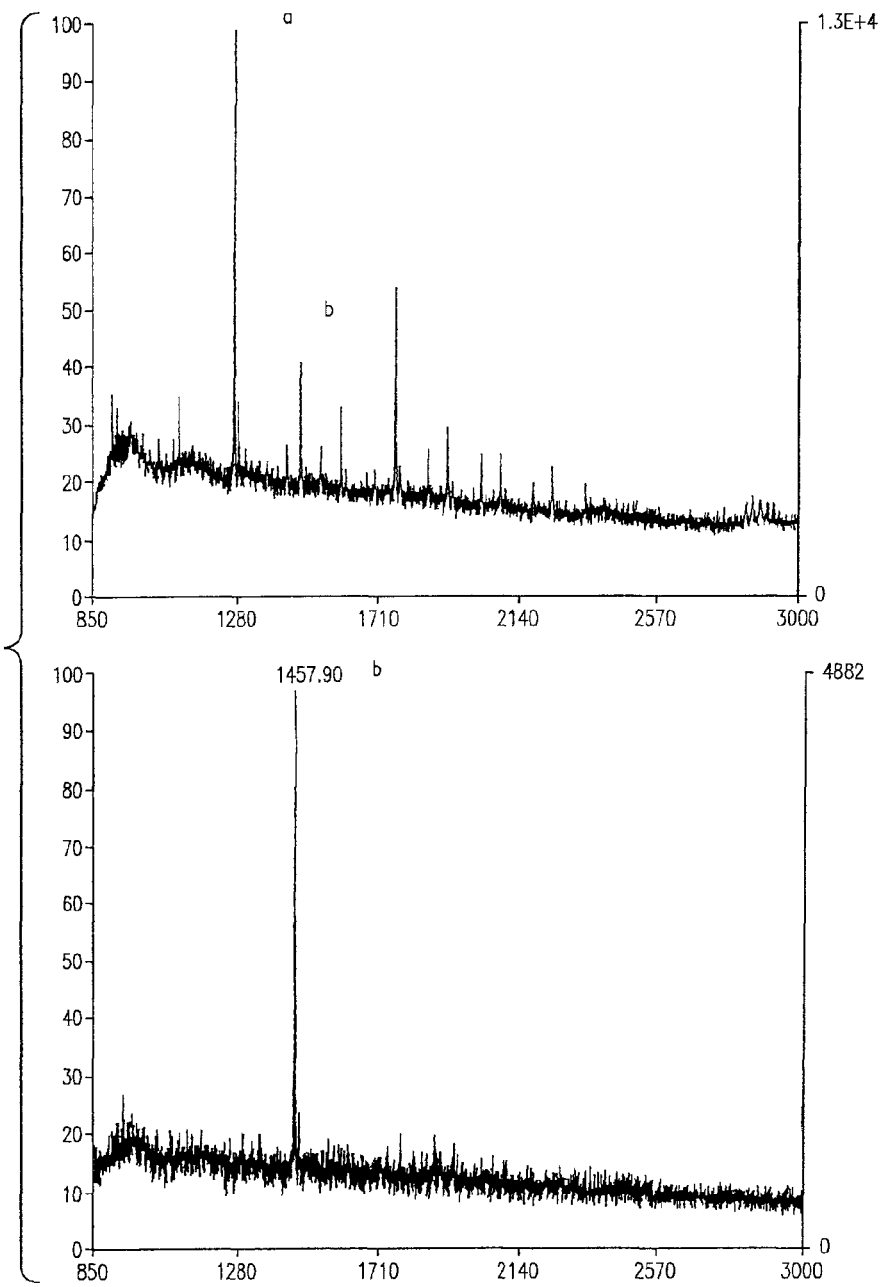

Similarly, the same approach was used to produce another secreted glycoprotein: IFN-β comprising predominantly Man$_5$GlcNAc$_2$. The Man$_5$GlcNAc$_2$ was removed by PNGase digestion (Papac et al. 1998) and subjected to MALDI-TOF as shown in FIG. 6A-6F. A single prominent peak at 1254 (m/z) confirms Man$_5$GlcNA$_2$ production on IFN-β in FIGS. 6E (pGC5) (*Saccharomyces* MNS1(m)/mouse mannosidase IB Δ99) and 6F (pFB8) (*Saccharomyces* SEC12 (m)/mouse mannosidase IA Δ187). Furthermore, in the *P. pastoris* strain PBP-3 comprising pFB8 (*Saccharomyces* SEC12 (m)/mouse mannosidase IA Δ187), pPB104 (*Saccharomyces* MNN9 (s)/human GnTI Δ38) and pPB103 (*K. lactis* MNN2-2 gene), the hybrid N-glycan GlcNAcMan$_5$GlcNAc$_2$ [b] was detected by MALDI-TOF (FIG. 10).

After identifying transformants with a high degree of mannose trimming, additional experiments were performed to confirm that mannosidase (trimming) activity occurred in vivo and was not predominantly the result of extracellular activity in the growth medium (Example 13; FIGS. 7-9).

Sequential Glycosylation Reactions

In a preferred embodiment, such targeting peptide/catalytic domain libraries are designed to incorporate existing information on the sequential nature of glycosylation reactions in higher eukaryotes. Reactions known to occur early in the course of glycoprotein processing require the targeting of enzymes that catalyze such reactions to an early part of the Golgi or the ER. For example, the trimming of Man$_8$GlcNAc$_2$ to Man$_5$GlcNAc$_2$ by mannosidases is an early step in complex N-glycan formation. Because protein processing is initiated in the ER and then proceeds through the early, medial and late Golgi, it is desirable to have this reaction occur in the ER or early Golgi. When designing a library for mannosidase I localization, for example, one thus attempts to match ER and early Golgi targeting signals with the catalytic domain of mannosidase I. As another example, the sialylation of glycoproteins occurs in Golgi. Thus, when designing a library for expression of sialyltransferase, one thus attempts to match Golgi targeting signals with the catalytic domain of a sialyltransferase.

Codon Optimization and Nucleotide Substitution

The methods of the invention may be performed in conjunction with optimization of the base composition for efficient transcription/translation of the encoded protein in a particular host, such as a fungal host. This includes codon optimization to ensure that the cellular pools of tRNA are sufficient. The foreign genes (ORFs) may contain motifs detrimental to complete transcription/translation in the fungal host and, thus, may require substitution to more amenable sequences. The expression of each introduced protein can be followed both at the transcriptional and translational stages by well known Northern and Western blotting techniques, respectively (Sambrook, J. and Russell, D. W., 2001).

Vectors

In another aspect, the present invention provides vectors (including expression vectors), comprising genes encoding activities glycosylation enzymes, a promoter, a terminator, a selectable marker and targeting flanking regions. Such promoters, terminators, selectable markers and flanking regions are readily available in the art. In a preferred embodiment, the promoter in each case is selected to provide optimal expression of the protein encoded by that particular ORF to allow sufficient catalysis of the desired enzymatic reaction. This step requires choosing a promoter that is either constitutive or inducible, and provides regulated levels of transcription. In another embodiment, the terminator selected enables sufficient termination of transcription. In yet another embodiment, the selectable markers used are unique to each ORF to enable the subsequent selection of a fungal strain that contains a specific combination of the ORFs to be introduced. In a further embodiment, the locus to which each fusion construct (encoding promoter, ORF and terminator) is localized, is determined by the choice of flanking region. The present invention is not limited to the use of the vectors disclosed herein.

Integration Sites

As one ultimate goal of this genetic engineering effort is a robust protein production strain that is able to perform well in an industrial fermentation process, the integration of multiple genes into the host (e.g., fungal) chromosome preferably involves careful planning. The engineered strain may likely have to be transformed with a range of different genes, and these genes will have to be transformed in a stable fashion to ensure that the desired activity is maintained throughout the fermentation process. As described herein, any combination of various desired enzyme activities may be engineered into the fungal protein expression host, e.g., sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. Genes which encode enzymes known to be characteristic of non-human glycosylation reactions in fugal hosts and their corresponding proteins have been extensively characterized in a number of lower eukaryotes (e.g., *Saccharomyces cerevisiae, Trichoderma reesei, Aspergillus nidulans, P. pastoris*, etc.), thereby providing a list of known glycosyltransferases in lower eukaryotes, their activities and their respective genetic sequence. These genes are likely to be selected from the group of mannosyltransferases e.g., 1,3 mannosyltransferases (e.g., MNN1 in *S. cerevisiae*) (Graham, 1991), 1,2 mannosyltransferases (e.g., the KTR/KRE family from *S. cerevisiae*), 1,6 mannosyltransferases (OCH1 from *S. cerevisiae*), mannosylphosphate transferases and their regulators (MNN4 and MNN6 from *S. cerevisiae*) and additional enzymes that are involved in aberrant (i.e. non-human) glycosylation reactions. Examples of preferred methods for modifying glycosylation in a lower eukaryotic host cell, such as *Pichia pastoris*, are shown in Table 6. (The HDEL and KDEL signal peptides in the second row of the third column are shown in SEQ ID NOS: 5 and 6, respectively).

TABLE 6

Some Preferred Embodiments For Modifying Glycosylation In A Lower Eukaroytic Microorganism

| Desired Structure | Suitable Catalytic Activities | Suitable Sources of Localization Sequences | Suitable Gene Deletions | Suitable Transporters and/or Phosphatases |
|---|---|---|---|---|
| $Man_5GlcNAc_2$ | α-1,2-mannosidase (murine, human, *Bacillus* sp., *A. nidulans*) | Mns1 (N-terminus, *S. cerevisiae*) Och1 (N-terminus, *S. cerevisiae*, *P. pastoris*) Ktr1 Mnn9 Mnt1 (*S. cerevisiae*) KDEL, HDEL (C-terminus) | OCH1 MNN4 MNN6 | none |
| $GlcNAcMan_5$ $GlcNAc_2$ | GlcNAc Transferase I, (human, murine, rat etc.) | Och1 (N-terminus, *S. cerevisiae*, *P. pastoris*) KTR1 (N-terminus) Mnn1 (N-terminus, *S. cerevisiae*) Mnt1 (N-terminus, *S. cerevisiae*) GDPase (N-terminus, *S. cerevisiae*) | OCH1 MNN4 MNN6 | UDP-GlcNAc transporter (human, murine, *K. lactis*) UDPase (human) |
| $GlcNAcMan_3$ $GlcNAc_2$ | mannosidase II | Ktr1 Mnn1 (N-terminus, *S. cerevisiae*) Mnt1 (N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-GlcNAc transporter (human, murine, *K. lactis*) UDPase (human) |
| $GlcNAc_{(2-4)}$ $Man_3GlcNAc_2$ | GlcNAc Transferase II, III, IV, V (human, murine) | Mnn1 (N-terminus, *S. cerevisiae*) Mnt1 (N-terminus, *S. cerevisiae*) Kre2/Mnt1 (*S. cerevisiae*) Kre2 (*P. pastoris*) Ktr1 (*S. cerevisiae*) Ktr1 (*P. pastoris*) Mnn1 (*S. cerevisiae*) | OCH1 MNN4 MNN6 | UDP-GlcNAc transporter (human, murine, *K. lactis*) UDPase (human) |
| $Gal_{(1-4)}$ $GlcNAc_{(2-4)}$- | β-1,4-Galactosyl transferase (human) | Mnn1 (N-terminus, | OCH1 MNN4 | UDP-Galactose transporter |

TABLE 6-continued

Some Preferred Embodiments For Modifying Glycosylation
In A Lower Eukaroytic Microorganism

| Desired Structure | Suitable Catalytic Activities | Suitable Sources of Localization Sequences | Suitable Gene Deletions | Suitable Transporters and/or Phosphatases |
|---|---|---|---|---|
| Man$_3$GlcNAc$_2$ | | S. cerevisiae) Mnt1 (N-terminus, S. cerevisiae) Kre2/Mnt1 (S. cerevisiae) Kre2 (P. pastoris) Ktr1 (S. cerevisiae) Ktr1 (P. pastoris) Mnn1 (S. cerevisiae) | MNN6 | (human, S. pombe) |
| NANA$_{(1-4)}$-Gal$_{(1-4)}$ GlcNAc$_{(2-4)}$-Man$_3$GlcNAc$_2$ | α-2,6-Sialyltransferase (human) α-2,3-Sialyltransferase | KTR1 MNN1 (N-terminus, S. cerevisiae) MNT1 (N-terminus, S. cerevisiae) Kre2/Mnt1 (S. cerevisiae) Kre2 (P. pastoris) Ktr1 (S. cerevisiae) Ktr1 (P. pastoris) MNN1 (S. cerevisiae) MNN2 (S. cerevisiae) | OCH1 MNN4 MNN6 | CMP-Sialic acid transporter (human) |

Methods for Producing CMP-Sia for the Generation of Recombinant N-Glycans

The present invention provides methods for production of a functional CMP-Sia biosynthetic pathway in a host cell that lacks endogenous CMP-Sia, such as a fungal cell. The present invention also provides a method for creating a host cell that has been modified to express a new or altered CMP-Sia pathway. The invention further provides a method for creating a host cell that comprises a cellular pool of CMP-Sia.

Figure 14:
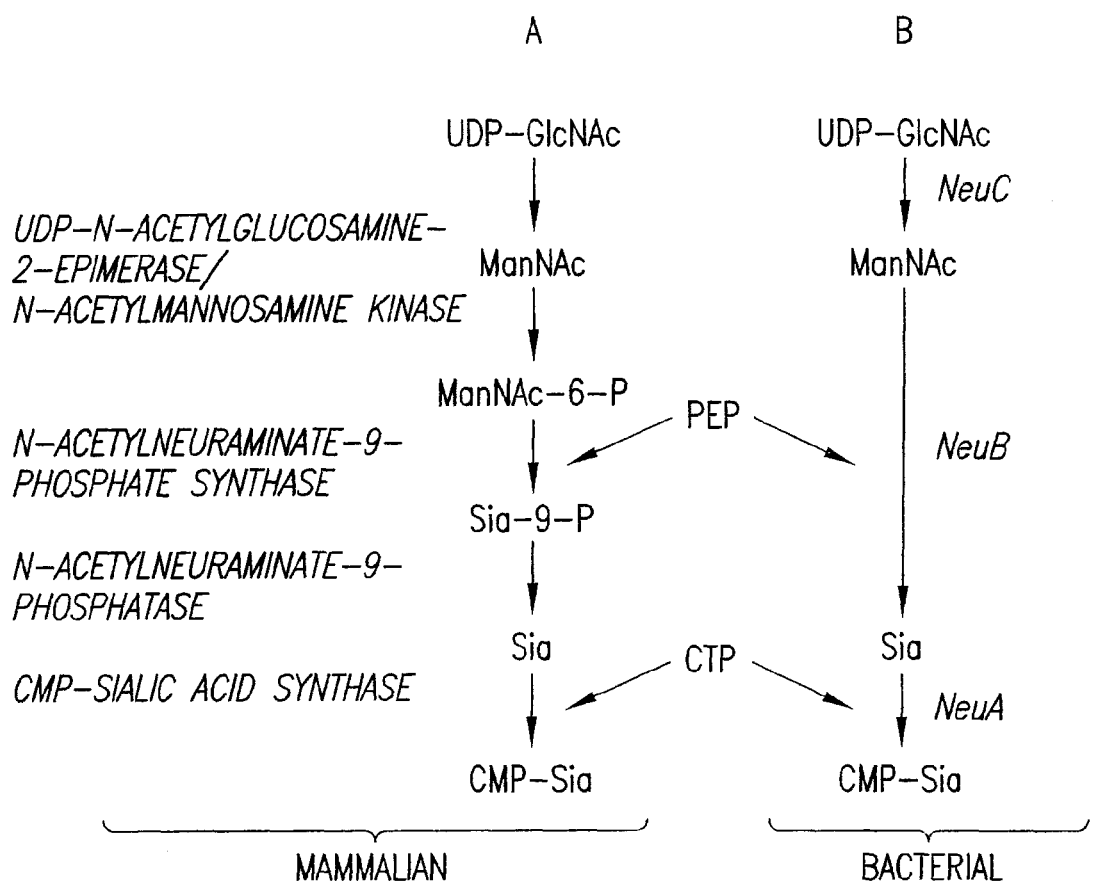
FIG. 14 illustrates the CMP-sialic acid biosynthetic pathway in mammals and bacteria. Enzymes involved in each pathway are italicized. The primary substrates, intermediates and products are in bold. (PEP: phosphoenol pyruvate; CTP: cytidine triphosphate).

The methods involve the cloning and expression in a host cell of several genes encoding enzymes of the CMP-Sia biosynthetic pathway resulting in a cellular pool of CMP-Sia in the host cell which can be utilized in the production of sialylated glycans on proteins of interest. In general, the addition of sialic acids to glycans requires the presence of the sialyltransferase, a glycan acceptor (e.g., Gal$_2$GlcNAc$_2$Man$_3$GlcNAc$_2$) and the sialyl donor molecule, CMP-Sia. The synthesis of the CMP-Sia donor molecule in higher organisms (e.g., mammals) is a four enzyme, multiple reaction process starting with the substrate UDP-GlcNAc and resulting in CMP-Sia (FIG. 14A). The process initiates in the cytoplasm producing sialic acid which is then translocated into the nucleus where Sia is converted to CMP-Sia by CMP-sialic acid synthase. Subsequently, CMP-Sia exits the nucleus into the cytoplasm and is then transported into the Golgi where sialyltransferases catalyze the transfer of sialic acid onto the acceptor glycan. In contrast, the bacterial pathway for synthesizing CMP-Sia from UDP-GlcNAc involves only three enzymes and two intermediates (FIG. 14), with all reactions occurring in the cytoplasm.

Accordingly, the methods of the invention involve generating a pool of CMP-Sia in a non-human host cell that lacks endogenous CMP-Sia by introducing a functional CMP-Sia biosynthetic pathway. With readily available DNA sequence information from genetic databases (e.g., GenBank, Swissprot), enzymes and/or activities involved in the CMP-Sia pathways (Example 16) are cloned. Using standard techniques known to those skilled in the art, nucleic acid molecules encoding one or more enzymes (or catalytically active fragments thereof) involved in the biosynthesis or transport of CMP-Sia are inserted into appropriate expression vectors under the transcriptional control of promoters and/or other expression control sequences capable of driving transcription in a selected host cell of the invention (e.g., a fungal host cell). The functional expression of such enzymes in the selected host cells of the invention can be detected. In one embodiment, the functional expression of such enzymes in the selected host cells of the invention can be detected by measuring the intermediate formed by the enzyme. The methods of the invention are not limited to the use of the specific enzyme sources disclosed herein. In certain preferred embodiments, combinatorial libraries of the invention are utilized to select and/or optimize CMP-Sia pathway activity in the selected host cell.

Engineering a Mammalian CMP-Sialic Acid Biosynthetic Pathway in a Host Cell

In one embodiment of the invention, the method involves cloning several genes encoding enzymes in the CMP-Sia biosynthetic pathway, including UDP-N-acetylglucosamine-2-epimerase/N-acetylmannosamine kinase, N-acetylneuraminate-9-phosphate synthase, N-acetylneuraminate-9-phosphatase, CMP-sialic acid phosphatase and CMP-sialic acid synthase, and expressing one or more of said cloned genes in a host cell which lacks endogenous CMP-Sia, such as a fungal host cell. The genes are expressed to generate each enzyme, producing intermediates that are used for subsequent enzymatic reactions. Example 16 describe methods for the introduction of these enzymes into a fungal host (e.g., P.

*pastoris*) using a selection marker. Alternatively, the enzymes are expressed together to produce or increase downstream intermediates whereby subsequent enzymes are able to act upon them.

The first enzyme in the pathway is a bi-functional enzyme that is both a UDP-GlcNAc epimerase and an N-acetylmannosamine kinase, converting UDP-GlcNAc through N-acetylmannosamine (ManNAc) to N-acetylmannosamine-6-phosphate (ManNAc-6-P) (Hinderlich, 1997). This enzyme was originally cloned from a rat liver cDNA library (Stasche, 1997). Homologs to this enzyme have subsequently been found to exist in other species, for example, human (NM_005476); *E. coli* (Ringenberg et al. 2003); *Mannheimia haemolytica* (McKerrell and Lo, Infect Immun. 2002 May; 70(5):2622-9). In a preferred embodiment, a gene encoding the functional UDP-N-acetylglucosamine-2-epimerase enzyme, including homologs, variants and derivatives thereof, is cloned and expressed in a host cell (for example, a non-human host cell which lacks endogenous CMP-Sia, such as a fungal host cell). In another preferred embodiment, a gene encoding the functional N-acetylmannosamine kinase enzyme, including homologs, variants and derivatives thereof, is cloned and expressed in a host cell, such as a fungal host cell. In a more preferred embodiment, a gene encoding the bifunctional UDP-N-acetylglucosamine-2-epimerase/N-acetylmannosamine kinase enzyme, including homologs, variants and derivatives thereof, is cloned and expressed in a host cell, such as a fungal host cell (e.g., *P. pastoris*). The functional expression of these genes can be detected using a functional assay. In one embodiment, the functional expression of such genes can be detected by monitoring the formation of ManNAc and ManNAc-6-P intermediates.

The second enzyme in the pathway, N-acetylneuraminic acid phosphate synthase, was cloned from human liver based on its homology to the *E. coli* sialic acid synthase gene, NeuB (Lawrence, 2000). Homologs of the N-acetylneuraminic acid phosphate synthase enzyme are also known in rat liver (Chen et al., Glycobiology. 2002 12(2):65-71) and mouse (Nakata et al., Biochem. Biophys. Res. Commun. 2000; 273(2):642-8). This enzyme catalyzes the conversion of ManNAc-6-P to sialate 9-phosphate (also referred to as Sia-9P, N-acetylneuraminate 9-phosphate, or Neu5Ac-9P). Accordingly, in a preferred embodiment, a gene encoding the functional N-acetylneuraminate 9-phosphate synthase enzyme, including homologs, variants and derivatives thereof, is cloned and expressed in a host cell (for example a non-human host cell which lacks endogenous CMP-Sia, such as a fungal host cell). The expression of N-acetylneuraminic acid phosphate synthase in the host can be detected using a functional assay. In one embodiment, the functional expression of N-acetylneuraminic acid phosphate synthase can be detected by monitoring the formation of Sia-9P.

The third enzyme in the pathway, N-acetylneuraminate 9-phosphatase (Sia-9-phosphatase), is involved in the conversion of Sia-9-P to sialic acid. The cloning of this enzyme has recently been reported by Maliekal et al., 2006 (See GenBank AN NM_152667). Although the activity of this enzyme has been detected in mammalian cells, no such activity has been identified in fungal cells. Therefore, the lack of Sia-9-phosphatase would cause a break in the pathway. Accordingly, in a preferred embodiment, the method of the present invention involves isolating and cloning a Sia-9-phosphatase gene and expressing it in a non-human host cell, such as a fungal host cell. (See Example 16.) Such hosts include, e.g., yeast, fungal, insect and bacterial cells. In a more preferred embodiment, the Sia-9-phosphatase gene, including homologs, variants and derivatives thereof, is expressed in a non-human host cell that lacks endogenous CMP-Sia or that expresses inadequate levels of CMP-Sia, such as a fungal host. The expression of Sia-9-phosphatase in the host can be detected using a functional assay. In one embodiment, the functional expression of Sia-9-phosphatase can be detected by monitoring the formation of sialic acid.

The next enzyme in the mammalian pathway, CMP-Sia synthase, was originally cloned from the murine pituitary gland by functional complementation of a cell line deficient in this enzyme (Munster, 1998). Homologs have been found to exist in *E. coli* (Mercker and Troy, 1990); and human (Raju et al., 2001). This enzyme converts sialic acid to CMP-Sia, which is the donor substrate in a sialyltransferase reaction in the Golgi. Accordingly, in an even more preferred embodiment, a gene encoding the functional CMP-Sia synthase enzyme, including homologs, variants and derivatives thereof, is cloned and expressed in a host cell (for example a non-human that lacks endogenous CMP-Sia, such as a fungal host cell). The expression of CMP-Sia synthase in the host can be detected using a functional assay. In one embodiment, the functional expression of CMP-Sia synthase can be detected by monitoring the formation of CMP-Sia.

The method of the present invention further involves the production of the intermediates produced in a host cell as a result of expressing the above enzymes in the CMP-Sia pathway. Preferably, the intermediates produced include one or more of the following: UDP-GlcNAc, ManNAc, ManNAc-6-P, Sia-9-P, Sia and CMP-Sia. Additionally, each intermediate produced by the enzymes is preferably detected. For example, to detect the presence or absence of an intermediate, an assay as described in Example 16 is used. Accordingly, the invention also provides assays to detect the N-glycan intermediates produced in a non-human host cell that lacks endogenous CMP-Sia, such as a fungal host cell.

A skilled artisan recognizes that the mere availability of one or more enzymes in the CMP-sialic acid biosynthetic pathway does not suggest that such enzymes can be functionally expressed in a host cell that lacks endogenous CMP-Sia, such as a fungal host cell. To date, the ability of such host cell to express these mammalian enzymes to create a functional de novo CMP-Sia biosynthetic pathway has not been described. The present invention provides for the first time the functional expression of at least one mammalian enzyme involved in CMP-Sia biosynthesis in a fungal host: the mouse CMP-Sia synthase (Example 16), indicating that production of CMP-Sia via the mammalian pathway (in whole or in part) is possible in a fungal host and thus in other non-human hosts that lack endogenous CMP-Sia.

The invention described herein is not limited to the use of the specific enzymes, genes, plasmids and constructs disclosed herein. A person of skill would readily understand how to use any homologs, variants, derivatives and functional equivalents of the genes involved in the synthesis of CMP-Sia.

To produce sialylated, recombinant glycoproteins in a host cell that lacks endogenous CMP-Sia (e.g., a fungal host such as *P. pastoris*) or in a host cell that needs or can benefit from increased levels of CMP-Sia, the above mentioned mammalian enzymes can be expressed using a combinatorial DNA library approach as disclosed herein, generating a pool of CMP-Sia, which is transferred onto galactosylated N-glycans in the presence of a sialyltransferase. Accordingly, the present invention provides a method for engineering a CMP-Sia biosynthetic pathway into a host cell by expressing one or more of each of the enzymes such that they function, preferably so that they function optimally, in the subcellular location to which they are targeted in the selected host cell. Mammalian, bacterial or hybrid engineered CMP-Sia biosynthetic pathways are provided.

Engineering a Bacterial CMP-Sialic Acid Biosynthetic Pathway in a Host Cell

Figure 15:
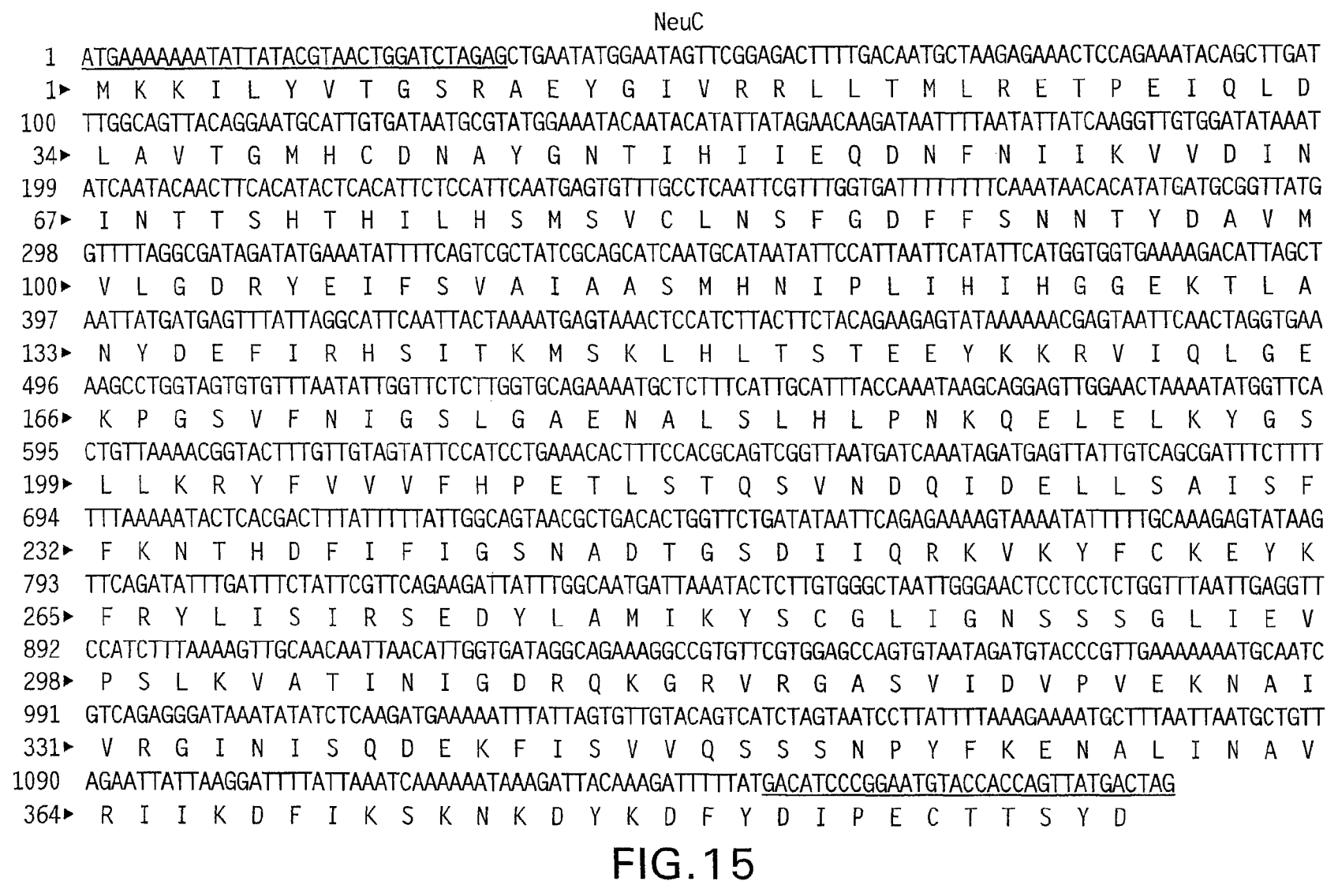

The metabolic intermediate UDP-GlcNAc is common to eukaryotes and prokaryotes, providing an endogenous substrate from which to initiate the synthesis of CMP-Sia (FIG. 14). Based on the presence of this common intermediate, the CMP-Sia biosynthetic pathway can be engineered into non-human host cells that lack endogenous CMP-Sia by introducing the genes encoding the bacterial UDP-GlcNAc epimerase (NeuC), sialate synthase (NeuB) and CMP-Sia (NeuA) synthase into the host cell, e.g., by transformation methods such as on plasmids, and preferably, by integration into the host cell chromosome. Accordingly, another aspect of the present invention involves engineering a bacterial CMP-Sia biosynthetic pathway into host cells that lack an endogenous CMP-Sia pathway or into host cells that need or would benefit from increased levels of CMP-Sia. The expression of bacterial Neu genes in cells that lack an endogenous CMP-Sia biosynthetic pathway enables the generation of a cellular CMP-Sia pool, which can subsequently facilitate the production of recombinant N-glycans having detectable level of sialylation on a protein of interest, such as recombinantly expressed glycoproteins. The bacterial enzymes involved in the synthesis of CMP-Sia include UDP-GlcNAc epimerase (NeuC), sialate synthase (NeuB) and CMP-Sia synthase (NeuA). In one embodiment, the NeuC, NeuB, and NeuA genes, which encode these functional enzymes, respectively, including homologs, variants and derivatives thereof, are cloned and expressed in non-human host cells that lack an endogenous CMP-Sia pathway, such as a fungal host cell. The sequences of NeuC, NeuB and NeuA genes are shown in FIGS. 15-17, respectively. The expression of these genes in the host cell generates the intermediate molecules in the biosynthetic pathway of CMP-sialic acid (FIG. 14B).

In addition to these three enzymes, the method for synthesizing the bacterial CMP-Sia biosynthetic pathway from UDP-GlcNAc involves generating two intermediates: ManNAc and Sia (FIG. 14B). The conversion of UDP-GlcNAc to ManNAc is facilitated by the NeuC gene. The conversion of ManNAc to Sia is facilitated by the NeuB gene and the conversion of Sia to CMP-Sia is facilitated by the NeuA gene. These three enzymes (or homologs thereof) have thus far been found linked together in pathogenic bacteria—i.e., not single gene has been found without the other two. Introducing the bacterial pathway into a host cell, such as a fungal host, thus requires the manipulation of fewer genes than introducing mammalian pathway.

The E. coli UDP-GlcNAc epimerase, encoded by the E. coli NeuC gene, is the first enzyme involved in the bacterial synthesis of polysialic acid (Ringenberg, 2001). The NeuC gene (Genbank AN: M84026.1; SEQ ID NO:57) encoding this enzyme was isolated from the pathogenic E. coli K1 strain and encodes a protein of 391 amino acids (SEQ ID NO:58) (FIG. 15) (Zapata, 1992). The encoded UDP-GlcNAc epimerase catalyzes the conversion of UDP-GlcNAc to ManNAc. Homologs of this enzyme have been identified in several pathogenic bacteria, including Streptococcus agalactiae, Synechococcus sp. WH 8102, Clostridium thermocellum, Vibrio vulnificus, Legionella pnuemophila, and Campylobacter jejuni. In one embodiment, a gene encoding the functional E. coli UDP-GlcNAc epimerase enzyme (NeuC), including homologs, variants and derivatives thereof, is cloned and expressed in a host cell (for example a non-human host cell, such as a fungal host). The expression of NeuC in the host can be detected using a functional assay. In one embodiment, the functional expression NeuC can be detected by monitoring the formation of ManNAc.

The second enzyme in the bacterial pathway is sialate synthase, which directly converts ManNAc to Sia, bypassing several enzymes and intermediates present in the mammalian pathway. This enzyme of 346 amino acids (SEQ ID NO:60), is encoded by the E. coli NeuB gene (Genbank AN: U05248.1; SEQ ID NO:59) (FIG. 16) (Annunziato, 1995). In another embodiment, a gene encoding a functional E. coli sialate synthase enzyme (NeuB), including homologs, variants and derivatives thereof, is cloned and expressed in a host cell (for example, a non-human host cell, such as a fungal host cell). The expression of NeuB in the host can be detected using a functional assay. In one embodiment, the functional expression NeuB can be detected by monitoring the formation of Sia.

The third enzyme in this bacterial pathway is CMP-Sia synthase, consisting of 419 amino acids (SEQ ID NO:62) and encoded by the E. coli NeuA gene (Genbank AN: J05023; SEQ ID NO:61) (FIG. 17). CMP-Sia synthase converts Sia to CMP-Sia (Zapata, 1989). The NeuA gene is found in the same organisms as the NeuC and NeuB genes. Accordingly, in yet another embodiment, a gene (NeuA) encoding a functional E. coli CMP-Sia synthase enzyme, including homologs, variants and derivatives thereof, is cloned and expressed in a host cell (for example, a non-human host cell, such as a fungal host cell). In one embodiment, the expression NeuA can be detected by monitoring the formation of CMP-Sia.

In yet another embodiment, the gene encoding a functional bacterial CMP-Sia synthase (e.g. NeuA) encodes a fusion protein comprising a: catalytic domain having the activity of a bacterial CMP-Sia synthase and a cellular targeting signal peptide (not normally associated with the catalytic domain) selected to target the enzyme to the nucleus of the host cell. In one embodiment, said cellular targeting signal peptide comprises a domain of the SV40 capside polypeptide VP1. In another embodiment, the signal peptide comprises one or more endogenous signaling motifs from a mammalian CMP-Sia synthase that ensure correct localization of the enzyme to the nucleus. Methods for making said fusion protein are well known in the art.

After PCR amplification of the E. coli NeuA, NeuB and NeuC genes, the amplified fragments were ligated into a selectable yeast integration vector under the control of a promoter (Example 16). After transforming a host strain (e.g., P. pastoris), with each vector carrying the Neu gene fragments, colonies were screened by applying positive selection for the presence of vectors and then screening transformants for Neu gene enzymatic activity. The ability of a non-human host cell that lacks endogenous sialylation to express the bacterial enzymes involved in creating a de novo CMP-Sia biosynthetic pathway is provided for the first time by this invention.

Figure 25:
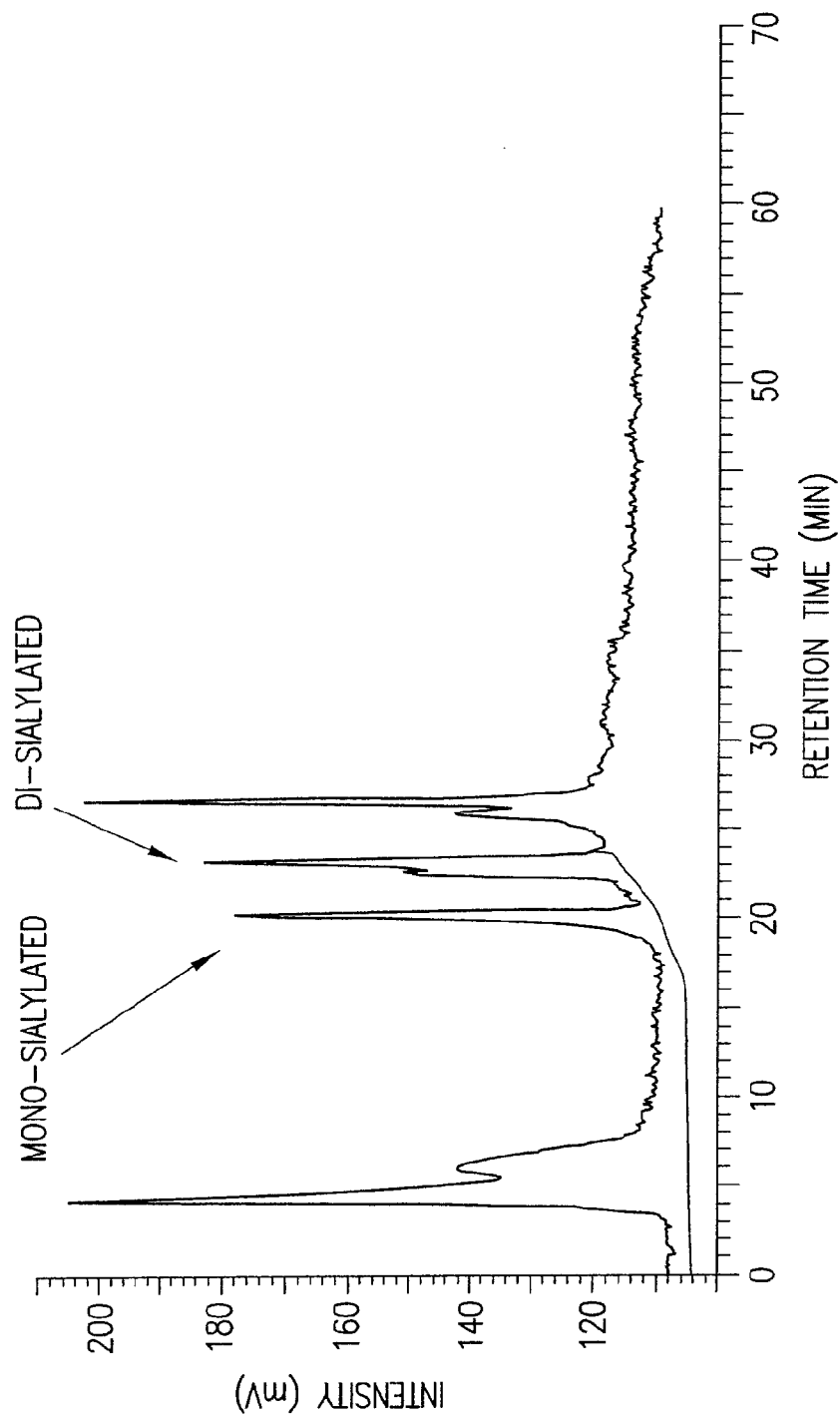
FIG. 25 shows a HPLC of a cell extract from strain YSH99a incubated under assay conditions (Example 16) in the presence of acceptor glycan with no exogenous CMP-sialic acid. The peaks eluting at 20 and 23 min correspond to mono- and di-sialylation of a biantennary galactosylated N-glycan. The doublet peak eluting at 26.5 min results from contaminating cellular component(s).

Engineering a Hybrid Mammalian/Bacterial
CMP-Sialic Acid Biosynthetic Pathway in a Host Cell Both mammalian and bacterial CMP-Sia biosynthetic pathways require that both CTP and sialic acid be available to the CMP-Sia synthase. Although similar in enzymatic function to the corresponding bacterial enzyme, the mammalian CMP-Sia synthase may include one or more endogenous signaling motifs that ensure correct localization to the nucleus. Because eukaryotes have a nucleus-localized pool of CTP and the prokaryotic CMP-Sia synthase may not localize to this compartment, a hybrid CMP-Sia biosynthetic pathway combining both mammalian and bacterial enzymes is a preferred method for the production of sialic acid and its intermediates in a non-human host cell that lacks endegenous sialylation, such as a fungal host cell. To this end, a pathway can be engineered into the host cell which involves the integration of both NeuC and NeuB as well as a mammalian CMP-Sia synthase. The CMP-Sia synthase enzyme may be selected from several mammalian homologs that have been cloned and characterized (Genbank AN: AJ006215; SEQ ID NO:63) (Munster, 1998) (see e.g., the murine CMP-Sia synthase) (FIG. 18). In one preferred embodiment, the host cell is transformed with UDP-GlcNAc epimerase (*E. coli* NeuC) and sialate synthase (*E. coli* NeuB) in combination with the mouse CMP-Sia synthase. The host engineered with this hybrid CMP-Sia biosynthetic pathway produces a cellular pool of the donor molecule CMP-Sia (FIG. 25). In a more preferred embodiment, the combination of the enzymes expressed in the host is selected for enhanced production of the donor molecule CMP-Sia.

Engineering Enzymes Involved in Alternative Routes for Enhancing the Production of CMP-Sialic Acid Pathway Intermediates in Host Cells In yet another aspect of the invention, enzymes involved in alternate pathways of CMP-sialic acid biosynthesis are engineered into non-human host cells that lack endogenous sialylation, such as fungal host cells; or in host cells in which endogenous sialylation may be altered, e.g., enhanced. For example, it is contemplated that when an intermediate becomes limiting during one of the methods outlined above, the introduction of an enzyme that uses an alternate mechanism to produce that intermediate will serve as a sufficient substitute in the production of CMP-sialic acid, or any intermediate along this pathway. Embodiments are described herein for the production of the intermediates ManNAc and Sia, though this approach may be extended to produce other intermediates. Furthermore, any of these enzymes can be incorporated into either the mammalian, bacterial or hybrid pathways, either in the absence of the enzymes mentioned previously (i.e., enzymes producing the same intermediate) or in the presence of enzymes mentioned previously, i.e., to enhance overall production.

In the above mentioned embodiments, ManNAc is produced from UDP-GlcNAc by either the mammalian enzyme UDP-GlcNAc-2-epimerase/ManNAc kinase or by the bacterial enzyme NeuC. The substrate for this reaction, UDP-GlcNAc, is predicted to be present in sufficient quantities in cells for the synthesis of CMP-Sia due to its requirement in producing several classes of molecules, including endogenous N-glycans. However, if ManNAc does become limiting—potentially due to the increased demand for ManNAc from the sialic acid biosynthetic pathway—then the cellular supply of ManNAc may be increased by introducing a GlcNAc epimerase which reacts with the substrate GlcNAc to produce ManNAc.

Figure 19:
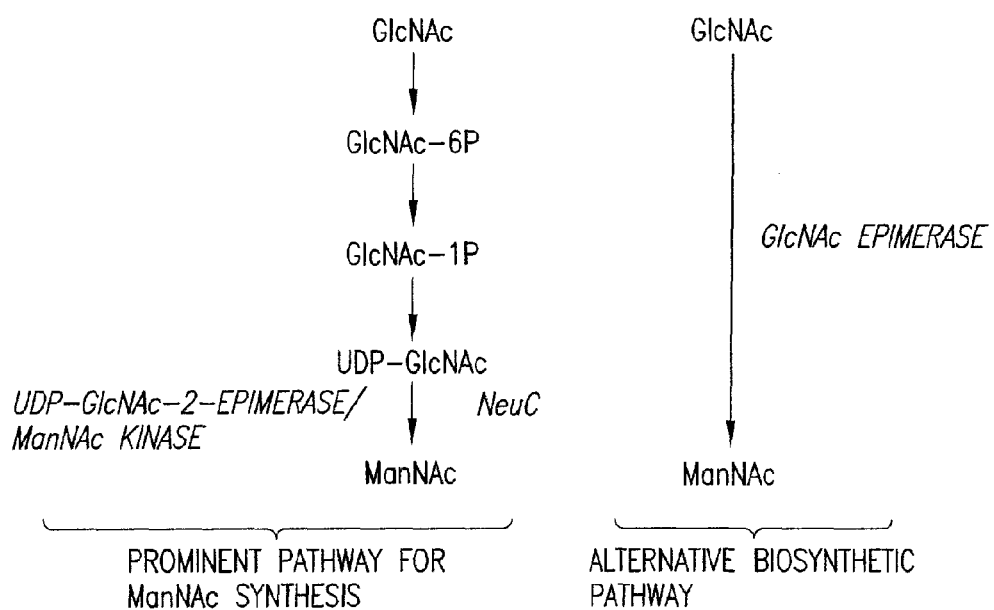
FIG. 19 illustrates an alternative biosynthetic route for generating N-acetylmannosamine (ManNAc) in vivo. Enzymes involved in each pathway are italicized. The primary substrates, intermediates and products are in bold.

Accordingly, in one embodiment, a gene encoding a functional GlcNAc epimerase enzyme, including homologs, variants and derivatives thereof, is cloned and expressed in a host cell. Using GlcNAc epimerase to directly convert GlcNAc to ManNAc is a shorter, more efficient approach compared with the two-step process involving the synthesis of UDP-GlcNAc (FIG. 19). The GlcNAc epimerase is readily available and, to date, the only confirmed GlcNAc epimerase to have been cloned is from the pig kidney (Maru, 1996) (Example 16). The gene (Genbank AN: D83766; SEQ ID NO: 65) isolated from pig kidney encodes a protein of 402 amino acids (SEQ ID NO: 64) (FIG. 20). When this enzyme was cloned, it was found to be identical to the pig renin-binding protein cloned previously (Inoue, 1990). Although this is the only protein with confirmed GlcNAc epimerase activity, several other renin-binding proteins have been isolated from other organisms, including humans, mouse, rat and bacteria, among others. All are shown to have significant homology. For example, the human GlcNAc epimerase homolog (Genbank AN: D10232.1) has 87% identity and 92% similarity to the pig GlcNAc epimerase protein. Although these homologs are very similar in sequence, the pig protein is the only one having demonstrable epimerase activity to date. The methods of the invention may be performed using any gene encoding a functional GlcNAc epimerase activity. Based on the presence of GlcNAc epimerase activity, the cloning and expression of this gene in a non-human host cell, such as a fungal host cell, is predicted to enhance the cellular levels of ManNAc, thereby, providing sufficient substrate for the enzymes that utilize ManNAc in the CMP-sialic acid biosynthetic pathway.

Figure 21:
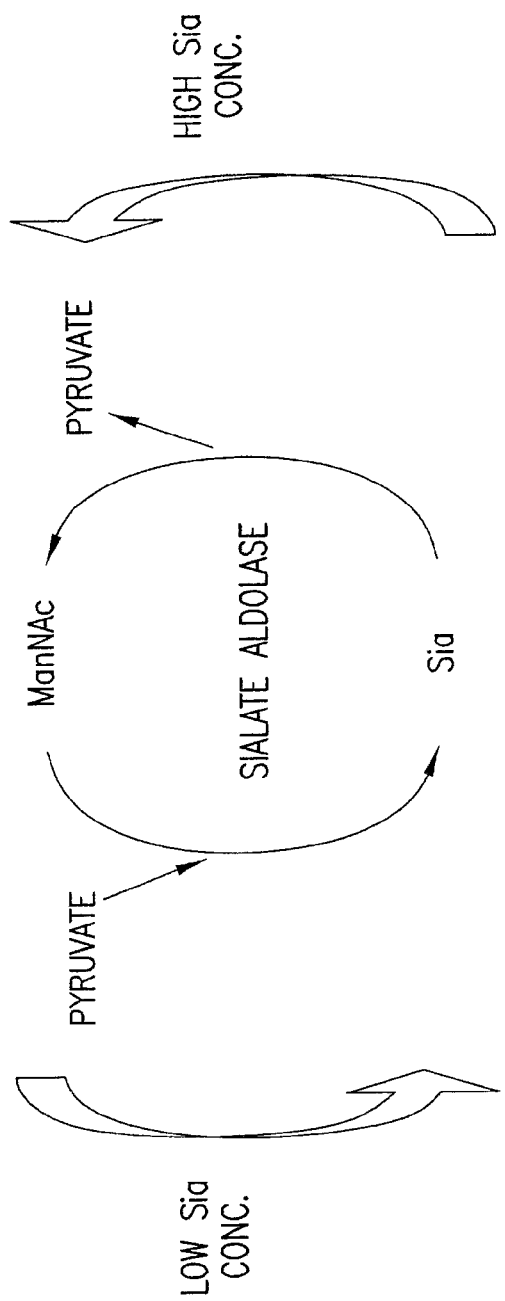
FIG. 21 illustrates the reversible reaction catalyzed by sialate aldolase and its dependence on sialic acid (Sia) concentration. Enzymes involved in each pathway are italicized. The primary substrates, intermediates and products are in bold.
Figure 22:
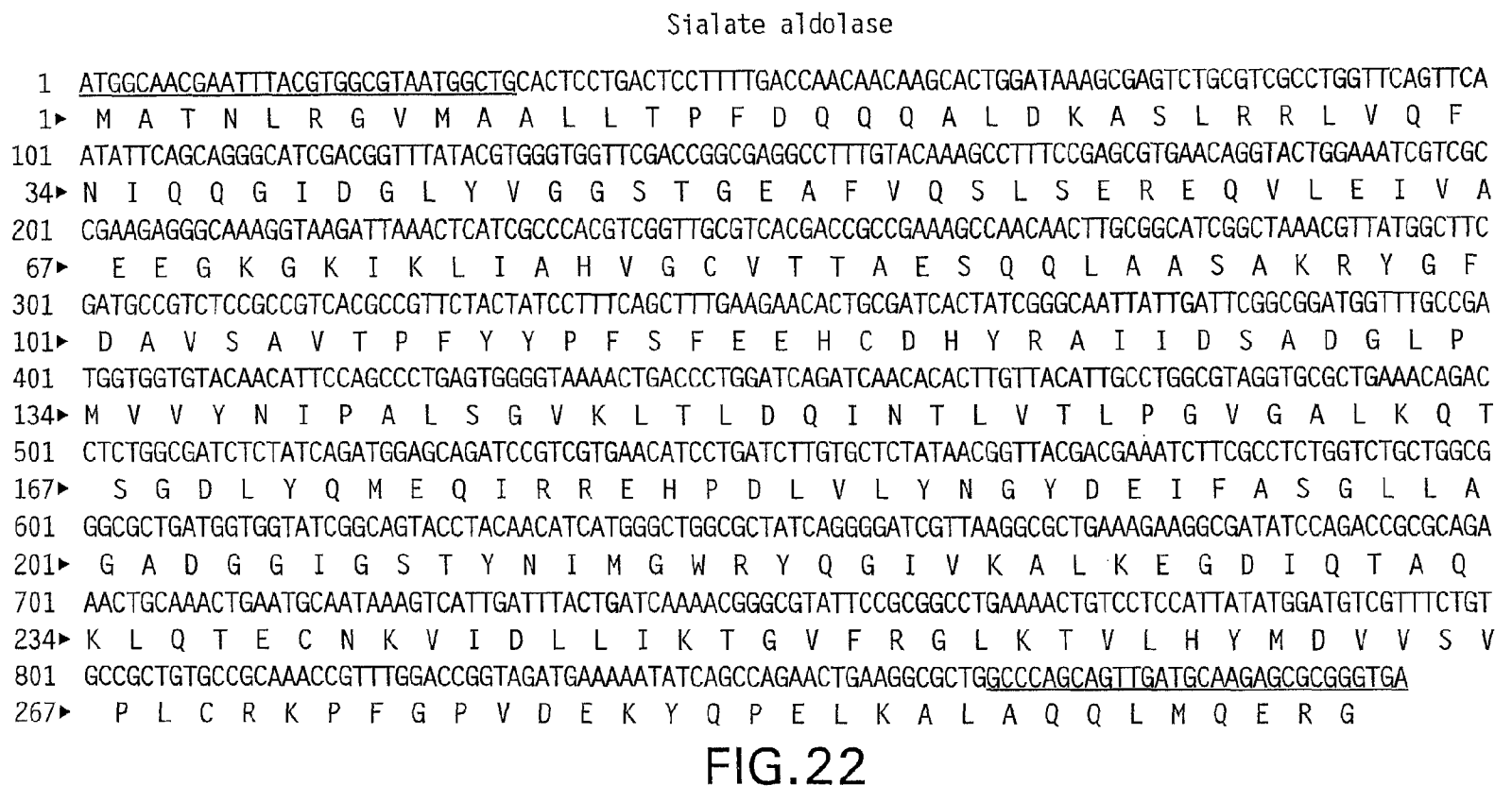
Figure 23:
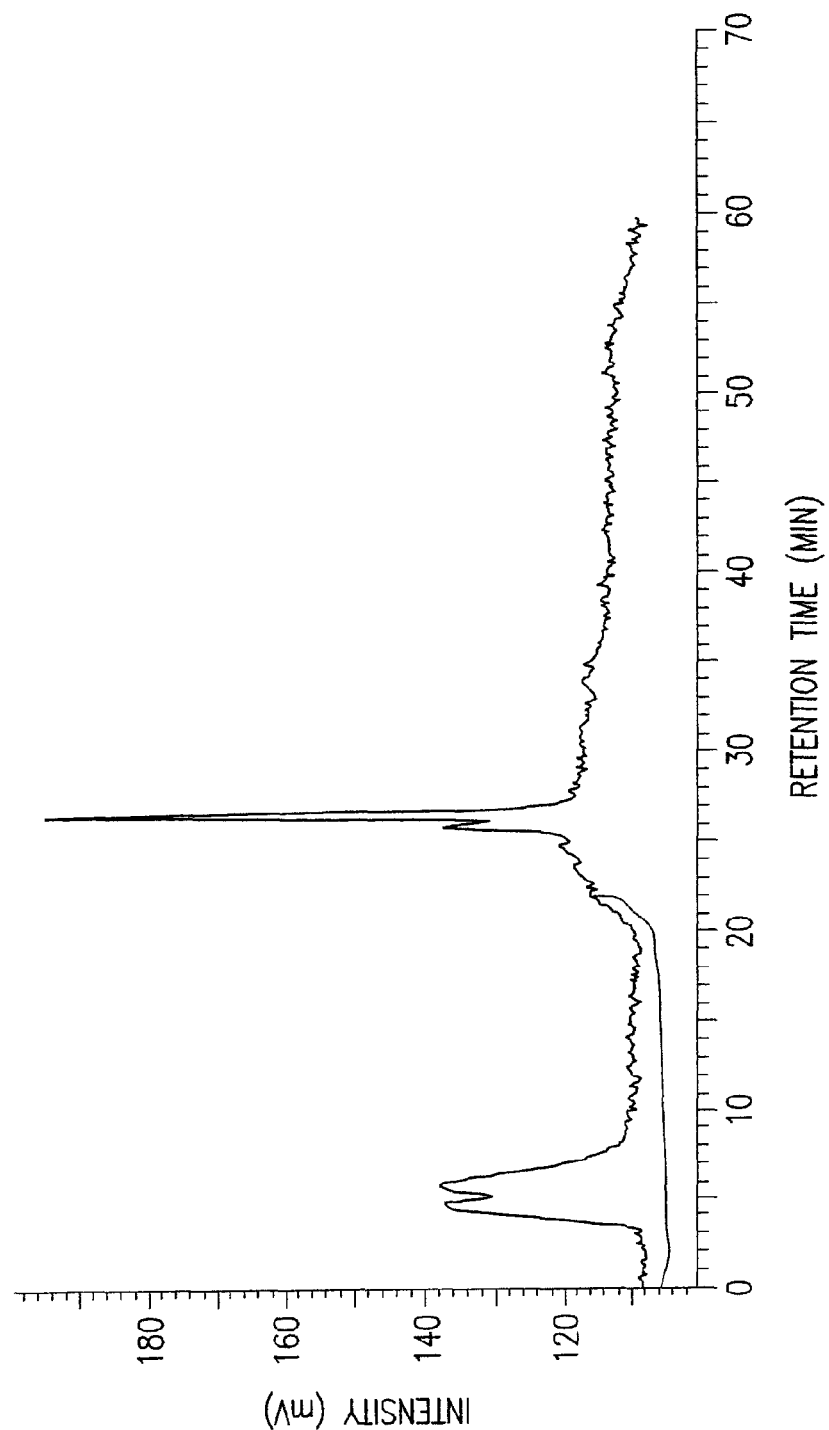
FIG. 23 shows a HPLC of negative control of cell extracts from strain YSH99a incubated under assay conditions (Example 16) in the absence of acceptor glycan. The doublet peak eluting at 26.5 min results from contaminating cellular component(s).
Figure 24:
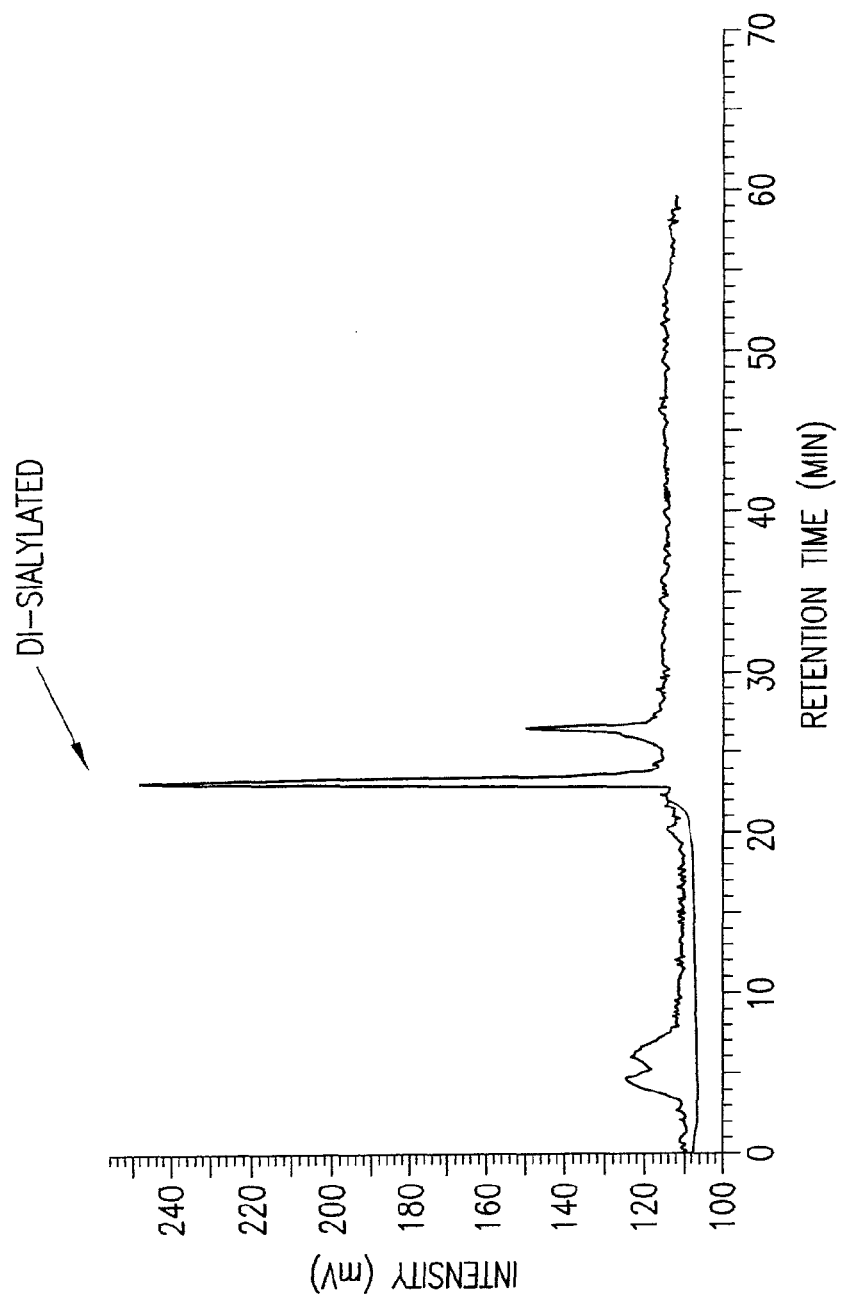
FIG. 24 shows a HPLC of positive control cell extract from strain YSH99a incubated under assay conditions (Example 16) in the presence of 2-AB (aminobenzamide) labeled acceptor glycan and supplemented with CMP-sialic acid. The peak eluting at 23 min corresponds to sialylation on each branch of a biantennary galactosylated N-glycan. The doublet peak eluting at 26.5 min results from contaminating cellular component(s).

In another embodiment, sialate aldolase is used to increase cellular levels of sialic acid, as illustrated in FIG. 21. This enzyme (also known as sialate lyase and sialate pyruvate-lyase) directly catalyzes the reversible reaction of ManNAc to sialic acid. In the presence of low concentrations of Sia, this enzyme catalyzes the condensation of ManNAc and pyruvate to produce Sia. Conversely, when Sia concentrations are high, the enzyme causes the reverse reaction to proceed, producing ManNAc and pyruvate (Vimr, 1985). In the above embodiments, the presence of CMP-Sia synthase converts substantially all Sia to CMP-Sia, thus shifting the equilibrium of the aldolase reaction to the condensation of ManNAc and pyruvate to produce Sia. Preferably, the sialate aldolase used in this embodiment is expressed from the *E. coli* NanA gene, but the invention is not limited to this enzyme source. The gene (Genbank AN: X03345; SEQ ID NO:67) for this enzyme encodes a 297 amino acid protein (SEQ ID NO:68) (FIG. 22) (Ohta, 1985). Close homologs to this enzyme are found in many pathogenic bacteria, including, *Salmonella typhimurium, Staphylococcus aureus, Clostridium perfringens, Haemophilus influenzae* among others. In addition, homologs are also present in mammals, including mice and humans. In one embodiment, cloning a gene encoding a sialate aldolase activity and expressing it in a fungal host cell enhances the cellular levels of Sia, thereby providing sufficient substrate for the enzymes that utilize Sia in the CMP-sialic acid biosynthetic pathway (Example 16).

Regulation of CMP-Sialic Acid Synthesis:
Feedback Inhibition and Inducible Promoters In mammalian cells, the production of CMP-sialic acid is highly regulated. CMP-sialic acid acts as a feedback inhibitor, acting on UDP-GlcNAc epimerase/ManNAc kinase to prevent further production of CMP-Sia (Hinderlich, 1997; Keppler, 1999). In contrast, the bacterial CMP-Sia biosynthetic pathway (FIG. 14B) does not appear to have a feedback inhibitory control mechanism that would limit the production of CMP-Sia (Ringenberg, 2001). However, incorporation of the *E. coli* sialate aldolase into one of the pathways mentioned above could cause a shift in the direction of the reaction that it catalyzes, depending on the balance of the equilibrium, thus potentially causing hydrolysis of Sia back to ManNAc. Accordingly, the methods involving sialate aldolase as outlined above will prevent this reverse reaction from occurring, given the presence of CMP-sialate synthase, which rapidly converts Sia to CMP-Sia.

The embodiments described thus far have detailed the constitutive overexpression of the enzymes in a particular biosynthetic pathway of CMP-Sia. Though no literature is currently available that suggests that the presence of any of the mentioned intermediates, and/or the final product could be detrimental to a non-human host, such as a fungal host, a preferred embodiment of the invention has one or more of the enzymes under the control of a regulatable (e.g., an inducible) promoter. In this embodiment, the gene (or ORF) encoding the protein of interest (including but not limited to: UDP-GlcNAc 2-epimerase/ManNAc kinase, NeuC, and GlcNAc epimerase) is cloned downstream of an inducible or regulatable promoter (including but not limited to: the alcohol oxidase promoter (AOX1 or AOX2; Tschopp, 1987), galactose-inducible promoter (GAL10; Yocum, 1984), tetracycline-inducible promoter (TET; Belli, 1998)) to facilitate the controlled expression of that enzyme, and thus to regulate the production of CMP-Sia.

Detection of CMP-Sialic Acid and the Intermediate Compounds in its Synthesis

The methods of the present invention provide engineered pathways to produce a cellular pool of CMP-Sia in non-human host cells that lack an endogenous CMP-Sia biosynthetic pathway, and/or to enhance production of CMP-Sia in host cells that have an endegenous pathway. To assess the production of each intermediate in the pathway, these intermediates must be detectable. Accordingly, the present invention also provides a method for detecting such intermediates. A method for detecting a cellular pool of CMP-Sia, for example, is provided in Example 16). Currently, the literature describes only a few methods for measuring cellular CMP-Sia and its precursors. Early methods involved paper chromatography and thiobarbituric acid analysis and were found to be complicated and time consuming (Briles, 1977; Harms, 1973). HPLC (high pressure liquid chromatography) has also been used, though earlier methods employed acid elution resulting in the rapid hydrolysis of the CMP-Sia (Rump, 1986). Most recently, a more robust method has been described using high-performance anion-exchange chromatography using an alkaline elution protocol combined with pulsed amperometric detection (HPAEC-PAD) (Fritsch, 1996). This method, in addition to detecting CMP-Sia, can also detect the precursor sialic acid, thus being useful for confirming cellular synthesis of either or both of these compounds.

Methods for In Vivo Transfer of Sialic Acid to N-Glycans Using Sialyltrasferase

The present invention provides a method for producing a sialylated glycoprotein in a recombinant non-human eukaryotic host cell. In one embodiment, the non-human eukaryotic host cell does not normally display sialyltransferase activity.

In one embodiment, said method comprises introducing into the host a nucleic acid encoding a sialyltransferase enzyme. The enzyme having sialyltransferase activity can be any enzyme having sialyltransferase activity including, but not limited to, any α-2,3 ST, any α-2,6 ST, human ST6Gal (GenBank AN: NM_00302) or a homologue thereof, human ST3Gal (GenBank AN: L23767) or a homologue thereof, or Xenopus ST3Gal (GenBank AN: CAF22058) or a homologue thereof.

As used herein, a homologue of human ST6Gal refers to a nucleic acid having significant alignment with human ST6Gal (NM_003032). Homologues of human ST6Gal include the enzymes identified by GenBank Accession Nos.: AAH40009.1, CAF29492.1, CAI29584.1, CAA38246.1, CAA75385.1, AAH92222.1, P13721, Q64685, NP_990572.1, XP_535839.1, XP_517005.1, NP_775324.1, XP_516938.1, NP_001003853.1, CAI39643.1, CAI29183.1, CAG32836.1, XP_545243.1, CAF29496.1, XP_416927.1, CAF29497.1, AAB22858.1, NP_671738.1, CAI29184.1, AAB22859.1, BAC24793.1, BAB47506.1, CAF29493.1, XP_515705.1, XP_614392.1, CAF29495.1, XP_236826.2, BAC87752.1, CAI29185.1, CAF97336.1, CAI39644.1, CAD54408.1, CAG05808.1, XP_538436.1, BAC98272.1, XP_604448.1, AAD33059.1, BAC28828.1, BAB00636.1, AAH08680.1, NP_766417.1, EAA04038.2, CAH25390.1, NP_726474.1, and NP_523853.1.

As used herein, a homologue of human ST3Gal refers to a nucleic acid having significant alignment with human ST3Gal (L23767). Homologues of human ST3Gal include the enzymes identified by GenBank Accession Nos.: AAA16460.1, AAM81378.1, AAH10645.1, CAH90316.1, AAM66433.1, CAF25182.1, AAK93790.1, AAM66431.1, CAA52662.1, AAM66432.1, AAF28871.1, NP_976082.1, AAH11121.1, NPO33204.2, AAP22942.1, CAA65076.1, NP_998922.1, NP_991375.1, CAB53395.1, XP_522245.1, AAC14162.1, CAI29182.1, XP_417860.1, AAC14163.1, BAB25732.1, BAB13940.1, CAF22058.1, NP_001003854.1, CAG00953.1, CAI26289.1, XP_546408.1, YP_227525.1, AAH84840.1, CAF25054.1, NP_989810.1, CAF25503.1, Q6 KB54, NP_001002883.1, AAH23312.1, CAH89922.1, CAF25178.1, AAH53179.1, AAO13870.1, AAO13869.1, AAO13867.1, AAO13866.1, AAO13861.1, AAO13859.1, NP_777631.1, and NP_777628.1.

As used herein, a homologue of Xenopus ST3Gal refers to a nucleic acid having significant alignment with Xenopus ST3Gal (CAF22058). Homologues of Xenopus ST3Gal include the enzymes identified by GenBank Accession Nos.: CAF22058.1, CAI29182.1, XP_417860.1, AAH10645.1, AAA16460.1, AAF28871.1, CAH90316.1, CAA52662.1, AAM66433.1, AAM66432.1, AAH11121.1, NP_976082.1, AAP22942.1, NP_033204.2, NP_998922.1, CAF25182.1, NP_991375.1, AAK93790.1, AAM81378.1, CAA65076.1, AAM66431.1, CAB53395.1, AAC14162.1, XP_522245.1, BAB25732.1, NP_001003854.1, AAC14163.1, CAI26289.1, CAG00953.1, YP_227525.1, BAB13940.1, AAH84840.1, CAE51388.1, CAF25181.1, Q6 KB54, NP_001002882.1, AAH23312.1, NP_998924.1, CAH89922.1, AAF18019.1, NP_001002883.1, AAO13870.1, AAO13869.1, AAO13867.1, AAO13866.1, AAO13861.1, AAO13859.1, NP_777631.1, NP_777628.1, and NP_777623.1.

In one embodiment, said enzyme having sialyltransferase activity is obtained using the combinatorial DNA library approach of the invention as described herein. In one embodiment, said enzyme having sialyltransferase activity is a fusion protein. In a preferred embodiment, said fusion protein comprises a sialyltransferase catalytic domain and a cellular targeting signal peptide to target the sialyltransferase activty to the Golgi apparatus of the host cell. In one embodiment, said cellular targeting signal peptide is derived from the Mnn2 (leader 53) gene. More preferably, said cellular targeting signal peptide is encoded by the first 108 bases of Mnn2 (leader 53) from Genbank Accession Number NP_009571.

Host cells may comprise a cellular pool of CMP-sialic acid that may be enhanced. In another embodiment, said host cell lacks an endogenous cellular pool of CMP-sialic acid, and may be modified to express CMP-sialic acid. In another embodiment, said host cell has been modified to express one or more enzyme activities involved in the CMP-Sia pathway. (See Example 16.)

In other embodiments, said host cell may be further modified to express one or more glycosylation enzymes selected from the group consisting of glycosyltransferases, glycosidases such as manosidases, sugar transporters and the like. In yet other embodiments, said host cell may be modified to produce a glycoprotein comprising a terminal galactose. In other embodiments, said host cell may be modified to produce a glycoprotein comprising the $Gal_{(1-4)}GlcNAc_{(1-4)}Man_{(3-5)}GlcNAc_2$. In a preferred embodiment, said host has been modified to produce a complex glycoprotein comprising $Gal_2GlcNAc_2Man_3GlcNAc_2$ or a hybrid glycoprotein comprising $Gal_1GlcNAc_1Man_5GlcNAc_2$.

In other embodiments, the invention provides a method for producing a sialylated glycoprotein in a recombinant non-human eukaryotic host cell comprising introducing into the host a nucleic acid encoding an enzyme having sialyltransferase activity; and further comprising introducing into the host cell one or more additional nucleic acids encoding one or more enzymes involved in the biosynthesis or transport of CMP-Sialic acid.

In other embodiments, the host cell to be used in the methods described herein lacks the activity of one or more enzymes selected from the group consisting of mannosyltransferases and phosphomannosyltransferases. In other embodiments, the host cell to be used in the methods described herein is an OCH1 mutant of *P. pastoris*.

In other embodiments, the host cell to be used in the methods described herein is selected from the group consisting of: any *Pichia* sp., including but not limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis* and *Pichia methanolica*; any *Saccharomyces* sp. including but not limited to *Saccharomyces cerevisiae Hansenula polymorpha*; any *Kluyveromyces* sp. including but not limited to *Kluyveromyces lactis; Candida albicans*; any *Aspergillus* sp. species including but not limited to *Aspergillus nidulans; Aspergillus niger*; and *Aspergillus oryzae; Trichoderma reseei; Chrysosporium lucknowense*; any *Fusarium* sp. including but not limited to *Fusarium gramineum* and *Fusarium venenatum*; and *Neurospora crassa*.

The invention also provides a nucleic acid encoding a fusion protein comprising a sialyltransferase catalytic domain functionally linked to a cellular targeting signal. The invention also provides a host cell comprising said nucleic acid sequence. The invention further provides a non-human eukaryotic host cell comprising said nucleic acid, and further expressing CMP-sialic acid.

The invention further provides non-human host cell genetically engineered to produce a complex glycoprotein comprising $NANA_{(1-4)}Gal_{(1-4)}GlcNAc_{(1-4)}Man_3GlcNAc_2$ or a hybrid glycoprotein comprising $NANAGalGlcNAcMan_5GlcNAc_2$.

The invention also provides a recombinant glycoprotein produced by any one of the methods described herein.

Example 17 illustrates a method of the claimed invention, whereby a sialylated glycoprotein is produced in vivo.
Methods for In Vivo Transfer of Sialic Acid to N-Glycans Using Trans-Sialidase An alternative method for obtaining sialylated proteins in non-human host cells that lack the CMP-Sia pathway is to use a trans-sialidase to transfer sialic acid onto an acceptable substrate glycoprotein. Protozoa, such as *Trypanosoma cruzi*, possess a cell-surface trans-sialidase which transfers sialic acid from host glycoproteins in an α 2,3 linkage to cell surface glycoproteins and glycolipids in a CMP-independent manner (see, e.g., Parodi, 1993, Schenkman, 1994). The gene encoding trans-sialidase contains an amino terminal region with catalytic activity and a C-terminal region with a plasma membrane anchoring domain (Pereira, 1991). *T. cruzi* trans-sialidase expressed in the baculovirus-insect cell system in the presence of sialic acid donors results in the sialylation of exogenous galactosylated acceptors (Marchal, I. 2001). *T. cruzi* trans-sialidase has also been expressed in *P. pastoris* (Laroy, W. 2000) as a means for obtaining high amounts of trans-sialidase for study. Thus, trans-sialidase can be used in host cells (e.g., a fungal host such as *P. pastoris*) engineered herein, to produce recombinant proteins having desirable N-glycan structures, as a means for sialylating glycoproteins with attached oligosaccharides bearing terminal galactose. Trans-sialidases other than that found in *T. cruzi* may be used. Transialidases suitable for use in the present invention are described for example in Colli, 1993. The disclosures of these references are hereby incorporated herein by reference.

Accordingly, the invention provides a method for producing a sialylated glycoprotein in a recombinant eukaryotic host cell comprising the step of introducing into the host a nucleic acid encoding an enzyme having trans-sialidase activity. The enzyme having trans-sialidase activity can be any enzyme having trans-sialidase activity including, but not limited to, *T. cruzi* trans-sialidase (e.g., GenBank Accession Nos. AJ276679, AJ002174), *T. rangeli* trans-sialidase (e.g., GenBank Accession No. L14943); *T. brucei* trans-sialidase (e.g., GenBank Accession No. XM_340626), and *T. carasasii* trans-sialidase (e.g., GenBank Accession No. AY249142, AY14111), or homologues and variants thereof. In one embodiment, said method further comprises supplementing the medium for growing the host cell with a sialic acid donor.

In one embodiment, said enzyme having trans-sialidase activity is a fusion protein. In a preferred embodiment, said enzyme having trans-sialidase activity is a fusion protein comprising a trans-sialidase catalytic domain functionally linked to a cellular targeting signal peptide. In one embodiment said cellular targeting signal peptide is capable of targeting the trans-sialidase activity to the cell wall of the host cell.

In another embodiment, said host cell has been engineered or selected to produce a glycoprotein comprising a terminal galactose. In another embodiment, said host cell has been modified to produce a glycoprotein comprising the structure $Gal_{(1-4)}GlcNAc_{(1-4)}Man_{(2-5)}GlcNAc_2$. In preferred embodiments, said host cell produces a complex glycoprotein comprising $Gal_2GlcNAc_2Man_3GlcNAc_2$ or a hybrid glycoprotein comprising $Gal_1GlcNAc_1Man_5GlcNAc_2$.

The invention provides a method for producing a sialylated glycoprotein in a recombinant eukaryotic host cell comprising introducing into the host a nucleic acid encoding an enzyme having trans-sialidase activity; and further comprising introducing into the host cell one or more additional nucleic acids encoding one or more enzymes selected from the group consisting of glycosyltransferases, glycosidases such as manossidases, sugar transporters, and enzymes involved in the biosynthesis or transport of CMP-Sialic acid.

In one embodiment, said host cell further comprises a sialic acid donor. In one embodiment, a sialic acid donor is added to the medium used to grow the host cell. In other embodiments, one or more precursors to CMP-Sialic acid may be added to the medium. Such CMP-Sia precursors include glucosamine [GlcN]; GlcNAc, UDP-GlcNAc and ManNAc. As described earlier, in other embodiments, said host cell has been adapted to comprise one or more sugar precursors, such as glucosamine or ManNAc, UDP-N-acetylglucosamine, UDP-N-acetylgalactosamine, CMP-N-acetylneuraminic acid, or UDP-galactose.

The invention also provides a method for producing a sialylated glycoprotein in a recombinant non-human eukaryotic host cell comprising introducing into a medium used for growing the host cell an enzyme having a trans-sialidase activity and a sialic acid donor. The sialic acid donor may be CMP-Sia or the presence of sialic acid donor may be increased by the addition of a sugar nucleotide precursor such as CMP-Sia, glucosamine, GlcNAc, UDP-GlcNAc and Man-NAc. In addition, the host cell may be adapted to comprise one or more sugar precursors, such as glucosamine or Man-NAc, UDP-N-acetylglucosamine, UDP-N-acetylgalactosamine, CMP-N-acetylneuraminic acid, or UDP-galactose.

In one embodiment, the host cell to be used in the methods described herein is selected from the group consisting of: Pichia sp., including but limited to: Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis and Pichia methanolica; any Saccharomyces sp including but not limited to Saccharomyces cerevisiae; Hansenula polymorpha; any Kluyveromyces sp. including but not limited to Kluyveromyces lactis; Candida albicans; any Aspergillus sp. including but not limited to Aspergillus nidulans, Aspergillus niger and Aspergillus oryzae; Trichoderma reseei; Chrysosporium lucknowense; any Fusarium sp. including but not limited to Fusarium gramineum and Fusarium venenatum; and Neurospora crassa.

In one embodiment, the host cell to be used in the methods described herein lacks the activity of one or more enzymes selected from the group consisting of mannosyltransferases and phosphomannosyltransferases. In one embodiment, the host cell to be used in the methods described herein is an OCH1 mutant of P. pastoris.

Introduction into a host cell of trans-sialidase activity may also be useful even if a CMP-Sia pathway is endogenous or has been engineered into the host cell. Trans-sialidase activity can increase the yield of secreted sialic acid terminated glycoproteins by transferring sialic acid from a donor protein onto recombinantly produced glycoproteins that did not sialylate within the secretory pathway or which had incomplete sialylation.

Whether a trans-sialidase activity is used alone, or in conjunction with an engineered CMP-Sia pathway and sialyl transferase activity, trans-sialidase may be (1) engineered to reside in the cell wall by fusion with the C-terminal domain of heat shock protein 150 (Mattila, 1996) or to another cell wall anchored protein (Bgl2, CRH1 and SCW19, (Weig, 2004)); (2) fed into the culture medium; or (3) immobilized in a column for use in a chromatography step during protein purification. When the trans-sialidase is fed into the culture medium for growing a host, the trans-sialidase is preferentially bound to a resin for simplified removal during protein purification. When the trans-sialidase is immobilized in a column, the supernatant of the host cell producing a recombinant glycoprotein is passed through the column in the presence of a sialic acid donor to effectuate the in vitro transfer of sialic acid onto the recombinantly produced glycoprotein.

As any strategy to engineer the formation of complex N-glycans into a host cell such as a lower eukaryote involves both the elimination as well as the addition of particular glycosyltransferase activities, a comprehensive scheme will attempt to coordinate both requirements. Genes that encode enzymes that are undesirable serve as potential integration sites for genes that are desirable. For example, 1,6 mannosyltransferase activity is a hallmark of glycosylation in many known lower eukaryotes. The gene encoding alpha-1,6 mannosyltransferase (OCH1) has been cloned from S. cerevisiae and mutations in the gene give rise to a viable phenotype with reduced mannosylation. The gene locus encoding alpha-1,6 mannosyltransferase activity therefore is a prime target for the integration of genes encoding glycosyltransferase activity. In a similar manner, one can choose a range of other chromosomal integration sites that, based on a gene disruption event in that locus, are expected to: (1) improve the cells ability to glycosylate in a more human-like fashion, (2) improve the cells ability to secrete proteins, (3) reduce proteolysis of foreign proteins and (4) improve other characteristics of the process that facilitate purification or the fermentation process itself.

Host Cells

Although the present invention is exemplified using a P. pastoris host organism, it is understood by those skilled in the art that other eukaryotic host cells, including plants, algae, insects and other species of yeast and fungal hosts, may be altered as described herein to produce human-like glycoproteins. The techniques described herein for identification and disruption of undesirable host cell glycosylation genes, e.g. OCH1, is understood to be applicable for these and/or other homologous or functionally related genes in other eukaryotic host cells such as other yeast and fungal strains. Preferably, robust protein production strains of fungal hosts that are capable of performing well in an industrial fermentation process are selected. These strains include, without limitation: any Pichia sp. including but limited to: Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis and Pichia methanolica; any Saccharomyces sp. including but not limited to Saccharomyces cerevisiae; Hansenula polymorpha; any Kluyveromyces sp. including but not limited to Kluyveromyces lactis; Candida albicans; any Aspergillus sp. including but not limited to Aspergillus nidulans, Aspergillus niger, and Aspergillus oryzae; Trichoderma reseei; Chrysosporium lucknowense; any Fusarium sp. including but not limited to Fusarium gramineum and Fusarium venenatum; and Neurospora crassa.

Another aspect of the present invention thus relates to a non-human eukaryotic host strain expressing glycoproteins comprising modified N-glycans that resemble those made by human-cells. Performing the methods of the invention in species other than yeast and fungal cells is thus contemplated and encompassed by this invention. It is contemplated that a combinatorial nucleic acid library of the present invention may be used to select constructs that modify the glycosylation pathway in any eukaryotic host cell system. For example, the combinatorial libraries of the invention may also be used in plants, algae and insects, and in other eukaryotic host cells, including mammalian and human cells, to localize proteins, including glycosylation enzymes or catalytic domains thereof, in a desired location along a host cell secretory pathway. Preferably, glycosylation enzymes or catalytic domains and the like are targeted to a subcellular location along the host cell secretory pathway where they are capable of functioning, and preferably, where they are designed or selected to function most efficiently.

As described in Examples 19 and 20, plant and insect cells may be engineered to alter the glycosylation of expressed proteins using the combinatorial library and methods of the invention. Furthermore, glycosylation in mammalian cells, including human cells, may also be modified using the combinatorial library and methods of the invention. It may be possible, for example, to optimize a particular enzymatic activity or to otherwise modify the relative proportions of various N-glycans made in a mammalian host cell using the combinatorial library and methods of the invention.

Examples of modifications to glycosylation which can be affected using a method according to this embodiment of the invention are: (1) engineering a eukaryotic host cell to trim mannose residues from $Man_8GlcNAc_2$ to yield a $Man_5GlcNAc_2$ N-glycan; (2) engineering eukaryotic host cell to add an N-acetylglucosamine (GlcNAc) residue to Man$_5$GlcNAc$_2$ by action of GlcNAc transferase I; (3) engineering a eukaryotic host cell to functionally express an enzyme such as an N-acetylglucosaminyl Transferase (GnTI, GnTII, GnTIII, GnTIV, GnTV, GnTVI), mannosidase II, fucosyltransferase (FT), galactosyl tranferase (GalT) or a sialyltransferase (ST); (4) an engineering or CMP-Sia pathway.

The invention also provides a host cell which lacks (or lacks an efficient) endogenous CMP-Sia biosynthetic pathway and which expresses a functional recombinant CMP-Sia biosynthetic pathway. Preferably, the host produces a cellular pool of CMP-Sia that may be used as a donor molecule in the presence of a sialyltransferase and a glycan acceptor (e.g., Gal$_2$GlcNAc$_2$Man$_3$GlcNAc$_2$) in a sialylation reaction. Using the methods of the invention, a variety of different hosts producing CMP-Sia may be generated.

By repeating the method, increasingly complex glycosylation pathways can be engineered into a target host, such as a lower eukaryotic microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

Target Glycoproteins and Glycoprotein Compositions

The methods described herein are useful for producing glycoproteins, especially glycoproteins used therapeutically in humans, as well as compositions comprising such glycoproteins. Glycoproteins having specific glycoforms may be especially useful, for example, in the targeting of therapeutic proteins. Glycoprotein compositions of the present invention will comprise predominantly a specific glycoform. For example, mannose-6-phosphate has been shown to direct proteins to the lysosome, which may be essential for the proper function of several enzymes related to lysosomal storage disorders such as Gaucher's, Hunter's, Hurler's, Scheie's, Fabry's and Tay-Sachs disease, to mention just a few. Likewise, the addition of one or more sialic acid residues to a glycan side chain may increase the lifetime of a therapeutic glycoprotein in vivo after administration. Accordingly, host cells (e.g., lower eukaryotic or mammalian) may be genetically engineered to increase the extent of terminal sialic acid in glycoproteins expressed in the cells. Alternatively, sialic acid may be conjugated to the protein of interest in vitro prior to administration using a sialic acid transferase and an appropriate substrate. Changes in growth medium composition may be employed in addition to the expression of enzyme activities involved in human-like glycosylation to produce glycoproteins more closely resembling human forms (Weikert, 1999; Werner, 1998; Andersen, 1994; Yang, 2000). Specific glycan modifications to monoclonal antibodies (e.g. the addition of a bisecting GlcNAc) have been shown to improve antibody dependent cell cytotoxicity (Umana, 1999), which may be desirable for the production of antibodies or other therapeutic proteins.

Therapeutic proteins are typically administered by injection, orally, pulmonary, or other means. Examples of suitable target glycoproteins which may be produced according to the invention include, without limitation: erythropoietin, cytokines such as interferon-α, interferon-β, interferon-γ, interferon-ω, TNFα and granulocyte-CSF, coagulation factors such as factor VIII, factor IX, and human protein C, antithrombin III and thrombopoietin soluble IgE receptor α-chain, IgG, IgG fragments, IgM, interleukins such as IL-1ra, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-proteins, AAT, rhTBP-1 (onercept, aka TNF Binding protein 1), TACI-Ig (transmembrane activator and calcium modulator and cyclophilin ligand interactor), FSH (follicle stimulating hormone), GM-CSF, GLP-1 w/ and w/o FC (glucagon like protein 1) IL-1 receptor agonist, sTNFr (enbrel, aka soluble TNF receptor Fc fusion) ATIII, rhThrombin, glucocerebrosidase and CTLA4-Ig (Cytotoxic T Lymphocyte associated Antigen 4-Ig)

The following are examples which illustrate the compositions and methods of this invention. These examples should not be construed as limiting: the examples are included for the purposes of illustration only. For example, while the examples illustrate embodiments of the compositions and methods of this invention relating to complex glycoproteins, one skilled in the art will recognize that the methods and compositions illustrated in the examples may be adapted to compositions and methods relating to hybrid glycoproteins, as described earlier herein.

EXAMPLE 1

Cloning and Disruption of the OCH1 Gene In *P. pastoria*

Generation of an OCH1 Mutant of *P. pastoris*

A 1215 bp ORF of the *P. pastoris* OCH1 gene encoding a putative α-1,6 mannosyltransferase was amplified from *P. pastoris* genomic DNA (strain X-33, Invitrogen, Carlsbad, Calif.) using the oligonucleotides 5'-ATGGCGAAGGCA-GATGGCAGT-3' (SEQ ID NO:7) and 5'-TTAGTCCTTC-CAACTTCCTTC-3' (SEQ ID NO:8) which were designed based on the *P. pastoris* OCH1 sequence (Japanese Patent Application Publication No. 8-336387). Subsequently, 2685 bp upstream and 1175 bp downstream of the ORF of the OCH1 gene were amplified from a *P. pastoris* genomic DNA library (Boehm, 1999) using the internal oligonucleotides 5'-ACTGCCATCTGCCTTCGCCAT-3' (SEQ ID NO:9) in the OCH1 gene, and 5'-GTAATACGACTCACTATAGGGC-3' T7 (SEQ ID NO:10) and 5'-AATTAACCCTCAC-TAAAGGG-3' T3 (SEQ ID NO:11) oligonucleotides in the backbone of the library bearing plasmid lambda ZAP II (Stratagene, La Jolla, Calif.). The resulting 5075 bp fragment was cloned into the pCR2.1-TOPO vector (Invitrogen, Carlsbad, Calif.) and designated pBK9.

After assembling a gene knockout construct that substituted the OCH1 reading frame with a HIS4 resistance gene, *P. pastoris* was transformed and colonies were screened for temperature sensitivity at 37° C. OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. About 20 temperature sensitive strains were further subjected to a colony PCR screen to identify colonies with a deleted och1 gene. Several och1 deletions were obtained.

The linearized pBK9.1, which has 2.1 kb upstream sequence and 1.5 kb down stream sequence of OCH1 gene cassette carrying *Pichia* HIS4 gene, was transformed into *P. pastoris* BK1 [GS115 (his4 Invitrogen Corp., San Diego, Calif.) carrying the human IFN-β gene in the AOX1 locus] to knock out the wild-type OCH1 gene. The initial screening of transformants was performed using histidine drop-out medium followed by replica plating to select the temperature sensitive colonies. Twenty out of two hundred histidine-positive colonies showed a temperature sensitive phenotype at 37° C. To exclude random integration of pBK9.1 into the *Pichia* genome, the 20 temperature-sensitive isolates were subjected to colony PCR using primers specific to the upstream sequence of the integration site and to HIS4 ORF. Two out of twenty colonies were och1 defective and further analyzed using a Southern blot and a Western blot indicating the functional och1 disruption by the och1 knock-out construct. Genomic DNA were digested using two separate restriction enzymes BglII and ClaI to confirm the och1 knock-out and to confirm integration at the open reading frame. The Western Blot showed och1 mutants lacking a discrete band produced in the GS115 wild type at 46.2 kDa.

EXAMPLE 2

Engineering of *P. Pastoris* with α-1,2-Mannosidase to Produce $Man_5GlcNAc_2$-Containing IFN-β Precursors An α-1,2-mannosidase is required for the trimming of $Man_6GlcNAc_2$ to yield $Man_5GlcNAc_2$, an essential intermediate for complex N-glycan formation. While the production of a $Man_5GlcNAc_2$ precursor is essential, it is not necessarily sufficient for the production of hybrid and complex glycans because the specific isomer of $Man_5GlcNAc_2$ may or may not be a substrate for GnTI. An och1 mutant of *P. pastoris* is engineered to express secreted human interferon-β under the control of an aox promoter. A DNA library is constructed by the in-frame ligation of the catalytic domain of human mannosidase IB (an α-1,2-mannosidase) with a sub-library including sequences encoding early Golgi and ER localization peptides. The DNA library is then transformed into the host organism, resulting in a genetically mixed population wherein individual transformants each express interferon-β as well as a synthetic mannosidase gene from the library. Individual transformant colonies are cultured and the production of interferon is induced by addition of methanol. Under these conditions, over 90% of the secreted protein is glycosylated interferon-β.

Supernatants are purified to remove salts and low-molecular weight contaminants by $C_{18}$ silica reversed-phase chromatography. Desired transformants expressing appropriately targeted, active α-1,2-mannosidase produce interferon-β including N-glycans of the structure $Man_5GlcNAc_2$, which has a reduced molecular mass compared to the interferon-β of the parent strain. The purified interferon-β is analyzed by MALDI-TOF mass spectroscopy and colonies expressing the desired form of interferon-β are identified.

EXAMPLE 3

Generation of an och1 Mutant Strain Expressing an α-1,2-Mannosidase, GnTI and GnTII for Production of a Human-Like Glycoprotein The 1215 bp open reading frame of the *P. pastoris* OCH1 gene as well as 2685 bp upstream and 1175 bp downstream was amplified by PCR (see also WO 02/00879), cloned into the pCR2.1-TOPO vector (Invitrogen) and designated pBK9. To create an och1 knockout strain containing multiple auxotrophic markers, 100 μg of pJN329, a plasmid containing an och1::URA3 mutant allele flanked with SfiI restriction sites was digested with SfiI and used to transform *P. pastoris* strain JC308 (Cereghino et al. *Gene* 263 (2001) 159-169) by electroporation. Following incubation on defined medium lacking uracil for 10 days at room temperature, 1000 colonies were picked and re-streaked. $URA^+$ clones that were unable to grow at 37° C., but grew at room temperature, were subjected to colony PCR to test for the correct integration of the och1::URA3 mutant allele. One clone that exhibited the expected PCR pattern was designated YJN153. The Kringle 3 domain of human plasminogen (K3) was used as a model protein. A $Neo^R$ marked plasmid containing the K3 gene was transformed into strain YJN153 and a resulting strain, expressing K3, was named BK64-1.

Plasmid pPB103, containing the *Kluyveromyces* lactic MNN2-2 gene which encodes a Golgi UDP-N-acetylglucosamine transporter was constructed by cloning a blunt BglII-HindIII fragment from vector pDL02 (Abeijon et al. (1996) Proc. Natl. Acad. Sci. U.S.A. 93:5963-5968) into BglII and BamHI digested and blunt ended pBLADE-SX containing the *P. pastoris* ADE1 gene (Cereghino et al. (2001) *Gene* 263:159-169). This plasmid was linearized with EcoNI and transformed into strain BK64-1 by electroporation and one strain confirmed to contain the MNN2-2 by PCR analysis was named PBP1.

A library of mannosidase constructs was generated, comprising in-frame fusions of the leader domains of several type I or type II membrane proteins from *S. cerevisiae* and *P. pastoris* fused with the catalytic domains of several α-1,2-mannosidase genes from human, mouse, fly, worm and yeast sources (see, e.g., WO02/00879, incorporated herein by reference). This library was created in a *P. pastoris* HIS4 integration vector and screened by linearizing with SalI, transforming by electroporation into strain PBP1, and analyzing the glycans released from the K3 reporter protein. One active construct chosen was a chimera of the 988-1296 nucleotides (C-terminus) of the yeast SEC12 gene fused with a N-terminal deletion of the mouse α-1,2-mannosidase IA gene (FIG. 3), which was missing the 187 nucleotides. A *P. pastoris* strain expressing this construct was named PBP2.

A library of GnTI constructs was generated, comprising in-frame fusions of the same leader library with the catalytic domains of GnTI genes from human, worm, frog and fly sources (WO 02/00879). This library was created in a *P. pastoris* ARG4 integration vector and screened by linearizing with AatII, transforming by electroporation into strain PBP2, and analyzing the glycans released from K3. One active construct chosen was a chimera of the first 120 bp of the *S. cerevisiae* MNN9 gene fused to a deletion of the human GnTI gene, which was missing the first 154 bp. A *P. pastoris* strain expressing this construct was named PBP3.

A library of GnTII constructs was generated, which comprised in-frame fusions of the leader library with the catalytic domains of GnTII genes from human and rat sources (WO 02/00879). This library was created in a *P. pastoris* integration vector containing the $NST^R$ gene conferring resistance to the drug nourseothricin. The library plasmids were linearized with EcoRI, transformed into strain RDP27 by electroporation, and the resulting strains were screened by analysis of the released glycans from purified K3.

Materials for the Following Reactions

MOPS, sodium cacodylate, manganese chloride, UDP-galactose and CMP-N-acetylneuraminic acid were from Sigma. Trifluoroacetic acid (TFA) was from Sigma/Aldrich, Saint Louis, Mo. Recombinant rat α2,6-sialyltransferase from *Spodoptera frugiperda* and β1,4-galactosyltransferase from bovine milk were from Calbiochem (San Diego, Calif.). Protein N-glycosidase F, mannosidases, and oligosaccharides were from Glyko (San Rafael, Calif.). DEAE ToyoPearl resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wis.).

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (4) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media is diluted 3:2, media/PBS (60 mM PO4, 16 mM KCl, 822 mM NaCl pH7.4) and loaded onto the columns. After draining, the columns are washed with 10 volumes of binding buffer and 6 volumes of wash buffer (30 mM imidazole, 0.5M NaCl, 20 mM Tris-HCl pH7.9) and the protein is eluted with 6 volumes of elution buffer (1M imidazole, 0.5M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, 1998). The wells of a 96-well MultiScreen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM $NH_4HCO_3$ pH 8.3 containing one milliunit of N-glycanase (Glyko). After 16 hours at 37° C., the solution containing the glycans was removed by centrifugation and evaporated to dryness.

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875 Da. Spectra were generated from the sum of 100-200 laser pulses and acquired with a 2 GHz digitizer. $Man_5GlcNAc_2$ oligosaccharide was used as an external molecular weight standard.

All spectra were generated with the instrument in the positive ion mode. The estimated mass accuracy of the spectra was 0.5%.

EXAMPLE 4

Engineering a Strain to Produce Galactosyltransferase

Galactosyltransferase Reaction

Approximately 2 mg of protein (r-K3:hPg [PBP6-5]) was purified by nickel-affinity chromatography, extensively dialyzed against 0.1% TFA, and lyophilized to dryness. The protein was redissolved in 150 μL of 50 mM MOPS, 20 mM MnCl2, pH7.4. After addition of 32.5 μg (533 nmol) of UDP-galactose and 4 mU of β 1,4-galactosyltransferase, the sample was incubated at 37° C. for 18 hours. The samples were then dialyzed against 0.1% TFA for analysis by MALDI-TOF mass spectrometry.

The spectrum of the protein reacted with galactosyltransferase showed an increase in mass consistent with the addition of two galactose moieties when compared with the spectrum of a similar protein sample incubated without enzyme. Protein samples were next reduced, carboxymethylated and deglycosylated with PNGase F. The recovered N-glycans were analyzed by MALDI-TOF mass spectrometry. The mass of the predominant glycan from the galactosyltransferase reacted protein was greater than that of the control glycan by a mass consistent with the addition of two galactose moieties (325.4 Da).

Bobrowicz et al. (2004), which is incorporated by reference herein, discloses engineering a strain of *P. pastoris* capable of producing glycoproteins containing terminal galactose. This strain expressed a β1, 4GalT, a UDP galactose transporter and UDP-galactose-4-epimerase using the methods of the invention, as disclosed herein. See also the disclosure of Davidson, U.S. Ser. No. 11/108,088, filed on Apr. 15, 2005, the disclosure of which is hereby incorporated by reference herein.

EXAMPLE 5

Engineering a Strain to Express Functional and Active Mannosidase II

To generate a human-like glycoform, a microorganism is engineered to express a mannosidase II enzyme which removes the two remaining terminal mannoses from the structure $GlcNAcMan_5GlcNAc_2$ (see FIG. 1B). A DNA library including sequences encoding cis and medial Golgi localization signals is fused in-frame to a library encoding mannosidase II catalytic domains. The host organism is a strain, e.g. a yeast, that is deficient in hypermannosylation (e.g. an och1 mutant) and provides N-glycans having the structure $GlcNAcMan_5GlcNAc_2$ in the Golgi and/or ER. After transformation, organisms having the desired glycosylation phenotype are selected. An in vitro assay is used in one method. The desired structure $GlcNAcMan_3GlcNAc_2$ (but not the undesired $GlcNAcMan_5GlcNAc_2$) is a substrate for the enzyme GlcNAc Transferase II (see FIG. 1B). Accordingly, single colonies may be assayed using this enzyme in vitro in the presence of the substrate, UDP-GlcNAc. The release of UDP is determined either by HPLC or an enzymatic assay for UDP. Alternatively, radioactively labeled UDP-GlcNAc or MALDI-TOF may be used. See Davidson et al., WO05/00584, the disclosure of which is hereby incorporated by reference.

The foregoing in vitro assays are conveniently performed on individual colonies using high-throughput screening equipment. Alternatively a lectin binding assay is used. In this case the reduced binding of lectins specific for terminal mannoses allows the selection of transformants having the desired phenotype. For example, *Galantus nivalis* lectin binds specifically to terminal α-1,3-mannose, the concentration of which is reduced in the presence of operatively expressed mannosidase II activity. In one suitable method, *G. nivalis* lectin attached to a solid agarose support (available from Sigma Chemical, St. Louis, Mo.) is used to deplete the transformed population of cells having high levels of terminal α-1,3-mannose.

EXAMPLE 6

Engineering a Strain to Express Sialyltransferase

The enzymes α2,3-sialyltransferase and α2,6-sialyltransferase add terminal sialic acid to galactose residues in nascent human N-glycans, leading to mature glycoproteins (see "α 2,3 ST; α2,6 ST" in FIG. 1B). In human cells, the reactions occur in the trans Golgi or TGN. Accordingly, a DNA library is constructed by the in-frame fusion of sequences encoding sialyltransferase catalytic domains with sequences encoding trans Golgi or TGN localization signals (Malissard, 2000; Borsig, 1995). The host organism is a strain, e.g. a yeast, that is deficient in hypermannosylation (e.g., an och1 mutant), which provides N-glycans having terminal galactose residues in the late Golgi or TGN, and provides a sufficient concentration of CMP-sialic acid in the late Golgi or TGN. Following transformation, transformants having the desired phenotype are selected, e.g., using a fluorescent antibody specific for N-glycans having a terminal sialic acid. In addition, the strains are engineered to produce the CMP-NANA precursors as described in Example 16.

Example 17 further illustrates the engineering of a strain that expresses α2,6 ST and CMP-Sia and is able to produce glycoproteins comprising the $NANA_2Gal_2GlcNAc_2Man_3GlcNAc_2$ glycoform.

Sialyltransferase Reaction

After resuspending the (galactosyltransferase reacted) (Example 4) proteins in 10 µL of 50 mM sodium cacodylate buffer pH6.0, 300 µg (488 nmol) of CMP-N-acetylneuraminic acid (CMP-NANA) dissolved in 15 µL of the same buffer, and 5 µL (2 mU) of recombinant α2,6 sialyltransferase were added. After incubation at 37° C. for 15 hours, an additional 200 µs of CMP-NANA and 1 mU of sialyltransferase were added. The protein samples were incubated for an additional 8 hours and then dialyzed and analyzed by MALDI-TOF-MS as above. The spectrum of the glycoprotein reacted with sialyltransferase showed an increase in mass when compared with that of the starting material (the protein after galactosyltransferase reaction). The N-glycans were released and analyzed as above. The increase in mass of the two ion-adducts of the predominant glycan was consistent with the addition of two sialic acid residues (580 and 583 Da).

EXAMPLE 7

Engineering a Strain to Express UDP-GlcNAc Transporter

Figure 10A:
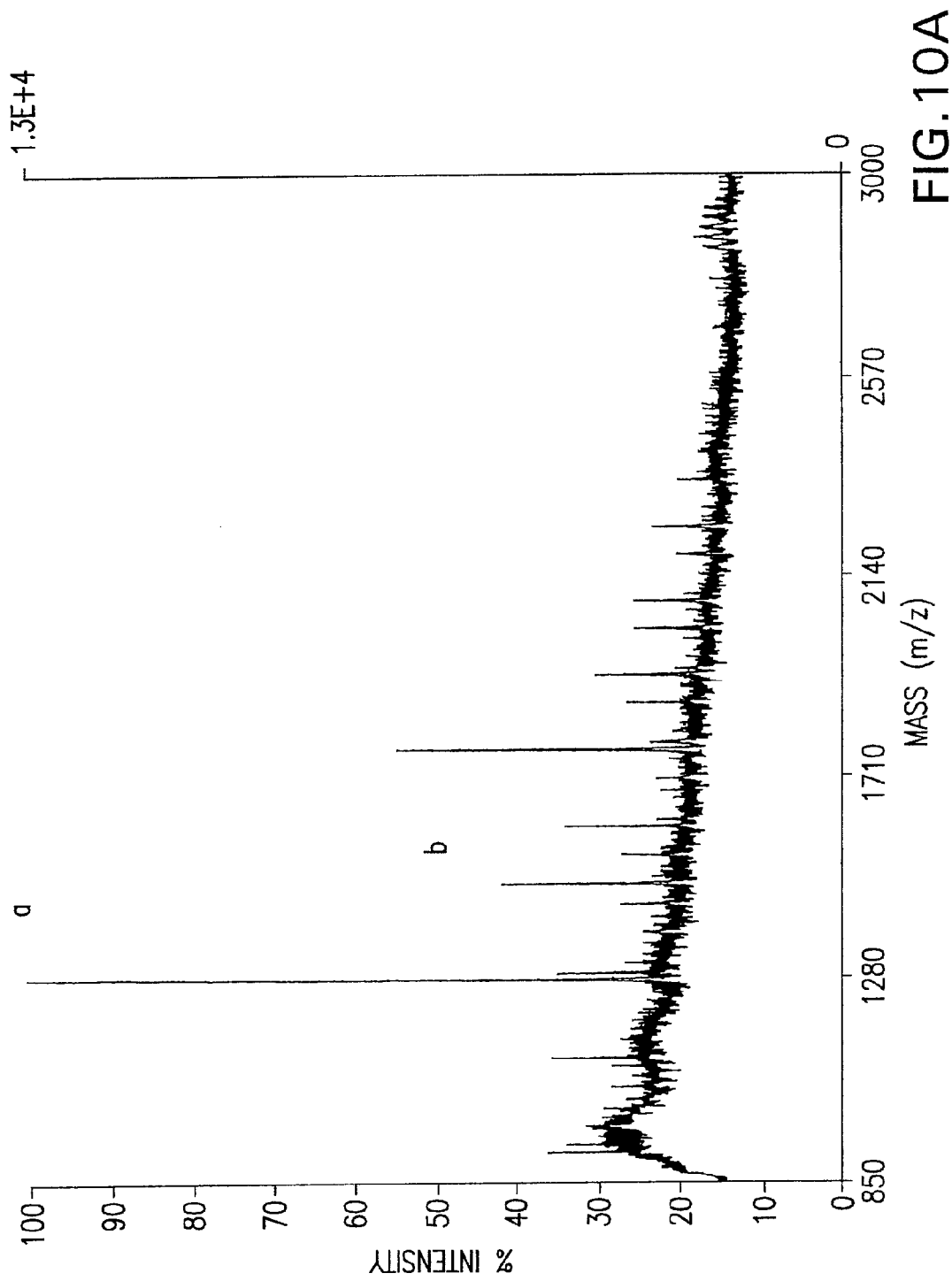

The cDNA of human Golgi UDP-GlcNAc transporter has been cloned by Ishida and coworkers. (Ishida, N., et al. 1999 *J. Biochem.* 126(1): 68-77). Guillen and coworkers have cloned the canine kidney Golgi UDP-GlcNAc transporter by phenotypic correction of a *Kluyveromyces lactis* mutant deficient in Golgi UDP-GlcNAc transport. (Guillen, E., et al. 1998). Thus a mammalian Golgi UDP-GlcNAc transporter gene has all of the necessary information for the protein to be expressed and targeted functionally to the Golgi apparatus of yeast. These or other cloned transporter genes may be engineered into a host organism to provide UDP-GlcNAc substrates for efficient GnT reactions in the Golgi and/or ER of the host. FIG. 10B demonstrates the effect of a strain expressing a *K. lactis* UDP-GlcNAc transporter. In comparison to FIG. 10A, which lacks a UDP-GlcNAc transporter, the effect of adding a UDP-GlcNAc transporter shows a dramatic increase in the production of $GlcNAcMan_5GlcNAc_2$.

EXAMPLE 8

Engineering a Strain to Express GDP-Fucose Transporter

The rat liver Golgi membrane GDP-fucose transporter has been identified and purified by Puglielli, L. and C. B. Hirschberg 1999 *J. Biol. Chem.* 274(50):35596-35600. The corresponding gene can be identified using standard techniques, such as N-terminal sequencing and Southern blotting using a degenerate DNA probe. The intact gene is then expressed in a host microorganism that also expresses a fucosyltransferase.

EXAMPLE 9

Engineering a Strain to Express UDP-Galactose Transporter

Human UDP-galactose (UDP-Gal) transporter has been cloned and shown to be active in *S. cerevisiae*. (Kainuma, M., et al. 1999 Glycobiology 9(2): 133-141). A second human UDP-galactose transporter (hUGT1) has been cloned and functionally expressed in Chinese Hamster Ovary Cells. Aoki, K., et al. 1999 *J. Biochem.* 126(5): 940-950. Likewise, Segawa and coworkers have cloned a UDP-galactose transporter from *Schizosaccharomyces pombe* (Segawa, H., et al. 1999 *Febs Letters* 451(3): 295-298). These or other sequences encoding UDP-galactose transporter activities may be introduced into a host cell directly or may be used as a component of a sub-library of the invention to engineer a strain having increased UDP-galactose transporter activity.

EXAMPLE 10

Engineering a Strain to Express CMP-Sialic Acid Transporter

Human CMP-sialic acid transporter (hCST) has been cloned and expressed in Lec 8 CHO cells by Aoki and coworkers (1999). Molecular cloning of the hamster CMP-sialic acid transporter has also been achieved (Eckhardt, 1997). The functional expression of the murine CMP-sialic acid transporter was achieved in *Saccharomyces cerevisiae* by Berninsone, 1997. These or other sequences encoding CMP-sialic acid transporter activities may be introduced into a host cell directly or may be used as a component of a sub-library of the invention to engineer a strain having increased CMP-sialic acid transporter activity.

EXAMPLE 11

Engineering of P. pastoris to Produce Man$_5$GlcNA$_2$ as the Predominant N-Glycan Structure Using a Combinatorial DNA Library An och1 mutant of P. pastoris (see Examples 1 and 3) was engineered to express and secrete proteins such as the kringle 3 domain of human plasminogen (K3) under the control of the inducible AOXI promoter. The Kringle 3 domain of human plasminogen (K3) was used as a model protein. A DNA fragment encoding the K3 was amplified using Pfu turbo polymerase (Strategene, La Jolla, Calif.) and cloned into EcoRI and XbaI sites of pPICZaA (Invitrogen, Carlsbad, Calif.), resulting in a C-terminal 6-His tag. In order to improve the N-linked glycosylation efficiency of K3 (Hayes, 1975), Pro$_{46}$ was replaced with Ser$_{46}$ using site-directed mutagenesis. The resulting plasmid was designated pBK64. The correct sequence of the PCR construct was confirmed by DNA sequencing.

A combinatorial DNA library was constructed by the in-frame ligation of murine α-1,2-mannosidase IB (Genbank: 6678787) and IA (Genbank: 6754619) catalytic domains with a sub-library including sequences encoding Cop II vesicle, ER, and early Golgi localization peptides according to Table 6. The combined DNA library was used to generate individual fusion constructs, which were then transformed into the K3 expressing host organism, resulting in a genetically mixed population wherein individual transformants each express K3 as well as a localization signal/mannosidase fusion gene from the library. Individual transformants were cultured and the production of K3 was induced by transfer to a methanol containing medium. Under these conditions, after 24 hours of induction, over 90% of the protein in the medium was K3. The K3 reporter protein was purified from the supernatant to remove salts and low-molecular weight contaminants by Ni-affinity chromatography. Following affinity purification, the protein was desalted by size exclusion chromatography on a Sephadex G10 resin (Sigma, St. Louis, Mo.) and either directly subjected to MALDI-TOF analysis described below or the N-glycans were removed by PNGase digestion as described below (Release of N-glycans) and subjected to MALDI-TOF analysis (Miele, 1997).

Following this approach, a diverse set of transformants were obtained; some showed no modification of the N-glycans compared to the och1 knockout strain; and others showed a high degree of mannose trimming (FIG. 5D, 5E). Desired transformants expressing appropriately targeted, active α-1,2-mannosidase produced K3 with N-glycans of the structure Man$_5$GlcNAc$_2$. This confers a reduced molecular mass to the glycoprotein compared to the K3 of the parent och1 deletion strain, a difference which was readily detected by MALDI-TOF mass spectrometry (FIG. 5). Table 7 indicates the relative Man$_5$GlcNAc$_2$ production levels.

TABLE 7

A Representative Combinatorial DNA Library Of Sequences/Catalytic Domains Localization Exhibiting Relative Levels Of Man$_5$GlcNAc$_2$ Production.

| Catalytic Domains | Targeting peptide sequences | | | | |
|---|---|---|---|---|---|
| | MNS1(s) | MNS1(m) | MNS1(l) | SEC12(s) | SEC12(m) |
| Mouse mannosidase 1A Δ187 | FB4 ++ | FB5 + | FB6 − | FB7 ++ | FB8 ++++ |
| Mouse mannosidase 1B Δ58 | GB4 ++ | GB5 + | GB6 + | GB7 ++ | GB8 + |
| Mouse mannosidase 1B Δ99 | GC4 − | GC5 +++ | GC6 + | GC7 + | GC8 + |
| Mouse mannosidase 1B Δ170 | GD4 − | GD5 − | GD6 − | GD7 + | GD8 + |

TABLE 8

Another Combinatorial DNA Library Of Localization Exhibiting Sequences/Catalytic Domains Relative Levels Of Man$_5$GlcNAc$_2$ Production.

| Catalytic Domains | Targeting peptide sequences | | | | | |
|---|---|---|---|---|---|---|
| | VAN1(s) | VAN1(m) | VAN1(l) | MNN10(s) | MNN10(m) | MNN10(l) |
| C. elegans mannosidase 1B Δ80 | BC18-5 +++++ | BC19 ++++ | BC20 +++ | BC27 +++++ | BC28 +++++ | BC29 +++ |
| C. elegans mannosidase 1B Δ31 | BB18 +++++ | BB19 +++++ | BB20 ++++ | BB18 +++++ | BB19 +++++ | BB20 ++++ |

Targeting peptides were selected from MNS I (SwissProt P32906) in S. cerevisiae (long, medium and short) (see supra Nucleic Acid Libraries; Combinatorial DNA Library of Fusion Constructs) and SEC12 (SwissProt P11655) in S. cerevisiae (988-1140 nucleotides: short) and (988-1296: medium). Although majority of the targeting peptide sequences were N-terminal deletions, some targeting peptide sequences, such as SEC12 were C-terminal deletions. Catalytic domains used in this experiment were selected from mouse mannosidase 1A with a 187 amino acid N-terminal deletion; and mouse mannosidase 1B with a 58, 99 and 170 amino acid deletion. The number of (+)s, as used herein, indicates the relative levels of Man$_5$GlcNA$_2$ production. The notation (−) indicates no apparent production of Man$_5$GlcNAc$_2$. The notation (+) indicates less than 10% production of Man$_5$GlcNAc$_2$. The notation (++) indicates about 10-20% production of Man$_5$GlcNA$_2$. The notation with (+++)

indicates about 20-40% production of $Man_5GlcNA_2$. The notation with (++++) indicates about 50% production of $Man_5GlcNA_2$. The notation with (+++++) indicates greater than 50% production of $Man_5GlcNA_2$.

Table 9 shows relative amount of $Man_5GlcNAc_2$ on secreted K3. Six hundred and eight (608) different strains of *P. pastoris*, Δoch1 were generated by transforming them with a single construct of a combinatorial genetic library that was generated by fusing nineteen (19) α-1,2 mannosidase catalytic domains to thirty-two (32) fungal ER, and cis-Golgi leaders.

TABLE 9

Amount of $Man_5GlcNAc_2$ on secreted K3

| (% of total glycans) | Number of constructs (%) |
|---|---|
| N.D.* | 19 (3.1) |
| 0-10% | 341 (56.1) |
| 10-20% | 50 (8.2) |
| 20-40& | 75 (12.3) |
| 40-60% | 72 (11.8) |
| More than 60% | 51 (8.4)† |
| Total | 608 (100) |

*Several fusion constructs were not tested because the corresponding plasmids could not be propagated in *E. coli* prior to transformation into *P. pastoris*.
†Clones with the highest degree of $Man_5GlcNAc_2$ trimming (30/51) were further analyzed for mannosidase activity in the supernatant of the medium. The majority (28/30) displayed detectable mannosidase activity in the supernatant (e.g. FIG. 4B).

Figure 4A:
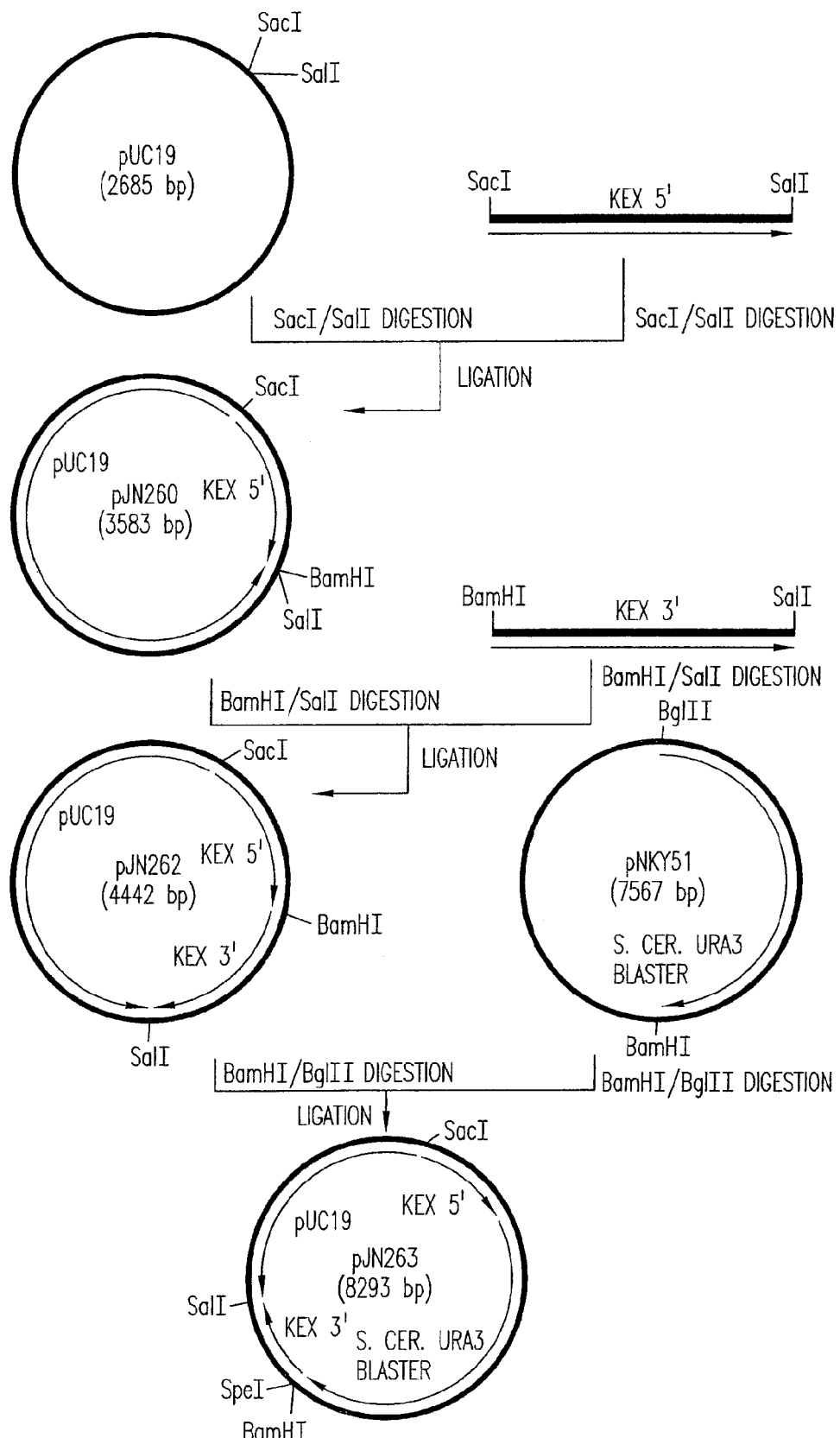
FIGS. 4A-4F illustrates engineering of vectors with multiple auxotrophic markers and genetic integration of target proteins in the *P. pastoris* OCH1 locus.
Figure 4B:
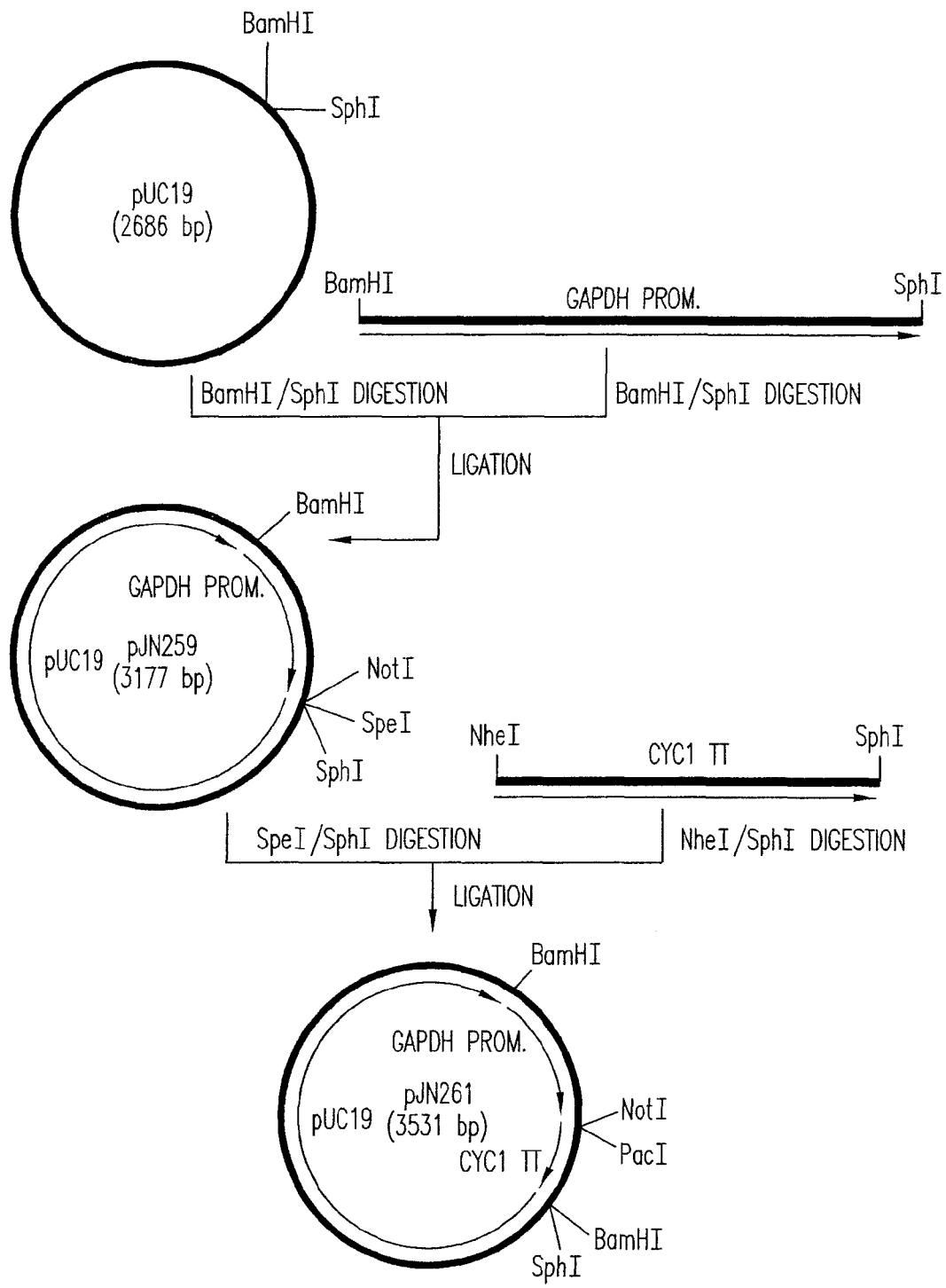
Figure 4C:
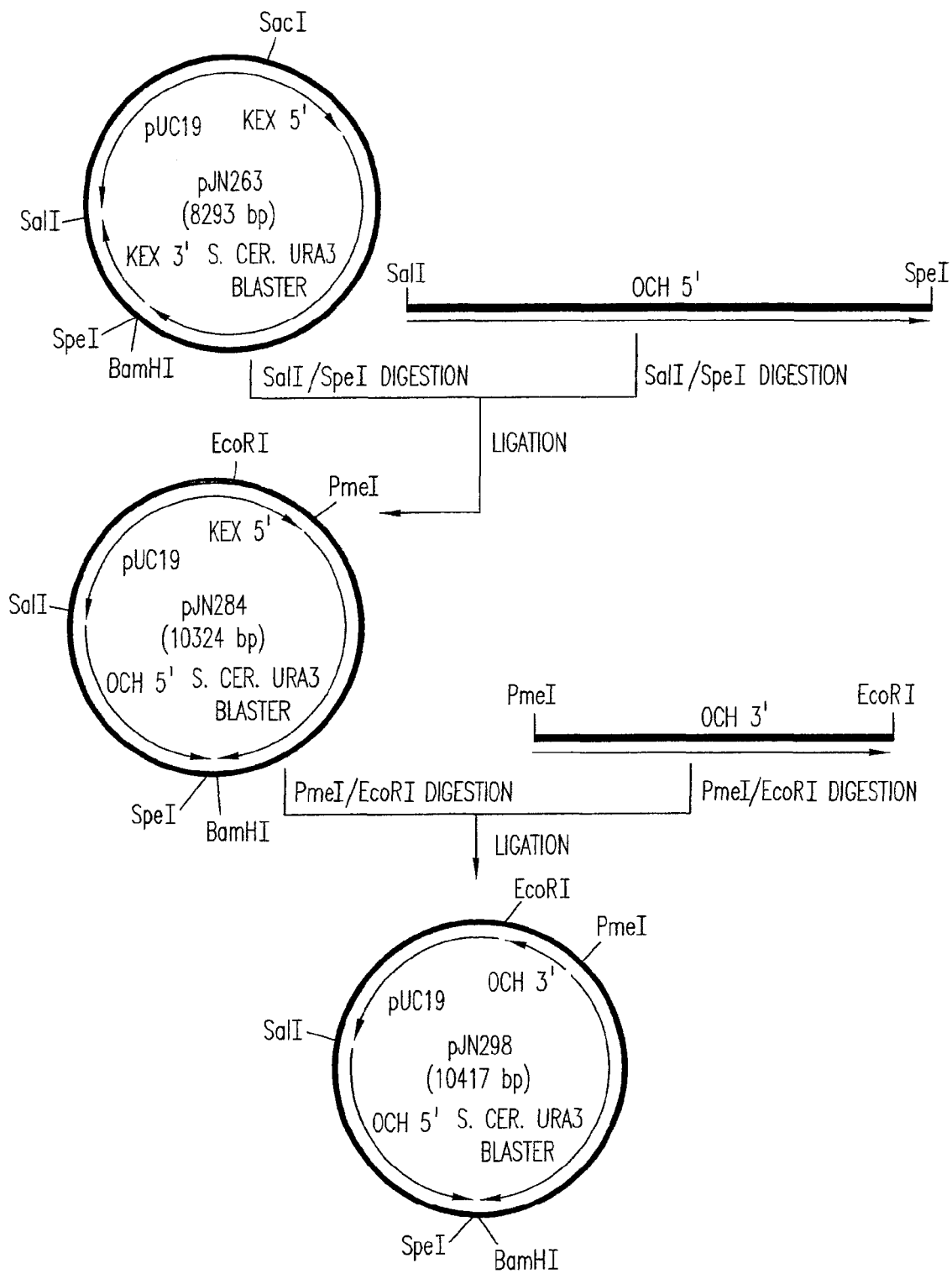

Only two constructs displayed high $Man_5GlcNAc_2$ levels, while lacking mannosidase activity in the medium (e.g. FIG. 4C).

Table 7 shows two constructs pFB8 and pGC5, among others, displaying $Man_5GlcNA_2$. Table 8 shows a more preferred construct, pBC18-5, a *S. cerevisiae* VAN1(s) targeting peptide sequence (from SwissProt 23642) ligated in-frame to a *C. elegans* mannosidase IB (Genbank AN: CAA98114) 80 amino acid N-terminal deletion (*Saccharomyces* Van1(s)/*C. elegans* mannosidase IB Δ80). This fusion construct also produces a predominant $Man_5GlcNA_2$ structure, as shown in FIG. 5E. This construct was shown to produce greater than 50% $Man_5GlcNA_2$ (+++++).

Generation of a Combinatorial Localization/Mannosidase Library:

Generating a combinatorial DNA library of α-1,2-mannosidase catalytic domains fused to targeting peptides required the amplification of mannosidase domains with varying lengths of N-terminal deletions from a number of organisms. To approach this goal, the full length open reading frames (ORFs) of α-1,2-mannosidases were PCR amplified from either cDNA or genomic DNA obtained from the following sources: *Homo sapiens, Mus musculus, Drosophila melanogaster, Caenorhabditis elegans, Aspergillus nidulans* and *Penicillium citrinum*. In each case, DNA was incubated in the presence of oligonucleotide primers specific for the desired mannosidase sequence in addition to reagents required to perform the PCR reaction. For example, to amplify the ORF of the *M. musculus* α-1,2-mannosidase IA, the 5'-primer ATGCCCGTGGGGGGCCTGTTGC-CGCTCTTCAGTAGC (SEQ ID NO:12) and the 3'-primer TCATTTCTCTTTGCCATCAATTTCCT-TCTTCTGTTCACGG (SEQ ID NO:13) were incubated in the presence of Pfu DNA polymerase (Stratagene, La Jolla, Calif.) and amplified under the conditions recommended by Stratagene using the cycling parameters: 94° C. for 1 min (1 cycle); 94° C. for 30 sec, 68° C. for 30 sec, 72° C. for 3 min (30 cycles). Following amplification the DNA sequence encoding the ORF was incubated at 72° C. for 5 min with 1 U Taq DNA polymerase (Promega, Madison, Wis.) prior to ligation into pCR2.1-TOPO (Invitrogen, Carlsbad, Calif.) and transformed into TOP10 chemically competent *E. coli*, as recommended by Invitrogen. The cloned PCR product was confirmed by ABI sequencing using primers specific for the mannosidase ORF.

To generate the desired N-terminal truncations of each mannosidase, the complete ORF of each mannosidase was used as the template in a subsequent round of PCR reactions wherein the annealing position of the 5'-primer was specific to the 5'-terminus of the desired truncation and the 3'-primer remained specific for the original 3'-terminus of the ORF. To facilitate subcloning of the truncated mannosidase fragment into the yeast expression vector, pJN347 (FIG. 2C) AscI and PacI restriction sites were engineered onto each truncation product, at the 5'- and 3'-termini respectively. The number and position of the N-terminal truncations generated for each mannosidase ORF depended on the position of the transmembrane (TM) region in relation to the catalytic domain (CD). For instance, if the stem region located between the TM and CD was less than 150 bp, then only one truncation for that protein was generated. If, however, the stem region was longer than 150 bp then either one or two more truncations were generated depending on the length of the stem region.

An example of how truncations for the *M. musculus* mannosidase IA (Genbank: 6678787) were generated is described herein, with a similar approach being used for the other mannosidases. FIG. 3 illustrates the ORF of the *M. musculus* α-1,2-mannosidase IA with the predicted transmembrane and catalytic domains being highlighted in bold. Based on this structure, three 5'-primers were designed (annealing positions underlined in FIG. 3) to generate the Δ65-, Δ105- and Δ187-N-terminal deletions. Using the Δ65 N-terminal deletion as an example the 5'-primer used was 5'-GGCGCGC-CGACTCCTCCAAGCTGCTCAGCGGGGTC-CTGTTCCAC-3'(SEQ ID NO:14) (with the AscI restriction site highlighted in bold) in conjunction with the 3'-primer CCTTAATTAATCATTTCTCTTTGCCAT-CAATTTCCTTCTTCTGTTCACGG-3' (SEQ ID NO:15) (with the PacI restriction site highlighted in bold). Both of these primers were used to amplify a 1561 bp fragment under the conditions outlined above for amplifying the full length *M. musculus* mannosidase 1A ORF. Furthermore, like the product obtained for the full length ORF, the truncated product was also incubated with Taq DNA polymerase, ligated into pCR2.1-TOPO (Invitrogen, Carlsbad, Calif.), transformed into TOP10 and ABI sequenced. After having amplified and confirmed the sequence of the truncated mannosidase fragment, the resulting plasmid, pCR2.1-Δ65 mMannIA, was digested with AscI and PacI in New England Biolabs buffer #4 (Beverly, Mass.) for 16 h at 37° C. In parallel, the pJN347 (FIG. 2C) was digested with the same enzymes and incubated as described above. Post-digestion, both the pJN347 (FIG. 2C) back-bone and the truncated catalytic domain were gel extracted and ligated using the Quick Ligation Kit (New England Biolabs, Beverly, Mass.), as recommended by the manufacturers, and transformed into chemically competent DH5α cells (Invitrogen, Carlsbad, Calif.). Colony PCR was used to confirm the generation of the pJN347-mouse Mannosidase IAΔ65 construct.

Having generated a library of truncated α-1,2-mannosidase catalytic domains in the yeast expression vector pJN347 (FIG. 2C) the remaining step in generating the targeting peptide/catalytic domain library was to clone in-frame the targeting peptide sequences (FIG. 2). Both the pJN347-mannosidase constructs (FIG. 2D) and the pCR2.1TOPO-targeting peptide constructs (FIG. 2B) such as were incubated overnight at 37° C. in New England Biolabs buffer #4 in the presence of the restriction enzymes NotI and AscI. Following digestion, both the pJN347-mannosidase back-bone and the targeting peptide regions were gel-extracted and ligated using the Quick Ligation Kit (New England Biolabs, Beverly, Mass.), as recommended by the manufacturers, and transformed into chemically competent DH5α cells (Invitrogen, Carlsbad, Calif.). Subsequently, the pJN347-targeting peptide/mannosidase constructs were ABI sequenced to confirm that the generated fusions were in-frame. The estimated size of the final targeting peptide/alpha-1,2-mannosidase library contains over 1300 constructs generated by the approach described above. FIG. 2 illustrates construction of the combinatorial DNA library.

Engineering a *P. Pastoris* OCH1 Knock-Out Strain With Multiple Auxotrophic Markers.

The first step in plasmid construction involved creating a set of universal plasmids containing DNA regions of the KEX1 gene of *P. pastoris* (Boehm et al. Yeast 1999 May; 15(7):563-72) as space holders for the 5' and 3' regions of the genes to be knocked out. The plasmids also contained the *S. cerevisiae* Ura-blaster (Alani et al., *Genetics* 116, 541-545. 1987) as a space holder for the auxotrophic markers, and an expression cassette with a multiple cloning site for insertion of a foreign gene. A 0.9-kb fragment of the *P. pastoris* KEX1-5' region was amplified by PCR using primers GGC GAGCTCGGCCTACCCGGCCAAGGCTGAGATCATTT-GTCCAGCTTCA GA (SEQ ID NO:16) and GCCCAC GTCGACGGATCCGTTTAAACATCGATTGGAGAGGC-TGACACC GCTACTA (SEQ ID NO:17) and *P. pastoris* genomic DNA as a template and cloned into the SacI, SalI sites of pUC19 (New England Biolabs, Beverly, Mass.). The resulting plasmid was cut with BamHI and SalI, and a 0.8-kb fragment of the KEX1-3' region that had been amplified using primers CG-GGATCCACTAGTATTTAAATCATATGTGCGAGTGTA-CAACTCTTCCC ACATGG (SEQ ID NO:18) and GGACGC GTCGACGGCCTACCCGGCCGTACGAGGAATTTCTCGG ATGACTCTTTTC (SEQ ID NO:19) was cloned into the open sites creating pJN262. This plasmid was cut with BamHI and the 3.8-kb BamHI, BglII fragment of pNKY51 (Alani et al. 1987) was inserted in both possible orientations resulting in plasmids pJN263 (FIG. 4A) and pJN284 (FIG. 4B).

An expression cassette was created with NotI and PacI as cloning sites. The GAPDH promoter of *P. pastoris* was amplified using primers CG GGATCCCTCGAGAGATCTTTTTTGTAGAAATGTCTT-GGTGCCT (SEQ ID NO:20) and GGACAT GCATGCACTAGTGCGGCCGCCACGTGATAGTTGTT-CA ATTGATTGAAATAGGGACAA (SEQ ID NO:21) and plasmid pGAPZ-A (Invitrogen) as template and cloned into the BamHI, SphI sites of pUC19 (New England Biolabs, Beverly, Mass.) (FIG. 4B). The resulting plasmid was cut with SpeI and SphI and the CYC1 transcriptional terminator region ("TT") that had been amplified using primers CCT-TGCTAGCTTAATTAACCGCGGCACGTCCGAC-GGCGGCCCA CGGGTCCCA (SEQ ID NO:22) and GGA-CATGCATGCGGATCCCTTAAGAGCCGGCAGCTT-GCAAATT AAAGCCTTCGAGCGTCCC (SEQ ID NO:23) and plasmid pPICZ-A (Invitrogen) as a template was cloned into the open sites creating pJN261 (FIG. 4B).

Figure 4D:
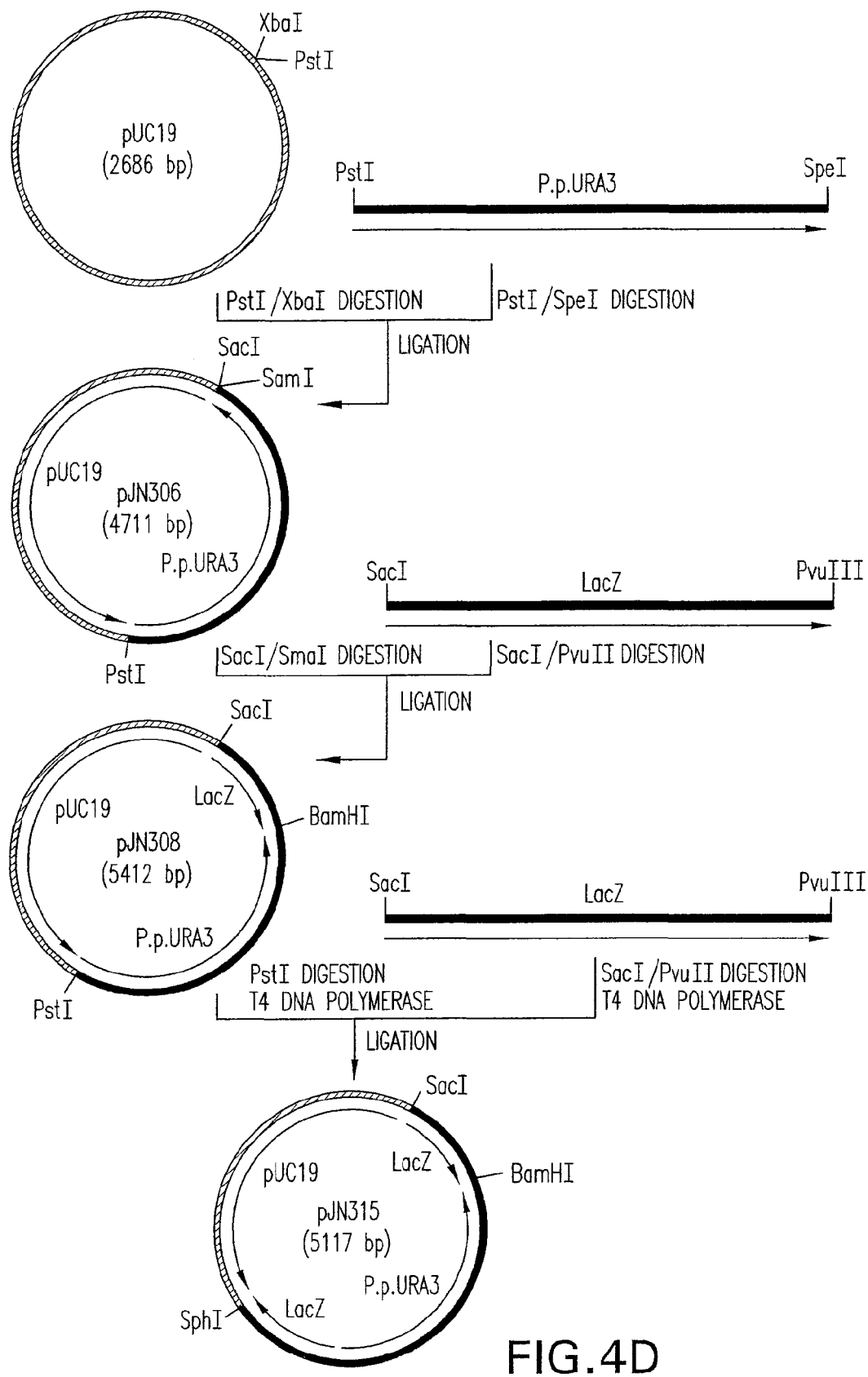
Figure 4E:
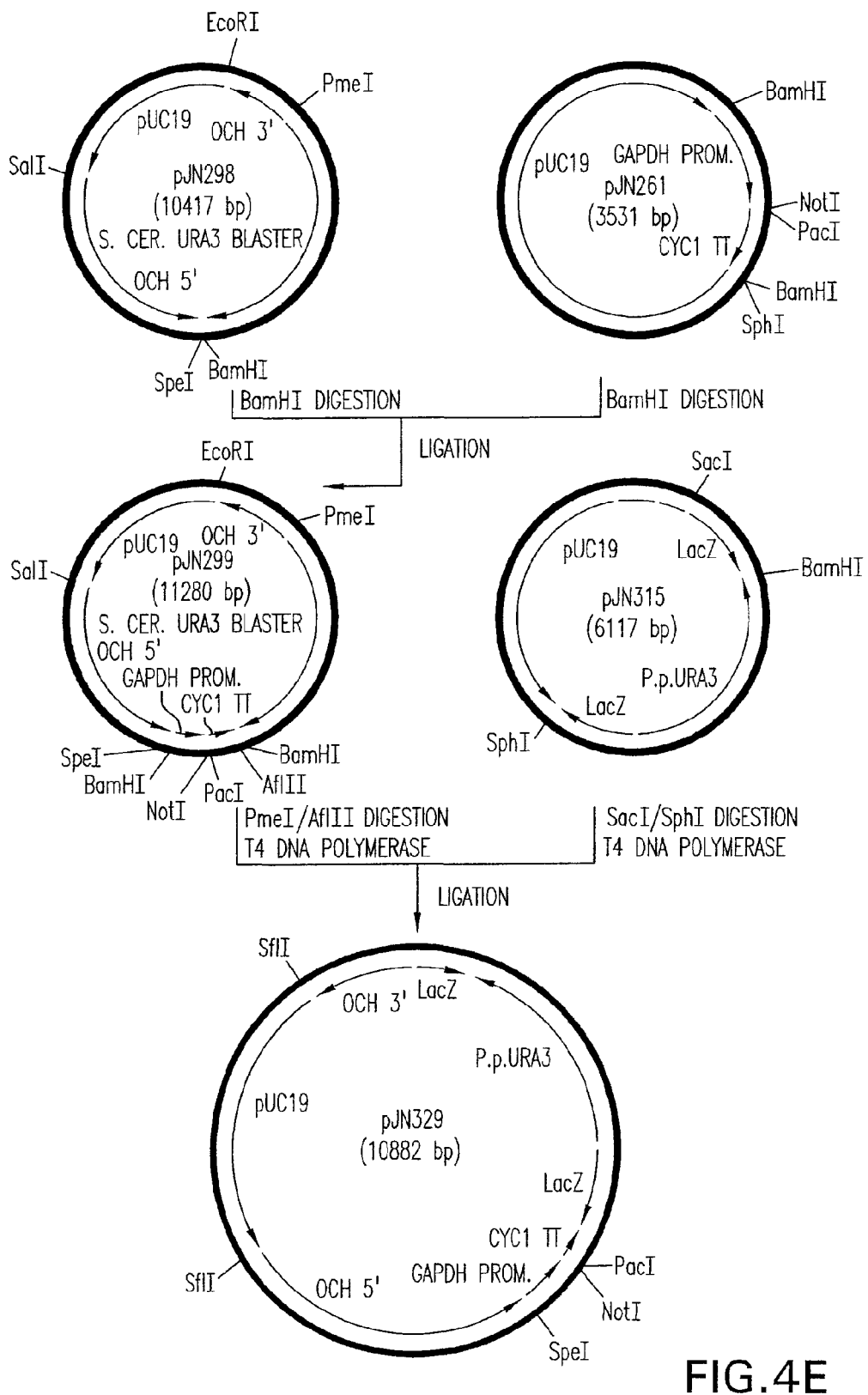

A knockout plasmid for the *P. pastoris* OCH1 gene was created by digesting pJN263 with SalI and SpeI and a 2.9-kb DNA fragment of the OCH1-5' region, which had been amplified using the primers GAACCAC GTCGACGGCCATTGCGGCCAAAACCTTTTTTCCTA-TT CAAACACAAGGCATTGC (SEQ ID NO:24) and CTC-CAAT ACTAGTCGAAGATTATCTTCTACGGTGCCTGGACTC (SEQ ID NO:25) and *P. pastoris* genomic DNA as a template, was cloned into the open sites (FIG. 4C). The resulting plasmid was cut with EcoRI and PmeI and a 1.0-kb DNA fragment of the OCH1-3' region that had been generated using the primers TGGAAG GTTTAAACAAAGCTAGAGTAAAATAGATATAGCGAG ATTAGAGAATG (SEQ ID NO:26) and AA GAATTCGGCTGGAAGGCCTTGTACCTTGATGTAGT-TCCCGTT TTCATC (SEQ ID NO:27) was inserted to generate pJN298 (FIG. 4C). To allow for the possibility to simultaneously use the plasmid to introduce a new gene, the BamHI expression cassette of pJN261 (FIG. 4B) was cloned into the unique BamHI site of pJN298 (FIG. 4C) to create pJN299 (FIG. 4E).

The *P. pastoris* Ura3-blaster cassette was constructed using a similar strategy as described in Lu. P., et al. 1998 (Cloning and disruption of the β-isopropylmalate dehydrogenase gene (Leu2) of *Pichia stipidis* with URA3 and recovery of the double auxotroph. Appl. Microbiol. Biotechnol. 49, 141-146.) A 2.0-kb PstI, SpeI fragment of *P. pastoris* URA3 was inserted into the PstI, XbaI sites of pUC19 (New England Biolabs, Beverly, Mass.) to create pJN306 (FIG. 4D). Then a 0.7-kb SacI, PvuII DNA fragment of the lacZ open reading frame was cloned into the SacI, SmaI sites to yield pJN$_{308}$ (FIG. 4D). Following digestion of pJN$_{308}$ (FIG. 4D) with PstI, and treatment with T4 DNA polymerase, the SacI-PvuII fragment from lacZ that had been blunt-ended with T4 DNA polymerase was inserted generating pJN315 (FIG. 4D). The lacZ/URA3 cassette was released by digestion with SacI and SphI, blunt ended with T4 DNA polymerase and cloned into the backbone of pJN299 that had been digested with PmeI and AflII and blunt ended with T4 DNA polymerase. The resulting plasmid was named pJN329 (FIG. 4E).

Figure 4F:
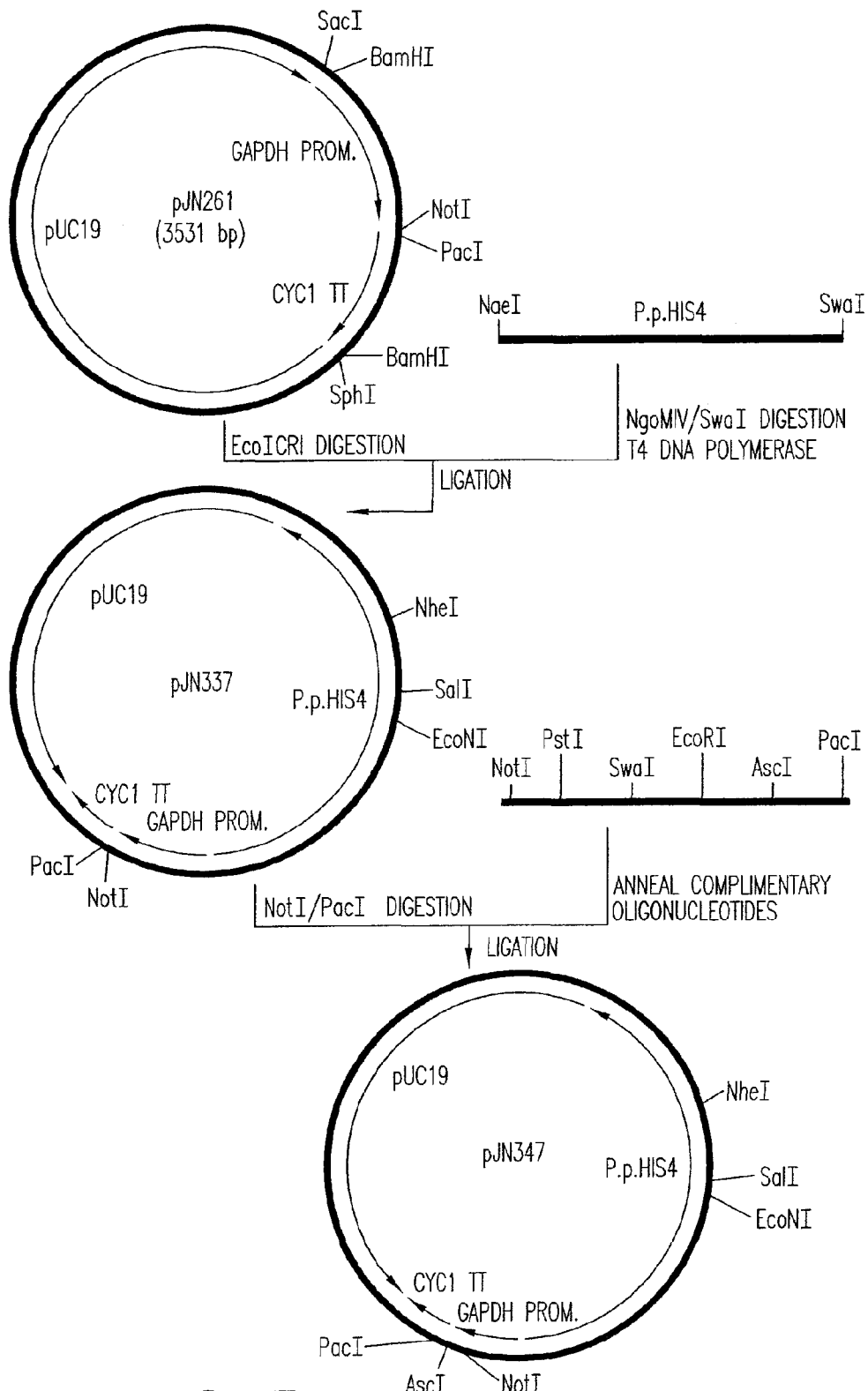

A HIS4 marked expression plasmid was created by cutting pJN261 (FIG. 4F) with EcoICRI (FIG. 4F). A 2.7 kb fragment of the *Pichia pastoris* HIS4 gene that had been amplified using the primers GCCCAA GCCGGCCTTAAGGGATCTCCTGATGACTGACTCAC-TGATAATA AAAATACGG (SEQ ID NO:28) and GGGCGCGTATTTAAATACTAGTGGATCTATCG-AATCTAAATGTAAGTTA AAATCTCTAA (SEQ ID NO:29) cut with NgoMIV and SwaI and then blunt-ended using T4 DNA polymerase, was then ligated into the open site. This plasmid was named pJN337 (FIG. 4F). To construct a plasmid with a multiple cloning site suitable for fusion library construction, pJN337 was cut with NotI and PacI and the two oligonucleotides GGCCGCCTGCAGATTTAAATGAATTCGGCGCGC CTTAAT (SEQ ID NO:30) and TAAGGCGCGCCGAATTCATTTAAATCTGCAGGGC (SEQ ID N0:31), that had been annealed in vitro were ligated into the open sites, creating pJN347 (FIG. 4F).

To create an och1 knockout strain containing multiple auxotrophic markers, 100 μg of pJN329 was digested with SfiI and used to transform *P. pastoris* strain JC308 (Cereghino, 2001) by electroporation. Following transformation, the URA dropout plates were incubated at room temperature for 10 days. One thousand (1000) colonies were picked and restreaked. All 1000 clones were then streaked onto 2 sets of URA dropout plates. One set was incubated at room temperature, whereas the second set was incubated at 37° C. The clones that were unable to grow at 37° C., but grew at room temperature, were subjected to colony PCR to test for the correct OCH1 knockout. One clone that showed the expected PCR signal (about 4.5 kb) was designated YJN153.

EXAMPLE 12

Characterization of the Combinatorial DNA Library

Positive transformants screened by colony PCR confirming integration of the mannosidase construct into the *P. pastoris* genome were subsequently grown at room temperature in 50 ml BMGY buffered methanol-complex medium consisting of 1% yeast extract, 2% peptone, 100 mM potassium phosphate buffer, pH 6.0, 1.34% yeast nitrogen base, 4× $10^{-5}$% biotin, and 1% glycerol as a growth medium) until $OD_{600\ nm}$ 2-6 at which point they were washed with 10 ml BMMY (buffered methanol-complex medium consisting of 1% yeast extract, 2% peptone, 100 mM potassium phosphate buffer, pH 6.0, 1.34% yeast nitrogen base, 4×$10^{-5}$% biotin, and 1.5% methanol as a growth medium) media prior to induction of the reporter protein for 24 hours at room temperature in 5 ml BMMY. Consequently, the reporter protein was isolated and analyzed by mass spectrophotometry and HPLC to characterize its glycan structure. Using the targeting peptides in Table 6, mannosidase catalytic domains localized to either the ER or the Golgi showed significant level of trimming of a glycan predominantly containing $Man_8GlcNAc_2$ to a glycan predominantly containing $Man_5GlcNAc_2$. This is evident when the glycan structure of the reporter glycoprotein is compared between that of *P. pastoris* och1 knock-out in FIGS. 5C, 6C and the same strain transformed with *M. musculus* mannosidase constructs as shown in FIGS. 5D, 5E, 6D-6F. FIGS. 5 and 6 show expression of constructs generated from the combinatorial DNA library which show significant mannosidase activity in *P. pastoris*. Expression of pGC5 (*Saccharomyces* MNS1(m)/mouse mannosidase IB Δ99) (FIG. 5D, 6E) produced a protein which has approximately 30% of all glycans trimmed to $Man_5GlcNAc_2$, while expression of pFB8 (*Saccharomyces* SEC12(m)/mouse mannosidase IA Δ187) (FIG. 6F) produced approximately 50% $Man_5GlcNAc_2$ and expression of pBC18-5 (*Saccharomyces* VAN1(s)/*C. elegans* mannosidase IB A80) (FIG. 5E) produced 70% $Man_5GlcNAc_2$.

Release of N-Glycans

The glycans were released and separated from the glycoproteins by a modification of a previously reported method (Papac et al. 1998 *Glycobiology* 8, 445-454). After the proteins were reduced and carboxymethylated and the membranes blocked, the wells were washed three time with water. The protein was deglycosylated by the addition of 30 μl of 10 mM NH4HCO3 pH 8.3 containing one milliunit of N-glycanase (Glyko, Novato, Calif.). After 16 hr at 37° C., the solution containing the glycans was removed by centrifugation and evaporated to dryness.

Matrix Assisted Laser Desorption Ionization Time of Flight Mass Spectrometry

After the N-glycans were released by PNGase digestion, they were analyzed by Matrix Assisted Laser Desorption Ionization Time of Flight Mass Spectrometry. Molecular weights of the glycans were determined using a Voyager DE PRO linear MALDI-TOF (Applied Biosciences) mass spectrometer using delayed extraction. The dried glycans from each well were dissolved in 15 μl of water and 0.5 μl was spotted on stainless steel sample plates and mixed with 0.5 μl of S-DHB matrix (9 mg/ml of dihydroxybenzoic acid, 1 mg/ml of 5-methoxysalicilic acid in 1:1 water/acetonitrile 0.1% TFA) and allowed to dry. Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.1%, the internal pressure was less than 5×10-7 torr, and the low mass gate was 875 Da. Spectra were generated from the sum of 100-200 laser pulses and acquired with a 500 MHz digitizer. $Man_5GlcNAc_2$ oligosaccharide was used as an external molecular weight standard. All spectra were generated with the instrument in the positive ion mode.

EXAMPLE 13

Trimming In Vivo by Alpha-1,2-Mannosidase

To ensure that the novel engineered strains of Example 11 in fact produced the desired $Man_5GlcNAc_2$ structure in vivo, cell supernatants were tested for mannosidase activity (see FIGS. 7-9). For each construct/host strain described below, HPLC was performed at 30° C. with a 4.0 mm×250 mm column of Altech (Avondale, Pa., USA) Econosil-NH2 resin (5 μm) at a flow rate of 1.0 ml/min for 40 min. In FIGS. 7 and 8, degradation of the standard $Man_9GlcNAc_2$ [b] was shown to occur resulting in a peak which correlates to $Man_5GlcNAc_2$. In FIG. 7, the $Man_9GlcNAc_2$ [b] standard eluted at 24.61 min and $Man_5GlcNAc_2$ [a] eluted at 18.59 min. In FIG. 8, $Man_9GlcNAc_2$ eluted at 21.37 min and $Man_5GlcNAc_2$ at 15.67 min. In FIG. 9, the standard $Man_8GlcNAc_2$ [b] was shown to elute at 20.88 min.

Figure 7C:
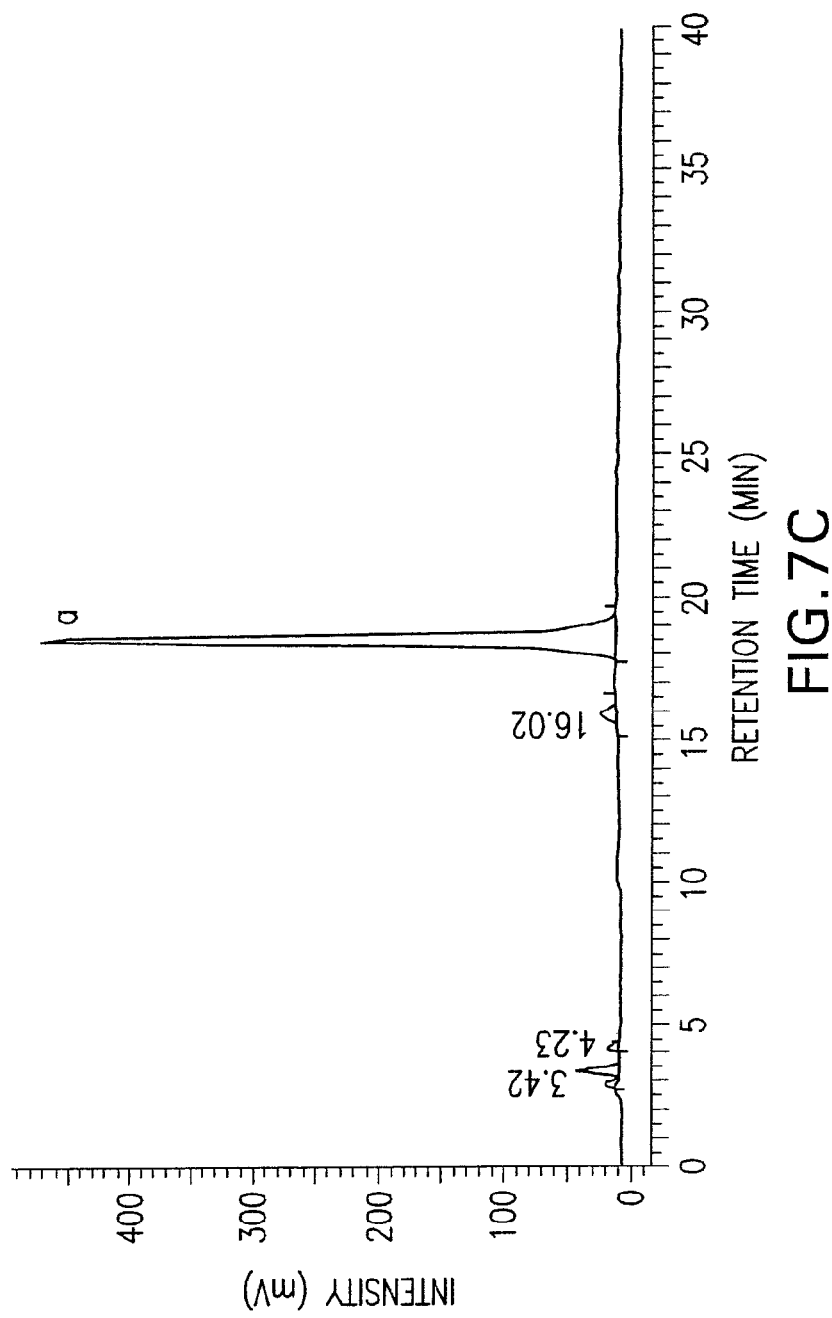

*P. pastoris* cells comprising plasmid pFB8 (*Saccharomyces* SEC12 (m)/mouse mannosidase IA Δ187) were grown at 30° C. in BMGY to an OD600 of about 10. Cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 6F. The earlier removed aliquot of the supernatant was further tested for the presence of secreted mannosidase activity. A commercially available standard of 2-aminobenzamide-labeled N-linked-type oligomannose 9 (Man-9-2-AB) (Glyko, Novato, Calif.) was added to: BMMY (FIG. 7A), the supernatant from the above aliquot (FIG. 7B), and BMMY containing 10 ng of 75 mU/mL of α-1,2-mannosidase from *Trichoderma reesei* (obtained from Contreras et al., WO 02/00856 A2) (FIG. 7C). After incubation for 24 hours at room temperature, samples were analyzed by amino silica HPLC to determine the extent of mannosidase trimming.

*P. pastoris* cells comprising plasmid pGC5 (*Saccharomyces* MNS1(m)/mouse mannosidase IB Δ99) were similarly grown and assayed. Cells were grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5D. The earlier removed aliquot of the supernatant was further tested for the presence of secreted mannosidase activity as shown in FIG. 5B. A commercially available standard of Man9-2-AB (Glyko, Novato, Calif.) were added to: BMMY (FIG. 8A), supernatant from the above aliquot (FIG. 8B), and BMMY containing 10 ng of 75 mU/mL of α-1,2-mannosidase from *Trichoderma reesei* (obtained from Contreras et al., WO 02/00856 A2) (FIG. 8C). After incubation for 24 hours at room temperature, samples were analyzed by amino silica HPLC to determine the extent of mannosidase trimming.

Man9-2-AB was used as a substrate and it is evident that after 24 hours of incubation, mannosidase activity was virtually absent in the supernatant of the pFB8 (*Saccharomyces* SEC12 (m)/mouse mannosidase IA Δ187) strain digest (FIG. 7B) and pGC5 (*Saccharomyces* MNS1(m)/mouse mannosidase IB Δ99) strain digest (FIG. 8B) whereas the positive control (purified α-1,2-mannosidase from *T. reesei* obtained from Contreras) leads to complete conversion of $Man_9GlcNAc_2$ to $Man_5GlcNAc_2$ under the same conditions, as shown in FIGS. 7C and 8C. This is conclusive data showing in vivo mannosidase trimming in *P. pastoris* pGC5 strain; and pFB8 strain, which is distinctly different from what has been reported to date (Contreras et al., WO 02/00856 A2).

Figure 9A:
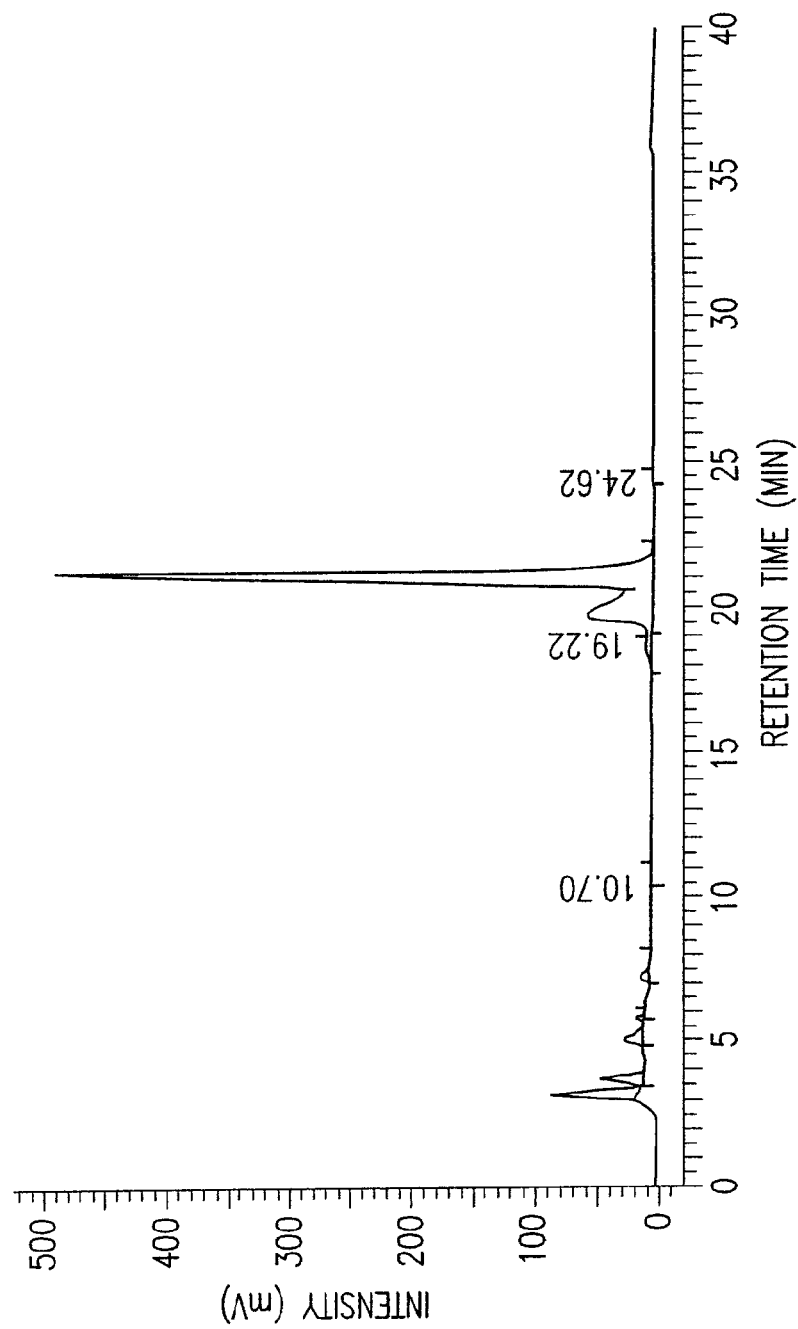
FIG. 9 shows a high performance liquid chromatogram for: (A) $Man_9GlcNAc_2$ standard labeled with 2-AB (negative control); (B) supernatant of medium *P. pastoris*, Δoch1 transformed with pBC18-5 mannosidase, which demonstrates lack of extracellular mannosidase activity in the supernatant; and (C) supernatant of medium *P. pastoris*, Δoch1 transformed with pDD28-3, which demonstrates activity in the supernatant (positive control).

FIG. 9 further substantiates localization and activity of the mannosidase enzyme. *P. pastoris* comprising pBC18-5 (*Saccharomyces* VAN1(s)/*C. elegans* mannosidase IB α80) was grown at room temperature in BMGY to an OD600 of about 10. Cells were harvested by centrifugation and transferred to BMMY to induce the production of K3 under control of an AOX1 promoter. After 24 hours of induction, cells were removed by centrifugation to yield an essentially clear supernatant. An aliquot of the supernatant was removed for mannosidase assays and the remainder was used for the recovery of secreted soluble 1(3. A single purification step using CM-sepharose chromatography and an elution gradient 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5E. The earlier removed aliquot of the supernatant was further tested for the presence of secreted mannosidase activity as shown in FIG. 9B. A commercially available standard of Man8-2-AB (Glyko, Novato, Calif.) was added to: BMMY (FIG. 9A), supernatant from the above aliquot pBC18-5 (*Saccharomyces* VAN1(s)/*C. elegans* mannosidase IB A80) (FIG. 9B), and BMMY containing media from a different fusion construct pDD28-3 (*Saccharomyces* MNN10(m) (from SwissProt 50108)/*H. sapiens* mannosidase IB Δ99) (FIG. 9C). After incubation for 24 hours at room temperature, samples were analyzed by amino silica HPLC to determine the extent of mannosidase trimming. FIG. 9B demonstrates intracellular mannosidase activity in comparison to a fusion construct pDD28-3 (*Saccharomyces* MNN10(m) *H. sapiens* mannosidase IB Δ99) exhibiting a negative result (FIG. 9C).

EXAMPLE 14 pH Optimum Assay of Engineered α-1,2-Mannosidase

*P. pastoris* cells comprising plasmid pBB27-2 (*Saccharomyces* MNN10 (s) (from SwissProt 50108)/*C. elegans* mannosidase IB Δ31) were grown at room temperature in BMGY to an OD600 of about 17. About 80 μL of these cells were inoculated into 600 μL BMGY and were grown overnight. Subsequently, cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant (pH 6.43). The supernatant was removed for mannosidase pH optimum assays. Fluorescence-labeled $Man_8GlcNAc_2$ (0.5 μg) was added to 20 μL of supernatant adjusted to various pH (FIG. 11) and incubated for 8 hours at room temperature. Following incubation the sample was analyzed by HPLC using an Econosil NH2 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (18). Solvent A (acetonitrile) and solvent B (ammonium formate, 50 mM, pH 4.5. The column was equilibrated with solvent (68% A:32% B) for 20 min between runs.

EXAMPLE 15

Engineering of *P. pastoris* to Produce N-Glycans with the Structure $GlcNAcMan_5GlcNAc_2$ GlcNAc Transferase I activity is required for the maturation of complex and hybrid N-glycans (U.S. Pat. No. 5,834, 251). $Man_5GlcNAc_2$ may only be trimmed by mannosidase II, a necessary step in the formation of human glycoforms, after the addition of N-acetylglucosamine to the terminal α-1,3 mannose residue of the trimannose stem by GlcNAc Transferase I (Schachter, 1991 Glycobiology 1(5):453-461). Accordingly, a combinatorial DNA library was prepared including DNA fragments encoding suitably targeted catalytic domains of GlcNAc Transferase I genes from *C. elegans* and *Homo sapiens*; and localization sequences from GLS, MNS, SEC, MNN9, VAN1, ANP1, HOC1, MNN10, MNN11, MNT1, KTR1, KTR2, MNN2, MNN5, YUR1, MNN1, and MNN6 from *S. cerevisiae* and *P. pastoris* putative α-1,2-mannosyltransferases based on the homology from *S. cerevisiae*: D2, D9 and J3, which are KTR homologs. Table 10 includes but does not limit targeting peptide sequences such as SEC and OCH1, from *P. pastoris* and *K. lactis* GnTI, (See Table 6 and Table 10)

TABLE 10

A Representative Combinatorial Library Of Targeting Peptide Sequences/Catalytic Domain For UDP-N-Acetylglucosaminyl Transferase I (GnTI)

| Catalytic Domains | Targeting peptide | | | | |
|---|---|---|---|---|---|
| | OCHI(s) | OCHI(m) | OCHI(l) | MNN9(s) | MNN9(m) |
| Human, GnTI, Δ38 | PB105 | PB106 | PB107 | PB104 | N/A |
| Human, GnTI, Δ86 | NB12 | NB13 | NB14 | NB15 | NB |
| C. elegans, GnTI, Δ88 | OA12 | OA13 | OA14 | OA15 | OA16 |
| C. elegans, GnTI, Δ35 | PA12 | PA13 | PA14 | PA15 | PA16 |
| C. elegans, GnTI, Δ63 | PB12 | PB13 | PB14 | PB15 | PB16 |
| X. leavis, GnTI, Δ33 | QA12 | QA13 | QA14 | QA15 | QA16 |
| X. leavis, GnTI, Δ103 | QB12 | QB13 | QB14 | QB15 | QB 16 |

Targeting peptide sequences were selected from OCH1 in *P. pastoris* (long, medium and short) (see Example 11) and MNN9 (SwissProt P39107) in *S. cerevisiae* short, and medium. Catalytic domains were selected from human GnTI with a 38 and 86 amino acid N-terminal deletion, *C. elegans*

(gly-12) GnTI with a 35 and 63 amino acid deletion as well as C. elegans (gly-14) GnTI with a 88 amino acid N-terminal deletion and X. leavis GnTI with a 33 and 103 amino acid N-terminal deletion, respectively.

A portion of the gene encoding human N-acetylglucosaminyl Transferase I (MGATI, GenBank Accession No. NM002406), lacking the first 154 bp, was amplified by PCR using oligonucleotides 5'-TGGCAGGCGCGCCTCAGT-CAGCGCTCTCG-3' (SEQ ID NO:32) and 5'-AGGT-TAATTA AGTGCTAATTCCAGCTAGG-3' (SEQ ID NO:33) and vector pHG4.5 (ATCC#79003) as template. The resulting PCR product was cloned into pCR2.1-TOPO and the correct sequence was confirmed. Following digestion with AscI and PacI the truncated GnTI was inserted into plasmid pJN346 to create pNA. After digestion of pJN271 with NotI and AscI, the 120 bp insert was ligated into pNA to generate an in-frame fusion of the MNN9 transmembrane domain with the GnTI, creating pNA15.

The host organism is a strain of P. pastoris that is deficient in hypermannosylation (e.g. an och1 mutant), provides the substrate UDP-GlcNAc in the Golgi and/or ER (i.e. contains a functional UDP-GlcNAc transporter), and provides N-glycans of the structure $Man_5GlcNAc_2$ in the Golgi and/or ER (e.g. P. pastoris pFB8 (Saccharomyces SEC12 (m)/mouse mannosidase IA Δ187) from above). First, P. pastoris pFB8 was transformed with pPB103 containing the Kluyveromyces lactis MNN2-2 gene (Genbank AN: AF106080) (encoding UDP-GlcNAc transporter) cloned into BamHI and BglII site of pBLADE-SX plasmid (Cereghino, 2001). Then the aforementioned combinatorial DNA library encoding a combination of exogenous or endogenous GnTI/localization genes was transformed and colonies were selected and analyzed for the presence of the GnTI construct by colony PCR. Our transformation and integration efficiency was generally above 80% and PCR screening can be omitted once robust transformation parameters have been established.

Protein Purification

K3 was purified from the medium by Ni-affinity chromatography utilizing a 96-well format on a Beckman BioMek 2000 laboratory robot. The robotic purification is an adaptation of the protocol provided by Novagen for their HisBind resin. Another screening method may be performed using a specific terminal GlcNAc binding antibody, or a lectin such as the GSII lectin from Griffonia simplificolia, which binds terminal GlcNAc (EY Laboratories, San Mateo, Calif.). These screens can be automated by using lectins or antibodies that have been modified with fluorescent labels such as FITC or analyzed by MALDI-TOF.

Secreted K3 can be purified by Ni-affinity chromatography, quantified and equal amounts of protein can be bound to a high protein binding 96-well plate. After blocking with BSA, plates can be probed with a GSII-FACS lectin and screened for maximum fluorescent response. A preferred method of detecting the above glycosylated proteins involves the screening by MALDI-TOF mass spectrometry following the affinity purification of secreted K3 from the supernatant of 96-well cultured transformants. Transformed colonies were picked and grown to an OD600 of 10 in a 2 ml, 96-well plate in BMGY at 30° C. Cells were harvested by centrifugation, washed in BMMY and resuspended in 250 ul of BMMY. Following 24 hours of induction, cells were removed by centrifugation, the supernatant was recovered and K3 was purified from the supernatant by Ni affinity chromatography. The N-glycans were released and analyzed by MALDI-TOF delayed extraction mass spectrometry as described herein.

In summary, the methods of the invention yield strains of P. pastoris that produce $GlcNAcMan_5GlcNAc_2$ in high yield, as shown in FIG. 10B. At least 60% of the N-glycans are $GlcNAcMan_5GlcNAc_2$. To date, no report exists that describes the formation of $GlcNAcMan_5GlcNAc_2$ on secreted soluble glycoproteins in any yeast. Results presented herein show that addition of the UDP-GlcNAc transporter along with GnTI activity produces a predominant $GlcNAcMan_5GlcNAc_2$ structure, which is confirmed by the peak at 1457 (m/z) (FIG. 10B).

Construction of Strain PBP-3:

The P. pastoris strain expressing K3, (Δoch1, arg-, ade-, his-) was transformed successively with the following vectors. First, pFB8 (Saccharomyces SEC12 (m)/mouse mannosidase IA M87) was transformed in the P. pastoris strain by electroporation. Second, pPB103 containing Kluyveromyces lactis MNN2-2 gene (Genbank AN: AF106080) (encoding UDP-GlcNAc transporter) cloned into pBLADE-SX plasmid (Cereghino et al. Gene 263 (2001) 159-169) digested with BamHI and BglII enzymes was transformed in the P. pastoris strain. Third, pPB104 containing Saccharomyces MNN9(s)/human GnTI Δ38 encoding gene cloned as NotI-PacI fragment into pJN336 was transformed into the P. pastoris strain.

EXAMPLE 16

Engineering a CMP-Sialic Acid Biosynthetic Pathway in P. pastoris

Cloning Enzymes Involved in CMP-Sialic Acid Synthesis

One method for cloning a CMP-sialic acid biosynthetic pathway into a fungal host cell involves amplifying the E. coli NeuA, NeuB and NeuC genes from E. coli genomic DNA using the polymerase chain reaction in conjunction with primer pairs specific for each open reading frame (ORF) (Table 12 below, and FIGS. 17, 16 and 15, respectively).

For cloning a mammalian CMP-sialic acid biosynthetic pathway, the mouse CMP-Sia synthase ORF (FIG. 18) was amplified from a mouse pituitary cDNA library in conjunction with the primer pairs set forth in Table 12. The GlcNAc epimerase (previously discussed in an alternate method for producing CMP-Sia intermediates), was amplified from porcine cDNA using PCR in conjunction with primer pairs specific for the corresponding gene (Table 12 and FIG. 20). The sialate aldolase gene (FIG. 22) was amplified from E. coli genomic DNA using the polymerase chain reaction in conjunction with the primer pairs set forth in Table 12. The mouse bifunctional UDP-N-acetylglucosamine-2-Epimerase/N-acetylmannosamine kinase gene was amplified from mouse liver using the polymerase chain reaction in conjunction with the primer pairs set forth in Table 12. The mouse N-acetylneuraminate-9-phosphate synthase gene was amplified from mouse liver using the polymerase chain reaction in conjunction with the primer pairs set forth in Table 12. The human CMP-Sia synthase gene was amplified from human liver using the polymerase chain reaction in conjunction with the primer pairs set forth in Table 12. In each case, the ORFs were amplified using a high-fidelity DNA polymerase enzyme under the following thermal cycling conditions: 97° C. for 1 min, 1 cycle; 97° C. for 20 sec, 60° C. for 30 sec, 72° C. for 2 min, 25 cycles; 72° C. for 2 min, 1 cycle. Following DNA sequencing to confirm the absence of mutations, each ORF is re-amplified using primers containing compatible restriction sites to facilitate the subcloning of each into suitable fungal expression vectors.

TABLE 12

| Primer name | Primer sequence |
| --- | --- |
| NeuA sense | 5'-ATGAGAACAAAAATTATTGCGATAATTCCAGCCCG-3' (SEQ ID NO: 45) |
| NeuA antisense | 5'-TCATTTAACAATCTCCGCTATTTCGTTTTC-3' (SEQ ID NO: 46) |
| NeuB sense | 5'-ATGAGTAATATATATATCGTTGCTGAAATTGGTTG-3' (SEQ ID NO: 47) |
| NeuB antisense | 5'-TTATTCCCCCTGATTTTTGAATTCGCTATG-3' (SEQ ID NO: 48) |
| NeuC sense | 5'-ATGAAAAAAATATTATACGTAACTGGATCTAGAG-3' (SEQ ID NO: 49) |
| NeuC antisense | 5'-CTAGTCATAACTGGTGGTACATTCCGGGATGTC-3' (SEQ ID NO: 50) |
| mouse CMP-Sia synthase sense | 5'-ATGGACGCGCTGGAGAAGGGGCCGTCACGTC-3' (SEQ ID NO: 51) |
| mouse CMP-Sia synthase antisense | 5'-CTATTTTTGGCATGAGTTATTAACTTTTTCTATCAG-3' (SEQ ID NO: 52) |
| porcine GlcNAc epimerase sense | 5'-ATGGAGAAGGAGCGCGAAACTCTGCAGG-3' (SEQ ID NO: 53) |
| porcine GlcNAc epimerase antisense | 5'-CTAGGCGAGGCGGCTCAGCAGGGCGCTC-3' (SEQ ID NO: 54) |
| *E. coli* Sialate aldolase sense | 5'-ATGGCAACGAATTTACGTGGCGTAATGGCTG-3' (SEQ ID NO: 55) |
| *E. coli* Sialate aldolase antisense | 5'-TCACCCGCGCTCTTGCATCAACTGCTGGGC-3' (SEQ ID NO: 56) |
| mouse bifunctional UDP-N-acetylglucosamine-2-epimerase/N-acetylmannosamine kinase sense | 5'-ATGGAGAAGAACGGGAACAACCGAAAGCTCCG-3' (SEQ ID NO: 69) |
| mouse bifunctional UDP-N-acetylglucosamine-2-epimerase/N-acetylmannosamine kinase antisense | 5'-CTAGTGGATCCTGCGCGTTGTGTAGTCCAG-3' (SEQ ID NO: 70) |
| mouse Sia9P syn sense | 5'-ATGCCGCTGGAACTGGAGCTGTGTCCCGGGC-3' (SEQ ID NO: 71) |
| mouse Sia9P syn antisense | 5'-TTAAGCCTTGATTTTCTTGCTGTGACTTTCCAC-3' (SEQ ID NO: 72) |
| human N-acetylneuraminic acid phosphatase (NANP) sense | 5'-GGGAGAATGCGGCCGCCACCATGGGGCTGAGCCGC GTGCGGGCGGTTTTC-3' (SEQ ID NO: 73) |
| human N-acetylneuraminic acid phosphatase (NANP) antisense | 5'-GTATAGACTGCAAAGTCAGTATGTCCACTTGATT AATTAACC-3' (SEQ ID NO: 74) |
| human CMP-Sia synthase sense | 5'-ATGGACTCGGTGGAGAAGGGGCCGCCACC-3' (SEQ ID NO: 75) |
| human CMP-Sia synthase antisense | 5'-CTATTTTTGGCATGAATTATTAACTTTTTCC-3' (SEQ ID NO: 76) |

Expression of Bacterial Neu Genes in *P. pastoris*

The 1176 bp PCR amplified fragment of the NeuC gene was ligated into the NotI-AscI site in the yeast integration vector pJN348 (a modified pUC19 vector comprising a GAPDH promoter, a NotI AscI PacI restriction site cassette, CycII transcriptional terminator, URA3 as a positive selection marker) producing pSH256. Similarly, the PCR amplified fragment (1041 bp) of the NeuB gene was ligated into the NotI-PacI site in the yeast integration vector pJN335, under the control of a GAPDH promoter using ADE as a positive selection marker, producing pSH255. The 1260 bp PCR amplified fragment of the NeuA gene was ligated into the NotI-PacI site in the yeast integration vector pJN346, under the control of a GAPDH promoter with ARG as a positive selection marker, to produce pSH254. After transforming *P. pastoris* with each vector by electroporation, the cells were plated onto the corresponding drop-out agar plates to facilitate positive selection of the newly introduced vector(s). To confirm the introduction of each gene, several hundred clones were repatched onto the respective dropout plates and grown for two days at 26° C. Once sufficient material had grown, each clone was screened by colony PCR using primers specific for the introduced gene. Conditions for colony PCR using the polymerase ExTaq™ from Takara (Madison, Wis.), were as follows: 97° C. for 3 min, 1 cycle; 97° C. for 20 sec, 50° C. for 30 sec, 72° C. for 2 min/kb, 30 cycles; 72° C. for 10 min, 1 cycle. Subsequently, several positive clones from colony PCR were grown in a baffled flask containing 200 ml of growth media. The base composition of growth media containing 2.68 g/l yeast nitrogen base, 200 mg/l biotin and 2 g/l dextrose was supplemented with appropriate amino acids depending on the strain used. The cells were grown in this media in the presence or absence of 20 mM ManNAc. Following growth in the baffle flask at 30° C. for 4-6 days, the cells were pelleted and analyzed for intermediates of the sialic acid pathway, as described below in this Example.

Expression of GlcNAc Epimerase Gene in *P. pastoris*

The PCR amplified fragment of the porcine GlcNAc epimerase gene is ligated into the NotI-PacI site in the yeast integration vector pJN348, under the control of the GAPDH promoter using URA3 as a positive selection marker. The *P. pastoris* strain producing endogenous GlcNAc is transformed with the vector carrying the GlcNAc epimerase gene fragment and screened for transformants.

Expression of Sialate Aldolase Gene in *P. Pastoris*

The PCR amplified fragment of the *E. coli* sialate aldolase gene is ligated into the NotI-PacI site in the yeast integration vector pJN335, under the control of the GAPDH promoter with ADE as a positive selection marker, producing pSH275. The *P. pastoris* strain producing ManNAc is transformed with the vector carrying the sialate aldolase gene fragment and screened for transformants.

Expression of the Gene Encoding UDP-N-Acetylglucosamine-2-Epimerase/N-Acetylmannosamine Kinase in *P. pastoris*

The PCR amplified fragment of the gene encoding the mouse bifunctional UDP-N-acetylglucosamine-2-Epimerase/N-acetylmannosamine Kinase enzyme was ligated into the NotI-PacI site in the yeast integration vector pJN348, under the control of the GAPDH promoter using URA as a positive selection marker, producing pSH284. The *P. pastoris* strain producing ManNAc was transformed with the vector carrying the gene fragment and screened for transformants.

Expression of the Gene Encoding N-Acetyl-Neuraminate-9-Phosphate Synthase in *P. pastoris*

The PCR amplified fragment of the mouse N-acetylneuraminate-9-phosphate synthase gene was ligated into the NotI-PacI site in the yeast integration vector pJN335, under the control of the GAPDH promoter with ADE as a positive selection marker producing, pSH285. The *P. pastoris* strain producing ManNAc-6-P was transformed with the vector carrying the above gene fragment and screened for transformants.

Identification, Cloning and Expression of the Gene Encoding N-Acetylneuraminate-9-Phosphatase N-acetylneuraminate-9-phosphatase activity has been detected in the cytosolic fraction of rat liver cells (Van Rinsum, 1984). We have repeated this method and isolated a cell extract fraction containing phosphatase activity selective against NeuAc-9-P. SDS-PAGE electrophoresis of this fraction identifies a single protein band. Subsequently, this sample was electroblotted onto a PDVF membrane, and the N-terminal amino acid sequence was identified by Edman degradation. The sequence identified allows the generation of degenerate oligonucleotides for the 5'-terminus of the ORF of the isolated protein. Using these degenerate primers in conjunction with the AP1 primer supplied in a rat liver Marathon-ready cDNA library (Clontech) according to the manufacturer's instructions, a full length ORF was isolated. The complete ORF was subsequently ligated into the yeast integration vector pJN347, under the control of the GAPDH promoter using a HIS gene as a positive selection marker. The *P. pastoris* strain producing NeuAc-9-P was transformed with the vector carrying the desired gene fragment and screened for transformants as described above in this Example.

Cloning and Expression of a CMP-Sialic Acid Synthase Gene in *P. Pastoris*

The PCR amplified fragment of the mouse CMP-Sia synthase gene was ligated into the NotI-PacI site in the yeast integration vector pJN346 under the control of the GAPDH promoter with the ARG gene as a positive selection marker. A *P. pastoris* strain producing sialic acid was transformed with the vector carrying the above gene fragment and screened for transformants as described above in this Example. Likewise, the human CMP-Sia synthase gene (Genbank AN AF397212) was amplified and ligated into the NotI-PacI site of the yeast expression vector pJN346 under the control of a GAPDH promoter with ARG as a positive selection marker, producing the vector pSH257. A *P. pastoris* strain capable of producing sialic acid is transformed with pSH257 by electroporation, producing a strain capable of generating CMP-Sia.

Expression of the Hybrid CMP-Sia Pathway in *P. Pastoris*

The *P. pastoris* strain JC308 (Cereghino, 2001) was super-transformed or simultaneously transformed with 20 mg of each of the vectors containing NeuC (pSH256), NeuB (pSH255) and hCMP-Sia synthase (pSH257) by electroporation. The resulting cells were plated on minimal media supplemented with histidine (containing 1.34 g/l yeast nitrogen base, 200 mg/l biotin, 2 g/l dextrose, 20 g/l agar and 20 mg/l L-histidine). Following incubation at 30° C. for 4 days, several hundred clones were isolated by repatching onto minimal media plates supplemented with histidine (see above for composition). The repatched clones were grown for 2 days prior to performing colony PCR (as described above in this Example) on the clones. Primers specific for NeuC, NeuB and hCMP-Sia synthase were used to confirm the presence of each ORF in the transformed clones. Twelve clones positive for all three ORFs (designated YSH99a-1) were grown in a baffled flask containing 200 ml of growth media (containing 2.68 g/l yeast nitrogen base, 200 mg/l biotin, 20 mg/l L-histidine and 2 g/l dextrose). The effect of supplementing the growth media with ManNAc was investigated by growing the cells in the presence or absence of 20 mM ManNAc. Following growth in the baffle flask at 30° C. for 4-6 days the cells are pelleted and analyzed for the presence of sialic acid pathway intermediates as described below in this Example.

Figure 26:
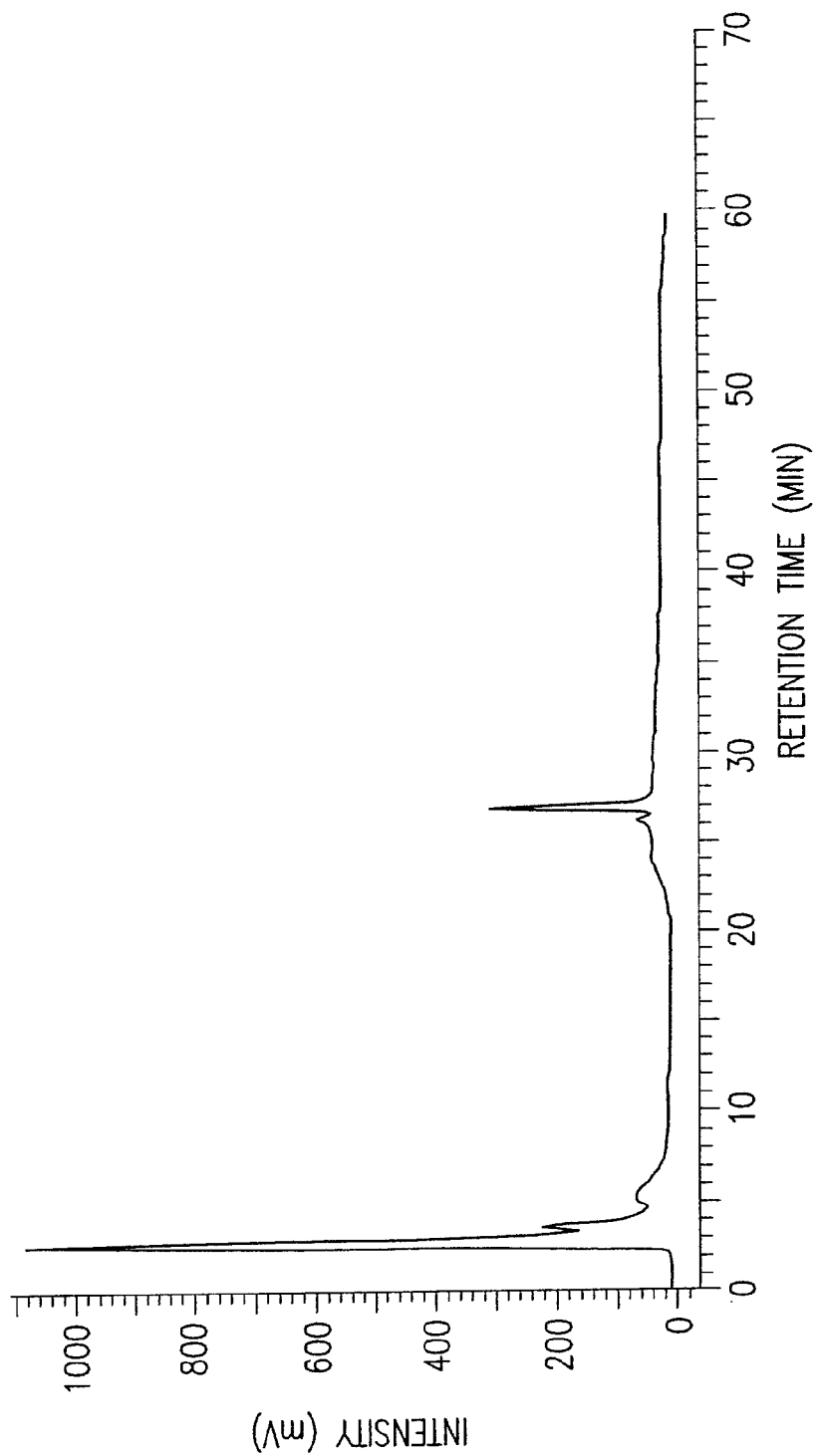
FIG. 26 shows sialidase treatment of N-glycans from YSH99a extract incubation. The sample illustrated in FIG. 25 was incubated overnight at 37° C. in the presence of 100 U sialidase (New England Biolabs, Beverley, Mass.). The peaks eluting at 20 and 23 min corresponding to mono- and di-sialylated N-glycan, have been removed in FIG. 25. The contaminating peak at 26 min remains.
Figure 27:
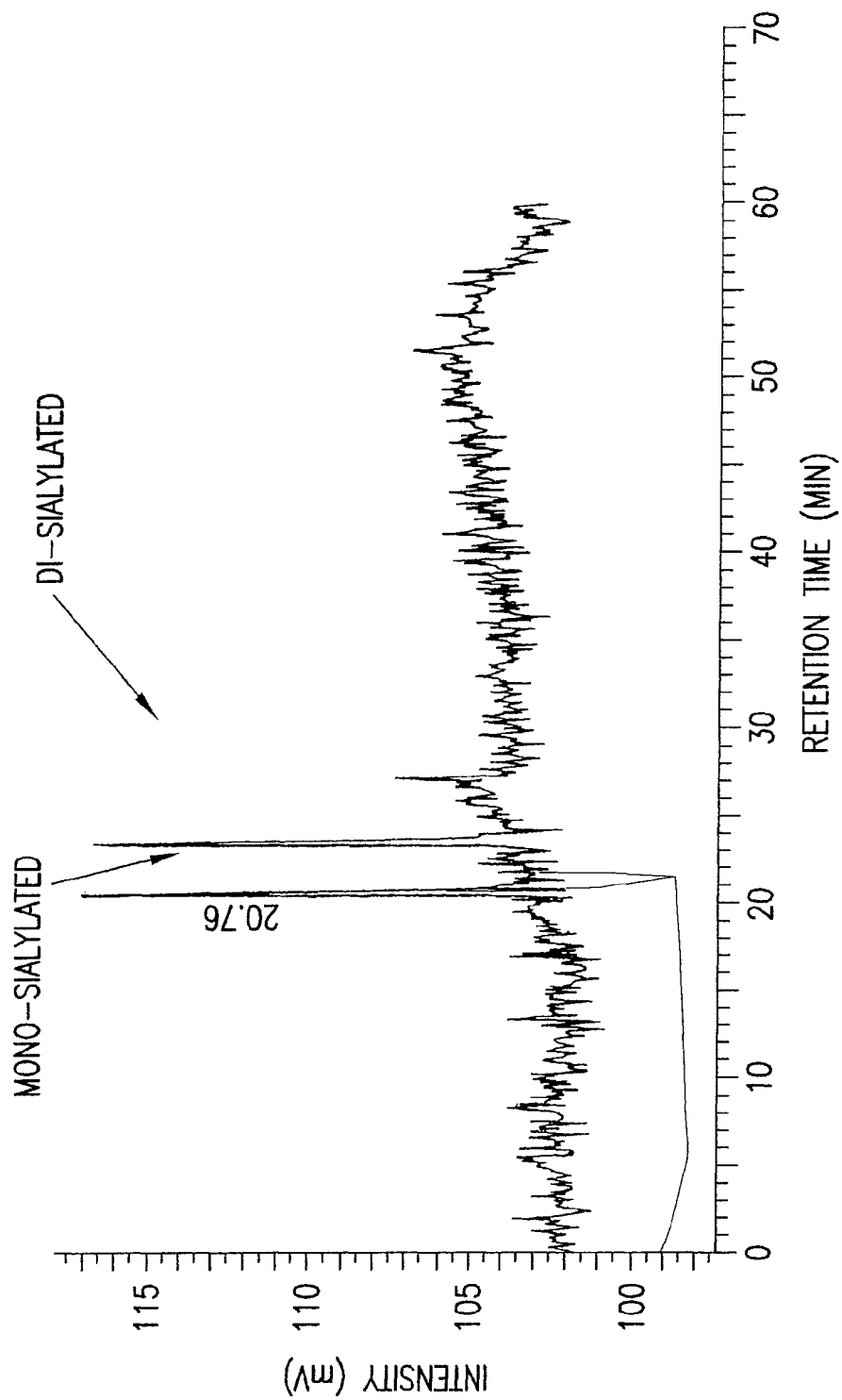
FIG. 27 shows commercial mono- and di-sialylated N-glycan standards. The peaks eluting at 20 and 23 min correspond to mono- and di-sialylation of the commercial standards A1 and A2 (Glyko Inc., San Rafael, Calif.).

Comparing the cell extracts using the assay outlined below in this Example, the cell extracts from *P. pastoris* YSH99a grown without exogenous CMP-Sia, showed transfer of Sia onto acceptor substrates, indicating the presence of endogenous CMP-Sia production (FIG. 25). Both mono- and di-sialylated biantennary N-glycans eluted at 20 min and 23 mM, their respective corresponding time. Additionally, subsequent sialidase treatment showed the removal of sialic acid (FIG. 26). Thus, a yeast strain engineered with a hybrid CMP-Sia biosynthetic pathway as described above, containing the NeuC, NeuB and hCMP-Sia synthase, was shown to be capable of generating an endogenous pool of CMP-sialic acid.

Assay for the Presence of Cytidine-5'-Monophospho-N-Acetylneuraminic Acid in Genetically Altered *P. Pastoris*

Yeast cells were washed three times with cold PBS buffer, and suspended in 100 mM ammonium bicarbonate pH 8.5 and kept on ice. The cells were lysed using a French pressure cell followed by sonication. Soluble cell contents were separated from cell debris by ultracentrifugation. Ice cold ethanol was added to the supernatant to a final concentration of 60% and kept on ice for 15 minutes prior to removal of insoluble proteins by ultracentrifugation. The supernatant was frozen and concentrated by lyophilization. The dried sample was resuspended in water (ensuring pH is 8.0) and then filtered through a pre-rinsed 10,000 MWCO Centricon cartridge. The filtrate was separated on a Mono Q ion-exchange column according to manufacturer's instructions and the elution fractions that co-eluted with authentic CMP-sialic acid were pooled and lyophilized.

The dried filtrate was dissolved in 100 µL of 100 mM ammonium acetate pH6.5, 11 µL (5 mU) of α2,6 sialyltransferase and 3.3 µL (12 mU) of α-2,3 sialyltransferase were added, and 10 µL of the mixture was removed for a negative control. Subsequently, 7 (1.4 µg) of 2-aminobenzamide-labeled asialo-biantennary N-glycan (NA2, Glyco Inc., San Rafael, Calif.) was added to the remaining mixture, followed by the removal of 10 µL for a positive control. The sample and control reactions were then incubated at 37° C. for 16 hr. 10 µL of each sample were then separated on a GlycoSep-C anion exchange column according to manufacturer's instructions. A separate control consisting of approximately 0.05 µg each of monosialylated and disialylated biantennary glycans was separated on the column to establish relative retention times. The results are shown in FIGS. 23-27.

Sialidase Treatment

The incubation of bi-antennary galactosylated N-glycans with an extract from the *P. pastoris* YSH99a strain in the presence of sialyltransferases produced sialylated N-glycans, which were subsequently desialylated as follows: a sialylated sample was passed through a Microcon cartridge, with 10,000 molecular weight cut-off, to remove the transferases. The cartridge was washed twice with 100 µl of water, which was pooled with the original eluate. Analysis of the eluate by HPLC (FIG. 26) produced a spectrum similar to the HPLC spectrum prior to the Microcon treatment. The remaining sample was lyophilized to dryness and resuspended in 25 µl of 1×NEB G1 buffer. After addition of 100 U of sialidase (New England Biolabs #P0720L, Beverley, Mass.), the resuspended sample was incubated overnight at 37° C. prior to HPLC analysis, as described previously.

EXAMPLE 17

Engineering a *P. Pastoris* Strain Capable of Transferring Sialic Acid to N-Glycan A *P. pastoris* strain capable of transferring sialic acid to N-glycans in vivo has been created as described in detail herein.

Generation of pSH321b for Expressing Human UDP-GlcNAc-2-Epimerase/N-Acetylmannosamine Kinase (hGNE) and N-Acetylneuraminate-9-Phosphate Synthase (HsiaPsyn)

The gene sequence encoding the human UDP-GlcNAc-2-epimerase/N-acetylmannosamine kinase (hGNE; Genbank Accession No. AJ238764) was amplified as NotI-PacI fragment from human liver cDNA using oligonucleotide primers GGGAGAATGCGGCCGCCACCATGGAGAA-GAATGGAAATAACCGAAAG CTGCG (hGNE NotI/Koz) (SEQ ID NO: 77) and CCTTAATTAACTAGTAGATCCT-GCGTGTTGTGTAGTCCAGAAC (hGNE PacI rev) (SEQ ID NO: 78) with Advantage™ DNA polymerase (BD Biosciences) according to manufacturer's instructions. The conditions used for thermocycling were as follows: 95° C. 2 min, 1 cycle; 97° C. 30 sec, 60° C. 30 sec, 72° C. 5 min, 25 cycles; 72° C. 5 min. The resulting 2.2 Kb fragment was cloned into pCR2.1 (Invitrogen), sequenced and designated pSH281. The hGNE was cloned from pSH281 into pJN348 (as described in US Publication No. 2004/0230042) as a NotI-PacI fragment, producing vector pSH284. Positive clones from colony PCR were grown in a baffled flask containing 200 mL of BMGY media consisting of 2.68 g/L yeast nitrogen base, 200 mg/L biotin and 2 g/L dextrose, supplemented with amino acids depending on the strains.

The gene sequence encoding the human N-acetylneuraminate-9-phosphate synthase (hSiaPsyn; Genbank Accession No. AF257466) was amplified as above using primers GGGAGAATGCGGCCGCCACCATGC-CGCTGGAGCTGGAGCTGTGTCCCG (hSiaPsyn NotI/Koz) (SEQ ID NO: 79) and CCTTAATTAATTAAGACT-TGATTTTTTTGCCATGATTATCTACC (hSiaPsyn PacI rev) (SEQ ID NO: 80). The conditions used for thermocycling were 2.5 min extension instead of 5 min. The resulting 1.1 Kb fragment was cloned into pCR2.1 (Invitrogen), sequenced and designated pSH282. The hSiaPsyn was cloned from pSH282 into pJN664 (as disclosed in US Publication No. 2004/230042) as a NotI-PacI fragment, giving the vector pSH302. This construct was used as template to amplify the PMA hSiaPsyn cassette flanked by XhoI sites using the primers: GGCTCGAGATTTAAATGCGTACCTCTTC-TACGAGATTC (pPMA for XhoI) (SEQ ID NO: 81) and CCCTCGAGATTTAAATCCAACCGATAAG-GTGTACAGGAG (PMAtt rev XhoI) (SEQ ID NO: 82). The resulting vector was designated pSH315.

Figure 28:
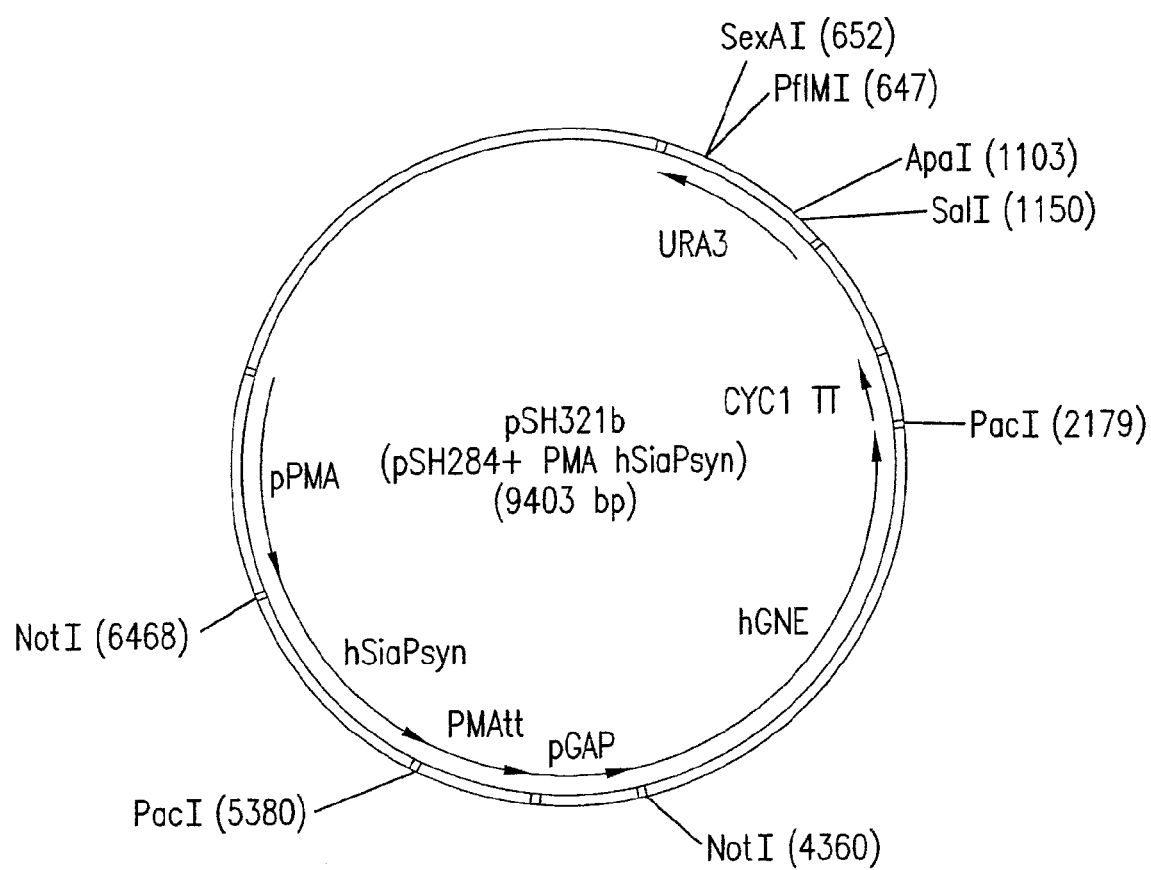
FIG. 28 illustrates vector pSH321b used in Example 17.

The 2.6 Kb XhoI fragment from pSH315, containing the PMA hSiaPsyn cassette, was ligated into the XhoI site of pSH284 to give the double expression cassette vector pSH321b (FIG. 28).

Generation of pJN711b for Expressing Genes Involved in Making Galactosylated Glycoproteins The *D. melanogaster* gene encoding the UDP Galactose Transporter (Genbank Accession No. BAB62747) (referred to as DmUGT) was PCR amplified from a *D. melanogaster* cDNA library (UC Berkeley *Drosophila* Genome Project, ovary λ-ZAP library GM), cloned into the pCR2.1 PCR cloning vector (Invitrogen) and sequenced. Primers DmUGT-5' (5'-GGCTCGAGCGGCCGCCACCATGAATAG-CATACACATGAACGCCAATAC G-3') (SEQ ID NO: 83)

and DmUGT-3' (5'-CCCTCGAGTTAATTAACTA-GACGCGCGGCAGCAGCTTCTCCTCATCG-3') (SEQ ID NO: 84) were used to amplify the gene, which introduced NotI and PacI sites at the 5' and 3' ends, respectively. The NotI and PacI sites were then used to subclone DmUGT fused downstream of the PpOCH1 and promoter at the NodI/PacI sites in pRCD393 to create plasmid pSH263. See Davidson et al., WO05/100584A2, which is incorporated by reference herein.

The *S. pombe* gene encoding UDP-galactose 4-epimerase (GenBank Accession No. ATCC24843) (referred to as SpGALE) was amplified from *S. pombe* genomic DNA using primers GALE2-L (5' ATG ACT GGT GTT CAT GAA GGG 3') (SEQ ID NO: 85) and GALE2-R (5' TTA CTT ATA TGT CTT GGT ATG 3') (SEQ ID NO: 86). The amplified product was cloned into pCR2.1 (Invitrogen) and sequenced. Sequencing revealed the presence of an intron (175 bp) at the +66 position. To eliminate the intron, upstream primer GD1 (94 bases) was designed. It has a NotI site, 66 bases upstream of the intron, followed by 20 bases preceding the intron. GD2 is the downstream primer and has a PacI site. Primers GD1 (5' GCG GCC GCA TGA CTG GTG TTC ATG AAG GGA CTG TGT TGG TTA CTG GCG GCG CTG GTT ATA TAG GTT CTC ATA CGT GCG TTG TFT TGT TAG AAA A 3') (SEQ ID NO: 87) and GD2 (5' TTA ATT AAT TAC TTA TAT GTC TTG GTA TG 3') (SEQ ID NO: 88) were used to amplify the SpGALE intronless gene from the pCR2.1 subclone and the product cloned again into pCR2.1 and sequenced.

The *H. sapiens* β-1,4-galactosyltransferase I gene (hGalTI, Genbank Accession No. AH003575) was PCR amplified from human kidney cDNA (Marathon-Ready cDNA, Clontech) using primers RCD192 (5'-GCCGCGAC-CTGAGCCGCCTGCCCCAAC-3') (SEQ ID NO: 89) and RCD186 (5'-CTAGCTCGGTGTCCCGATGTCCACTGT-3') (SEQ ID NO: 90). This PCR product was cloned into pCR2.1 vector (Invitrogen, Carlsbad, Calif.) and sequenced. From this clone, a PCR overlap mutagenesis was performed for three purposes: 1) to remove a NotI site within the open reading frame while maintaining the wild-type protein sequence; 2) to truncate the protein immediately downstream of the endogenous transmembrane domain; and 3) to introduce AscI and PacI sites at the 5' and 3' ends for modular cloning. To do this, the 5' end of the gene up to the NotI site was amplified using primers RCD198 (5'-CTTAGGCGCGC-CGGCCGCGACCTGAGCCGCCTGCCC-3') (SEQ ID NO: 91) and RCD201 (5'-GGGGCATATCTGCCGCCCATC-3') (SEQ ID NO: 92) and the 3' end was amplified with primers RCD200 (5'-GATGGGCGGCAGATATGCCCC-3') (SEQ ID NO: 93) and RCD199 (5'-CTTCTTAATTAAC-TAGCTCGGTGTCCCGATGTCCAC-3') (SEQ ID NO: 94). The products were overlapped together with primers 198 and 199 to resynthesize the ORF with the wild-type amino acid sequence while eliminating the NotI site. The new truncated hGalTI PCR product was cloned into pCR2.1 vector (Invitrogen, Carlsbad, Calif.) and sequenced. The introduced AscI/PacI sites were then used to subclone the fragment into plasmid pRCD259, which is a PpURA3/HYGR roll-in vector, to create pRCD260. A library of yeast targeting sequence transmembrane domains as described herein, was ligated into the NotI/AscI sites located upstream of the hGalTI gene to create plasmids pXB20-pXB67. pXB53 is a truncated *S. cerevisiae* Mnn2(s) targeting peptide (1-108 nucleotides of MNN2 from Genbank Accession No. NP_009571) ligated in-frame to a 43 N-terminal amino acid deletion of a human β1,4-galactosyltransferase I (Genbank Accession No. AH003575).

Figure 29:
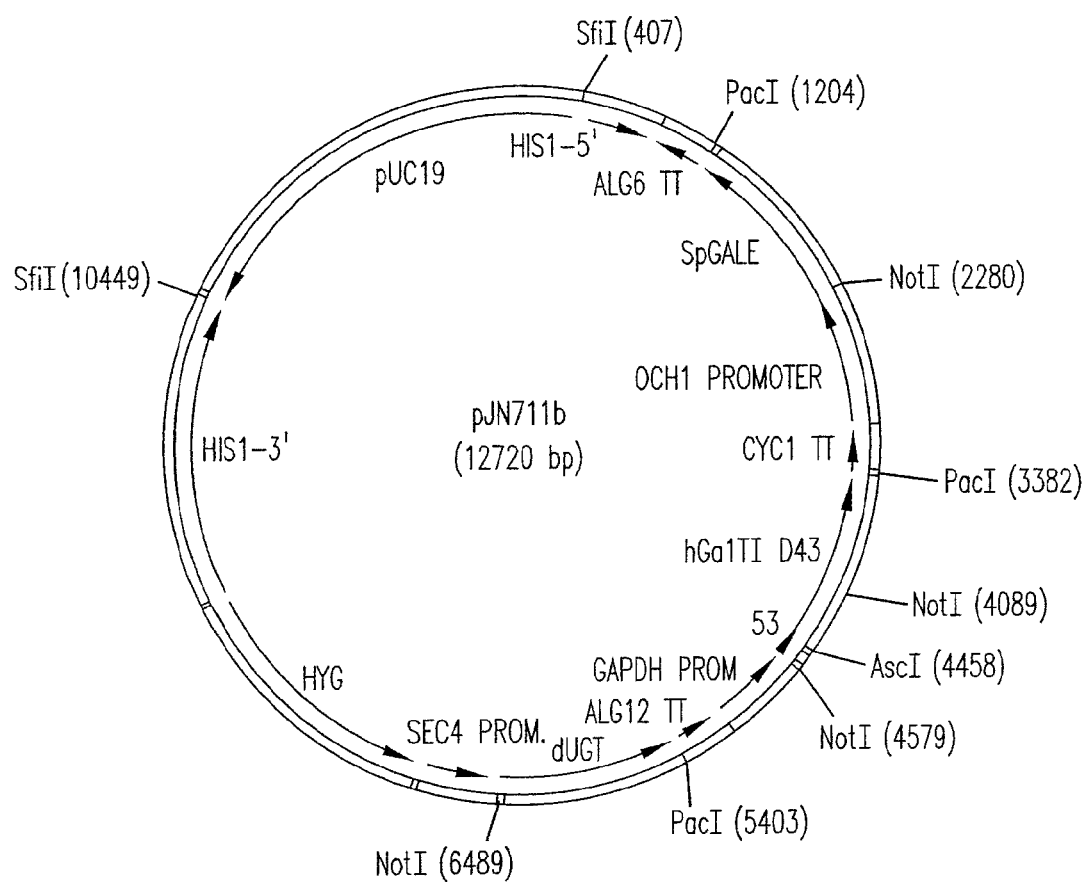
FIG. 29 depicts vector pJN711b used in Example 17.

Using the above vectors, pJN711b (FIG. 29) was constructed, which is a HYGR plasmid containing hGalTI-53, POCH1-SpGALE, and DmUGT.

Generation of pSH326b for Expressing Human CMP-Sialic Acid Synthase (hCMP-Sia syn) and Mouse CMP-Sialic Acid Transporter (mCMP-Sia Tr)

The gene encoding the human CMP-Sialic acid synthase (Genbank Accession No. AF397212) (referred to as hCMP-Sia syn) was amplified as a NotI-PacI fragment from human prostate cDNA. The conditions used for thermocycling were as follows: 95° C. 2 min, 1 cycle; 97° C. 30 sec, 60° C. 30 sec, 72° C. 2.5 min, 25 cycles; 72° C. 5 min. using oligonucleotide primers: GGGAGAATGCGGCCGCCACCATG-GACTCGGTGGAGAAGGGGGCCGCC ACCTC (hCMP-NANA syn NotI/Koz) (SEQ ID NO: 95) and CCTTAAT-TAACTATTTTTGGCATGAATTATTAACTTTTTCCATTA (hCMP-NANA syn PacI) (SEQ ID NO: 96) with Advantage™ DNA polymerase (BD Biosciences). The resulting 1.3 Kb fragment was cloned into pCR2.1 (Invitrogen), sequenced and designated pHW6. The hCMP-Sia syn was cloned from pHW6 into pPB140 (a Kanamycin resistance vector, containing a 1.2 Kb fragment of *P. pastoris* HIS3 loci to facilitate 'rolling-in' integration, and the GAPDH-CYC promoter-terminator expression cassette) as a NotI-PacI fragment, giving the vector pSH301.

The gene encoding the mouse CMP-Sialic acid transporter (Genbank Accession No. Z71268) (referred to as mCMP-Sia Tr) was amplified as above (using 2.5 min extension time) from mouse brain cDNA using oligonucleotide primers: CGGAATTCCACCATGGCTCCGGC-GAGAGAAAATGTCAG (mCMP-NANA trans Koz/for) (SEQ ID NO: 97) and CGGAATTCTCACACACCAATGAT-TCTCTCTTTTGAAG (mCMP-NANA trans rev) (SEQ ID NO: 98). The resulting fragment was cloned into pCR2.1 (Invitrogen), sequenced and designated pSH194. The mCMP-Sia syn was digested from pSH194 with EcoRI and blunted with T4 DNA polymerase prior to subcloning into pJN664, previously digested with NotI-PacI and blunted, giving the vector pSH306. This construct was used as template to amplify the PMA mCMP-Sia cassette flanked by XhoI sites using the primers: GGCTCGAGATTTAAATGCGTAC-CTCTTCTACGAGATTC (pPMA for XhoI) (SEQ ID NO: 99) and CCCTCGAGATTTAAATCCAACCGATAAG-GTGTACAGGAG (PMAtt rev XhoI) (SEQ ID NO: 100). The resulting vector was designated pSH317.

Figure 30:
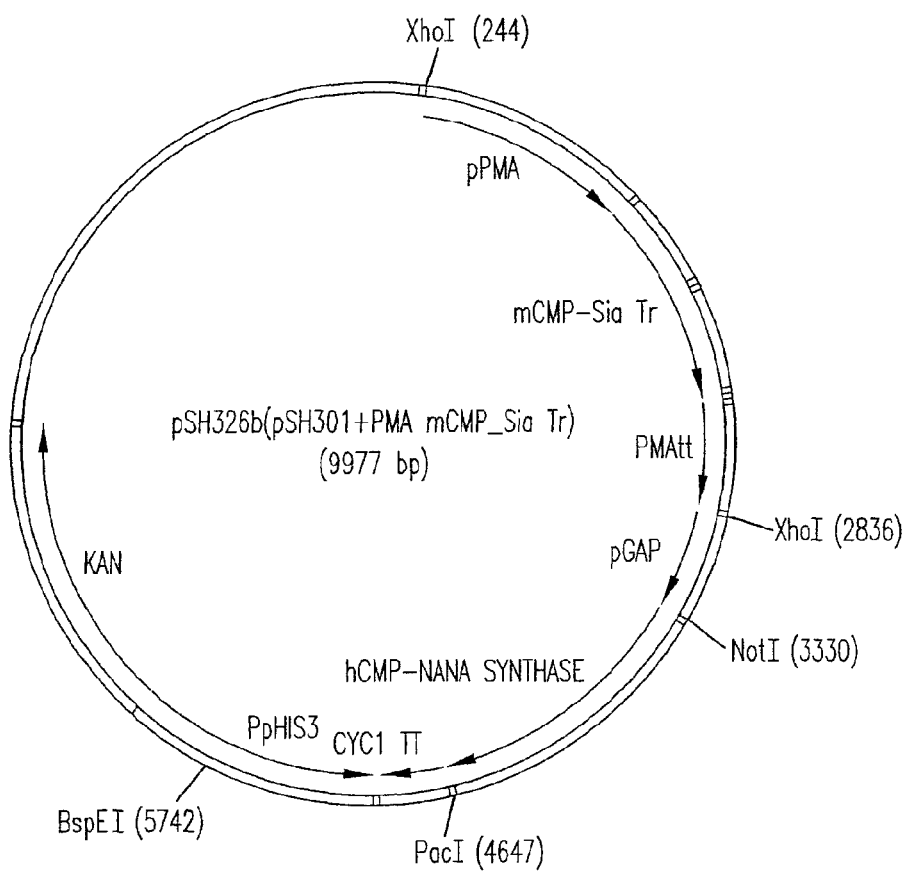
FIG. 30 depicts vector pSH326b used in Example 17.

The 2.6 Kb XhoI fragment from pSH317, containing the PMA mCMP-Sia transporter cassette, was ligated into the XhoI site of pSH301 (containing hCMP-Sia syn) to give the double expression cassette vector pSH326b (FIG. 30).

Generation of pSH370 for Expressing Rat ST6Gal

Figure 31:
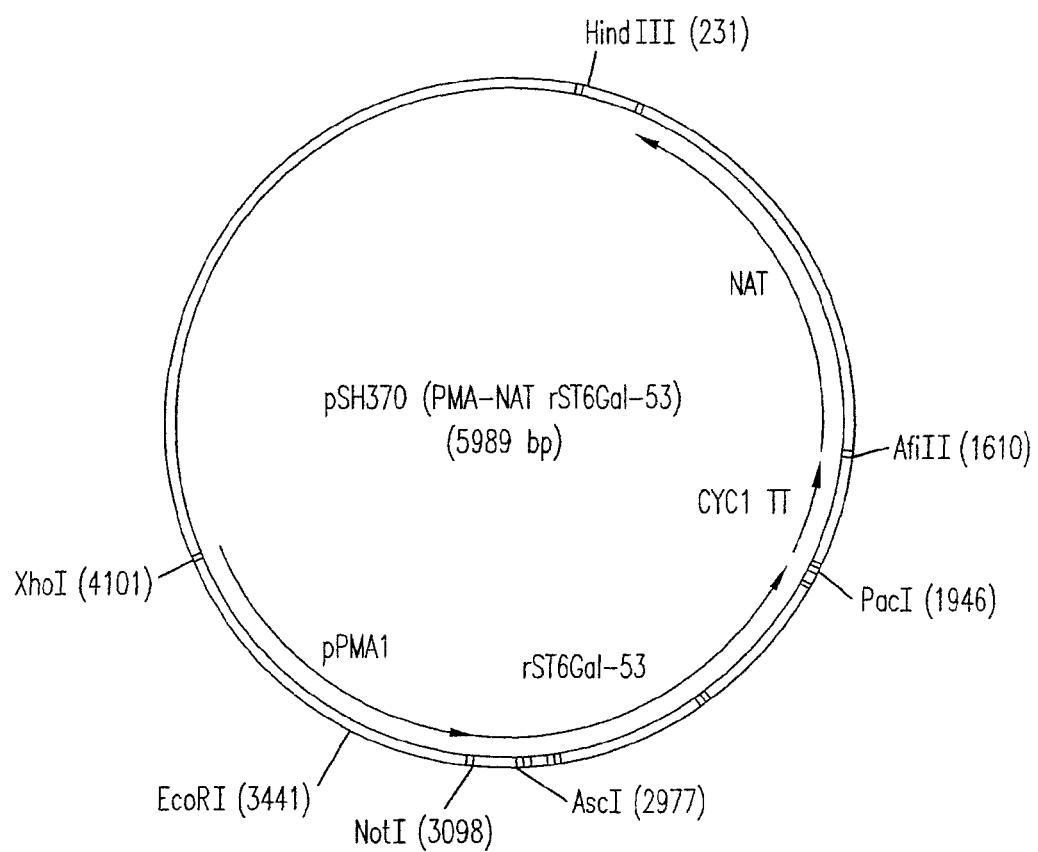
FIG. 31 depicts vector pSH370 used in Example 17.

An N-terminal deletion of the rat ST6Gal (Genbank Accession No. M18769) was amplified from rat liver cDNA using the conditions described above for the hGNE, but using a 2 min extension time instead of 5 min. The primers were: GGCGCGCCAGCAAGCAAGACCCTAAG-GAAGACATTCC (rST6GalI d63 AscI) (SEQ ID NO: 101) and CCTTAATTAATCAACAACGAATGTTCCG-GAAGCCAGAAAGG (rST6GalI Pace (SEQ ID NO: 102). The resulting fragment was cloned into pCR2.1 (Invitrogen), sequenced and designated pSH271. Subsequently, the 1 kb fragment containing the encoded rST6Gal catalytic domain was subcloned into a nourseothricin selectable vector (Hansen, 2003) generating a fusion of the rST6Gal to the first 108 base pairs of Mnn2 (leader 53), under the control of the PMA promoter. The resulting vector was designated pSH370 (FIG. 31).

Generation of pSH373 for Expressing Mannosidase II (MannII) and GnTII

*D. melanogaster* mannosidase II (Genbank Accession No. X77652) fused to leader 53 (K1353) was subcloned as a NotI-PacI fragment from pKD53 into the expression vector pJN702. The resulting vector was designated pSH368.

The rat GnTII (Genbank Accession No. U21662) fused to the first 108 base pairs of Mnn2 (leader 53) was digested from pTC53 (see Hamilton, 2003) as a NotI-PacI fragment and subcloned into pJN664 digested with the same enzymes. The resulting vector was designated pSH327.

Figure 32:
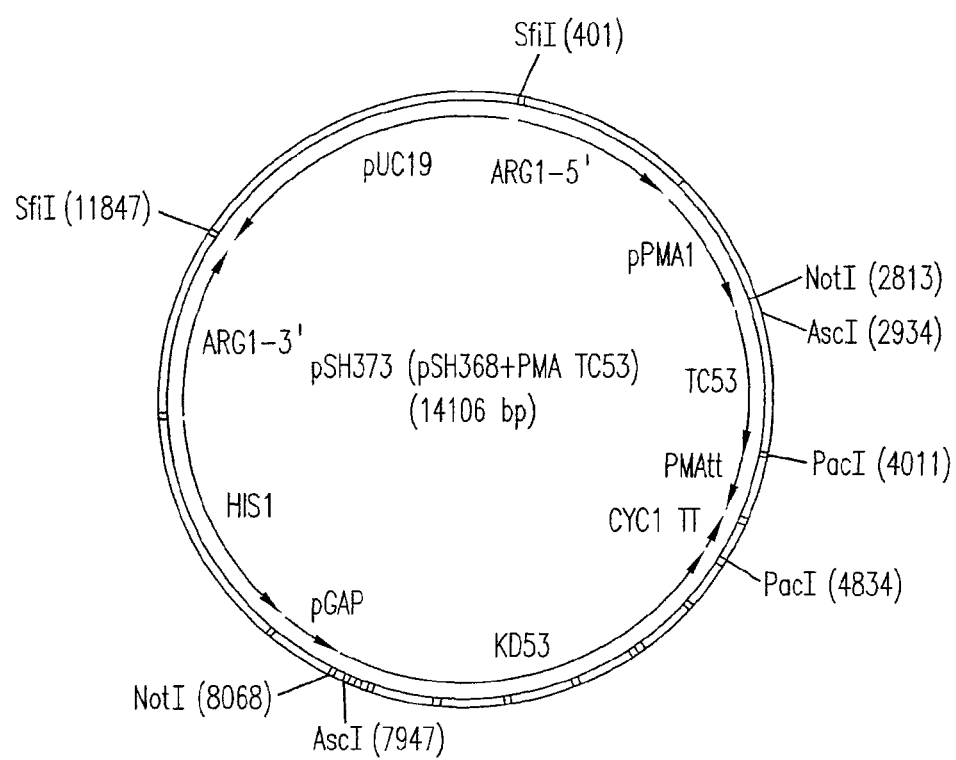
FIG. 32 depicts vector pSH373 used in Example 17.

The 2.7 kb SwaI fragment of pSH327, containing the PMA GnTII expression cassette, was ligated into the PmeI site of pSH368. The resulting vector was designated pSH373 (FIG. 32).

Generation of pSH568 for Expressing Codon-Optimized Human ST6Gal

Figure 34:
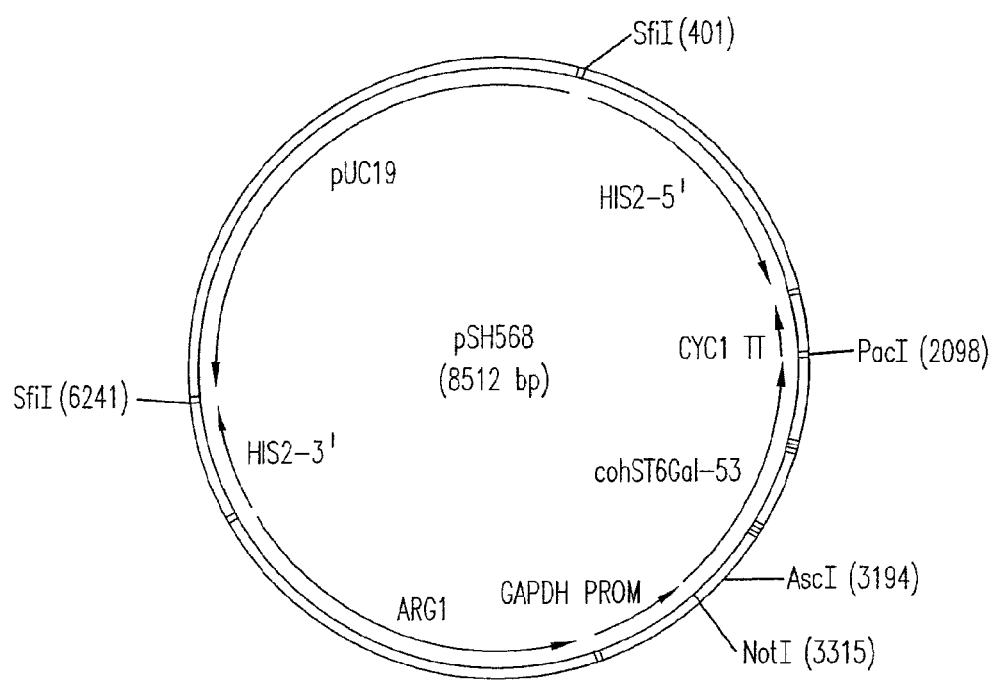
FIG. 34 depicts vector pSH568 used in Example 17.

A codon-optimized version of an N-terminal deletion of human ST6Gal (Genbank Accession No. NM_003032) fused to the first 108 base pairs of Mnn2 (leader 53) was generated by GENEART GmbH (Regensburg Germany). The nucleic acid and amino acid sequences of this codon optimized hST6Gal are shown in FIG. 33. The resulting NotI-PacI fragment was subcloned into the expression vector pJN703b, giving the construct pSH568 (FIG. 34).

pSH568 was digested with SfiI and transformed into the strain YSH272, which was generated in a similar fashion to YSH160, except that the introduction of rST6Gal was omitted and the vector pSH505 was used instead of pSH373. In vector pSH505, the MannII and GntII genes were introduced as leader 4 and leader 5 fusions, respectively. Leader 4 comprises *S. cerevisiae* mns1s leader, and leader 5 comprises *S. cerevisia* mns1m, respectively. See US 2002/0137134.

Engineering In Vivo Transfer of Sialic Acid to N-Glycans in Yeast

Figure 36:
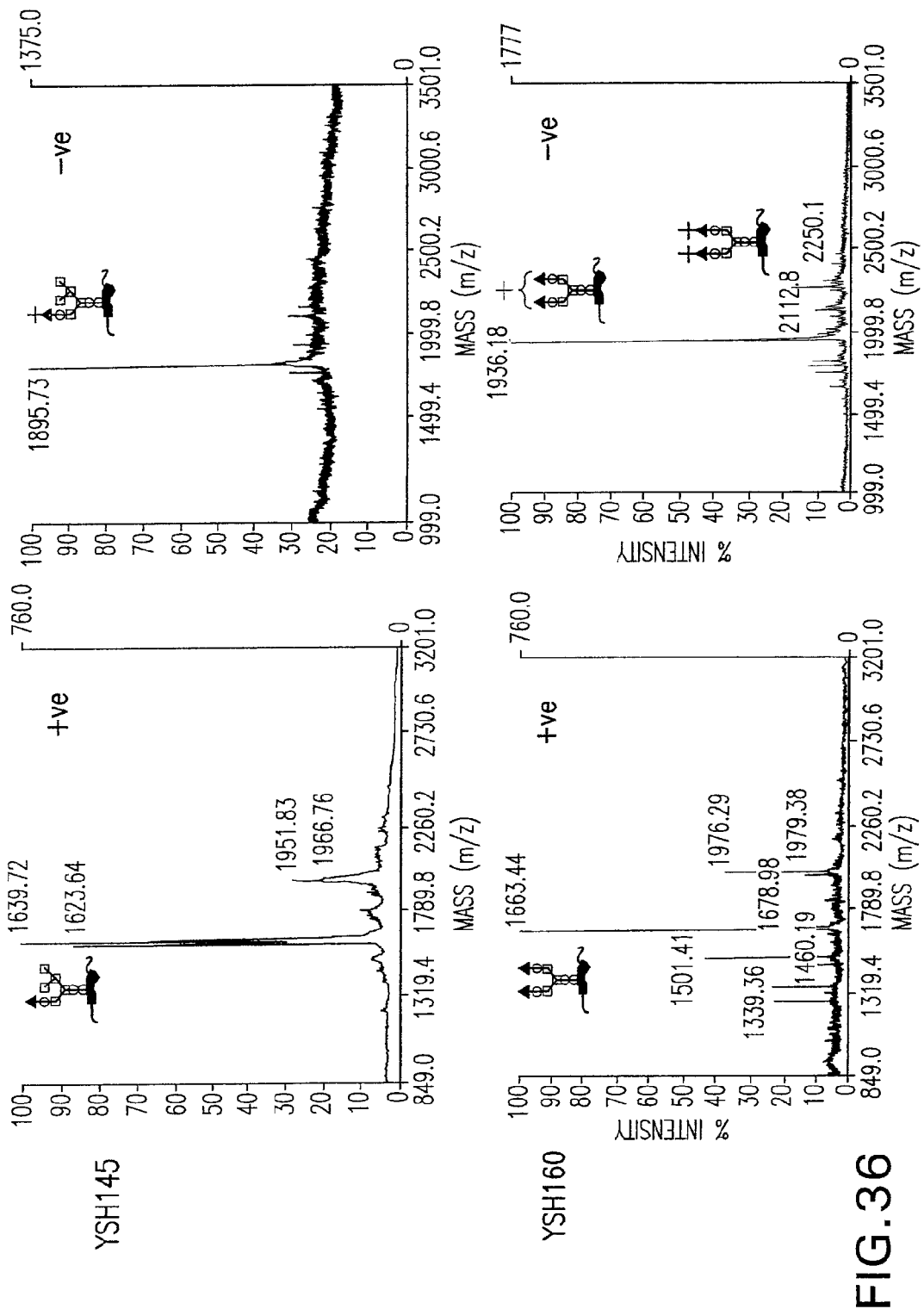
FIG. 36 shows MALDI-TOF MS analysis of the glycans produced in YSH145 and YSH160.

*P. pastoris* YSH1 (Hamilton, 2003) was used as the initial host strain to engineer the glycosylation machinery necessary to produce sialylated glycoproteins. YSH1 (Ura3-) was transformed with pSH321 (hGNE, hSiaPsyn, URA3; described above) digested with ApaI, and a positive clone designated YSH103 was identified using Ura3 as the selectable marker. YSH103 was then transformed with SfiI digested pJN711b (hGalTI-53, POCH1-SpGALE, DmUGT, Δhis1::Hyg; described above), using Hyg as the selectable marker. A transformant designated YSH116 (Δhis1) was selected and transformed with BspEI digested pSH326 (hCMP-Sia syn, mCMP-Sia Tr; described above), using Kan as the selectable marker. A transformant designated YSH125 (Δhis1) was selected and transformed with pSH370 (rST6Gal; described above) digested with EcoRI and a positive clone selected, using Nat as a selectable marker (Hansen, 2003). A transformant designated as YSH145 (Δhis1) was selected and subsequently transformed with SfiI digested pSH373 (MannII, GnTII, (Δarg1::His1); described above), using this as a selectable marker. The resulting transformant designated as YSH160 (Δarg1) produced glycoproteins exhibiting the oligosaccharide structure: NANA$_2$Gal$_2$GlcNAc$_2$Man$_3$GlcNAc$_2$ as shown in FIG. 36.

Figure 37:
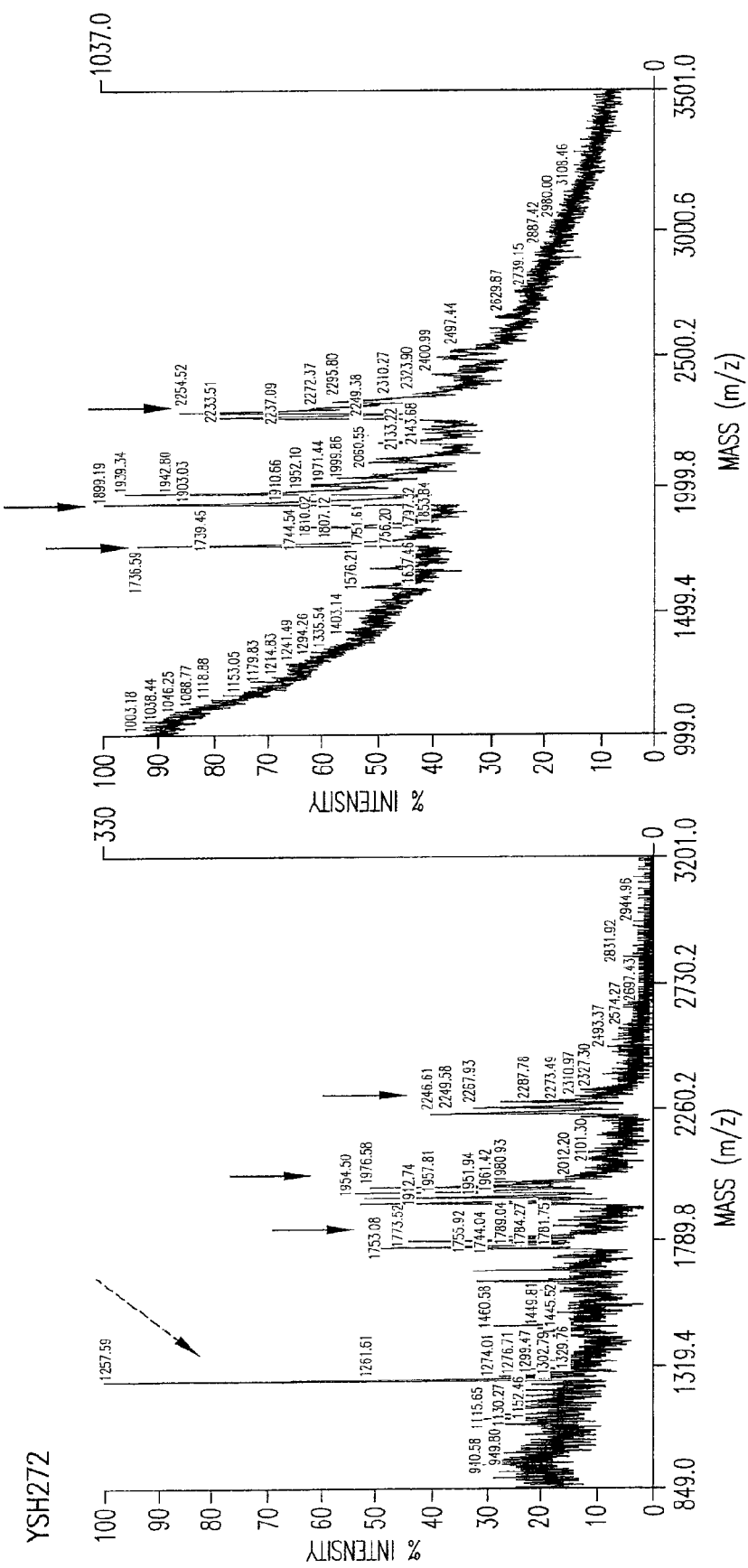
FIG. 37 shows MALDI-TOF MS analysis of the glycans produced in YSH272. The solid arrows represent sialic acid containing glycans. The dashed arrows represent neutral glycans.

Alternatively, YSH125 (Δhis1) was selected and transformed with pSH568 (codon optimized hST6Gal) digested with SfiI and a positive clone selected using Nat as a selectable marker. A transformant was selected and subsequently transformed with SfiI digested pSH505 (MannII, GnTII, (Δarg1::His1); described above). The resulting transformant designated as YSH272 (Δarg1) produced glycoproteins exhibiting the oligosaccharide structure: NANA$_2$Gal$_2$GlcNAc$_2$Man$_3$GlcNAc$_2$ as shown in FIG. 37.

All of the yeast strains were transformed by electroporation (as recommended by the manufacturer of the electroporator BioRad). Integration into the host genome was confirmed by PCR (Nett, 2005).

Glycan Analysis

Oligosaccharides on a recombinant Kringle 3 glycoprotein expressed in each of the strains described above were analyzed using MALDI-TOF MS.

Figure 35:
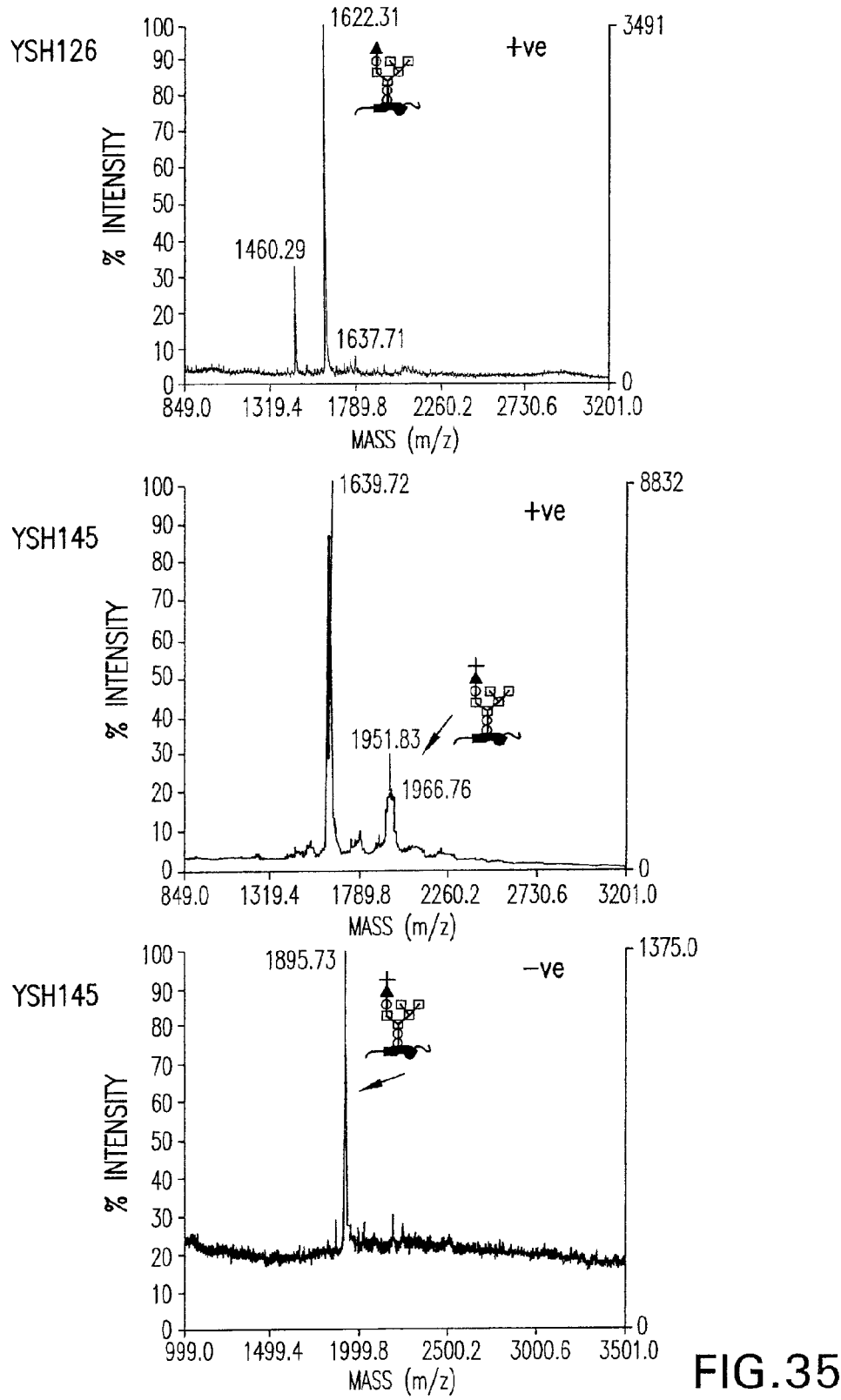
FIG. 35 depicts MALDI-TOF MS analysis of the glycans produced in YSH126 and YSH145. The "+ve" sign at the upper right corner of each MALDI-ROF indicates analysis of positive ions and the "−ve" sign indicates analysis of negative ions.

Glycan analysis of glycoproteins produced in strain YSH126, in which strain YSH116 is further transformed with pSH326, showed mass consistent with the glycan structure GalGlcNAcMan$_5$GlcNAc$_2$ confirming the in vivo transfer of a terminal galactose residue (FIG. 35).

Glycan analysis of glycoproteins produced in strain YSH145 showed mass consistent with the glycan structure NANAGalGlcNAcMan$_5$GlcNAc$_2$ confirming the in vivo transfer of sialic acid onto at least one oligosaccharide branch (FIGS. 35 and 36).

Glycan analysis of glycoproteins produced in strain YSH160 showed mass consistent with the glycan structure NANA$_2$Gal$_2$GlcNAc$_2$Man$_3$GlcNAc$_2$ confirming the in vivo transfer of sialic acid onto at least one oligosaccharide branch (FIG. 36).

Glycan analysis of glycoproteins produced in strain YSH272 showed mass consistent with the glycan structure NANA$_2$Gal$_2$GlcNAc$_2$Man$_3$GlcNAc$_2$ confirming the in vivo transfer of sialic acid onto at least one oligosaccharide branch (FIG. 37).

Table 13 summarizes the extent of in vivo sialic acid transfer onto a recombinant glycoprotein in an engineered *P. pastoris* strain made according to the invention disclosed herein. Values represent the percentages of total glycans that contained sialic acid; and thus sensitive to sialidase treatment.

TABLE 13

In Vivo Sialic Acid Transfer In Yeast

| Strain | Mono-sialylated | Bi-sialylated | Total transfer |
|---|---|---|---|
| YSH145 | 15% | — | 15% |
| YSH160 | 20% | 2% | 22% |
| YSH272 | 34% | 24% | 58% |

Materials and Method for the Experiments Described in Example 17

MOPS, sodium cacodylate, manganese chloride, UDP-galactose and CMP-N-acetylneuraminic acid were from Sigma. TFA was from Aldrich. β1,4-galactosyltransferase from bovine milk were from Calbiochem. Protein N-glycosidase F, mannosidases, and oligosaccharides were from Glyko (San Rafael, Calif.). DEAE ToyoPearl resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wis.).

Shake-Flask Cultivations

A single colony was picked from an YPD plate (<2 weeks old) containing the strain of interest and inoculated into 10 ml of BMGY media in a 50 ml "Falcon" centrifuge tube. The culture was grown to saturation at 24° C. (approx. 48 hours). The seed culture is transferred into a 500 ml baffled volumetric flask containing 150 ml of BMGY media and grown to OD600 of 5±2 at 24° C. (approx. 18 hours). The growth rate of the cells was determined as the slope of a plot of the natural logarithm of OD600 against time. The cells were harvested from the growth medium (BMGY) by centrifugation at 3000 g for 10 minutes, washed with BMMY and suspended in 15 ml of BMMY in a 250 ml baffled volumetric flask. After 24 hours, the expression medium is harvested by centrifugation (3000 g for 10 minutes) and the supernatant analyzed for K3 production.

Bioreactor Cultivations

A 500 ml baffled volumetric flask with 150 ml of BMGY media was inoculated with 1 ml of seed culture (see flask cultivations). The inoculum was grown to an OD600 of 4-6 at 24° C. (approx 18 hours). The cells from the inoculum culture was then centrifuged and resuspended into 50 ml of fermentation media (per liter of media: CaSO4.2H2O 0.30 g, K2SO4 6.00 g, MgSO4.7H2O 5.00 g, Glycerol 40.0 g, PTM1 salts 2.0 ml, Biotin 4×10-3 g, H3PO4 (85%) 30 ml, PTM1 salts per liter: CuSO4.H2O 6.00, NaI 0.08 g, MnSO4.7H2O 3.00 g, NaMoO4.2H2O 0.20 g, H3BO3 0.02 g, CoCl2.6H2O 0.50 g, ZnCl2 20.0 g, FeSO4.7H2O 65.0 g, Biotin 0.20 g, H2SO4 (98%) 5.00 ml).

Fermentations were conducted in 3 liter dished bottom (1.5 liter initial charge volume) Applikon bioreactors. The fermentors were run in a fed-batch mode at a temperature of 24° C., and the pH was controlled at 4.5±0.1 using 30% ammonium hydroxide. The dissolved oxygen was maintained above 40% relative to saturation with air at 1 atm by adjusting agitation rate (450-900 rpm) and pure oxygen supply. The air flow rate was maintained at 1 vvm. When the initial glycerol (40 g/l) in the batch phase is depleted, which is indicated by an increase of DO, a 50% glycerol solution containing 12 ml/l of PTM1 salts was fed at a feed rate of 12 ml/l/h until the desired biomass concentration was reached. After a half an hour starvation phase, the methanol feed (100% Methanol with 12 ml/l PTM1) is initiated. The methanol feed rate is used to control the methanol concentration in the fermentor between 0.2 and 0.5%. The methanol concentration is measured online using a TGS gas sensor (TGS822 from Figaro Engineering Inc.) located in the offgass from the fermentor. The fermentors were sampled every eight hours and analyzed for biomass (OD600, wet cell weight and cell counts), residual carbon source level (glycerol and methanol by HPLC using Aminex 87H) and extracellular protein content (by SDS page, and Bio-Rad protein assay).

Reporter Protein Expression, Purification and Release of N-Linked Glycans

The K3 domain, under the control of the alcohol oxidase 1 (AOX1) promoter, was used as a model protein and was purified using the 6× Histidine tag as reported previously (Choi, 2003). The glycans were released and separated from the glycoproteins by a modification of a previously reported method (Papac and Briggs 1998). After the proteins were reduced and carboxymethylated, and the membranes blocked, the wells were washed three time with water. The protein was deglycosylated by the addition of 30 μl of 10 mM NH4HCO3 pH 8.3 containing one milliunit of N-glycanase (Glyko). After 16 hr at 37° C., the solution containing the glycans was removed by centrifugation and evaporated to dryness.

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (μL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media is diluted 3:2, media/PBS (60 mM PO4, 16 mM KCl, 822 mM NaCl pH7.4) and loaded onto the columns. After draining, the columns are washed with 10 volumes of binding buffer and 6 volumes of wash buffer (30 mM imidazole, 0.5M NaCl, 20 mM Tris-HCl pH7.9) and the protein is eluted with 6 volumes of elution buffer (1M imidazole, 0.5M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, et al. A. J. S. (1998) Glycobiology 8, 445-454). The wells of a 96-well MultiScreen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1 M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM NH4HCO3 pH 8.3 containing one milliunit of N-glycanase (Glyko). After 16 hours at 37° C., the solution containing the glycans was removed by centrifugation and evaporated to dryness.

Miscellaneous

Proteins were separated by SDS/PAGE according to Laemmli (Laemmli 1970).

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875 Da. Spectra were generated from the sum of 100-200 laser pulses and acquired with a 2 GHz digitizer. Man5GlcNAc2 oligosaccharide was used as an external molecular weight standard. All spectra were generated with the instrument in the positive ion mode. The estimated mass accuracy of the spectra was 0.5%.

EXAMPLE 18

Engineering *K. lactis* Cells to Produce N-Glycans with the Structure Man$_5$GlcNAc$_2$ Identification and Disruption of the *K. lactis* OCH1 Gene The OCH1 gene of the budding yeast *S. cerevisiae* encodes a 1,6-mannosyltransferase that is responsible for the first Golgi localized mannose addition to the Man$_8$GlcNAc$_2$ N-glycan structure on secreted proteins (Nakanishi-Shindo, 1993). This mannose transfer is generally recognized as the key initial step in the fungal specific polymannosylation of N-glycan structures (Nakanishi-Shindo et al., 1993; Nakayama, 1992; Morin-Ganet, 2000). Deletion of this gene in *S. cerevisiae* results in a significantly shorter N-glycan structure that does not include this typical polymannosylation or a growth defect at elevated temperatures (Nakayama, 1992).

The Och1p sequence from *S. cerevisiae* was aligned with known homologs from *Candida albicans* (Genbank Accession No. AAL49987), and *P. pastoris* (Choi, 2003) along with the Hoc1 proteins of *S. cerevisiae* (Neiman, 1997) and *K. lactis* (PENDANT EST database) which are related but distinct mannosyltransferases. Regions of high homology that were in common among Och1p homologs but distinct from the Hoc1p homologs were used to design pairs of degenerate primers that were directed against genomic DNA from the *K. lactis* strain MG1/2 (Bianchi, 1987). PCR amplification with primers RCD33 (CCAGAAGAATTCAATTYTGY-CARTGG) (SEQ ID NO:34) and RCD34 (CAGT-GAAAATACCTGGNCCNGTCCA) (SEQ ID NO:35) resulted in a 302 bp product that was cloned and sequenced and the predicted translation was shown to have a high degree of homology to Och1 proteins (>55% to *S. cerevisiae* Och1p).

Figure 12:
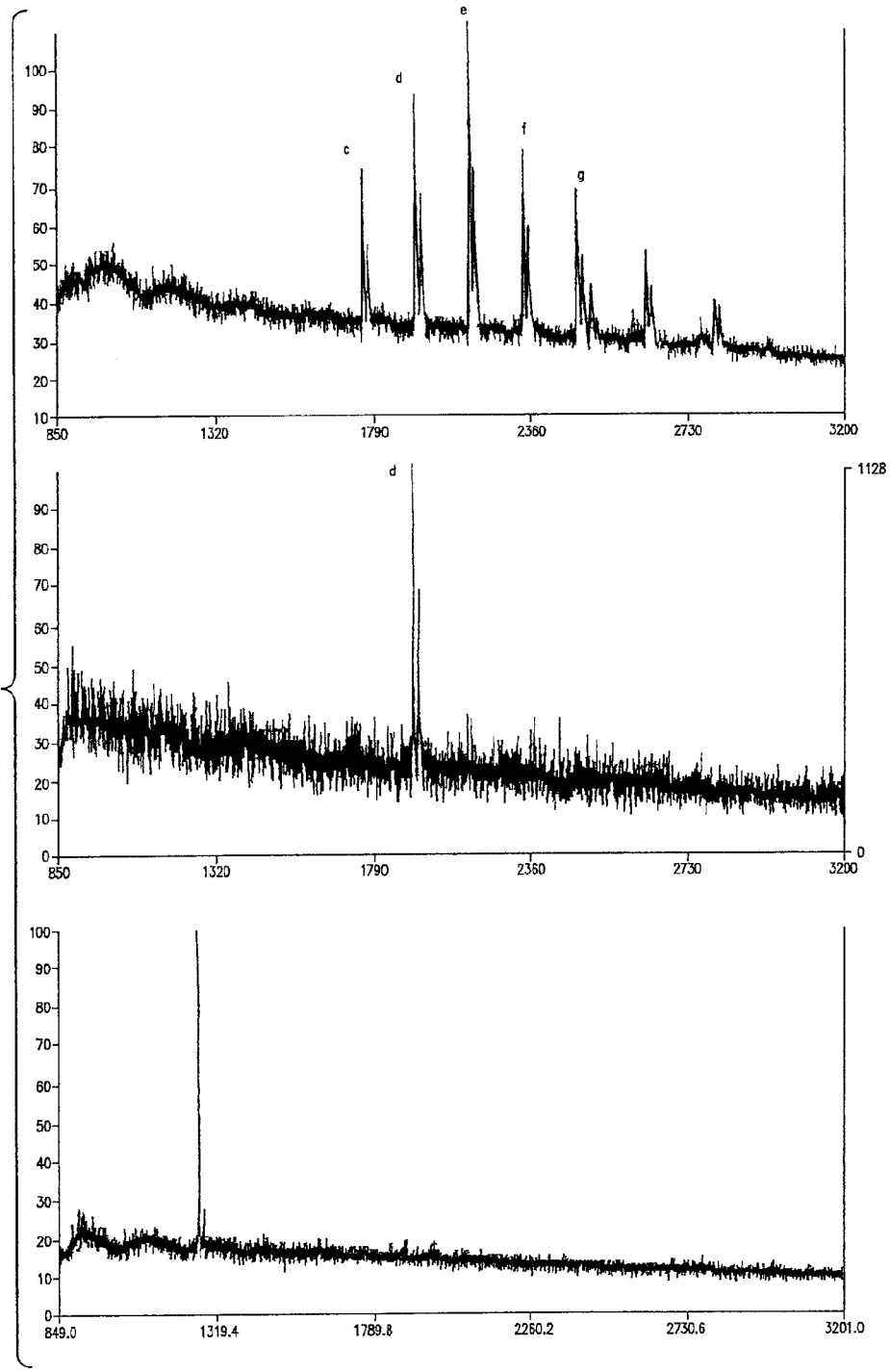
FIGS. 12 and 12A-12C show MALDI-TOF analysis of N-glycans released from a cell free extract of *K. lactis*.
Figure 12A:
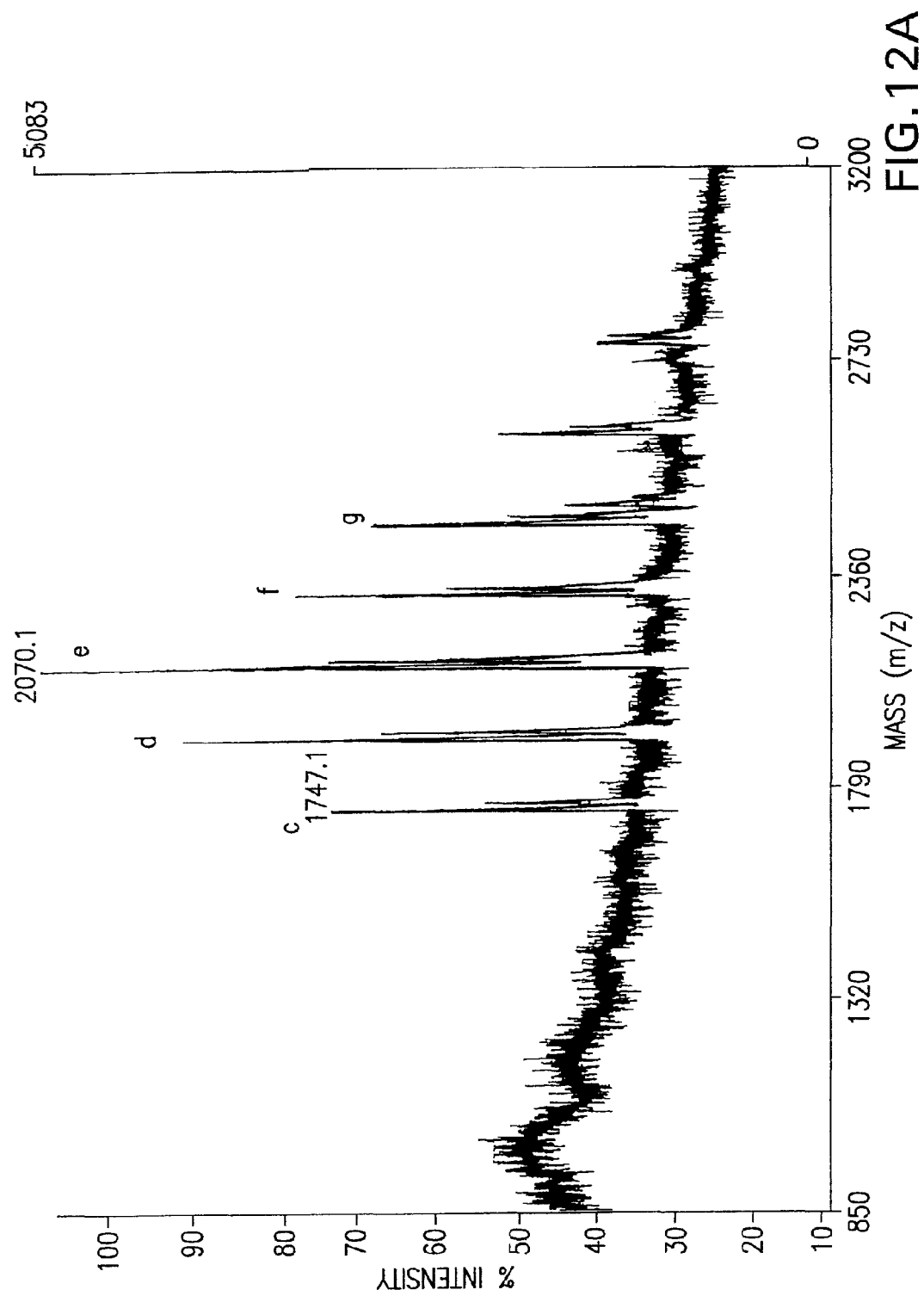

The 302 bp PCR product was used to probe a Southern blot of genomic DNA from *K. lactis* strain (MG1/2) with high stringency (Sambrook et al., 1989). Hybridization was observed in a pattern consistent with a single gene indicating that this 302 bp segment corresponds to a portion of the *K. lactis* genome and *K. lactis* (KlOCH1) contains a single copy of the gene. To clone the entire KlOCH1 gene, the Southern blot was used to map the genomic locus. Accordingly, a 5.2 kb BamHI/PstI fragment was cloned by digesting genomic DNA and ligating those fragments in the range of 5.2 kb into pUC19 (New England Biolabs, Beverly, Mass.) to create a *K. lactis* subgenomic library. This subgenomic library was transformed into *E. coli* and several hundred clones were tested by colony PCR using RCD 33/34. The 5.2 kb clone containing the predicted KlOCH1 gene was sequenced and an open reading frame of 1362 bp encoding a predicted protein that is 46.5% identical to the *S. cerevisiae* OCH1 gene. The 5.2 kb sequence was used to make primers for construction of an och1::KAN$^R$ deletion allele using a PCR overlap method (Davidson, 2002). This deletion allele was transformed into two *K. lactis* strains and G418 resistant colonies selected. These colonies were screened by both PCR and for temperature sensitivity to obtain a strain deleted for the OCH1 ORF. The results of the experiment show strains which reveal a mutant PCR pattern, which were characterized by analysis of growth at various temperatures and N-glycan carbohydrate analysis of secreted and cell wall proteins following PNGase digestion. The och1 mutation conferred a temperature sensitivity which allowed strains to grow at 30° C. but not at 35° C. FIG. 12A shows a MALDI-TOF analysis of a wild type *K. lactis* strain producing N-glycans of Man$_8$GlcNAc$_2$ [c] and higher.

Identification, Cloning, and Disruption of the *K. lactis* MNN1 Gene

*S. cerevisiae* MNN1 is the structural gene for the Golgi α-1,3-mannosyltransferase. The product of MNN1 is a 762-amino acid type II membrane protein (Yip, 1994). Both N-linked and O-linked oligosaccharides isolated from mnn1 mutants lack α-1,3-mannose linkages (Raschke, 1973).

The Mnn1p sequence from *S. cerevisiae* was used to search the *K. lactis* translated genomic sequences (PEDANT). One 405 bp DNA sequence encoding a putative protein fragment of significant similarity to Mnn1p was identified. An internal segment of this sequence was subsequently PCR amplified with primers KMN1 (TGCCATCTTTTAGGTCCAGGC-CCGTTC) (SEQ ID NO:36) and KMN2 (GATCCCAC-GACGCATCGTATTTCTTTC), (SEQ ID NO:37) and used to probe a Southern blot of genomic DNA from *K. lactis* strain (MG1/2). Based on the Southern hybridization data a 4.2 Kb BamHI-PstI fragment was cloned by generating a size-selected library as described herein. A single clone containing the *K. lactis* MNN1 gene was identified by whole colony PCR using primers KMN1 (SEQ ID NO:36) and KMN2 (SEQ ID NO:37) and sequenced. Within this clone a 2241 bp ORF was identified encoding a predicted protein that was 34% identical to the *S. cerevisiae* MNN1 gene. Primers were designed for construction of a mnn1::NAT$^R$ deletion allele using the PCR overlap method (Davidson, 2002).

This disruption allele was transformed into a strain of *K. lactis* by electroporation and Noursethoicin resistant transformants were selected and PCR amplified for homologous insertion of the disruption allele. Strains that reveal a mutant PCR pattern may be subjected to N-glycan carbohydrate analysis of a known reporter gene.

Figure 12B:
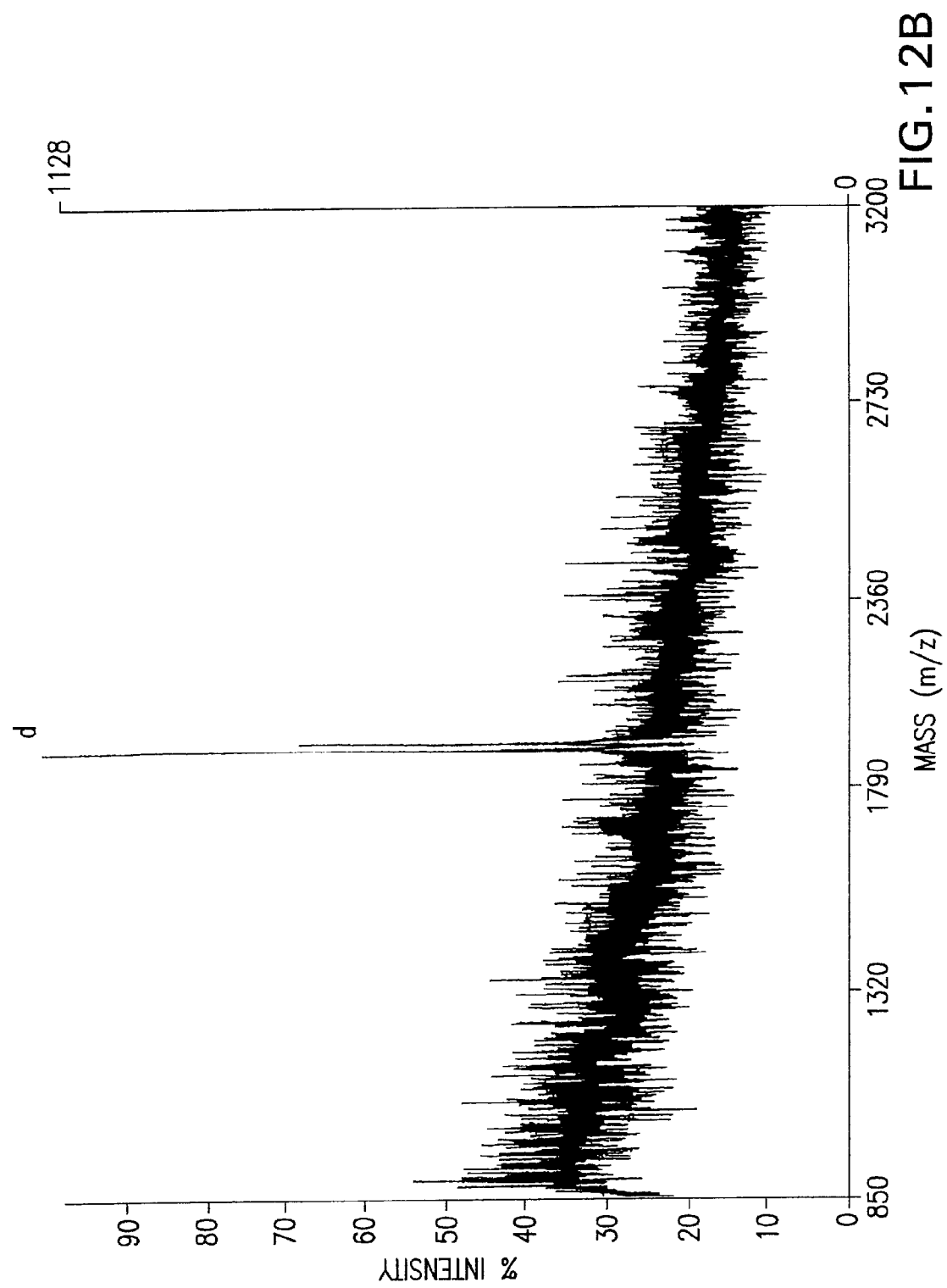
Figure 12C:
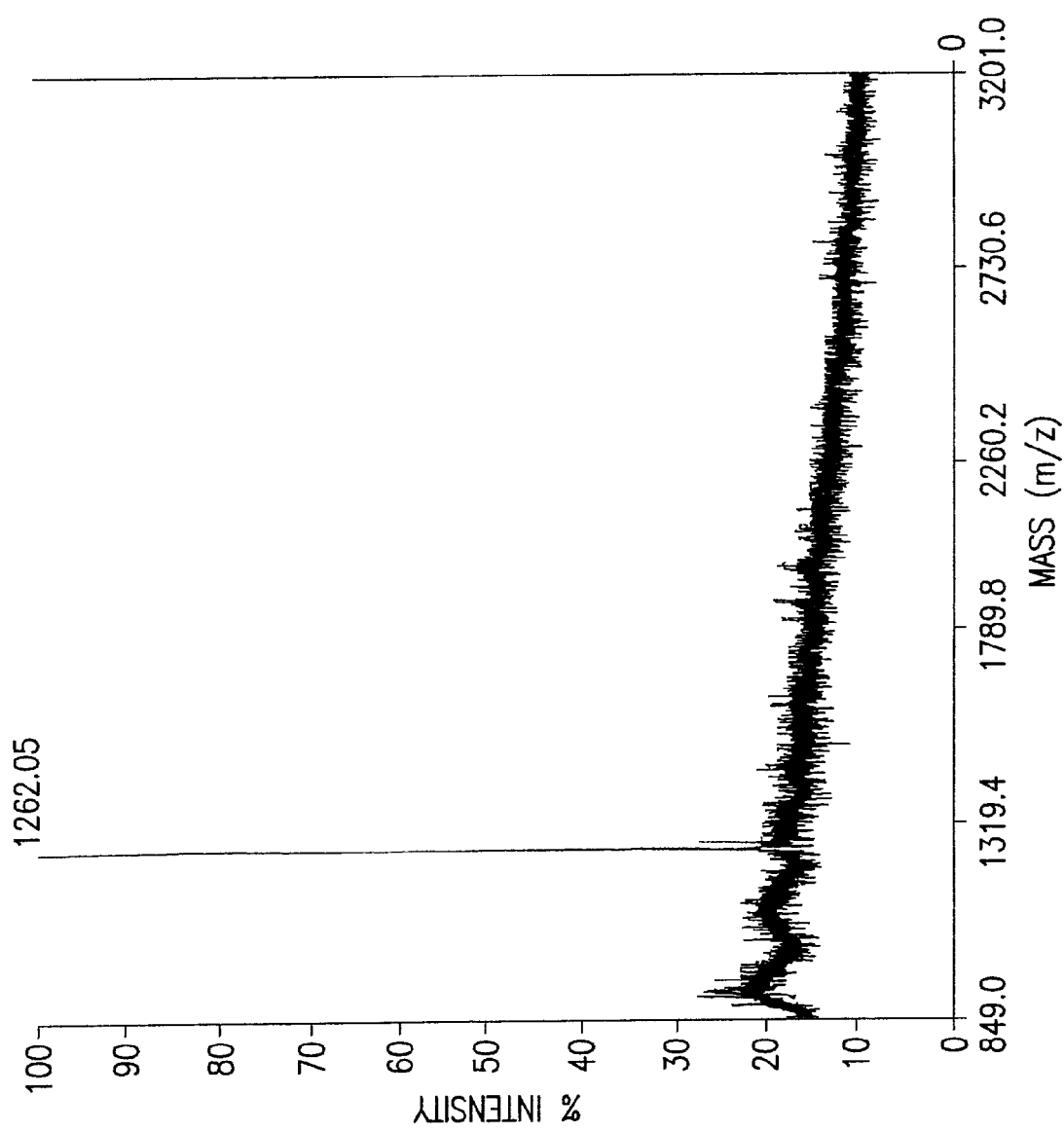

FIG. 12B depicts the N-glycans from the *K. lactis* och1 mnn1 deletion strain observed following PNGase digestion and MALDI-TOF as described herein. The predominant peak at 1908 (m/z) indicated as [d] is consistent with the mass of Man$_9$GlcNAc$_2$.

EXAMPLE 19

Engineering Plant Cells to Express GlcNAc Transferases or Galactosyltransferases GlcNAc transferase IV is required for the addition of β1,4 GlcNAc to the α-1,6 mannose residue and the α-1,3 mannose residues in complex N-glycans in humans. So far, GlcNAc transferase IV has not been detected in or isolated from plants. A transgenic plant that is capable of adding human-like N-glycans must therefore be engineered to express GlcNAc transferase IV. Thus, the plant host cell or transgenic plant must also localize an expressed GlcNAc transferase IV to the correct intracellular compartment in the host so that the enzyme can add the β1,4 GlcNAc to the appropriate mannose residues.

There is some evidence that glycosyltransferases from mammals and plants have similar targeting signals. For example, a full-length rat α2,6-sialyltransferase has been shown to correctly localize to the trans Golgi network in transgenic *Arabidopsis* plant cells, but was not necessarily active there (Wee™, 1998). A fusion construct having fifty-two N-terminal amino acids from α2,6-sialyltransferase fused to a green fluorescent reporter protein (GFP) was also shown to correctly localize to the plant Golgi (Boevink, 1998). Two mammalian proteins—TGN30 and furin—and AtELP, an *Arabidopsis* integral membrane protein (Sanderfoot, 1998), which localize to the trans Golgi network, each contain a tyrosine tetrapeptide motif which targets them to the Golgi, probably by a recycling mechanism via the plasma membrane. Although mammals and plants appear to share some common mechanisms related to protein targeting, exogenous glycosylases may nonetheless not target correctly in a plant cell, however, localization does not necessarily equate with enzyme activity. It therefore becomes essential to devise means to correctly target in a plant cell these enzymes and/or other enzymes that participate in forming complex, human-like N-glycans.

Glycosylation enzymes are integral membrane proteins which reside in the endoplasmic reticulum and Golgi apparatus. The targeting and localization signals are normally contained in the cytoplasmic and/or transmembrane domains and in some cases are contained in some lumenal domains. For example, fifty-two amino acids that make up the transmembrane domain, nine cytoplasmic amino acids and twenty-six lumenal amino acids of α2,6-sialyltransferase are required to target GFP to the trans Golgi network (Boevink, 1998).

Figure 13:
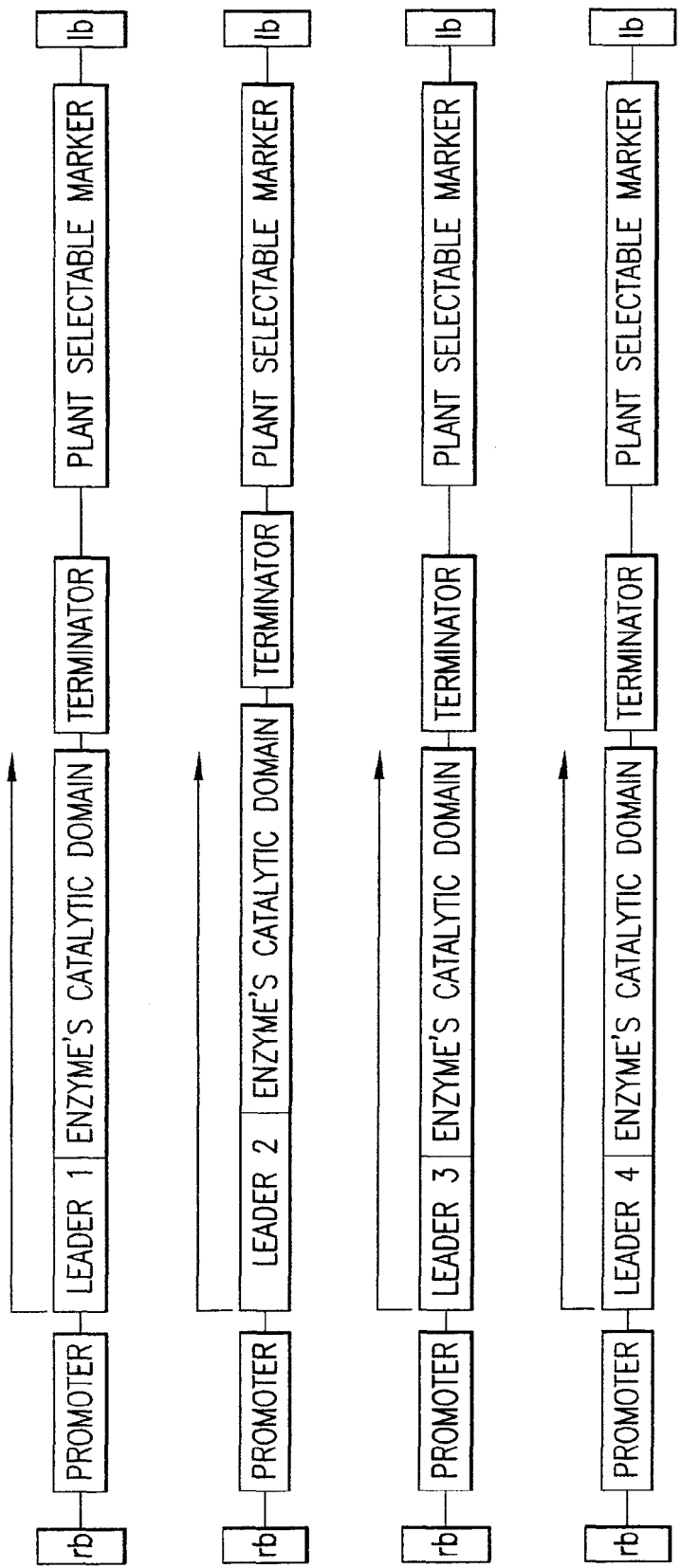
FIG. 13 represents T-DNA cassettes with catalytic domain(s) of glycosylation enzymes fused in-frame to different leader sequences. The ends of the T-DNA are marked by the right (rb) and left borders (lb). Various promoters and terminators may also be used. The plant selectable marker can also be varied. The right and left borders are required only for *agrobacterium*-mediated transformation and not for particle bombardment or electroporation.

Thus, a library of sequences encoding cellular targeting signal peptides comprising either just the cytoplasmic and transmembrane domains or the cytoplasmic, transmembrane and lumenal domains of endoplasmic reticulum and Golgi specific proteins is generated, as described in Example 11. The targeting peptide sequences may be chosen from ER and Golgi-resident plant, yeast or animal proteins. A glycosylation related protein, e.g., an enzyme (or catalytic domain thereof) such as a glycosylase or integral membrane enzyme can be fused in-frame to the library of targeting peptide sequences and introduced into plants (FIG. 13). Plant targeting peptide sequences may be most efficient in localizing the chimeric enzymes to the ER and Golgi, although targeting peptide sequences from fungi and mammals may also be effective. For example, the N-terminal 77 amino acids from tobacco N-acetylglucosaminyl Transferase I have been shown to correctly target a reporter protein to the Golgi (Essl, 1999). In one embodiment, one or more N-terminal fragments comprising these 77 amino acids (or subsets of these amino acids) is fused to one or more fragments comprising a catalytic domain of GlcNAc transferase IV. At least one resulting fusion protein correctly localizes a functional GlcNAc transferase IV to the Golgi apparatus in a plant cell, as evidenced by monitoring the glycosylation state of a reporter glycoprotein resident or introduced into the plant host cell using techniques described herein.

Another plant enzyme shown to localize to the Golgi is *Arabidopsis* GlcNAc transferase II (Strasser, 1999). Thus, in another embodiment, one or more different fragments of the *Arabidopsis* GlcNAc transferase II targeting peptide are fused to a GlcNAc transferase IV catalytic domain and fusion constructs produced and tested as described above. The plant specific β1,2-xylosyltransferase from *Arabidopsis thaliana* is another protein that localizes to the Golgi and its localization and retention in the Golgi is dependent on its cytoplasmic and transmembrane sequences (Dimberger, 2002). Thus, in another embodiment, one or more fragments comprising the cytoplasmic and transmembrane sequences of β1,2-xylosyltransferase are fused to one or more fragments comprising a GlcNAc transferase IV catalytic domain and resulting fusion constructs are transformed into plant cells and tested for their ability to produce a human-like N-glycan and to otherwise modulate glycosylation in the plant host cell.

Because GlcNAc transferase IV or Galactosyltransferase from one organism may function more efficiently in a specific plant host than one from another organism, fragments comprising GlcNAc transferase IVs (or catalytic domains) from various eukaryotic organisms are fused in-frame to the library of endoplasmic reticulum (ER) and Golgi targeting peptide sequences and are then introduced into plants. The use of a library of nucleic acids encoding enzyme domains isolated or derived from different species increases the chances of efficient glycosylation—in addition to correct localization and glycosylation by GlcNAc transferase IV.

The methods and combinatorial nucleic acid libraries of the invention may be used to introduce and localize, sequentially or en masse, multiple enzymes required to glycosylate proteins in a plant cell with human-like N-glycans. As different plant species may require different growth conditions, protocols for transformation may vary depending on the species being transformed (Potrykus, 1990). The commonly used methods for generating transgenic plants include *Agrobacterium* mediated transformation, particle bombardment (Sanford, 1990) and electroporation.

*Agrobacterium* Method

The catalytic domains of GlcNAc transferase IVs are fused in-frame to multiple different targeting peptide sequences known to target proteins to the ER and Golgi in plants. Each of these fusion constructs is introduced under the control of the ubiquitously expressed promoters like the $^{35}$S CaMV, ubiquitin or actin promoters, tissue specific promoters or inducible promoters. A plant specific terminator region is also used. This cassette (promoter::targeting peptide-GlcNAc transferase IV::terminator) is cloned into a vector suitable for *Agrobacterium* mediated transformation (FIG. 13). The vector also contains a selectable marker that allows one to select for transformed plants. The common selectable markers used include those resulting in kanamycin, hygromycin and basta resistance. The construct is introduced into *Agrobacterium* via well-established transformation methods, which are available in the art. An *Agrobacterium* library of Golgi-targeted GlcNAc transferase IVs is thereby generated.

Embryonic and meristematic tissue may be transformed and can regenerate transgenic plants. To transform tissue, tissue explants (these could be plumules and radicals from germinated seeds) are first soaked and coated with an *Agrobacterium* innoculum. They are then cultured on plates containing the innoculum to form an undifferentiated mass of cells termed the callus. Transformed plant cells are selected for by adding to the medium the relevant kanamycin, hygromycin or basta (depending on the selectable marker used on the construct). The transformed plant cells can either be grown in culture and remain undifferentiated or they are treated with shoot regenerating and shoot elongation medium. Explants that differentiate are transferred onto rooting medium to generate transgenic plants. Some plants like *Arabidopsis* can be transformed by dipping flowers into an *Agrobacterium* solution. Seeds from the transformed plants are germinated on plates containing the relevant herbicide or antibiotic selection. Transgenic plants are those that grow on the selection media. The transgenic plants are then screened for those with properly glycosylated proteins (i.e., those which have complex, human-like N-glycans) by isolating glycoproteins from plant extracts and analyzing glycoprotein patterns as described elsewhere herein, e.g., by using a specific antibody or lectin. Although the *Agrobacterium* method is economical and simple, it is limited to certain species of plants. Accordingly, plants that cannot be transformed using *Agrobacterium* can be transformed by ballistics or electroporation.

Particle Bombardment Method and Electroporation

Compared to *Agrobacterium* mediated transformation, these methods have a greater tendency to insert multiple copies of the transgene into the genome. This could result in gene silencing and cosuppression. However, unlike *Agrobacterium* mediated transformation, these methods are not species limited and are therefore useful when an *Agrobacterium* method cannot be employed to generate transgenic plants. In the particle bombardment method, cultured plant cells are bombarded with very small tungsten or gold particle that have been coated with DNA (promoter:: targeting peptide-GlcNAc transferase IV-terminator:: selectable marker) (FIG. 13) (rb and lb not required) while in the electroporation method, plant cells in a DNA (promoter::targeting peptide-GlcNAc transferase IV-terminator::selectable marker) solution are treated with an electric pulse that perforates the cell, allowing it to take up DNA. The cells are then cultured and allowed to recover. Stable transformants are selected for by culturing and regenerating plants on appropriate selection medium.

Engineering Soybeans to Express GlcNAc Transferase IV Using a Soybean Cotyledonary Node *Agrobacterium* Mediated Transformation System An *Agrobacterium* library of Golgi-targeted GlcNAc transferase IV is generated as described above. Soybean explants are transformed with the library using a protocol described by Hinchee, 1988. A reporter protein is expressed with a His tag, purified and then analyzed. Transgenic plants are assayed for proteins with the α-1,6 mannose and the α-1,3 mannose residues using, e.g., mass spectroscopy.

Engineering Pea to Express GlcNAc Transferase IV Using Particle Bombardment

A GlcNAc transferase IV plasmid library is coated onto tungsten or gold particles and used as microprojectiles to bombard calli derived from pea embryonic tissue as described (Molnar, 1999). A reporter protein is expressed with a His tag, purified and then analyzed. Transgenic plants are assayed for proteins with the α-1,6 mannose and the α-1,3 mannose residues using, e.g., MALDI.

Engineering Plants to Express GlcNAc Transferase I

GlcNAc transferase I is involved in the addition of GlcNAc to the terminal α-1,3 mannose residue to form $Man_5GlcNAc_2$, an essential step in the maturation of complex N-glycans. Although GlcNAc transferase I has been isolated from plants and appears to have the same function as its mammalian homolog, it may not be the most efficient enzyme for glycosylation of mammalian or exogenous proteins and may not be found in every plant species. As the addition of GlcNAc to the terminal α-1,3 mannose residue is a controlling step in the mammalian glycosylation pathway, it is advantageous to have transgenic plants that can carry out this step efficiently. To create transgenic plants that express GlcNAc transferase I that can function efficiently to promote the formation of complex N-glycans, a library of GlcNAc transferase I isolated or derived from various organisms is fused in-frame to multiple plant Golgi targeting peptide sequences according to the methods described herein. The combinatorial library thus created is introduced into a plant cell or organism as described above for GlcNAc transferase IV.

Engineering Maize to Express GlcNAc Transferase I Using Particle Bombardment

Transgenic maize can be obtained using a protocol similar to the one used to generate peas that express GlcNAc transferase IV. Here the GlcNAc transferase I plasmid library is coated onto tungsten or gold particles and used to bombard calli derived from maize embryonic tissue, e.g., using a protocol specific for the generation of transgenic maize (Gordon-Kamm, 1990). Transgenic plants are assayed for proteins having GlcNAc on the terminal α-1,3 mannose residue, e.g., using specific antibodies or by assaying reduced binding of the N-glycans to certain lectins or by using MALDI-TOF.

Other useful references for using plant host cells according to the invention include: Dirnberger, 2002; Frame, 2002; Gomord, 1999; Laursen, 1994; Orci, 2000; Newell, 2002; Pawlowski, 1996; Schroeder, 1993; Sorokin, 2000; Strasser, 1999; Tomes, 1990.

Engineering Plant Cells to Produce β1,4-Galactosyltransferases

β1,4-galactosyltransferase is an important human glycosyltransferase that is absent in plants. Lerouge, 1998. In mammals, β1,4-galactosyltransferase is localized in the Golgi and is responsible for the transfer of galactose residues to the terminal N-acetylglucosamine of the core $Man_3GlcNAc_2$ of complex N-glycans. In plants, the $Man_3GlcNAc_2$ core contains β1,2-xylose and α-1,3-fucose residues and lacks the β1,4-galactose. The xylose and fucose modifications are implicated in allergies and act as antigenic epitopes and are therefore not desirable modifications of therapeutic proteins.

The galactose modifications carried out by β1,4-galactosyltransferase can be important for the proper functioning of the therapeutic proteins. In mammals, β1,4-galactosyltransferase acts after N-acetylglucosaminyltransferase I and N-acetylglucosaminyltransferase II and has been shown to initiate branching of the complex N-glycan. Lerouge, 1998; Palacpac, 1999. In tobacco cells, expression of human β1,4-galactosyltransferase has been shown to result in galactosylated N-glycans with reduced fucose and xylose modifications. Bakker, 2001; Fujiyama, 2001; Palacpac, 1999. In these studies, a 1.2 kb fragment of human β1,4-galactosyltransferase was cloned downstream of the cauliflower mosaic virus promoter (35SCaMV), introduced into the binary vector pGA482, and finally into tobacco cells. Palacpac, 1999.

Tobacco cells were transformed using the *agrobacterium* method described by Rempel et al. (Rempel, 1995). Transformation of tobacco cells has also been described (An, 1985). Expression of β1,4-galactosyltransferase under the 35SCaMV resulted in ubiquitous expression of the gene in tobacco cells. Tobacco cells expressing human β1,4-galactosyltransferase showed the presence of galactosylated N-glycans. (Palacpac, 1999; Bakker 1991), showed that crossing tobacco plants expressing human β1,4-galactosyltransferase with plants expressing the heavy and light chain of a mouse antibody resulted in plants in which the antibody showed 30% galactosylation (Bakker, 2001).

A combinatorial DNA library can be constructed to obtain a β1,4-galactosyltransferase plant cell line for the addition of galactose residues. The combinatorial DNA library can effectively produce cell lines which are more efficient in the addition of galactose residues. Once such a cell line is made it can be easily crossed to cell lines expressing other glycosylation enzymes and to those expressing therapeutic proteins to produce therapeutic proteins with human-like glycosylation. The final line can then be grown as plants and harvested to extract proteins or can be cultured as plant cells in suspension cultures to produce proteins in bioreactors. By expressing the therapeutic proteins using the library of signal peptides, it is possible to retain the therapeutic protein within the cells or have them secreted into the medium. Tobacco cells expressing β1,4-galactosyltransferase secrete galactosylated N-glycans (Ryo, 2002). While horseradish peroxidase isozyme C expressed in tobacco plants expressing β1,4-galactosyltransferase contained xylose and fucose modifications, no xylose or fucose could be detected in horseradish peroxidase isozyme C expressed in tobacco cells expressing β1,4-galactosyltransferase (GT6 cells). (Fujiyama, 2001). This indicates that it may be advantageous to express therapeutic proteins in cell lines instead of whole plants.

Engineering Plants to Produce Sialyltransferase

In mammals, sialyltransferase is a trans Golgi enzyme that adds terminal sialic acid residues to glycosylated polypeptides. Thus far, terminal sialic acid residues have not been detected in plants (Wee, 1998). Wee et al. expressed the rat α2,6-sialyltransferase in transgenic *Arabidopsis* and showed that the enzyme properly localized to the Golgi and was functional. Wee et al. demonstrated that membranes isolated from transgenic *Arabidopsis*, when incubated with CMP-$^3$H-sialic acid and asialofetuin acceptor, resulted in the addition of sialic acid residues while membrane isolated from wildtype *Arabidopsis* did not. While expressing the rat α2,6-sialyltransferase in *Arabidopsis* resulted in a functional enzyme that was able to incorporate sialic acid residues, fusing the mammalian enzymes α-2,3-sialyltransferase and α2,6-sialyltransferase to a variety of transit peptides using the library approach of the present invention (described above) can result in more efficient sialylation in other plant species. Wee et al. had to isolate membranes and incubate them with CMP-$^3$H-sialic acid and asialofetuin acceptor since *Arabidopsis* does not have CMP-sialic acid or its transporter. In order to overcome this additional step and obtain sialic acid addition in the plant, CMP-sialic acid biosynthetic pathway and the CMP-sialic acid transporter can be co-expressed in transgenic plants expressing α-2,3-sialyltransferase and α-2,6-sialyltransferase (see Examples 6, 16 and 17). As an alternative, the CMP-sialic acid transporter can be co-expressed with α-2,3-sialyltransferase and α-2,6-sialyltransferase in plant cells grown in suspension culture, and CMP-sialic acid or other precursors of CMP-sialic acid supplied in the medium.

Expressing α-2,3-Sialyltransferase and α-2,6-Sialyltransferase in Lemna

As described in the U.S. Pat. No. 6,040,498 ("the '498 patent"), lemna (duckweed) can be transformed using both *agrobacterium* and ballistic methods. Using protocols described in the '498 patent, lemna will be transformed with a library of Golgi targeted α-2,3-sialyltransferase and/or α-2,6-sialyltransferase and a library of mammalian CMP-sialic acid transporters. Transgenic plants can be assayed for those that produce proteins with terminal sialic acid residues according to screening techniques discussed herein (Example 17).

Expressing α-2,3-Sialyltransferase and α-2,6-Sialyltransferase in Tobacco Cells

Alpha-2,3-sialyltransferase and/or α-2,6-sialyltransferase and/or a library of mammalian CMP-sialic acid transporters can also be introduced into tobacco cells grown in suspension culture as described for β1,4-galactosyltransferases. CMP-sialic acid can be added to the medium. Both the cells and the culture medium (secreted proteins) can be assayed for proteins with terminal sialic acid residues according to screening techniques discussed herein (Example 17).

EXAMPLE 20

Engineering Insect Cells to Produce Glycosyltransferases

Insect cells provide another mechanism for producing glycoproteins but the resulting glycoproteins are not complex human-like glycoproteins. (Marz, 1995; Jarvis, 1997.) It is another feature of the present invention to provide enzymes in insect cells, which are targeted to the organelles in the secretory pathway. In a preferred embodiment, enzymes such as glycosyltransferases, galactosyltransferases and sialyltransferases are targeted to the ER, Golgi or the trans Golgi network in lepidopteran insect cells (Sf9). Expression of mammalian β1,4-galactosyltransferase has been shown in Sf9 cells. Hollister, 1998. These enzymes are targeted by means of a chimeric protein comprising a cellular targeting signal peptide not normally associated with the enzyme. The chimeric proteins are made by constructing a nucleic acid library comprising targeting sequences as described herein and the glycosylation enzymes. Baculovirus expression in insect cells is commonly used for stable transformation for adding mammalian glycosyltransferases in insect cells. (Hollister, 2001.)

TABLE 11

DNA And Protein Sequence Resources

1. European Bioinformatics Institute (EBI) (a centre for research and services in bioinformatics)
2. Swissprot database
3. List of known glycosyltransferases and their origin.
4. human cDNA, Kumar et al (1990) Proc. Natl. Acad. Sci. USA 87: 9948-9952
5. human gene, Hull et al (1991) Biochem. Biophys. Res. Commun. 176: 608-615
6. mouse cDNA, Kumar et al (1992) Glycobiology 2: 383-393
7. mouse gene, Pownall et al (1992) Genomics 12: 699-704
8. murine gene (5' flanking, non-coding), Yang et al (1994) Glycobiology 5: 703-712
9. rabbit cDNA, Sarkar et al (1991) Proc. Natl. Acad. Sci. USA 88: 234-238
10. rat cDNA, Fukada et al (1994) Biosci. Biotechnol. Biochem. 58: 200-201

1,2 (GnTII) EC 2.4.1.143

11. human gene, Tan et al ( 1995) Eur. J. Biochem. 231: 317-328
12. rat cDNA, D'Agostaro et al (1995) J. Biol. Chem. 270: 15211-15221
13. *arabadopsis* cDNA Strasser et al (1999) J. Glycoconj. 16: 787-791
14. *C. elegans* gene Chen et al., (2002) Biochim. Biophys. Acta. 1573: 271- 279

β1,4 (GnTII) EC 2.4.1.144

15. human cDNA, Ihara et al (1993) J. Biochem. 113: 692-698
16. murine gene, Bhaumik et al (1995) Gene 164: 295-300
17. rat cDNA, Nishikawa et al (1992) J. Biol. Chem. 267: 18199-18204

β1,4 (GnTIV) EC 2.4.1.145

18. human cDNA, Yoshida et al (1998) Glycoconjugate Journal 15: 1115-1123
19. bovine cDNA, Minowa et al., European Patent EP 0 905 232
20. β1,6 (GnT V) EC 2.4. 1.155
21. human cDNA, Saito et al (1994) Biochem. Biophys. Res. Commun. 198: 318-327
22. rat cDNA, Shoreibah et al (1993) J. Biol. Chem. 268: 15381-15385

β1,4 Galactosyltransferase, EC 2.4.1.90 (LacNAc synthetase) EC 2.4.1.22 (lactose synthetase)

23. bovine cDNA, D'Agostaro et al (1989) Eur. J. Biochem. 183: 211-217
24. bovine cDNA (partial), Narimatsu et al (1986) Proc. Natl. Acad. Sci. USA 83: 4720-4724
25. bovine cDNA (partial), Masibay & Qasba (1989) Proc. Natl. Acad. Sci. USA 86: 5733-5377
26. bovine cDNA (5' end), Russo et al (1990) J. Biol. Chem. 265: 3324
27. chicken cDNA (partial), Ghosh et al (1992) Biochem. Biophys. Res. Commun. 1215-1222
28. human cDNA, Masri et al (1988) Biochem. Biophys. Res. Commun. 157: 657-663
29. human cDNA, (HeLa cells) Watzele & Berger (1990) Nucl. Acids Res. 18: 7174
30. human cDNA, (partial) Uejima et al (1992) Cancer Res. 52: 6158-6163
31. human cDNA, (carcinoma) Appert et al (1986) Biochem. Biophys. Res. Commun. 139: 163-168
32. human gene, Mengle-Gaw et al (1991) Biochem. Biophys. Res. Commun. 176: 1269-1276
33. murine cDNA, Nakazawa et al (1988) J. Biochem. 104: 165-168
34. murine cDNA, Shaper et al (1988) J. Biol. Chem. 263: 10420-10428
35. murine cDNA (novel), Uehara & Muramatsu unpublished
36. murine gene, Hollis et al (1989) Biochem. Biophys. Res. Commun. 162: 1069-1075
37. rat protein (partial), Bendiak et al (1993) Eur. J. Biochem. 216: 405-417

2,3-Sialyltransferase, (ST3Gal II) (N-linked) (Gal-1,3/4-GlcNAc) EC 2.4.99.6

38. human cDNA, Kitagawa & Paulson (1993) Biochem. Biophys. Res. Commun. 194: 375-382
39. rat cDNA, Wen et al (1992) J. Biol. Chem. 267: 21011-21019
40. murine cDNA Lee et al., (1994) J. Biol. Chem. 269: 10028-10033

2,6-Sialyltransferase, (ST6Gal I) EC 2.4.99.1

41. chicken, Kurosawa et al (1994) Eur. J. Biochem 219: 375-381
42. human cDNA (partial), Lance et al (1989) Biochem. Biophys. Res. Commun. 164: 225-232
43. human cDNA, Grundmann et al (1990) Nucl. Acids Res. 18: 667

TABLE 11-continued

DNA And Protein Sequence Resources 44. human cDNA, Zettlmeisl et al (1992) Patent EPO475354-A/3
45. human cDNA, Stamenkovic et al (1990) J. Exp. Med. 172: 641-643 (CD75)
46. human cDNA, Bast et al (1992) J. Cell Biol. 116: 423-435
47. human gene (partial), Wang et al (1993) J. Biol. Chem. 268: 4355-4361
48. human gene (5' flank), Aasheim et al (1993) Eur. J. Biochem. 213: 467-475
49. human gene (promoter), Aas-Eng et al (1995) Biochim. Biophys. Acta 1261: 166-169
50. mouse cDNA, Hamamoto et al (1993) Bioorg. Med. Chem. 1: 141-145
51. rat cDNA, Weinstein et al (1987) J. Biol. Chem. 262: 17735-17743
52. rat cDNA (transcript fragments), Wang et al (1991) Glycobiology 1: 25-31, Wang et al (1990) J. Biol. Chem. 265: 17849-17853
53. rat cDNA (5' end), O'Hanlon et al (1989) J. Biol. Chem. 264: 17389-17394; Wang et al (1991) Glycobiology 1: 25-31
54. rat gene (promoter), Svensson et al (1990) J. Biol. Chem. 265: 20863-20688

TABLE 11-continued

DNA And Protein Sequence Resources 55. rat mRNA (fragments), Wen et al (1992) J. Biol. Chem. 267: 2512-2518

Additional methods and reagents that can be used in the methods for modifying the glycosylation are described in the literature, such as U.S. Pat. No. 5,955,422, U.S. Pat. No. 4,775,622, U.S. Pat. No. 6,017,743, U.S. Pat. No. 4,925,796, U.S. Pat. No. 5,766,910, U.S. Pat. No. 5,834,251, U.S. Pat. No. 5,910,570, U.S. Pat. No. 5,849,904, U.S. Pat. No. 5,955,347, U.S. Pat. No. 5,962,294, U.S. Pat. No. 5,135,854, U.S. Pat. No. 4,935,349, U.S. Pat. No. 5,707,828, and U.S. Pat. No. 5,047,335. Appropriate yeast expression systems can be obtained from sources such as the American Type Culture Collection, Rockville, Md. Vectors are commercially available from a variety of sources.

```
SEQUENCE LISTINGS

SEQ ID NO: 1-6 can be found in U.S. patent application Ser. No. 09/892,591

SEQ ID NO: 7
Primer: regions of high homology within 1,6 mannosyltransferases
5'-atggcgaaggcagatggcagt-3'

SEQ ID NO: 8
Primer: regions of high homology within 1,6 mannosyltransferases
5'-ttagtccttccaacttccttc-3'

SEQ ID NO: 9
internal primer: 5'-actgccatctgccttcgccat-3'

SEQ ID NO: 10
internal primer: 5'-GTAATACGACTCACTATAGGGC-3' T7

SEQ ID NO: 11
Internal primer: 5'-AATTAACCCTCACTAAAGGG-3' T3

SEQ ID NO: 12
Primer: atgcccgtgg ggggcctgtt gccgctcttc agtagc

SEQ ID NO: 13
Primer: tcatttctct ttgccatcaa tttccttctt ctgttcacgg

SEQ ID NO: 14
Primer: ggcgcgccga ctcctccaag ctgctcagcg ggtcctgtt ccac

SEQ ID NO: 15
Primer: ccttaattaa tcatttctct ttgccatcaa tttccttctt ctgttcacgg

SEQ ID NO: 16
Primer: ggcgagctcg gcctacccgg ccaaggctga gatcatttgt ccagcttcaga

SEQ ID NO: 17
Primer: gcccacgtcg acggatccgt ttaaacatcg attggagagg ctgacaccgc tacta SEQ ID NO: 18
Primer: cgggatccac tagtatttaa atcatatgtg cgagtgtaca actcttccca catgg SEQ ID NO: 19
Primer: ggacgcgtcg acggcctacc cggccgtacg aggaatttct cggatgactc ttttc SEQ ID NO: 20
Primer: cgggatccct cgagagatct tttttgtaga aatgtcttgg tgcct SEQ ID NO: 21
Primer: ggacatgcat gcactagtgc ggccgccacg tgatagttgt tcaattgatt gaaatagga caa SEQ ID NO: 22
Primer: ccttgctagc ttaattaacc gcggcacgtc cgacggcggc ccacgggtcc ca SEQ ID NO: 23
Primer: ggacatgcat gcggatccct taagagccgg cagcttgcaa attaaagcct tcgagcgtcc c
```

SEQ ID NO: 24
Primer: gaaccac<u>gtc gacggccatt gcggcc</u>aaaa ccttttttcc tattcaaaca caaggcattg c SEQ ID NO: 25
Primer: ctccaat<u>act agt</u>cgaagat tatcttctac ggtgcctgga ctc SEQ ID NO: 26
Primer: tggaag<u>gttt aaac</u>aaagct agagtaaaa tagatatagc gagattagag aatg SEQ ID NO: 27
Primer: aa<u>gaattc</u>gg ctggaaggcc ttgtaccttg atgtagttcc cgttttcatc SEQ ID NO: 28
Primer: gcccaa<u>gccg gcct</u>taaggg atctcctgat gactgactca ctgataataa aaatacgg SEQ ID NO: 29
Primer: gggcgcgt<u>a tttaaatacta gt</u>ggatctat cgaatctaaa tgtaagttaa aatctctaa SEQ ID NO: 30
Primer: <u>ggccgcctgc agatttaaat gaattcgg cgcgccttaat</u>

SEQ ID NO: 31
Primer: <u>taaggcgcgc cgaattcatt taaatctgca gggc</u>

SEQ ID NO: 32
Primer: 5'-tggcaggcgcgcctcagtcagcgctctcg-3'

SEQ ID NO: 33
Primer: 5'-aggttaatta agtgctaattccagctagg-3'

SEQ ID NO: 34
primer for *K. lactis* OCH1 gene: ccagaagaat tcaattytgy cartgg

SEQ ID NO: 35
primer for *K. lactis* OCH1 gene: cagtgaaaat acctggnccn gtcca

SEQ ID NO: 36
primer for *K. lactis* MNN1 gene: tgccatcttt taggtccagg cccgttc

SEQ ID NO: 37
primer for *K. lactis* MNN1 gene: gatcccacga cgcatcgtat ttctttc

SEQ ID NO: 38
DNA sequence of the 302 bp segment of the putative KlOCH1 gene:
gcccttcagtgaaaatacctggcccggtccagttcataatatcggtaccatctgtattttggcggttttcttttgttgatgttt
gtaattttgttgaacttcttttatccctcatgttgacattataatcatctgcaatgtcttttaatacttcagc
atcatctaaaggaatgctgcttttaacatttgccacgctctccaatgttgttgcggtgatatttgtgatcaattcgcgcaataa
tggatggccagattttgattgtattgtccactgacaaaattgaattctctggaagggc SEQ ID NO: 39
Translation of putative KlOCH1 gene (excluding primers):
TIQSKSGHPLLRELITNITATTLESVANVKSSIPLDDAEVLKDIADDYNVNM
RDKKKFNKNYKHQQKKTAKNTDGTDIMN SEQ ID NO: 40
DNA sequence of the 405 bp segment of the putative KlMNN1 gene:
cccagcgtgccattaccgtatttgccgccgtttgaaatactcaatattcatgatggttgtaaggcgttttttatcattcgcgat
ataatatgccatcttttaggtccaggcccgttctcttagctatcttttggtgtctgtgctaccgtgatggtacct
attcttttttccagtctaatctgaagatggcagatttgaaaaaggtagcaacttcaaggtatctttcacaagaaccgtcgttat
cagaacttatgtcaaatgtgaagatcaagcctattgaagaaaccccggtttcgccattggagttgattccagatatcgaaa
tatcgactagaaagaaatacgatgcgtcgtgggatctgttgttccgtggtagaaaatataaatcgttcaacgattatgat SEQ ID NO: 41
DNA sequence of the *K. lactis* OCH1 gene:
atgggggttaccaaagatttcaagaagaacgaggtacattattgtcattgtgctgatactgtacttattgttttctgtgcaatg
gaatactgcgaaagtgaatcacctttctataacagcattggcacggtgcttcccagtacagctcgcgtggatcacttga
acttgaaaaacttggacttagcaggtacgagcaataacggtgatcatttgatggatctacgagttcaattggctagtcaat
tccccctacgattctcgagtacccatccccaaaaaggtatggcagaccgtgaagattgatccagttcaaagtcacaggtt
tcttccatttcaaaatgccagaatgattggaaacatttcagtgcatccgaggaaccgccatatcaataccaattaatcaca
gatgatcaaatgataccacttctagagcagctatatggtggggtcccacaagtgataaaggcttttgaatccttgccactt
ccaattcttaaagcagacttttcagatacttgatcctttatgcaagaggtggtatatattctgacatggatacgttcccatta
aagccattgtcgtcatggccatcgacttctcagtcctactttctcagtttaaagaatccacaaaggtatagaaattccttgga
caaccttgaaacgctagaagcttcagaacctggctttgtcattggtatcgaggctgatccggatagaagcgattgggca
gagtggtacgccaggagaatacaattctgtcagtggacaatacaatcaaaatctggccatccattattgcgcgaattgat
cacaaatatcaccgcaacaacattggagagcgtggcaaatgttaaaagcagcattcctttagatgatgctgaagtattaa
aagacattgcagatgattataatgtcaacatgagggataaaaagaagttcaacaaaaattacaaacatcaacaaaagaa
aaccgccaaaaatacagatggtaccgatattatgaactggactggtccaggtattttttcagatgttattttccagtatctta
ataacgttatccagaagaatgatgacattttaattttcaatgataatcttaatgttatcaacaaacatggatccaaacatgata

```
caactatgagattctataaagacattgttaaaaatttacaaaacgacaaaccctcattgttctggggattcttttcattgatga
cagagcctattctagtggacgacatcatggtacttccgattacttctttctcaccaggtatcagaacaatgggcgctaaag
aagacaacgacgagatggcatttgttaagcatattttgaaggaagttggaaagactga
```

SEQ ID NO: 42
Translation of putative *K. lactis* OCH1 gene:
MGLPKISRRTRYIIVIVLILYLLFSVQWNTAKVNHHFYNSIGTVLPSTARVD
HLNLKNLDLAGTSNNGDHLMDLRVQLASQFPYDSRVPIPKKVWQTWKID
PSSKSQVSSISKCQNDWKHFSASEEPPYQYQLITDDQMIPLLEQLYGGVPQ
VIKAFESLPLPILKADFFRYLILYARGGIYSDMDTFPLKPLSSWPSTSQSYFS
SLKNPQRYRNSLDNLETLEASEPGFVIGIEADPDRSDWAEWYARRIQFCQW
TIQSKSGHPLLRELITNITATTLESVANVKSSIPLDDAEVLKDIADDYNVNM
RDKKKFNKNYKHQQKKTAKNTDGTDIMNWTGPGIFSDVIFQYLNNVIQK
NDDILIFNDNLNVINKHGSKHDTTMRFYKDIVKNLQNDKPSLFWGFFSLMT
EPILVDDIMVLPITSFSPGIRTMGAKEDNDEMAFVKHIFEGSWKDZ SEQ ID NO: 43
DNA sequence of the *K. lactis* MNN1 gene:
```
atgatggttgtaaggcgtttttttatcagcttcgcgatataatatgccatcttttaggtccaggcccgttctcttagctatctttg
gtgtctgtgctaccgtgatatggtacctattcttttttccagtctaatctgaagatggcagatttgaaaaaggtag
caacttcaaggtatctttcacaagaaccgtcgttatcagaacttatgtcaaatgtgaagatcaagcctattgaagaaaccc
cggtttcgccattggagttgattccagatatcgaaatatcgactagaaaagaaatacgatgcgtcgtgggatctgttgttcc
gtggtagaaaatataaatcgttcaacgattatgatcttcatacgaaatgtgagttttatttccagaatttatacaatttgaacg
aggattggaccaataatattcggacgttcactttcgatattaacgatgtagacacgtctacgaaaattgacgctcttaaag
attccgatggggttcaattggtggacgagaaggctatacgtttatacaagagaacgcataacgttgccttggctacgga
aaggttacgtctcttatgataaatgttttgtcaatagtccaggttcaaacccattgaaaatggatcaccttttcagatcgaaca
agaagagtaagactacggctttggatgacgaagtcactgggaaccgtcgatacttttaccaagacgaagaaaacttcgtt
cttaagcgatatggacacgagtagtttccagaagtacgatcaatgggatttcgaacatagaatgttcccccatgatcccata
tttcgaggaacacaatttcaccaacgtgatgcctattttcaccggctcaaacggtggggaacctttacctcaagggaaatt
cccggtattagatccaaaatccggtgaattgttacgtgtagagactttcagatatgataaatcgaaatcgcttttggaagaa
ctggaatgatatgtcctctgcttctggtaaacgtggtattatcttggctgctggcgacggccaagtggaccaatgcatcc
gtcttattgctacgttgagagctcaaggaaacgctctaccattcaaattatccacaacaaccaattgaatgagaaatctgt
gaaactgttatcggaggccgctaaatctaccgaattctcatccggtagagctcaatctctttggttagtgaatgtgggccc
cacgttggaatcttcaatgaagagcaattttgggagatttaagaataagtggtgtcagttattttcaacacttttgaagaatt
tatattcatagatacagatgccatctcctacattaatatggctgattatttcaacttcaaggagtacaaatctactggaacact
cttctttaaggataggtctttggcaattggaactgaacagaaatgtggtcctttgttcgaaactcttgaaccaagaattcttg
aaatgtactatttcaatactttacctatgatcaatggtgattacgtggaacagcaatgtatgggcatgctcacccccagagg
aaaaagtttacaaacgtttcttgaagttggtcatcaacacaacttggaaagtggattattggccatcaacaaaaacgaac
acatcatgggattggttactgcaacagtcttaaatatcgcacgaagtcggaggttcggttgggtgacaagagttt
ttctggcttggtttgttggttgctggccaacgctactcgatctatgatatagatgcaagtgcaattggtgttcctcaacagaa
gcaatctatcgctaacggagacgaatttgatgaatataggatttgttctttacaagtggcacatacttcatacgacggacat
ttactatggataaatggtggctctcagtactgtaagaaaccagagacttttgaaggtgattggaccaacattaaggagctt
cgtgaatcgtattctgatgataaagaaaaggctctgaaggcttataggtgaaggggaagcagcaatcgtgc
cagattccagaagtaatggttggggtagagacgatcaaagatgtaaaggctacttctggtgcggcaaatttacttcaaa
gctgaaaccgtatacttataacacggtggtaactaaaggtgatttgatccgtttcggagacgaggaaatcgaaagtatct
ccaagattaataagatctggaatgatgctattattccagacggagcttaa
```

SEQ ID NO: 44
Translation of putative *K. lactis* MNN1 gene:
MMVVRRFLSASRYNMPSFRSRPVLLAIFGVCATVIWYLFFFQSNLKMADL
KKVATSRYLSQEPSLSELMSNVKIKPIEETPVSPLELIPDIEISTRKKYDASW
DLLFRGRKYKSFNDYDLHTKCEFYFQNLYNLNEDWTNNIRTFTFDINDVD
TSTKIDALKDSDGVQLVDEKAIRLYKRTHNVALATERLRLYDKCFVNSPG
SNPLKMDHLFRSNKKSKTTALDDEVTGNRDTFTKTKKTSFLSDMDTSSFQ
KYDQWDFEHRMFPMIPYFEEHNFTNVMPIFTGSNGGEPLPQGKFPVLDPKS
GELLRVETFRYDKSKSLWKNWNDMSSASGKRGIILAAGDGQVDQCIRLIA
TLRAQGNALPIQIIHNNQLNEKSVKLLSEAAKSTEFSSGRAQSLWLVNVGP
TLESSMKSNFGRFKNKWLSVIFNTFEEFIFIDTDAISYINMADYFNFKEYKST
GTLFFKDRSLAIGTEQKCGPLFETLEPRILEMYYFNTLPMINGDYVEQQCM
GMLTPEEKVYKRFFEVGHQHNLESGLLAINKNEHIMGLVTATVLNIAPKV
GGCGWGDKEFFWLGLLVAGQRYSIYDIDASAIGVPQQKQSIANGDEFDEY
RICSLQVAHTSYDGHLLWINGGSQYCKKPETFEGDWTNIKELRESYSDDKE
KALKAYSDTVKVEAAIVPDSRSNGWGRDDQRCKGYFWCGKFTSKLKPYT
YNTVVTKGDLIRFGDEEIESISKINKIWNDAIIPDGA SEQ ID NO: 45-56: See Table 12.

| Primer name | Primer sequence |
| --- | --- |
| NeuA sense | 5'-ATGAGAACAAAAATTATTGCGATAATTCCAGCCCG-3' (SEQ ID NO: 45) |
| NeuA antisense | 5'-TCATTTAACAATCTCCGCTATTTCGTTTTC-3' (SEQ ID NO: 46) |
| NeuB sense | 5'-ATGAGTAATATATATATCGTTGCTGAAATTGGTTG-3' (SEQ ID NO: 47) |

| | |
|---|---|
| NeuB antisense | 5'-TTATTCCCCCTGATTTTTGAATTCGCTATG-3' (SEQ ID NO: 48) |
| NeuC sense | 5'-ATGAAAAAAATATTATACGTAACTGGATCTAGAG-3' (SEQ ID NO: 49) |
| NeuC antisense | 5'-CTAGTCATAACTGGTGGTACATTCCGGGATGTC-3' (SEQ ID NO: 50) |
| mouse CMP-Sia synthase sense | 5'-ATGGACGCGCTGGAGAAGGGGGCCGTCACGTC-3' (SEQ ID NO: 51) |
| mouse CMP-Sia synthase antisense | 5'-CTATTTTTGGCATGAGTTATTAACTTTTTCTATCAG-3' (SEQ ID NO: 52) |
| porcine GlcNAc epimerase sense | 5'-ATGGAGAAGGAGCGCGAAACTCTGCAGG-3' (SEQ ID NO: 53) |
| porcine GlcNAc epimerase antisense | 5'-CTAGGCGAGGCGGCTCAGCAGGGCGCTC-3' (SEQ ID NO: 54) |
| E. coli Sialate aldolase sense | 5'-ATGGCAACGAATTTACGTGGCGTAATGGCTG-3' (SEQ ID NO: 55) |
| E. coli Sialate aldolase antisense | 5'-TCACCCGCGCTCTTGCATCAACTGCTGGGC-3' (SEQ ID NO: 56) |

SEQ ID NO: 57-68: Are disclosed throughout the specification.

SEQ ID NO: 69-76: See Table 12.

| | |
|---|---|
| mouse bifunctional UDP-N-acetylglucosamine-2-epimerase/N-acetylmannosamine kinase sense | 5'-ATGGAGAAGAACGGGAACAACCGAAAGCTCCG-3' (SEQ ID NO: 69) |
| mouse bifunctional UDP-N-acetylglucosamine-2-epimerase/N-acetylmannosamine kinase antisense | 5'-CTAGTGGATCCTGCGCGTTGTGTAGTCCAG-3' (SEQ ID NO: 70) |
| mouse Sia9P syn sense | 5'-ATGCCGCTGGAACTGGAGCTGTGTCCCGGGC-3' (SEQ ID NO: 71) |
| mouse Sia9P syn antisense | 5'-TTAAGCCTTGATTTTCTTGCTGTGACTTTCCAC-3' (SEQ ID NO: 72) |
| human N-acetylneuraminic acid phosphatase (NANP) sense | 5'-GGGAGAATGCGGCCGCCACCATGGGGCTGAGCCGC GTGCGGGCG GTTTTC-3' (SEQ ID NO: 73) |
| human N-acetylneuraminic acid phosphatase (NANP) antisense | 5'-GTATAGACTGCAAAGTCAGTATGTCCACTTGATT AATTAACC-3' (SEQ ID NO: 74) |
| human CMP-Sia synthase sense | 5'-ATGGACTCGGTGGAGAAGGGGGCCGCCACC-3' (SEQ ID NO: 75) |
| human CMP-Sia synthase antisense | 5'-CTATTTTTGGCATGAATTATTAACTTTTTCC-3' (SEQ ID NO: 76) |

SEQ ID NO: 77
Primer for hGNE:
GGGAGAATGCGGCCGCCACCATGGAGAAGAATGGAAATAACCGAAAG
CTGCG SEQ ID NO: 78
Primer for hGNE:
CCTTAATTAACTAGTAGATCCTGCGTGTTGTGTAGTCCAGAAC SEQ ID NO: 79
Primer for hSiaPsyn
GGGAGAATGCGGCCGCCACCATGCCGCTGGAGCTGGAGCTGTGTCCCG SEQ ID NO: 80
Primer for hSiaPsyn
CCTTAATTAATTAAGACTTGATTTTTTTGCCATGATTATCTACC SEQ ID NO: 81
Primer
GGCTCGAGATTTAAATGCGTACCTCTTCTACGAGATTC SEQ ID NO: 82
Primer
CCCTCGAGATTTAAATCCAACCGATAAGGTGTACAGGAG SEQ ID NO: 83
Primer
GGCTCGAGCGGCCGCCACCATGAATAGCATACACATGAACGCCAATAC
G SEQ ID NO: 84
Primer
CCCTCGAGTTAATTAACTAGACGCGCGGCAGCAGCTTCTCCTCATCG-3')

SEQ ID NO: 85
Primer
ATG ACT GGT GTT CAT GAA GGG

SEQ ID NO: 86
Primer
TTA CTT ATA TGT CTT GGT ATG

SEQ ID NO: 87
Primer
GCG GCC GCA TGA CTG GTG TTC ATG AAG GGA CTG TGT TGG TTA
CTG GCG GCG CTG GTT ATA TAG GTT CTC ATA CGT GCG TTG TTT
TGT TAG AAA A SEQ ID NO: 88
Primer
TTA ATT AAT TAC TTA TAT GTC TTG GTA TG 3')

SEQ ID NO: 89
Primer
GCCGCGACCTGAGCCGCCTGCCCCAAC

SEQ ID NO: 90
Primer
CTAGCTCGGTGTCCCGATGTCCACTGT

SEQ ID NO: 91
Primer
CTTAGGCGCGCCGGCCGCGACCTGAGCCGCCTGCCC

SEQ ID NO: 92
Primer
GGGGCATATCTGCCGCCCATC

SEQ ID NO: 93
Primer
GATGGGCGGCAGATATGCCCC

SEQ ID NO: 94
Primer
CTTCTTAATTAACTAGCTCGGTGTCCCGATGTCCAC

SEQ ID NO: 95
Primer
GGGAGAATGCGGCCGCCACCATGGACTCGGTGGAGAAGGGGGCCGCC
ACCTC

SEQ ID NO: 96
Primer
CCTTAATTAACTATTTTTGGCATGAATTATTAACTTTTTCCATTA

SEQ ID NO: 97
Primer

```
CGGAATTCCACCATGGCTCCGGCGAGAGAAAATGTCAG

SEQ ID NO: 98
Primer
CGGAATTCTCACACACCAATGATTCTCTCTTTTGAAG

SEQ ID NO: 99
Primer
GGCTCGAGATTTAAATGCGTACCTCTTCTACGAGATTC

SEQ ID NO: 100
Primer
CCCTCGAGATTTAAATCCAACCGATAAGGTGTACAGGAG

SEQ ID NO: 101
Primer
GGCGCGCCAGCAAGCAAGACCCTAAGGAAGACATTCC

SEQ ID NO: 102
Primer
CCTTAATTAATCAACAACGAATGTTCCGGAAGCCAGAAAGG

SEQ ID NO: 103 and 104
Nucleic acid (SEQ ID NO: 103) and amino acid sequence (SEQ ID NO: 104) of the
codon-optimized hST6Gal leader 53 fusion (FIG. 33)
```

REFERENCES

Abeijon (1996) *Proc. Natl. Acad. Sci. U.S.A.* 93:5963-5968.

Aebi M. et al. (1996) "Cloning and characterization of the ALG3 gene of *Saccharomyces cerevisiae*." *Glycobiology* 6(4): 439-444.

Alani and Kleckner (1987) *Genetics* 116:541-545

Altmann F. et al. (1999) "Insect cells as hosts for the expression of recombinant glycoproteins." *Glycoconjugate J.* 16(2): 109-123.

Altschul, S. F. et al. (1990) *J. Mol. Biol.* 215:403-410.

Altschul, S. F. et al. (1997) *Nucleic Acids Res.* 25:3389-3402.

Alviano C. S. et al. (1999) Sialic acids in fungi: A minireview. *Glycoconjugate J.* 16: 545-554.

An G. 1985. *Plant Physiol.* 79:568-570.

Andersen D. C. and C. F. Goochee (1994) "The effect of cell-culture conditions on the oligosaccharide structures of secreted glycoproteins." *Current Opinion in Biotechnology* 5: 546-549.

Annunziato P. W., et al. (1995) "Nucleotide sequence and genetic analysis of the neuD and neuB genes in region 2 of the polysialic acid gene cluster of *Escherichia coli* K1." *J. Bacteriol.* 177: 312-319.

Aoki (1999) *J. Biochem.* 126(5): 940-950

Bakker H. et al. (2001) *Proc. Natl. Acad. Sci. USA* 98(5): 2899-904

Ballou C. E. (1990) "Isolation, characterization, and properties of *Saccharomyces cerevisiae* mnn mutants with non-conditional protein glycosylation defects." *Methods Enzymology* 185: 440-470.

Bardor M. et al. (1999) "Analysis of the N-glycosylation of recombinant glycoproteins produced in transgenic plants." *Trends in Plant Science* 4(9): 376-380.

Beaudet L. et al. 1998 *Abc Transporters: Biochemical, Cellular, and Molecular Aspects.* 292: 397-413.

Belli G. et al. (1998) "An activator/repressor dual system allows tight tetracycline-regulated gene expression in budding yeast." *Nucleic Acids Res.* 26: 942-947.

Berka R. M. et al. (1992) *Abstr. Papers Amer. Chem. Soc.* 203: 121-BIOT.

Beminsone P. et al. (1994) *J. Biol. Chem.* 269(1):207-211.

Beminsone P. et al. (1995) *J. Biol. Chem.* 270(24): 14564-14567.

Beminsone P. et al. (1997) *J. Biol. Chem.* 272 (19):12616-12619.

Bianchi et al. (1987) *Current Genetics* 12: 185-192.

Boehm T. et al. (1999) *Yeast* 15(7):563-72.

Boevink et al. (1998) *Plant J.* 15(3):441-7.

Borsig et al. (1995) *Biochem. Biophys. Res. Commun.* 210 (1):14-20.

Bonneaud N. et al. (1991) *Yeast* 7: 609-615.

Bretthauer R. K. and F. J. Castellino (1999) "Glycosylation of *Pichia pastoris*-derived proteins." *Biotechnology and Applied Biochemistry* 30: 193-200.

Briles E. B. et al. (1977) "Isolation of wheat germ agglutinin-resistant clones of Chinese hamster ovary cells deficient in membrane sialic acid and galactose." *J. Biol. Chem.* 252: 1107-1116.

Burda P. and Aebi M. (1999) "The dolichol pathway of N-linked glycosylation."*Biochimica Et Biophysica Acta-General Subjects* 1426(2): 239-257.

Caldwell R. C. and Joyce G. F. (1992) *PCR Methods Applic.*, 2, pp. 28-33.

Cereghino G. P. et al. (2001) "New selectable marker/auxotrophic host strain combinations for molecular genetic manipulation of *Pichia pastoris*." *Gene* 263: 159-169.

Cereghino J. L. and J. M. Cregg (2000) *FEMS Microbiology Reviews* 24(1): 45-66.

Chandrasekaran et al. (1984) *Cancer Res.* 44(9):4059-68.

Chiba Y. et al. (1998) "Production of human compatible high mannose-type (Man(5)GlcNAc(2)) sugar chains in *Saccharomyces cerevisiae*." *J. Biol. Chem.* 273(41): 26298-26304.

Choi B. K. et al. (2003) "Use of combinatorial genetic libraries to humanize N-linked glycosylation in the yeast *Pichia pastoris*." *Proc. Nat'l Acad. Sci. USA.* 100(9):5022-7.

Chowrira G. M. et al. (1995) *Mol. Biotechnol.* 3(1):17-23.

Christou P. (1997) *Plant. Mol. Biol.* 35(1-2):197-203.

Cole E. S. et al. (1994) "Glycosylation Patterns of Human Proteins Expressed in Transgenic Goat Milk." *J. of Cell. Biochem.* 265:S18D.

Colli, (1993) FASEB J, 7:1257-1264

Cregg J. M. et al. (2000) "Recombinant protein expression in *Pichia pastoris.*" *Mol. Technol.* 16: 23-52.

Davidson et al. (2002) *Microbiology* 148(Pt 8):2607-15.

Davies et al. (2001) *Biotechnol Bioeng.* August 20; 74(4): 288-294. "Expression of GnTIII in a Recombinant Anti-CD20 CHO Production Cell Line: Expression of Antibodies with Altered Glycoforms Leads to an Increase in ADCC Through Higher Affinity for FcgRIII."

Dente L. et al. (1988). "Expression of Human Alpha-1-Acid Glycoprotein Genes in Cultured-Cells and in Transgenic Mice." *Genes & Development* 2(2): 259-266.

Dirnberger et al. (2002) *Plant Mol. Biol.* 50(2):273-81.

Eades and Hintz (2000) *Gene* 255(1):25-34.

Eckhardt and Gerardy Schahn (1997) *Eur. I Biochem.* 248(1): 187-192.

Essl D. et al. (1990) *FEBS Lett* 18; 453(1-2):169-73.

Frame B. R. et al. (2002 May) *Plant Physiol* 129(1):13-22.

Fritsch M. et al. (1996) "Determination of cytidine 5'-monophospho-N-acetylneuraminic acid pool size in cell culture scale using high-performance anion-exchange chromatography with pulsed amperometric detection." *J. Chromatogr. A.* 727: 223-230.

Fujiyama K. et al. (2001) *Biochem. Biophys. Res. Commun.* 289(2):553-7.

Fukuda M. N. et al. (1989) "Survival of recombinant erythropoietin in the circulation: the role of carbohydrates." *Blood,* 73, 84-89.

Gish and States (1993) *Nature Genet.* 3:266-272.

Gleeson P. A. (1998) *Histochem. Cell Biol.* 109: 517-532.

Gomord V. et al. (1999 June) *Biochimie* 81(6):607-18.

Gordon-Kamm W. J. et al. (1990 July) *Plant Cell* 2(7):603-618.

Graham T. and Emr S. (1991) "Compartmental organization of Golgi-specific protein modification and vacuolar protein sorting events defined in a yeast sec18 (NSF) mutant." *J. Cell. Biol.* 114(2):207-218.

Guillen et al. (1998) *Proc. Natl. Acad. Sci. USA* 95(14): 7888-7892.

Hamilton S. R., Bobrowicz P., et al. (2003) "Production of Complex Human Glycoproteins in Yeast." *Science* 301: 1244-1246.

Hanset et al., FEMS Yeast Res 2003 4(3):323-37.

Harduin-Lepers, 2001, Biochimie 83:727-37.

Hardeuin-Lepers, 2005, Glycobiology 15:8705-17.

Harkki A. et al. (1989) *Bio-Technology* 7(6): 596.

Harms E. et al. (1973) "Biosynthesis of N-acetylneuraminic acid in Morris hepatomas." *Eur. J. Biochem.* 32: 254-262.

Hayes et al. (1975) *J. Arch. Biochem. Biophys.* 171, 651-655.

Hinchee et al. (1988) *Bio/Technology* 6:915.

Hinderlich S., Stasche, R., et al. (1997) "A bifunctional enzyme catalyzes the first two steps in N-acetylneuraminic acid biosynthesis of rat liver. Purification and characterization of UDP-N-acetylglucosamine 2-epimerase/N-acetylmannosamine kinase." *J. Biol. Chem.* 272: 24313-24318.

Hollister et al. (2001) *Glycobiology* 11(1):1-9.

Hollister et al. (1998) *Glycobiology* 8(5):473-480.

Huffaker T. C. and Robbins P. W. (1983) "Yeast Mutants Deficient in Protein Glycosylation." *Proc. Nal. Acad. Sci. USA* 80(24): 7466-7470.

Huffaker T. C. and Robbins, P. W., (1983) *Proc. Nat'l. Acad. Sci. USA.* 80(24):7466-70.

Ichishima et al. (1999) *Biochem.* 1339(Pt 3):589-597

Inoue H., Fukui K., et al. (1990) "Molecular cloning and sequence analysis of a cDNA encoding a porcine kidney renin-binding protein." *J. Biol. Chem.* 265: 6556-6561.

Ishida (1999) *J. Biochem.* 126(1): 68-77.

Jarvis D. L., Kawar Z. S., et al. (1998). "Engineering N-glycosylation pathways in the baculovirus-insect cell system." *Current Opinion in Biotechnology* 9(5): 528-533.

Jarvis (1997) *The Baculoviruses* 389-431.

Kainuma, 1999 *Glycobiology* 9(2): 133-141

Kalsner et al. (1995) *Glycoconj. J.* 12:360-70

Kelm S, and Schauer R. (1997) "Sialic acids in molecular and cellular interactions." *Int. Rev. Cytol.* 175: 137-240.

Keppler O. T., Hinderlich S. et al. (1999) "UDP-GlcNAc 2-epimerase: A regulator of cell surface sialylation." *Science* 284: 1372-1376.

Kimura T., N. Kitamoto, et al. (1997) "A novel yeast gene, RHK1, is involved in the synthesis of the cell wall receptor for the HM-1 killer toxin that inhibits beta-1,3-glucan synthesis." *Molecular & General Genetics* 254(2): 139-147.

Kimura, T., T. Komiyama, et al. (1999) "N-glycosylation is involved in the sensitivity of *Saccharomyces cerevisiae* to HM-1 killer toxin secreted from *Hansenula mrakii* IFO 0895." *Applied Microbiology and Biotechnology* 51(2): 176-184.

Krezdorn (1994) Eur. J. Biochem., 220:809-17

Laroy et al., (2001) *Glycobiology* 11(3):175-82

Laursen C. M. et al. (1994) *Plant Mol. Biol.* 24(1):51-61.

Lawrence S. M. et al. (2000) "Cloning and expression of the human N-acetylneuraminic acid phosphate synthase gene with 2-keto-3-deoxy-D-glycero-D-galacto-nononic acid biosynthetic ability." *J. Biol. Chem.* 275, 17869-17877.

Lehele and Tanner (1974) *Biochim. Biophys. Acta* 350(1): 225-235.

Lerouge P. et al. (1998) *Plant Mol. Biol.* 38(1-2):31-48.

Leung D. W. et al. (1989) *Technique* 1: 11-15.

MacDougall I. C., Gray S. J., et al. (1999). "Pharmacokinetics of Novel Erythropoeisis Stimulating Protein Compared with Epoetin Alfa in Dialysis Patients." *J. Am. Soc. Nephrol.* 10: 2392-2395.

Madden T. L. et al. (1996) *Meth. Enzymol.* 266:131-141.

Maliekal et al. (2006) *Glycobiology* 16(2):165-172.

Malissard M., S. Zeng, et al. (2000). "Expression of functional soluble forms of human beta-1,4-galactosyltransferase I, alpha-2,6-sialyltransferase, and alpha-1,3-fucosyltransferase VI in the methylotrophic yeast *Pichia pastoris.*" *Biochemical and Biophysical Research Communications* 267(1): 169-173.

Maras M. et al. (2000) *J. Biotechnol.* 77(2-3):255-263.

Maras, M. and R. Contreras (1994). "Methods of Modifying Carbohydrate Moieties." United States, Alko Group Ltd., Helsinki, Finland.

Maras, M., A. De Bruyn, et al. (1999) "In vivo synthesis of complex N-glycans by expression of human N-acetylglucosaminyltransferase I in the filamentous fungus *Trichoderma reesei.*" *Febs Letters* 452(3): 365-370.

Maras M., Saelens X., et al. (1997) "In vitro conversion of the carbohydrate moiety of fungal glycoproteins to mammalian-type oligosaccharides—Evidence for N-acetylglucosaminyltransferase-1-accepting glycans from *Trichoderma reesei.*" *European Journal of Biochemist?),* 249(3): 701-707.

Martinet W., Maras M., et al. (1998) "Modification of the protein glycosylation pathway in the methylotrophic yeast *Pichia pastoris.*" *Biotechnology Letters* 20(12): 1171-1177.

Marchal et al., (2001) *Glycobiology* 1(7): 593-603.

Maru I., Ohta Y., et al. (1996) "Molecular cloning and identification of N-acyl-D-glucosamine 2-epimerase from porcine kidney as a renin-binding protein." *J. Biol. Chem.* 271: 16294-16299.

Maruyama et al. (1994) *Carbohydrate Res.* 251:89-98.

Marz et al. (1995) *Glycoproteins* 29:543-563.

Mattila P et al. (1996) "Targeting of active rat alpha 2,3-sialyltransferase to the yeast cell wall by the aid of the hsp 150 delta-carrier: toward synthesis of sLe(x)-decorated L-selectin ligands." *Glycobiology* 6(8):851-9.

McGarvey, P. B., J. Hammond, et al. (1995). "Expression of the Rabies Virus Glycoprotein in Transgenic Tomatoes." *Bio-Technology* 13(13): 1484-1487.

Mercker and Troy (1990) *Glycobiology* 1:93-100.

Miele et al. (1997) *Biotechnol. Appl. Biochem.* 25: 151-157.

Moens S, and Vanderleyden J. (1997) "Glycoproteins in prokaryotes." *Archives of Microbiology* 168(3): 169-175.

Molnar et al. (Sep. 4-11, 1999) *Symposium on Recent Advances in Plant Biotechnology* Stara Lesna, Slovak Republic.

Morin-Ganet et al. (2000) *Traffic* 1(1):56-68

Munster A. K., Eckhardt M., et al. (1998) "Mammalian cytidine 5'-monophosphate N-acetylneuraminic acid synthetase: a nuclear protein with evolutionarily conserved structural motifs." *Proc. Nat'l. Acad. Sci. USA* 95: 9140-9145.

Nakanishi-Shindo Y., Nakayama K., et al. (1993) "Structure of the N-Linked Oligosaccharides That Show the Complete Loss of Alpha-1,6-Polymannose Outer Chain From Och1, Och1 Mnn1, and Och1 Mnn1 Alg3 Mutants of *Saccharomyces-Cerevisiae.*" *J. Biol. Chem.* 268: 26338-26345.

Nakayama et al. (1992) *EMBO J.* 11(7):2511-9.

Neiman et al. (1997) *Genetics* 145(3):637-45.

Nett et al. (2005) *Yeast* 22(4):295-304.

Newell C A. (2000 September) *Mol Biotechnol* 16(1):53-65.

Ohta Y., Watanabe K. et al. (1985) "Complete nucleotide sequence of the *E. coli* N-acetylneuraminate lyase." *Nucleic Acids Res.* 13: 8843-8852.

Orci et al. (2000) J. Cell Biol. 150(6):1263-70.

Palacpac N. et al. (1999) *Proc. Natl. Acad. Sci. USA* 96(8): 4692-7.

Papac et al. A. J. S. (1998) *Glycobiology* 8 445-454.

Parodi A. J. (1993) "N-glycosylation in trypanosomatid protozoa." *Glycobiology* 3: 193-199.

Pawlowski W. et al. (1996) *Mol. Biotechnol.* 6(1):17-30.

Pearson (1990) *Methods Enzymol.* 183:63-98.

Pearson et al. (1994) *Genomics* 46(1):24-36.

Pereira et al. (1991) "The *Trypanosoma cruzi* neuraminidase contains sequences similar to bacterial neuraminidases, YWTD repeats of the low density lipoprotein receptor, and type III modules of fibronectin." *J. Exp. Med.* 174:179-91.

Perez and Hirschberg (1987) *Methods in Enzymology* 138: 709-715.

Potrykus (1990) "Gene transfer methods for plants and cell cultures." *Ciba Found Symp* 154:198-12.

Puglielli (1999) *J. Biol. Chem.* 274(50):35596-35600.

Raju T. S., J. B. Briggs, et al. (2000) "Species-specific variation in glycosylation of IgG: evidence for the species-specific sialylation and branch-specific galactosylation and importance for engineering recombinant glycoprotein therapeutics." *Glycobiology* 10(5): 477-486.

Raju (2001) *Biochemistry* 40:8868-76.

Raschke et al. (1973) *J. Biol. Chem.* 248(13):4660-6.

Reidhaar-Olson, J. F. & Sauer, R. T., et al. (1988) *Science* 241: 53-57.

Rempel H. C. et al. (1995) *Transgenic Res.* 4(3):199-207.

Ren et al. (1995) *Biochem.* 34(8):2489-2495.

Ringenberg M., Lichtensteiger C., et al. (2001) "Redirection of sialic acid metabolism in genetically engineered *Escherichia coli.*" *Glycobiology* 11: 533-539.

Ringenberg et al. (2003) *Mol. Microbiol.* 50:961-75.

Romero et al. (1997) *Biochem. J.* 321(Pt 2):289-295.

Rothstein R. (1991) *Methods in Enzymology* vol. 194: 281.

Rump J. A., Phillips J., et al. (1986) "Biosynthesis of gangliosides in primary cultures of rat hepatocytes. Determination of the net synthesis of individual gangliosides by incorporation of labeled N-acetylmannosamine." *Biol. Chem. Hoppe Seyler* 367: 425-432.

Ryo, Misaki et al. (2002) *Glycobiology* 10:1093.

Sambrook J. and Russell, D. W. (2001) Molecular Cloning: A laboratory manual. 3rd Edition. Cold Spring Harbor Laboratory Press, Cold Spring Harbor N. Y.

Sanderfoot et al. (1998) *Proc. Natl. Acad. Sci. USA* 95(17): 9920-5

Sanford J. C. et al. (1990) Biolistic plant transformation. *Physiol. Plant.* 79: 206-209.

Schauer, R. (2000) "Achievements and challenges of sialic acid research."*Glycoconj. J.* 17: 485-99.

Schenkman S., Eichinger D. (1994) M. E. A. Pereira, Structural and Functional Properties *Trypanosoma* Trans-Sialidase *Annu Rev Microbiol.* 48:499-523

Schneikert and Herscovics (1994) *Glycobiology* 4(4):445-50

Schroeder H. E. et al. (1993) *Plant Physiol* 101(3):751-757

Segawa, 1999 *Febs Letters* 451(3): 295-298

Sharma C. B., Knauer R., et al. (2001) "Biosynthesis of lipid-linked oligosaccharides in yeast: the ALG3 gene encodes the DoI-P-Man: Man(5)GlcNAc(2)-PP-DoI mannosyltransferase." *Biological Chemistry* 382(2): 321-328.

Sikorski R. S., and Hieter, P. (1989) *Genetics* 122: 19-27.

Sommers and Hirschberg (1982) *J. Biol. Chem.* 257(18): 811-817.

Sommers and Hirschberg (1981) *J. Cell. Biol.* 91(2): A406-A406.

Sorokin, A. P. et al. (2000 Jul. 28) *Plant Sci.* 156(2):227-233.

Spivak J. L. and Hogans B. B. (1989) "The in vivo metabolism of recombinant human erythropoietin in the rat." *Blood* 73: 90-99.

Stanley P. and Siminovitch L. (1977) *Somatic Cell Genet.* 3(4):391-405

Stasche R., Hinderlich S., et al. (1997) "A bifunctional enzyme catalyzes the first two steps in N-acetylneuraminic acid biosynthesis of rat liver. Molecular cloning and functional expression of UDP-N-acetyl-glucosamine 2-epimerase/N-acetylmannosamine kinase." *J. Biol. Chem.* 272: 24319-24324.

Staub J. M., Garcia B., et al. (2000). "High-yield production of a human therapeutic protein in tobacco chloroplasts." *Nature Biotechnology* 18(3): 333-338.

Strasser R et al. (1999) *Glycoconj. J.* 16(12):787-91.

Svetina M. et al. (2000) *J. Biotechnol.* 76(2-3): 245-251.

Takeuchi, M. (1997) "Trial for molecular breeding of yeast for the production of glycoprotein therapeutics." *Trends in Glycoscience and Glycotechnology* 9: S29-S35.

Tsji, 1996, J. Biochem. (Tokyo) 120:1-13

Tomes D. T. et al. (1990) *Plant Mol. Biol.* 14(2):261-8.

Tschopp J. F., Brust P. F., et al. (1987) "Expression of the lacZ gene from two methanol-regulated promoters in *Pichia pastoris.*" *Nucleic Acids Res.* 15: 3859-3876.

Umana et al. (1999a) "Engineered glycoforms of an antineuroblastoma IgG1 with optimized antibodydependent cellular cytotoxic activity" *Nat. Biotechnol.* (17)176-180.

Umana et al. (1999b) "Regulated Overexpression of glycosyltransferase."*Biotechnol Bioeng.* 65(5):542-549.

Van Rinsum J., Van Dijk W., et al. (1984) "Subcellular localization and tissue distribution of sialic acid forming enzymes." *Biochem. J.* 223: 323-328.

Verostek M. F., Atkinson P. H., et al. (1993) "Glycoprotein-Biosynthesis in the Alg3 *Saccharomyces*-Cerevisiae Mutant 0.2. Structure of Novel Man6-10glcnac2 Processing Intermediates On Secreted Invertase." *Journal of Biological Chemistry* 268(16): 12104-12115.

Vimr E., Steenbergen S., et al. (1995) "Biosynthesis of the polysialic acid capsule in *Escherichia coli* K1." *J. Ind. Microbiol.* 15: 352-360.

Vimr E. R. and Troy F. A. (1985) "Regulation of sialic acid metabolism in *Escherichia coli*: Role of N-acylneuraminate pyruvate-lyase." *J. Bacteriol.* 164: 854-860.

Warren L. (1994) Bound Carbohydrates in Nature. Cambridge University Press, Cambridge, U.K.

Wee E. et al. (1998) *Plant Cell* 10(10):1759-68.

Weig M et al. (2004) "Systematic identification in silico of covalently bound cell wall proteins and analysis of protein-polysaccharide linkages of the human pathogen *Candida glabrata.*" *Microbiology* 150(Pt 10):3129-44.

Weikert S., Papac D., et al. (1999). "Engineering Chinese hamster ovary cells to maximize sialic acid content of recombinant glycoproteins." *Nature Biotechnology* 17(11): 1116-1121.

Werner R. G., Noe W., et al. (1998). "Appropriate mammalian expression systems for biopharmaceuticals." *Arzneimittel-Forschung-Drug Research* 48(8): 870-880.

Yang M. and Butler M. (2000). "Effects of ammonia on CHO cell growth, erythropoietin production, and glycosylation." *Biotechnology and Bioengineering* 68(4): 370-380.

Yip et al. (1994) *Proc. Natl. Acad. Sci. USA* 91(7):2723-7.

Yocum R. R., Hanley S. et al. (1984) "Use of lacZ fusions to delimit regulatory elements of the inducible divergent GAL1-GAL10 promoter in *Saccharomyces cerevisiae.*" *Mol. Cell. Biol.* 4: 1985-1998.

Yoko-o T., Tsukahara K., et al. (2001) "*Schizosaccharomyces pombe* och1(+) encodes alpha-1,6-mannosyltransferase that is involved in outer chain elongation of N-linked oligosaccharides." *FEBS Lett* 489: 75-80.

Yoshida et al. (1993) *Biochem. J.* 290(Pt 2):349-354.

Zapata G., Vann W. F., et al. (1989) "Sequence of the cloned *Escherichia coli* K1 CMP-N-acetylneuraminic acid synthetase gene." *J. Biol. Chem.* 264: 14769-14774.

Zapata G., Crowley J. M., et al. (1992) "Sequence and expression of the *Escherichia coli* K1 neuC gene product." *J. Bacteriol.* 174: 315-319.

Zhang J. and Madden, T. L. (1997) *Genome Res.* 7:649-656.

Zufferey R., R. Knauer, et al. (1995) "Stt3, a Highly Conserved Protein Required for Yeast Oligosaccharyl Transferase-Activity in-Vivo." *EMBO Journal* 14(20): 4949-4960.

---

What is claimed is:

1. A method for producing a recombinant sialylated glycoprotein in a *Pichia pastoris* host cell, the host cell selected or engineered to produce glycoproteins comprising a GalGlcNAcMan$_5$GlcNAc$_2$ glycoform, the method comprising the step of transforming into the host cell:
   a. a nucleic acid encoding an enzyme having sialyltransferase activity, wherein the nucleic acid encodes a sialyltransferase enzyme comprising the amino acid sequence of SEQ ID NO:104 or a catalytic domain thereof; and
   b. a nucleic acid encoding a CMP-sialic acid transporter; and
   c. one or more nucleic acids encoding a CMP-sialic acid pathway consisting of: a bifunctional UDP-N-acetylglucosamine-2-epimerase/N-acetylmannosamine Kinase, an N-acetylneuraminate-9-phosphate synthase, and a CMP-Sialic acid synthase;
   wherein upon passage of the recombinant glycoprotein through the Golgi apparatus of the host cell, a recombinant glycoprotein comprising a NANAGalGlcNAcMan$_5$GlcNAc$_2$ glycoform is produced.

2. The method of claim 1, wherein said host cell comprises a cellular pool of CMP-sialic acid.

3. The method of claim 1, wherein the method further comprises culturing said host cell in the presence of a sialic acid donor or a precursor of a sialic acid donor.

4. The method of claim 1, wherein said method further comprises the step of introducing into the host cell one or more additional nucleic acids encoding one or more enzymes selected from the group consisting of glycosyltransferases, glycosidases and sugar transporters.

5. The method of claim 1, wherein said nucleic acid encoding a CMP-sialic acid transporter is mouse; and said one or more nucleic acids encoding a bifunctional UDP-N-acetylglucosamine-2-epimerase/N-acetylmannosamine Kinase, an N-acetylneuraminate-9-phosphate synthase, and a CMP-Sialic acid synthase is/are human.

* * * * *

SEQUENCE LISTING

```
<160> NUMBER OF SEQ ID NOS: 107

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
atggcgaagg cagatggcag t                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ttagtccttc caacttcctt c                                                   21

<210> SEQ ID NO 3
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: 9
<223> OTHER INFORMATION: n = a, c, g, t, unknown or other
<220> FEATURE:
<221> NAME/KEY: modified_base
<222> LOCATION: 12
<223> OTHER INFORMATION: n = a, c, g, t, unknown or other
<220> FEATURE:
<221> NAME/KEY: modified_base
<222> LOCATION: 18
<223> OTHER INFORMATION: n = a , c, g, t, unknown or other

<400> SEQUENCE: 3
```
taytggmgng tngarcynga yathaa 26

<210> SEQ ID NO 4
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: 6
<223> OTHER INFORMATION: n = a, c, g, t, unknown or other
<220> FEATURE:
<221> NAME/KEY: modified_base
<222> LOCATION: 12
<223> OTHER INFORMATION: n = a, c, g, t, unknown or other

<400> SEQUENCE: 4
gcrtcncccc anckytcrta 20

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

His Asp Glu Leu
 1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Lys Asp Glu Leu
 1

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
atggcgaagg cagatggcag t 21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ttagtccttc caacttcctt c 21

<210> SEQ ID NO 9
<211> LENGTH: 21
<212> TYPE: DNA
<213> ORGANISM: Artificial Sequence
<220> FEATURE:

```
<223> OTHER INFORMATION: Synthetic primer

<400> SEQUENCE: 9
actgccatct gccttcgcca t                                              21

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
gtaatacgac tcactatagg gc                                             22

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
aattaaccct cactaaaggg                                                20

<210> SEQ ID NO 12
<211> LENGTH: 36
<212> TYPE: DNA
<213> ORGANISM: Artificial Sequence
<220> FEATURE:
<223> OTHER INFORMATION: Synthetic primer

<400> SEQUENCE: 12
atgcccgtgg ggggcctgtt gccgctcttc agtagc                              36

<210> SEQ ID NO 13
<211> LENGTH: 40
<212> TYPE: DNA
<213> ORGANISM: Artificial Sequence
<220> FEATURE:
<223> OTHER INFORMATION: Synthetic primer

<400> SEQUENCE: 13
tcatttctct tgccatcaa tttccttctt ctgttcacgg                           40

<210> SEQ ID NO 14
<211> LENGTH: 44
<212> TYPE: DNA
<213> ORGANISM: Artificial Sequence
<220> FEATURE:
<223> OTHER INFORMATION: Synthetic primer

<400> SEQUENCE: 14
ggcgcgccga ctcctccaag ctgctcagcg gggtcctgtt ccac                     44

<210> SEQ ID NO 15
<211> LENGTH: 50
<212> TYPE: DNA
<213> ORGANISM: Artificial Sequence
<220> FEATURE:
<223> OTHER INFORMATION: Synthetic primer

<400> SEQUENCE: 15
ccttaattaa tcatttctct tgccatcaa tttccttctt ctgttcacgg                50
```

```
<210> SEQ ID NO 16
<211> LENGTH: 51
<212> TYPE: DNA
<213> ORGANISM: Artificial Sequence
<220> FEATURE:
<223> OTHER INFORMATION: Synthetic primer

<400> SEQUENCE: 16
ggcgagctcg gcctacccgg ccaaggctga gatcatttgt ccagcttcag a          51

<210> SEQ ID NO 17
<211> LENGTH: 55
<212> TYPE: DNA
<213> ORGANISM: Artificial Sequence
<220> FEATURE:
<223> OTHER INFORMATION: Synthetic primer

<400> SEQUENCE: 17
gcccacgtcg acggatccgt ttaaacatcg attggagagg ctgacaccgc tacta      55

<210> SEQ ID NO 18
<211> LENGTH: 55
<212> TYPE: DNA
<213> ORGANISM: Artificial Sequence
<220> FEATURE:
<223> OTHER INFORMATION: Synthetic primer

<400> SEQUENCE: 18
cgggatccac tagtatttaa atcatatgtg cgagtgtaca actcttccca catgg      55

<210> SEQ ID NO 19
<211> LENGTH: 55
<212> TYPE: DNA
<213> ORGANISM: Artificial Sequence
<220> FEATURE:
<223> OTHER INFORMATION: Synthetic primer

<400> SEQUENCE: 19
ggacgcgtcg acggcctacc cggccgtacg aggaatttct cggatgactc ttttc      55

<210> SEQ ID NO 20
<211> LENGTH: 45
<212> TYPE: DNA
<213> ORGANISM: Artificial Sequence
<220> FEATURE:
<223> OTHER INFORMATION: Synthetic primer

<400> SEQUENCE: 20
cgggatccct cgagagatct tttttgtaga aatgtcttgg tgcct                 45

<210> SEQ ID NO 21
<211> LENGTH: 63
<212> TYPE: DNA
<213> ORGANISM: Artificial Sequence
<220> FEATURE:
<223> OTHER INFORMATION: Synthetic primer

<400> SEQUENCE: 21
ggacatgcat gcactagtgc ggccgccacg tgatagttgt tcaattgatt gaaataggga 60
caa                                                               63

<210> SEQ ID NO 22
<211> LENGTH: 52
<212> TYPE: DNA
<213> ORGANISM: Artificial Sequence
<220> FEATURE:
```

<223> OTHER INFORMATION: Synthetic primer

<400> SEQUENCE: 22
ccttgctagc ttaattaacc gcggcacgtc cgacggcggc ccacgggtcc ca          52

<210> SEQ ID NO 23
<211> LENGTH: 61
<212> TYPE: DNA
<213> ORGANISM: Artificial Sequence
<220> FEATURE:
<223> OTHER INFORMATION: Synthetic primer

<400> SEQUENCE: 23
ggacatgcat gcggatccct taagagccgg cagcttgcaa attaaagcct tcgagcgtcc    60
c                                                                    61

<210> SEQ ID NO 24
<211> LENGTH: 61
<212> TYPE: DNA
<213> ORGANISM: Artificial Sequence
<220> FEATURE:
<223> OTHER INFORMATION: Synthetic primer

<400> SEQUENCE: 24
gaaccacgtc gacggccatt gcggccaaaa cctttttttcc tattcaaaca caaggcattg    60
c                                                                    61

<210> SEQ ID NO 25
<211> LENGTH: 43
<212> TYPE: DNA
<213> ORGANISM: Artificial Sequence
<220> FEATURE:
<223> OTHER INFORMATION: Synthetic primer

<400> SEQUENCE: 25
ctccaatact agtcgaagat tatcttctac ggtgcctgga ctc                      43

<210> SEQ ID NO 26
<211> LENGTH: 53
<212> TYPE: DNA
<213> ORGANISM: Artificial Sequence
<220> FEATURE:
<223> OTHER INFORMATION: Synthetic primer

<400> SEQUENCE: 26
tggaaggttt aaacaaagct agagtaaaat agatatagcg agattagaga atg           53

<210> SEQ ID NO 27
<211> LENGTH: 50
<212> TYPE: DNA
<213> ORGANISM: Artificial Sequence
<220> FEATURE:
<223> OTHER INFORMATION: Synthetic primer

<400> SEQUENCE: 27
aagaattcgg ctggaaggcc ttgtaccttg atgtagttcc cgttttcatc               50

<210> SEQ ID NO 28
<211> LENGTH: 58
<212> TYPE: DNA
<213> ORGANISM: Artificial Sequence
<220> FEATURE:
<223> OTHER INFORMATION: Synthetic primer

<400> SEQUENCE: 28

```
gcccaagccg gccttaaggg atctcctgat gactgactca ctgataataa aaatacgg      58

<210> SEQ ID NO 29
<211> LENGTH: 59
<212> TYPE: DNA
<213> ORGANISM: Artificial Sequence
<220> FEATURE:
<223> OTHER INFORMATION: Synthetic primer

<400> SEQUENCE: 29
gggcgcgtat ttaaatacta gtggatctat cgaatctaaa tgtaagttaa aatctctaa     59

<210> SEQ ID NO 30
<211> LENGTH: 39
<212> TYPE: DNA
<213> ORGANISM: Artificial Sequence
<220> FEATURE:
<223> OTHER INFORMATION: Synthetic primer

<400> SEQUENCE: 30
ggccgcctgc agatttaaat gaattcggcg cgccttaat                           39

<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
taaggcgcgc cgaattcatt taaatctgca gggc                                34

<210> SEQ ID NO 32
<211> LENGTH: 29
<212> TYPE: DNA
<213> ORGANISM: Artificial Sequence
<220> FEATURE:
<223> OTHER INFORMATION: Synthetic primer

<400> SEQUENCE: 32
tggcaggcgc gcctcagtca gcgctctcg                                      29

<210> SEQ ID NO 33
<211> LENGTH: 29
<212> TYPE: DNA
<213> ORGANISM: Artificial Sequence
<220> FEATURE:
<223> OTHER INFORMATION: Synthetic primer

<400> SEQUENCE: 33
aggttaatta agtgctaatt ccagctagg                                      29

<210> SEQ ID NO 34
<211> LENGTH: 26
<212> TYPE: DNA
<213> ORGANISM: Artificial Sequence
<220> FEATURE:
<223> OTHER INFORMATION: Synthetic primer

<400> SEQUENCE: 34
ccagaagaat tcaattytgy cartgg                                         26

<210> SEQ ID NO 35
<211> LENGTH: 25
<212> TYPE: DNA
```

```
<213> ORGANISM: Artificial Sequence
<220> FEATURE:
<223> OTHER INFORMATION: Synthetic primer
<220> FEATURE:
<221> NAME/KEY: modified_base
<222> LOCATION: 17
<223> OTHER INFORMATION: n = a, c, g, t, unknown or other
<220> FEATURE:
<221> NAME/KEY: modified_base
<222> LOCATION: 20
<223> OTHER INFORMATION: n = a, c, g, t, unknown or other

<400> SEQUENCE: 35
cagtgaaaat acctggnccn gtcca                                          25

<210> SEQ ID NO 36
<211> LENGTH: 27
<212> TYPE: DNA
<213> ORGANISM: Artificial Sequence
<220> FEATURE:
<223> OTHER INFORMATION: Synthetic primer

<400> SEQUENCE: 36
tgccatcttt taggtccagg cccgttc                                        27

<210> SEQ ID NO 37
<211> LENGTH: 27
<212> TYPE: DNA
<213> ORGANISM: Artificial Sequence
<220> FEATURE:
<223> OTHER INFORMATION: Synthetic primer

<400> SEQUENCE: 37
gatcccacga cgcatcgtat ttctttc                                        27

<210> SEQ ID NO 38
<211> LENGTH: 302
<212> TYPE: DNA
<213> ORGANISM: kluyveromyces lactis

<400> SEQUENCE: 38
gcccttcagt gaaaatacct ggcccggtcc agttcataat atcggtacca tctgtatttt    60
tggcggtttt cttttgttga tgtttgtaat ttttgttgaa cttcttttta tccctcatgt   120
tgacattata atcatctgca atgtctttta atacttcagc atcatctaaa ggaatgctgc   180
ttttaacatt tgccacgctc tccaatgttg ttgcggtgat atttgtgatc aattcgcgca   240
ataatggatg gccagatttt gattgtattg tccactgaca aaattgaatt ctctggaagg   300
gc                                                                 302

<210> SEQ ID NO 39
<211> LENGTH: 80
<212> TYPE: PRT
<213> ORGANISM: kluyveromyces lactis

<400> SEQUENCE: 39

Thr Ile Gln Ser Lys Ser Gly His Pro Leu Leu Arg Glu Leu Ile Thr
 1               5                  10                  15

Asn Ile Thr Ala Thr Thr Leu Glu Ser Val Ala Asn Val Lys Ser Ser
            20                  25                  30

Ile Pro Leu Asp Asp Ala Glu Val Leu Lys Asp Ile Ala Asp Asp Tyr
        35                  40                  45

Asn Val Asn Met Arg Asp Lys Lys Phe Asn Lys Asn Tyr Lys His
    50                  55                  60
```

Gln Gln Lys Lys Thr Ala Lys Asn Thr Asp Gly Thr Asp Ile Met Asn
65                  70                  75                  80

<210> SEQ ID NO 40
<211> LENGTH: 404
<212> TYPE: DNA
<213> ORGANISM: Kluyveromyces lactis

<400> SEQUENCE: 40

| | | | | | |
|---|---|---|---|---|---|
| cccagcgtgc | cattaccgta | tttgccgccg | tttgaaatac | tcaatattca | tgatggttgt | 60 |
| aaggcgtttt | ttatcattcg | cgatataata | tgccatcttt | taggtccagg | cccgttctct | 120 |
| tagctatctt | tggtgtctgt | gctaccgtga | tatggtacct | attctttttc | cagtctaatc | 180 |
| tgaagatggc | agatttgaaa | aaggtagcaa | cttcaaggta | tctttcacaa | gaaccgtcgt | 240 |
| tatcagaact | tatgtcaaat | gtgaagatca | agcctattga | agaaaccccg | gtttcgccat | 300 |
| tggagttgat | tccagatatc | gaaatatcga | ctagaaagaa | atacgatgcg | tcgtgggatc | 360 |
| tgttgttccg | tggtagaaaa | tataaatcgt | tcaacgatta | tgat |  | 404 |

<210> SEQ ID NO 41
<211> LENGTH: 1362
<212> TYPE: DNA
<213> ORGANISM: Kluyveromyces lactis

<400> SEQUENCE: 41

| | | | | | |
|---|---|---|---|---|---|
| atggggttac | caaagatttc | aagaagaacg | aggtacatta | ttgtcattgt | gctgatactg | 60 |
| tacttattgt | tttctgtgca | atggaatact | gcgaaagtga | atcaccattt | ctataacagc | 120 |
| attggcacgg | tgcttcccag | tacagctcgc | gtggatcact | tgaacttgaa | aaacttggac | 180 |
| ttagcaggta | cgagcaataa | cggtgatcat | ttgatggatc | tacgagttca | attggctagt | 240 |
| caattcccct | acgattctcg | agtacccatc | cccaaaaagg | tatggcagac | ctggaagatt | 300 |
| gatcccagtt | caaagtcaca | ggtttcttcc | atttcaaaat | gccagaatga | ttggaaacat | 360 |
| ttcagtgcat | ccgaggaacc | gccatatcaa | taccaattaa | tcacagatga | tcaaatgata | 420 |
| ccacttctag | agcagctata | tggtggggtc | ccacaagtga | taaaggcttt | tgaatccttg | 480 |
| ccacttccaa | ttcttaaagc | agactttttc | agatacttga | tcctttatgc | aagaggtggt | 540 |
| atatattctg | acatggatac | gttcccatta | aagccattgt | cgtcatggcc | atcgacttct | 600 |
| cagtcctact | tttctagttt | aaagaatcca | caaaggtata | gaaattcctt | ggacaacctt | 660 |
| gaaacgctag | aagcttcaga | acctggcttt | gtcattggta | tcgaggctga | tccggataga | 720 |
| agcgattggg | cagagtggta | cgccaggaga | atacaattct | gtcagtggac | aatacaatca | 780 |
| aaatctggcc | atccattatt | gcgcgaattg | atcacaaata | tcaccgcaac | aacattggag | 840 |
| agcgtggcaa | atgttaaaag | cagcattcct | ttagatgatg | ctgaagtatt | aaaagacatt | 900 |
| gcagatgatt | ataatgtcaa | catgagggat | aaaagaagt | tcaacaaaaa | ttacaaacat | 960 |
| caacaaaaga | aaaccgccaa | aaatacagat | ggtaccgata | ttatgaactg | gactggtcca | 1020 |
| ggtattttt | cagatgttat | tttccagtat | cttaataacg | ttatccagaa | gaatgatgac | 1080 |
| atttaatttt | tcaatgataa | tcttaatgtt | atcaacaaac | atggatccaa | acatgataca | 1140 |
| actatgagat | tctataaaga | cattgttaaa | aatttacaaa | acgacaaacc | ctcattgttc | 1200 |
| tggggattct | tttcattgat | gacagagcct | attctagtgg | acgacatcat | ggtacttccg | 1260 |
| attacttctt | tctcaccagg | tatcagaaca | atggcgcgta | aagaagacaa | cgacgagatg | 1320 |
| gcatttgtta | agcatatttt | tgaaggaagt | tggaaagact | ga | | 1362 |

<210> SEQ ID NO 42
<211> LENGTH: 454
<212> TYPE: PRT
<213> ORGANISM: Kluyveromyces lactis

<400> SEQUENCE: 42

```
Met Gly Leu Pro Lys Ile Ser Arg Arg Thr Arg Tyr Ile Ile Val Ile
1               5                   10                  15

Val Leu Ile Leu Tyr Leu Leu Phe Ser Val Gln Trp Asn Thr Ala Lys
            20                  25                  30

Val Asn His His Phe Tyr Asn Ser Ile Gly Thr Val Leu Pro Ser Thr
        35                  40                  45

Ala Arg Val Asp His Leu Asn Leu Lys Asn Leu Asp Leu Ala Gly Thr
    50                  55                  60

Ser Asn Asn Gly Asp His Leu Met Asp Leu Arg Val Gln Leu Ala Ser
65                  70                  75                  80

Gln Phe Pro Tyr Asp Ser Arg Val Pro Ile Pro Lys Lys Val Trp Gln
                85                  90                  95

Thr Trp Lys Ile Asp Pro Ser Ser Lys Ser Gln Val Ser Ser Ile Ser
            100                 105                 110

Lys Cys Gln Asn Asp Trp Lys His Phe Ser Ala Ser Glu Glu Pro Pro
        115                 120                 125

Tyr Gln Tyr Gln Leu Ile Thr Asp Asp Gln Met Ile Pro Leu Leu Glu
    130                 135                 140

Gln Leu Tyr Gly Gly Val Pro Gln Val Ile Lys Ala Phe Glu Ser Leu
145                 150                 155                 160

Pro Leu Pro Ile Leu Lys Ala Asp Phe Phe Arg Tyr Leu Ile Leu Tyr
                165                 170                 175

Ala Arg Gly Gly Ile Tyr Ser Asp Met Asp Thr Phe Pro Leu Lys Pro
            180                 185                 190

Leu Ser Ser Trp Pro Ser Thr Ser Gln Ser Tyr Phe Ser Ser Leu Lys
        195                 200                 205

Asn Pro Gln Arg Tyr Arg Asn Ser Leu Asp Asn Leu Glu Thr Leu Glu
    210                 215                 220

Ala Ser Glu Pro Gly Phe Val Ile Gly Ile Glu Ala Asp Pro Asp Arg
225                 230                 235                 240

Ser Asp Trp Ala Glu Trp Tyr Ala Arg Arg Ile Gln Phe Cys Gln Trp
                245                 250                 255

Thr Ile Gln Ser Lys Ser Gly His Pro Leu Leu Arg Glu Leu Ile Thr
            260                 265                 270

Asn Ile Thr Ala Thr Thr Leu Glu Ser Val Ala Asn Val Lys Ser Ser
        275                 280                 285

Ile Pro Leu Asp Asp Ala Glu Val Leu Lys Asp Ile Ala Asp Asp Tyr
    290                 295                 300

Asn Val Asn Met Arg Asp Lys Lys Phe Asn Lys Asn Tyr Lys His
305                 310                 315                 320

Gln Gln Lys Lys Thr Ala Lys Asn Thr Asp Gly Thr Asp Ile Met Asn
                325                 330                 335

Trp Thr Gly Pro Gly Ile Phe Ser Asp Val Ile Phe Gln Tyr Leu Asn
            340                 345                 350

Asn Val Ile Gln Lys Asn Asp Asp Ile Leu Ile Phe Asn Asp Asn Leu
        355                 360                 365

Asn Val Ile Asn Lys His Gly Ser Lys His Asp Thr Thr Met Arg Phe
```

```
                370             375             380
Tyr Lys Asp Ile Val Lys Asn Leu Gln Asn Asp Lys Pro Ser Leu Phe
385             390             395             400

Trp Gly Phe Phe Ser Leu Met Thr Glu Pro Ile Leu Val Asp Asp Ile
            405             410             415

Met Val Leu Pro Ile Thr Ser Phe Ser Pro Gly Ile Arg Thr Met Gly
            420             425             430

Ala Lys Glu Asp Asn Asp Glu Met Ala Phe Val Lys His Ile Phe Glu
            435             440             445

Gly Ser Trp Lys Asp Glx
            450

<210> SEQ ID NO 43
<211> LENGTH: 2241
<212> TYPE: DNA
<213> ORGANISM: Kluyveromyces lactis

<400> SEQUENCE: 43
atgatggttg taaggcgttt tttatcagct tcgcgatata atatgccatc ttttaggtcc     60
aggcccgttc tcttagctat ctttggtgtc tgtgctaccg tgatatggta cctattcttt    120
ttccagtcta atctgaagat ggcagatttg aaaaaggtag caacttcaag gtatctttca    180
caagaaccgt cgttatcaga acttatgtca aatgtgaaga tcaagcctat tgaagaaacc    240
ccggtttcgc cattggagtt gattccagat atcgaaatat cgactagaaa gaaatacgat    300
gcgtcgtggg atctgttgtt ccgtggtaga aaatataaat cgttcaacga ttatgatctt    360
catacgaaat gtgagtttta tttccagaat ttatacaatt gaacgagga ttggaccaat    420 aatattcgga cgttcacttt cgatattaac gatgtagaca cgtctacgaa aattgacgct    480
cttaaagatt ccgatggggt tcaattggtg gacgagaagg ctatacgttt atacaagaga    540
acgcataacg ttgccttggc tacggaaagg ttacgtctt tatgataaatg ttttgtcaat    600 agtccaggtt caaacccatt gaaaatggat caccttttca gatcgaacaa gaagagtaag    660
actacggctt tggatgacga agtcactggg aacgtgata cttttaccaa gacgaagaaa    720
acttcgttct taagcgatat ggacacgagt agtttccaga gtacgatca atgggatttc    780 gaacatagaa tgttccccat gatcccatat ttcgaggaac acaatttcac caacgtgatg    840
cctattttca ccggctcaaa cggtggggaa ccttttacctc aagggaaatt cccggtatta    900
gatccaaaat ccggtgaatt gttacgtgta gagactttca gatatgataa atcgaaatcg    960
ctttggaaga actggaatga tatgtcctct gcttctggta acgtggtat tatcttggct   1020 gctggcgacg gccaagtgga ccaatgcatc cgtcttattg ctacgttgag agctcaagga   1080
aacgctctac ctattcaaat tatccacaac aaccaattga atgagaaatc tgtgaaactg   1140
ttatcggagg ccgctaaatc taccgaattc tcatccggta gagctcaatc tctttggtta   1200
gtgaatgtgg gccccacgtt ggaatcttca atgaagagca attttgggag atttaagaat   1260
aagtggttgt cagttatttt caacactttt gaagaattta tattcataga tacagatgcc   1320
atctcctaca ttaatatggc tgattatttc aacttcaagg agtacaaatc tactggaaca   1380
ctcttcttta aggataggtc tttggcaatt ggaactgaac agaaatgtgg tcctttgttc   1440
gaaactcttg aaccaagaat tcttgaaatg tactatttca atactttacc tatgatcaat   1500
ggtgattacg tggaacagca atgtatgggc atgctcaccc cagaggaaaa agtttacaaa   1560
cgtttctttg aagttggtca tcaacacaac ttggaaagtg gattattggc catcaacaaa   1620
```

-continued

```
aacgaacaca tcatgggatt ggttactgca acagtcttaa atatcgcacc aaaggtcgga    1680
ggttgcggtt ggggtgacaa agagttttc tggcttggtt tgttggttgc tggccaacgc    1740
tactcgatct atgatataga tgcaagtgca attggtgttc ctcaacagaa gcaatctatc   1800
gctaacggag acgaatttga tgaatatagg atttgttctt tacaagtggc acatacttca   1860
tacgacggac atttactatg gataaatggt ggctctcagt actgtaagaa accagagact   1920
tttgaaggtg attggaccaa cattaaggag cttcgtgaat cgtattctga tgataaagaa   1980
aaggctctga aggcttatag tgatacagtt aaggtggaag cagcaatcgt gccagattcc   2040
agaagtaatg gttggggtag agacgatcaa agatgtaaag gctacttctg gtgcggcaaa   2100
tttacttcaa agctgaaacc gtatacttat aacacggtgg taactaaagg tgatttgatc   2160
cgtttcggag acgaggaaat cgaaagtatc tccaagatta ataagatctg gaatgatgct   2220
attattccag acggagctta a                                              2241
```

<210> SEQ ID NO 44
<211> LENGTH: 746
<212> TYPE: PRT
<213> ORGANISM: Kluyveromyces lactis

<400> SEQUENCE: 44

```
Met Met Val Val Arg Arg Phe Leu Ser Ala Ser Arg Tyr Asn Met Pro
 1               5                  10                  15

Ser Phe Arg Ser Arg Pro Val Leu Ala Ile Phe Gly Val Cys Ala
             20                  25                  30

Thr Val Ile Trp Tyr Leu Phe Phe Gln Ser Asn Leu Lys Met Ala
         35                  40                  45

Asp Leu Lys Lys Val Ala Thr Ser Arg Tyr Leu Ser Gln Glu Pro Ser
 50                  55                  60

Leu Ser Glu Leu Met Ser Asn Val Lys Ile Lys Pro Ile Glu Glu Thr
 65                  70                  75                  80

Pro Val Ser Pro Leu Glu Leu Ile Pro Asp Ile Glu Ile Ser Thr Arg
                 85                  90                  95

Lys Lys Tyr Asp Ala Ser Trp Asp Leu Leu Phe Arg Gly Arg Lys Tyr
            100                 105                 110

Lys Ser Phe Asn Asp Tyr Asp Leu His Thr Lys Cys Glu Phe Tyr Phe
        115                 120                 125

Gln Asn Leu Tyr Asn Leu Asn Glu Asp Trp Thr Asn Asn Ile Arg Thr
130                 135                 140

Phe Thr Phe Asp Ile Asn Asp Val Asp Thr Ser Thr Lys Ile Asp Ala
145                 150                 155                 160

Leu Lys Asp Ser Asp Gly Val Gln Leu Val Asp Glu Lys Ala Ile Arg
                165                 170                 175

Leu Tyr Lys Arg Thr His Asn Val Ala Leu Ala Thr Glu Arg Leu Arg
            180                 185                 190

Leu Tyr Asp Lys Cys Phe Val Asn Ser Pro Gly Ser Asn Pro Leu Lys
        195                 200                 205

Met Asp His Leu Phe Arg Ser Asn Lys Lys Ser Lys Thr Thr Ala Leu
    210                 215                 220

Asp Asp Glu Val Thr Gly Asn Arg Asp Thr Phe Lys Thr Lys Lys
225                 230                 235                 240

Thr Ser Phe Leu Ser Asp Met Asp Thr Ser Ser Phe Gln Lys Tyr Asp
                245                 250                 255

Gln Trp Asp Phe Glu His Arg Met Phe Pro Met Ile Pro Tyr Phe Glu
```

```
              260                 265                 270
Glu His Asn Phe Thr Asn Val Met Pro Ile Phe Thr Gly Ser Asn Gly
                275                 280                 285

Gly Glu Pro Leu Pro Gln Gly Lys Phe Pro Val Leu Asp Pro Lys Ser
290                 295                 300

Gly Glu Leu Leu Arg Val Glu Thr Phe Arg Tyr Asp Lys Ser Lys Ser
305                 310                 315                 320

Leu Trp Lys Asn Trp Asn Asp Met Ser Ser Ala Ser Gly Lys Arg Gly
                325                 330                 335

Ile Ile Leu Ala Ala Gly Asp Gly Gln Val Asp Gln Cys Ile Arg Leu
                340                 345                 350

Ile Ala Thr Leu Arg Ala Gln Gly Asn Ala Leu Pro Ile Gln Ile Ile
                355                 360                 365

His Asn Asn Gln Leu Asn Glu Lys Ser Val Lys Leu Leu Ser Glu Ala
                370                 375                 380

Ala Lys Ser Thr Glu Phe Ser Ser Gly Arg Ala Gln Ser Leu Trp Leu
385                 390                 395                 400

Val Asn Val Gly Pro Thr Leu Glu Ser Ser Met Lys Ser Asn Phe Gly
                405                 410                 415

Arg Phe Lys Asn Lys Trp Leu Ser Val Ile Phe Asn Thr Phe Glu Glu
                420                 425                 430

Phe Ile Phe Ile Asp Thr Asp Ala Ile Ser Tyr Ile Asn Met Ala Asp
                435                 440                 445

Tyr Phe Asn Phe Lys Glu Tyr Lys Ser Thr Gly Thr Leu Phe Phe Lys
                450                 455                 460

Asp Arg Ser Leu Ala Ile Gly Thr Glu Gln Lys Cys Gly Pro Leu Phe
465                 470                 475                 480

Glu Thr Leu Glu Pro Arg Ile Leu Glu Met Tyr Tyr Phe Asn Thr Leu
                485                 490                 495

Pro Met Ile Asn Gly Asp Tyr Val Glu Gln Gln Cys Met Gly Met Leu
                500                 505                 510

Thr Pro Glu Glu Lys Val Tyr Lys Arg Phe Phe Glu Val Gly His Gln
                515                 520                 525

His Asn Leu Glu Ser Gly Leu Leu Ala Ile Asn Lys Asn Glu His Ile
                530                 535                 540

Met Gly Leu Val Thr Ala Thr Val Leu Asn Ile Ala Pro Lys Val Gly
545                 550                 555                 560

Gly Cys Gly Trp Gly Asp Lys Glu Phe Phe Trp Leu Gly Leu Leu Val
                565                 570                 575

Ala Gly Gln Arg Tyr Ser Ile Tyr Asp Ile Asp Ala Ser Ala Ile Gly
                580                 585                 590

Val Pro Gln Gln Lys Gln Ser Ile Ala Asn Gly Asp Glu Phe Asp Glu
                595                 600                 605

Tyr Arg Ile Cys Ser Leu Gln Val Ala His Thr Ser Tyr Asp Gly His
                610                 615                 620

Leu Leu Trp Ile Asn Gly Gly Ser Gln Tyr Cys Lys Lys Pro Glu Thr
625                 630                 635                 640

Phe Glu Gly Asp Trp Thr Asn Ile Lys Glu Leu Arg Glu Ser Tyr Ser
                645                 650                 655

Asp Asp Lys Glu Lys Ala Leu Lys Ala Tyr Ser Asp Thr Val Lys Val
                660                 665                 670

Glu Ala Ala Ile Val Pro Asp Ser Arg Ser Asn Gly Trp Gly Arg Asp
                675                 680                 685
```

```
Asp Gln Arg Cys Lys Gly Tyr Phe Trp Cys Gly Lys Phe Thr Ser Lys
        690                 695                 700
Leu Lys Pro Tyr Thr Tyr Asn Thr Val Val Thr Lys Gly Asp Leu Ile
705                 710                 715                 720
Arg Phe Gly Asp Glu Glu Ile Glu Ser Ile Ser Lys Ile Asn Lys Ile
                725                 730                 735
Trp Asn Asp Ala Ile Ile Pro Asp Gly Ala
            740                 745
```

<210> SEQ ID NO 45
<211> LENGTH: 35
<212> TYPE: DNA
<213> ORGANISM: Artificial Sequence
<220> FEATURE:
<223> OTHER INFORMATION: Synthetic primer

<400> SEQUENCE: 45
atgagaacaa aaattattgc gataattcca gcccg          35

<210> SEQ ID NO 46
<211> LENGTH: 30
<212> TYPE: DNA
<213> ORGANISM: Artificial Sequence
<220> FEATURE:
<223> OTHER INFORMATION: Synthetic primer

<400> SEQUENCE: 46
tcatttaaca atctccgcta tttcgttttc          30

<210> SEQ ID NO 47
<211> LENGTH: 35
<212> TYPE: DNA
<213> ORGANISM: Artificial Sequence
<220> FEATURE:
<223> OTHER INFORMATION: Synthetic primer

<400> SEQUENCE: 47
atgagtaata tatatcgt tgctgaaatt ggttg          35

<210> SEQ ID NO 48
<211> LENGTH: 30
<212> TYPE: DNA
<213> ORGANISM: Artificial Sequence
<220> FEATURE:
<223> OTHER INFORMATION: Synthetic primer

<400> SEQUENCE: 48
ttattccccc tgattttga attcgctatg          30

<210> SEQ ID NO 49
<211> LENGTH: 34
<212> TYPE: DNA
<213> ORGANISM: Artificial Sequence
<220> FEATURE:
<223> OTHER INFORMATION: Synthetic primer

<400> SEQUENCE: 49
atgaaaaaaa tattatacgt aactggatct agag          34

<210> SEQ ID NO 50
<211> LENGTH: 33
<212> TYPE: DNA
<213> ORGANISM: Artificial Sequence
<220> FEATURE:

<223> OTHER INFORMATION: Synthetic primer

<400> SEQUENCE: 50
ctagtcataa ctggtggtac attccgggat gtc                    33

<210> SEQ ID NO 51
<211> LENGTH: 32
<212> TYPE: DNA
<213> ORGANISM: Artificial Sequence
<220> FEATURE:
<223> OTHER INFORMATION: Synthetic primer

<400> SEQUENCE: 51
atggacgcgc tggagaaggg ggccgtcacg tc                     32

<210> SEQ ID NO 52
<211> LENGTH: 36
<212> TYPE: DNA
<213> ORGANISM: Artificial Sequence
<220> FEATURE:
<223> OTHER INFORMATION: Synthetic primer

<400> SEQUENCE: 52
ctatttttgg catgagttat taacttttc tatcag                  36

<210> SEQ ID NO 53
<211> LENGTH: 28
<212> TYPE: DNA
<213> ORGANISM: Artificial Sequence
<220> FEATURE:
<223> OTHER INFORMATION: Synthetic primer

<400> SEQUENCE: 53
atggagaagg agcgcgaaac tctgcagg                          28

<210> SEQ ID NO 54
<211> LENGTH: 28
<212> TYPE: DNA
<213> ORGANISM: Artificial Sequence
<220> FEATURE:
<223> OTHER INFORMATION: Synthetic primer

<400> SEQUENCE: 54
ctaggcgagg cggctcagca gggcgctc                          28

<210> SEQ ID NO 55
<211> LENGTH: 31
<212> TYPE: DNA
<213> ORGANISM: Artificial Sequence
<220> FEATURE:
<223> OTHER INFORMATION: Synthetic primer

<400> SEQUENCE: 55
atggcaacga atttacgtgg cgtaatggct g                      31

<210> SEQ ID NO 56
<211> LENGTH: 30
<212> TYPE: DNA
<213> ORGANISM: Artificial Sequence
<220> FEATURE:
<223> OTHER INFORMATION: Synthetic primer

<400> SEQUENCE: 56
tcacccgcgc tcttgcatca actgctgggc                        30

```
<210> SEQ ID NO 57
<211> LENGTH: 1176
<212> TYPE: DNA
<213> ORGANISM: escherichia coli
<220> FEATURE:
<221> NAME/KEY: CDS
<222> LOCATION: (1)...(1173)

<400> SEQUENCE: 57 atg aaa aaa ata tta tac gta act gga tct aga gct gaa tat gga ata        48
Met Lys Lys Ile Leu Tyr Val Thr Gly Ser Arg Ala Glu Tyr Gly Ile
1               5                   10                  15 gtt cgg aga ctt ttg aca atg cta aga gaa act cca gaa ata cag ctt        96
Val Arg Arg Leu Leu Thr Met Leu Arg Glu Thr Pro Glu Ile Gln Leu
            20                  25                  30 gat ttg gca gtt aca gga atg cat tgt gat aat gcg tat gga aat aca       144
Asp Leu Ala Val Thr Gly Met His Cys Asp Asn Ala Tyr Gly Asn Thr
        35                  40                  45 ata cat att ata gaa caa gat aat ttt aat att atc aag gtt gtg gat       192
Ile His Ile Ile Glu Gln Asp Asn Phe Asn Ile Ile Lys Val Val Asp
    50                  55                  60 ata aat atc aat aca act tca cat act cac att ctc cat tca atg agt       240
Ile Asn Ile Asn Thr Thr Ser His Thr His Ile Leu His Ser Met Ser
65                  70                  75                  80 gtt tgc ctc aat tcg ttt ggt gat ttt ttt tca aat aac aca tat gat       288
Val Cys Leu Asn Ser Phe Gly Asp Phe Phe Ser Asn Asn Thr Tyr Asp
                85                  90                  95 gcg gtt atg gtt tta ggc gat aga tat gaa ata ttt tca gtc gct atc       336
Ala Val Met Val Leu Gly Asp Arg Tyr Glu Ile Phe Ser Val Ala Ile
            100                 105                 110 gca gca tca atg cat aat att cca tta att cat att cat ggt ggt gaa       384
Ala Ala Ser Met His Asn Ile Pro Leu Ile His Ile His Gly Gly Glu
        115                 120                 125 aag aca tta gct aat tat gat gag ttt att agg cat tca att act aaa       432
Lys Thr Leu Ala Asn Tyr Asp Glu Phe Ile Arg His Ser Ile Thr Lys
    130                 135                 140 atg agt aaa ctc cat ctt act tct aca gaa gag tat aaa aaa cga gta       480
Met Ser Lys Leu His Leu Thr Ser Thr Glu Glu Tyr Lys Lys Arg Val
145                 150                 155                 160 att caa cta ggt gaa aag cct ggt agt gtg ttt aat att ggt tct ctt       528
Ile Gln Leu Gly Glu Lys Pro Gly Ser Val Phe Asn Ile Gly Ser Leu
                165                 170                 175 ggt gca gaa aat gct ctt tca ttg cat tta cca aat aag cag gag ttg       576
Gly Ala Glu Asn Ala Leu Ser Leu His Leu Pro Asn Lys Gln Glu Leu
            180                 185                 190 gaa cta aaa tat ggt tca ctg tta aaa cgg tac ttt gtt gta gta ttc       624
Glu Leu Lys Tyr Gly Ser Leu Leu Lys Arg Tyr Phe Val Val Val Phe
        195                 200                 205 cat cct gaa aca ctt tcc acg cag tcg gtt aat gat caa ata gat gag       672
His Pro Glu Thr Leu Ser Thr Gln Ser Val Asn Asp Gln Ile Asp Glu
    210                 215                 220 tta ttg tca gcg att tct ttt ttt aaa aat act cac gac ttt att ttt       720
Leu Leu Ser Ala Ile Ser Phe Phe Lys Asn Thr His Asp Phe Ile Phe
225                 230                 235                 240 att ggc agt aac gct gac act ggt tct gat ata att cag aga aaa gta       768
Ile Gly Ser Asn Ala Asp Thr Gly Ser Asp Ile Ile Gln Arg Lys Val
                245                 250                 255 aaa tat ttt tgc aaa gag tat aag ttc aga tat ttg att tct att cgt       816
Lys Tyr Phe Cys Lys Glu Tyr Lys Phe Arg Tyr Leu Ile Ser Ile Arg
            260                 265                 270 tca gaa gat tat ttg gca atg att aaa tac tct tgt ggg cta att ggg       864
```

```
Ser Glu Asp Tyr Leu Ala Met Ile Lys Tyr Ser Cys Gly Leu Ile Gly
            275                 280                 285 aac tcc tcc tct ggt tta att gag gtt cca tct tta aaa gtt gca aca      912
Asn Ser Ser Ser Gly Leu Ile Glu Val Pro Ser Leu Lys Val Ala Thr
        290                 295                 300 att aac att ggt gat agg cag aaa ggc cgt gtt cgt gga gcc agt gta      960
Ile Asn Ile Gly Asp Arg Gln Lys Gly Arg Val Arg Gly Ala Ser Val
305                 310                 315                 320 ata gat gta ccc gtt gaa aaa aat gca atc gtc aga ggg ata aat ata     1008
Ile Asp Val Pro Val Glu Lys Asn Ala Ile Val Arg Gly Ile Asn Ile
                325                 330                 335 tct caa gat gaa aaa ttt att agt gtt gta cag tca tct agt aat cct     1056
Ser Gln Asp Glu Lys Phe Ile Ser Val Val Gln Ser Ser Ser Asn Pro
            340                 345                 350 tat ttt aaa gaa aat gct tta att aat gct gtt aga att att aag gat     1104
Tyr Phe Lys Glu Asn Ala Leu Ile Asn Ala Val Arg Ile Ile Lys Asp
        355                 360                 365 ttt att aaa tca aaa aat aaa gat tac aaa gat ttt tat gac atc ccg     1152
Phe Ile Lys Ser Lys Asn Lys Asp Tyr Lys Asp Phe Tyr Asp Ile Pro
370                 375                 380 gaa tgt acc acc agt tat gac tag                                      1176
Glu Cys Thr Thr Ser Tyr Asp
385                 390

<210> SEQ ID NO 58
<211> LENGTH: 391
<212> TYPE: PRT
<213> ORGANISM: escherichia coli

<400> SEQUENCE: 58

Met Lys Lys Ile Leu Tyr Val Thr Gly Ser Arg Ala Glu Tyr Gly Ile
1               5                   10                  15

Val Arg Arg Leu Leu Thr Met Leu Arg Glu Thr Pro Glu Ile Gln Leu
            20                  25                  30

Asp Leu Ala Val Thr Gly Met His Cys Asp Asn Ala Tyr Gly Asn Thr
        35                  40                  45

Ile His Ile Ile Glu Gln Asp Asn Phe Asn Ile Ile Lys Val Val Asp
    50                  55                  60

Ile Asn Ile Asn Thr Thr Ser His Thr His Ile Leu His Ser Met Ser
65                  70                  75                  80

Val Cys Leu Asn Ser Phe Gly Asp Phe Phe Ser Asn Asn Thr Tyr Asp
                85                  90                  95

Ala Val Met Val Leu Gly Asp Arg Tyr Glu Ile Phe Ser Val Ala Ile
            100                 105                 110

Ala Ala Ser Met His Asn Ile Pro Leu Ile His Ile His Gly Gly Glu
        115                 120                 125

Lys Thr Leu Ala Asn Tyr Asp Glu Phe Ile Arg His Ser Ile Thr Lys
    130                 135                 140

Met Ser Lys Leu His Leu Thr Ser Thr Glu Tyr Lys Lys Arg Val
145                 150                 155                 160

Ile Gln Leu Gly Glu Lys Pro Gly Ser Val Phe Asn Ile Gly Ser Leu
                165                 170                 175

Gly Ala Glu Asn Ala Leu Ser Leu His Leu Pro Asn Lys Gln Glu Leu
            180                 185                 190

Glu Leu Lys Tyr Gly Ser Leu Leu Lys Arg Tyr Phe Val Val Val Phe
        195                 200                 205

His Pro Glu Thr Leu Ser Thr Gln Ser Val Asn Asp Gln Ile Asp Glu
```

```
                210              215                220
Leu Leu Ser Ala Ile Ser Phe Phe Lys Asn Thr His Asp Phe Ile Phe
225                 230                 235                 240

Ile Gly Ser Asn Ala Asp Thr Gly Ser Asp Ile Ile Gln Arg Lys Val
                245                 250                 255

Lys Tyr Phe Cys Lys Glu Tyr Lys Phe Arg Tyr Leu Ile Ser Ile Arg
            260                 265                 270

Ser Glu Asp Tyr Leu Ala Met Ile Lys Tyr Ser Cys Gly Leu Ile Gly
        275                 280                 285

Asn Ser Ser Gly Leu Ile Glu Val Pro Ser Leu Lys Val Ala Thr
290                 295                 300

Ile Asn Ile Gly Asp Arg Gln Lys Gly Arg Val Arg Gly Ala Ser Val
305                 310                 315                 320

Ile Asp Val Pro Val Glu Lys Asn Ala Ile Val Arg Gly Ile Asn Ile
                325                 330                 335

Ser Gln Asp Glu Lys Phe Ile Ser Val Val Gln Ser Ser Asn Pro
            340                 345                 350

Tyr Phe Lys Glu Asn Ala Leu Ile Asn Ala Val Arg Ile Ile Lys Asp
        355                 360                 365

Phe Ile Lys Ser Lys Asn Lys Asp Tyr Lys Asp Phe Tyr Asp Ile Pro
    370                 375                 380

Glu Cys Thr Thr Ser Tyr Asp
385                 390

<210> SEQ ID NO 59
<211> LENGTH: 1041
<212> TYPE: DNA
<213> ORGANISM: Escherichia coli
<220> FEATURE:
<221> NAME/KEY: CDS
<222> LOCATION: (1)...(1038)

<400> SEQUENCE: 59 atg agt aat ata tat atc gtt gct gaa att ggt tgc aac cat aat ggt       48
Met Ser Asn Ile Tyr Ile Val Ala Glu Ile Gly Cys Asn His Asn Gly
 1               5                  10                  15 agt gtt gat att gca aga gaa atg ata tta aaa gcc aaa gag gcc ggt       96
Ser Val Asp Ile Ala Arg Glu Met Ile Leu Lys Ala Lys Glu Ala Gly
            20                  25                  30 gtt aat gca gta aaa ttc caa aca ttt aaa gct gat aaa tta att tca      144
Val Asn Ala Val Lys Phe Gln Thr Phe Lys Ala Asp Lys Leu Ile Ser
        35                  40                  45 gct att gca cct aag gca gag tat caa ata aaa aac aca gga gaa tta      192
Ala Ile Ala Pro Lys Ala Glu Tyr Gln Ile Lys Asn Thr Gly Glu Leu
    50                  55                  60 gaa tct cag tta gaa atg aca aaa aag ctt gaa atg aag tat gac gat      240
Glu Ser Gln Leu Glu Met Thr Lys Lys Leu Glu Met Lys Tyr Asp Asp
65                  70                  75                  80 tat ctc cat cta atg gaa tat gca gtc agt tta aat tta gat gtt ttt      288
Tyr Leu His Leu Met Glu Tyr Ala Val Ser Leu Asn Leu Asp Val Phe
                85                  90                  95 tct acc cct ttt gac gaa gac tct att gat ttt tta gca tct ttg aaa      336
Ser Thr Pro Phe Asp Glu Asp Ser Ile Asp Phe Leu Ala Ser Leu Lys
            100                 105                 110 caa aaa ata tgg aaa atc cct tca ggt gag tta ttg aat tta ccg tat      384
Gln Lys Ile Trp Lys Ile Pro Ser Gly Glu Leu Leu Asn Leu Pro Tyr
        115                 120                 125 ctt gaa aaa ata gcc aag ctt ccg atc cct gat aag aaa ata atc ata      432
```

```
                                  -continued

Leu Glu Lys Ile Ala Lys Leu Pro Ile Pro Asp Lys Lys Ile Ile Ile
    130             135                 140 tca aca gga atg gct act att gat gag ata aaa cag tct gtt tct att    480
Ser Thr Gly Met Ala Thr Ile Asp Glu Ile Lys Gln Ser Val Ser Ile
145                 150                 155                 160 ttt ata aat aat aaa gtt ccg gtt ggt aat att aca ata tta cat tgc    528
Phe Ile Asn Asn Lys Val Pro Val Gly Asn Ile Thr Ile Leu His Cys
                165                 170                 175 aat act gaa tat cca acg ccc ttt gag gat gta aac ctt aat gct att    576
Asn Thr Glu Tyr Pro Thr Pro Phe Glu Asp Val Asn Leu Asn Ala Ile
            180                 185                 190 aat gat ttg aaa aaa cac ttc cct aag aat aac ata ggc ttc tct gat    624
Asn Asp Leu Lys Lys His Phe Pro Lys Asn Asn Ile Gly Phe Ser Asp
        195                 200                 205 cat tct agc ggg ttt tat gca gct att gcg gcg gtg cct tat gga ata    672
His Ser Ser Gly Phe Tyr Ala Ala Ile Ala Ala Val Pro Tyr Gly Ile
    210                 215                 220 act ttt att gaa aaa cat ttc act tta gat aaa tct atg tct ggc cca    720
Thr Phe Ile Glu Lys His Phe Thr Leu Asp Lys Ser Met Ser Gly Pro
225                 230                 235                 240 gat cat ttg gcc tca ata gaa cct gat gaa ctg aaa cat ctt tgt att    768
Asp His Leu Ala Ser Ile Glu Pro Asp Glu Leu Lys His Leu Cys Ile
                245                 250                 255 ggg gtc agg tgt gtt gaa aaa tct tta ggt tca aat agt aaa gtg gtt    816
Gly Val Arg Cys Val Glu Lys Ser Leu Gly Ser Asn Ser Lys Val Val
                260                 265                 270 aca gct tca gaa agg aag aat aaa atc gta gca aga aag tct att ata    864
Thr Ala Ser Glu Arg Lys Asn Lys Ile Val Ala Arg Lys Ser Ile Ile
            275                 280                 285 gct aaa aca gag ata aaa aaa ggt gag gtt ttt tca gaa aaa aat ata    912
Ala Lys Thr Glu Ile Lys Lys Gly Glu Val Phe Ser Glu Lys Asn Ile
        290                 295                 300 aca aca aaa aga cct ggt aat ggt atc agt ccg atg gag tgg tat aat    960
Thr Thr Lys Arg Pro Gly Asn Gly Ile Ser Pro Met Glu Trp Tyr Asn
305                 310                 315                 320 tta ttg ggt aaa att gca gag caa gac ttt att cca gat gaa tta ata   1008
Leu Leu Gly Lys Ile Ala Glu Gln Asp Phe Ile Pro Asp Glu Leu Ile
                325                 330                 335 att cat agc gaa ttc aaa aat cag ggg gaa taa                       1041
Ile His Ser Glu Phe Lys Asn Gln Gly Glu
                340                 345

<210> SEQ ID NO 60
<211> LENGTH: 346
<212> TYPE: PRT
<213> ORGANISM: Escherichia coli

<400> SEQUENCE: 60

Met Ser Asn Ile Tyr Ile Val Ala Glu Ile Gly Cys Asn His Asn Gly
1               5                   10                  15

Ser Val Asp Ile Ala Arg Glu Met Ile Leu Lys Ala Lys Glu Ala Gly
                20                  25                  30

Val Asn Ala Val Lys Phe Gln Thr Phe Lys Ala Asp Lys Leu Ile Ser
            35                  40                  45

Ala Ile Ala Pro Lys Ala Glu Tyr Gln Ile Lys Asn Thr Gly Glu Leu
        50                  55                  60

Glu Ser Gln Leu Glu Met Thr Lys Lys Leu Glu Met Lys Tyr Asp Asp
65                  70                  75                  80

Tyr Leu His Leu Met Glu Tyr Ala Val Ser Leu Asn Leu Asp Val Phe
```

```
                    85                  90                  95
Ser Thr Pro Phe Asp Glu Asp Ser Ile Asp Phe Leu Ala Ser Leu Lys
            100                 105                 110

Gln Lys Ile Trp Lys Ile Pro Ser Gly Glu Leu Leu Asn Leu Pro Tyr
            115                 120                 125

Leu Glu Lys Ile Ala Lys Leu Pro Ile Pro Asp Lys Lys Ile Ile Ile
130                 135                 140

Ser Thr Gly Met Ala Thr Ile Asp Glu Ile Lys Gln Ser Val Ser Ile
145                 150                 155                 160

Phe Ile Asn Asn Lys Val Pro Val Gly Asn Ile Thr Ile Leu His Cys
                165                 170                 175

Asn Thr Glu Tyr Pro Thr Pro Phe Glu Asp Val Asn Leu Asn Ala Ile
            180                 185                 190

Asn Asp Leu Lys Lys His Phe Pro Lys Asn Asn Ile Gly Phe Ser Asp
            195                 200                 205

His Ser Ser Gly Phe Tyr Ala Ala Ile Ala Ala Val Pro Tyr Gly Ile
210                 215                 220

Thr Phe Ile Glu Lys His Phe Thr Leu Asp Lys Ser Met Ser Gly Pro
225                 230                 235                 240

Asp His Leu Ala Ser Ile Glu Pro Asp Glu Leu Lys His Leu Cys Ile
                245                 250                 255

Gly Val Arg Cys Val Glu Lys Ser Leu Gly Ser Asn Ser Lys Val Val
            260                 265                 270

Thr Ala Ser Glu Arg Lys Asn Lys Ile Val Ala Arg Lys Ser Ile Ile
            275                 280                 285

Ala Lys Thr Glu Ile Lys Lys Gly Glu Val Phe Ser Glu Lys Asn Ile
290                 295                 300

Thr Thr Lys Arg Pro Gly Asn Gly Ile Ser Pro Met Glu Trp Tyr Asn
305                 310                 315                 320

Leu Leu Gly Lys Ile Ala Glu Gln Asp Phe Ile Pro Asp Glu Leu Ile
                325                 330                 335

Ile His Ser Glu Phe Lys Asn Gln Gly Glu
            340                 345

<210> SEQ ID NO 61
<211> LENGTH: 1260
<212> TYPE: DNA
<213> ORGANISM: Escherichia coli
<220> FEATURE:
<221> NAME/KEY: CDS
<222> LOCATION: (1)...(1257)

<400> SEQUENCE: 61 atg aga aca aaa att att gcg ata att cca gcc cgt agt gga tct aaa     48
Met Arg Thr Lys Ile Ile Ala Ile Ile Pro Ala Arg Ser Gly Ser Lys
 1               5                  10                  15 ggg ttg aga aat aaa aat gct ttg atg ctg ata gat aaa cct ctt ctt     96
Gly Leu Arg Asn Lys Asn Ala Leu Met Leu Ile Asp Lys Pro Leu Leu
            20                  25                  30 gct tat aca att gaa gct gcc ttg cag tca gaa atg ttt gag aaa gta    144
Ala Tyr Thr Ile Glu Ala Ala Leu Gln Ser Glu Met Phe Glu Lys Val
        35                  40                  45 att gtg aca act gac tcc gaa cag tat gga gca ata gca gag tca tat    192
Ile Val Thr Thr Asp Ser Glu Gln Tyr Gly Ala Ile Ala Glu Ser Tyr
    50                  55                  60 ggt gct gat ttt ttg ctg aga ccg gaa gaa cta gca act gat aaa gca    240
Gly Ala Asp Phe Leu Leu Arg Pro Glu Glu Leu Ala Thr Asp Lys Ala
```

-continued

```
              65                  70                  75                  80
    tca tca ttt gaa ttt ata aaa cat gcg tta agt ata tat act gat tat      288
    Ser Ser Phe Glu Phe Ile Lys His Ala Leu Ser Ile Tyr Thr Asp Tyr
                        85                  90                  95 gag agc ttt gct tta tta caa cca act tca ccc ttt aga gat tcg acc      336
    Glu Ser Phe Ala Leu Leu Gln Pro Thr Ser Pro Phe Arg Asp Ser Thr
                100                 105                 110 cat att att gag gct gta aag tta tat caa act tta gaa aaa tac caa      384
    His Ile Ile Glu Ala Val Lys Leu Tyr Gln Thr Leu Glu Lys Tyr Gln
            115                 120                 125 tgt gtt gtt tct gtt act aga agc aat aag cca tca caa ata att aga      432
    Cys Val Val Ser Val Thr Arg Ser Asn Lys Pro Ser Gln Ile Ile Arg
    130                 135                 140 cca tta gat gat tac tcg aca ctg tct ttt ttt gac ctt gat tat agt      480
    Pro Leu Asp Asp Tyr Ser Thr Leu Ser Phe Phe Asp Leu Asp Tyr Ser
    145                 150                 155                 160 aaa tat aat cga aac tca ata gta gaa tat cat ccg aat gga gct ata      528
    Lys Tyr Asn Arg Asn Ser Ile Val Glu Tyr His Pro Asn Gly Ala Ile
                    165                 170                 175 ttt ata gct aat aag cag cat tat ctt cat aca aag cat ttt ttt ggt      576
    Phe Ile Ala Asn Lys Gln His Tyr Leu His Thr Lys His Phe Phe Gly
                180                 185                 190 cgc tat tca cta gct tat att atg gat aag gaa agc tct tta gat ata      624
    Arg Tyr Ser Leu Ala Tyr Ile Met Asp Lys Glu Ser Ser Leu Asp Ile
            195                 200                 205 gat gat aga atg gat ttc gaa ctt gca att acc att cag caa aaa aaa      672
    Asp Asp Arg Met Asp Phe Glu Leu Ala Ile Thr Ile Gln Gln Lys Lys
    210                 215                 220 aat aga caa aaa att gac ctt tat caa aac ata cat aat aga atc aat      720
    Asn Arg Gln Lys Ile Asp Leu Tyr Gln Asn Ile His Asn Arg Ile Asn
    225                 230                 235                 240 gag aaa cga aat gaa ttt gat agt gta agt gat ata act tta att gga      768
    Glu Lys Arg Asn Glu Phe Asp Ser Val Ser Asp Ile Thr Leu Ile Gly
                    245                 250                 255 cac tcg ctg ttt gat tat tgg gac gta aaa aaa ata aat gat ata gaa      816
    His Ser Leu Phe Asp Tyr Trp Asp Val Lys Lys Ile Asn Asp Ile Glu
                260                 265                 270 gtt aat aac tta ggt atc gct ggt ata aac tcg aag gag tac tat gaa      864
    Val Asn Asn Leu Gly Ile Ala Gly Ile Asn Ser Lys Glu Tyr Tyr Glu
            275                 280                 285 tat att att gag aaa gag ctg att gtt aat ttc gga gag ttt gtt ttc      912
    Tyr Ile Ile Glu Lys Glu Leu Ile Val Asn Phe Gly Glu Phe Val Phe
        290                 295                 300 atc ttt ttt gga act aat gat ata gtt gtt agt gat tgg aaa aaa gaa      960
    Ile Phe Phe Gly Thr Asn Asp Ile Val Val Ser Asp Trp Lys Lys Glu
    305                 310                 315                 320 gac aca ttg tgg tat ttg aag aaa aca tgc cag tat ata aag aag aaa     1008
    Asp Thr Leu Trp Tyr Leu Lys Lys Thr Cys Gln Tyr Ile Lys Lys Lys
                    325                 330                 335 aat gct gca tca aaa att tat tta ttg tcg gtt cct cct gtt ttt ggg     1056
    Asn Ala Ala Ser Lys Ile Tyr Leu Leu Ser Val Pro Pro Val Phe Gly
                340                 345                 350 cgt att gat cga gat aat aga ata att aat gat tta aat tct tat ctt     1104
    Arg Ile Asp Arg Asp Asn Arg Ile Ile Asn Asp Leu Asn Ser Tyr Leu
            355                 360                 365 cga gag aat gta gat ttt gcg aag ttt att agc ttg gat cac gtt tta     1152
    Arg Glu Asn Val Asp Phe Ala Lys Phe Ile Ser Leu Asp His Val Leu
    370                 375                 380 aaa gac tct tat ggc aat cta aat aaa atg tat act tat gat ggc tta     1200
```

```
Lys Asp Ser Tyr Gly Asn Leu Asn Lys Met Tyr Thr Tyr Asp Gly Leu
385                 390                 395                 400 cat ttt aat agt aat ggg tat aca gta tta gaa aac gaa ata gcg gag    1248
His Phe Asn Ser Asn Gly Tyr Thr Val Leu Glu Asn Glu Ile Ala Glu
                405                 410                 415 att gtt aaa tga                                                    1260
Ile Val Lys <210> SEQ ID NO 62
<211> LENGTH: 419
<212> TYPE: PRT
<213> ORGANISM: Escherichia coli

<400> SEQUENCE: 62

Met Arg Thr Lys Ile Ile Ala Ile Ile Pro Ala Arg Ser Gly Ser Lys
1               5                   10                  15

Gly Leu Arg Asn Lys Asn Ala Leu Met Leu Ile Asp Lys Pro Leu Leu
            20                  25                  30

Ala Tyr Thr Ile Glu Ala Ala Leu Gln Ser Glu Met Phe Glu Lys Val
        35                  40                  45

Ile Val Thr Thr Asp Ser Glu Gln Tyr Gly Ala Ile Ala Glu Ser Tyr
    50                  55                  60

Gly Ala Asp Phe Leu Leu Arg Pro Glu Glu Leu Ala Thr Asp Lys Ala
65                  70                  75                  80

Ser Ser Phe Glu Phe Ile Lys His Ala Leu Ser Ile Tyr Thr Asp Tyr
                85                  90                  95

Glu Ser Phe Ala Leu Leu Gln Pro Thr Ser Pro Phe Arg Asp Ser Thr
            100                 105                 110

His Ile Ile Glu Ala Val Lys Leu Tyr Gln Thr Leu Glu Lys Tyr Gln
        115                 120                 125

Cys Val Val Ser Val Thr Arg Ser Asn Lys Pro Ser Gln Ile Ile Arg
130                 135                 140

Pro Leu Asp Asp Tyr Ser Thr Leu Ser Phe Phe Asp Leu Asp Tyr Ser
145                 150                 155                 160

Lys Tyr Asn Arg Asn Ser Ile Val Glu Tyr His Pro Asn Gly Ala Ile
                165                 170                 175

Phe Ile Ala Asn Lys Gln His Tyr Leu His Thr Lys His Phe Phe Gly
            180                 185                 190

Arg Tyr Ser Leu Ala Tyr Ile Met Asp Lys Glu Ser Ser Leu Asp Ile
        195                 200                 205

Asp Asp Arg Met Asp Phe Glu Leu Ala Ile Thr Ile Gln Gln Lys Lys
    210                 215                 220

Asn Arg Gln Lys Ile Asp Leu Tyr Gln Asn Ile His Asn Arg Ile Asn
225                 230                 235                 240

Glu Lys Arg Asn Glu Phe Asp Ser Val Ser Asp Ile Thr Leu Ile Gly
                245                 250                 255

His Ser Leu Phe Asp Tyr Trp Asp Val Lys Lys Ile Asn Asp Ile Glu
            260                 265                 270

Val Asn Asn Leu Gly Ile Ala Gly Ile Asn Ser Lys Glu Tyr Tyr Glu
        275                 280                 285

Tyr Ile Ile Glu Lys Glu Leu Ile Val Asn Phe Gly Glu Phe Val Phe
    290                 295                 300

Ile Phe Phe Gly Thr Asn Asp Ile Val Val Ser Asp Trp Lys Lys Glu
305                 310                 315                 320

Asp Thr Leu Trp Tyr Leu Lys Lys Thr Cys Gln Tyr Ile Lys Lys Lys
```

```
                    325                 330                 335
Asn Ala Ala Ser Lys Ile Tyr Leu Leu Ser Val Pro Pro Val Phe Gly
                340                 345                 350

Arg Ile Asp Arg Asp Asn Arg Ile Ile Asn Asp Leu Asn Ser Tyr Leu
            355                 360                 365

Arg Glu Asn Val Asp Phe Ala Lys Phe Ile Ser Leu Asp His Val Leu
        370                 375                 380

Lys Asp Ser Tyr Gly Asn Leu Asn Lys Met Tyr Thr Tyr Asp Gly Leu
385                 390                 395                 400

His Phe Asn Ser Asn Gly Tyr Thr Val Leu Glu Asn Glu Ile Ala Glu
                405                 410                 415

Ile Val Lys

<210> SEQ ID NO 63
<211> LENGTH: 1299
<212> TYPE: DNA
<213> ORGANISM: Mus musculus
<220> FEATURE:
<221> NAME/KEY: CDS
<222> LOCATION: (1)...(126)

<400> SEQUENCE: 63 atg gac gcg ctg gag aag ggg gcc gtc acg tcg ggg ccc gcc ccg cgt     48
Met Asp Ala Leu Glu Lys Gly Ala Val Thr Ser Gly Pro Ala Pro Arg
1               5                   10                  15 gga cgg ccg tcc cgg ggc cgg ccc ccg aag ctg cag cgc agc cgg ggc     96
Gly Arg Pro Ser Arg Gly Arg Pro Pro Lys Leu Gln Arg Ser Arg Gly
            20                  25                  30 gcg ggg cgc ggc cta gag aag ccg ccg cac ctggcagcgc tggtgctggc      146
Ala Gly Arg Gly Leu Glu Lys Pro Pro His
        35                  40 ccgcggcggc agcaaaggca tcccactgaa gaacatcaag cgcctggcgg gggttccgct    206
cattggctgg gtcctgcgcg ccgccctgga tgcgggggtc ttccagagtg tgtgggtttc    266
aacagaccat gatgaaattg agaatgtggc caaacagttt ggtgcacagg tccatcgaag    326
aagttctgaa acgtccaaag acagctctac ctcactagac gccattgtag aattcctgaa    386
ttatcacaat gaggttgaca ttgtggggaa tatccaagcc acatctccat gtttacatcc    446
cactgacctc agaaagttg cagaaatgat ccgagaagaa ggatatgact ctgtcttctc     506
cgttgtgagg cgccatcagt ttcgatggag tgaaattcag aaaggagttc gtgaagtgac    566
tgagcctctg aacttgaatc cagcgaaacg gcctcgtcga caagactggg atggagagtt    626
atatgagaac ggctcatttt attttgctaa aagacatttg atagagatgg ttacttaca    686 gggtgggaaa atggcatatt atgaaatgcg agctgagcac agtgtggata tcgacgtgga    746
catcgattgg ccgatcgcag agcaaagagt tctgagattt ggctattttg gaaaagagaa    806
gctgaaggag ataaagcttt tggtttgtaa tattgatgga tgtctcacca atggccacat    866
ttatgtatca ggagaccaaa aagaataat atcttatgat gtaaaagacg ccattggcat     926
aagtttatta agaaaagcg gtattgaggt gaggctcatc tcagaacggg cctgctccaa    986
gcagacgctc tctgccctaa agctggactg taaaacagaa gtcagtgtgt ccgataagct   1046
ggccaccgtg gatgagtgga ggaaggagat gggcctgtgc tggaaagaag tggcctatct   1106
cggcaatgaa gtgtctgatg aagaatgcct caagagagtg ggcctgagcg ctgttcctgc   1166
cgacgcctgc tccggggccc agaaggctgt ggggtacatc tgcaaatgca gcggtggccg   1226
gggagccatc cgcgagtttg cagagcacat tttcctactg atagaaaaag ttaataactc   1286
```

-continued atgccaaaaa tag                                                            1299

<210> SEQ ID NO 64
<211> LENGTH: 42
<212> TYPE: PRT
<213> ORGANISM: Mus musculus

<400> SEQUENCE: 64

Met Asp Ala Leu Glu Lys Gly Ala Val Thr Ser Gly Pro Ala Pro Arg
1               5                   10                  15

Gly Arg Pro Ser Arg Gly Arg Pro Lys Leu Gln Arg Ser Arg Gly
            20                  25                  30

Ala Gly Arg Gly Leu Glu Lys Pro Pro His
            35                  40

<210> SEQ ID NO 65
<211> LENGTH: 1209
<212> TYPE: DNA
<213> ORGANISM: Sus scrofa
<220> FEATURE:
<221> NAME/KEY: CDS
<222> LOCATION: (1)...(1206)

<400> SEQUENCE: 65 atg gag aag gag cgc gaa act ctg cag gcc tgg aag gag cgt gtg ggc        48
Met Glu Lys Glu Arg Glu Thr Leu Gln Ala Trp Lys Glu Arg Val Gly
1               5                   10                  15 caa gag ctg gac cgc gtg atg gct ttc tgg ctg gag cac tcc cac gat        96
Gln Glu Leu Asp Arg Val Met Ala Phe Trp Leu Glu His Ser His Asp
            20                  25                  30 cgg gag cac ggg ggc ttc ttc acg tgc ctg ggc cgc gac ggg cgg gtg       144
Arg Glu His Gly Gly Phe Phe Thr Cys Leu Gly Arg Asp Gly Arg Val
            35                  40                  45 tat gac gac ctc aag tac gtc tgg ctg cag ggg agg cag gtg tgg atg       192
Tyr Asp Asp Leu Lys Tyr Val Trp Leu Gln Gly Arg Gln Val Trp Met
    50                  55                  60 tac tgt cgc ctg tac cgc aag ctt gag cgc ttc cac cgc cct gag ctt       240
Tyr Cys Arg Leu Tyr Arg Lys Leu Glu Arg Phe His Arg Pro Glu Leu
65              70                  75                  80 ctg gat gcg gct aaa gca ggg ggc gaa ttt ttg ctg cgc cat gcc cga       288
Leu Asp Ala Ala Lys Ala Gly Gly Glu Phe Leu Leu Arg His Ala Arg
                85                  90                  95 gtg gca cct cct gaa aag aag tgt gcc ttt gtg ctg acg cgg gac ggc       336
Val Ala Pro Pro Glu Lys Lys Cys Ala Phe Val Leu Thr Arg Asp Gly
            100                 105                 110 cgg ccc gtc aag gtg cag cgg agc atc ttc agt gag tgc ttc tac acc       384
Arg Pro Val Lys Val Gln Arg Ser Ile Phe Ser Glu Cys Phe Tyr Thr
            115                 120                 125 atg gcc atg aac gag ctg tgg agg gtg acg gcg gag gca cgg tac cag       432
Met Ala Met Asn Glu Leu Trp Arg Val Thr Ala Glu Ala Arg Tyr Gln
    130                 135                 140 agc gaa gcg gtg gac atg atg gat cag atc gtg cac tgg gtg cga gag       480
Ser Glu Ala Val Asp Met Met Asp Gln Ile Val His Trp Val Arg Glu
145                 150                 155                 160 gac ccc tct ggg ctg ggc cgg ccc cag ctc ccc ggg gcc gtg gcc tcg       528
Asp Pro Ser Gly Leu Gly Arg Pro Gln Leu Pro Gly Ala Val Ala Ser
                165                 170                 175 gag tcc atg gca gtg ccc atg atg ctg ctg tgc ctg gtg gag cag ctc       576
Glu Ser Met Ala Val Pro Met Met Leu Leu Cys Leu Val Glu Gln Leu
            180                 185                 190

```
ggg gag gag gac gag gag ctg gca ggc cgc tac gcg cag ctg ggg cac    624
Gly Glu Glu Asp Glu Glu Leu Ala Gly Arg Tyr Ala Gln Leu Gly His
            195                 200                 205 tgg tgc gct cgg agg atc ctg cag cac gtc cag agg gat gga cag gct    672
Trp Cys Ala Arg Arg Ile Leu Gln His Val Gln Arg Asp Gly Gln Ala
    210                 215                 220 gtg ctg gag aat gtg tcg gaa gat ggc gag gaa ctt tct ggc tgc ctg    720
Val Leu Glu Asn Val Ser Glu Asp Gly Glu Glu Leu Ser Gly Cys Leu
225                 230                 235                 240 ggg aga cac cag aac cca ggc cac gcg ctg gaa gct ggc tgg ttc ctg    768
Gly Arg His Gln Asn Pro Gly His Ala Leu Glu Ala Gly Trp Phe Leu
                245                 250                 255 ctc cgc cac agc agc cgg agc ggt gac gcc aaa ctt cga gcc cac gtc    816
Leu Arg His Ser Ser Arg Ser Gly Asp Ala Lys Leu Arg Ala His Val
            260                 265                 270 atc gac acg ttc ctg cta ctg cct ttc cgc tcc gga tgg gac gct gat    864
Ile Asp Thr Phe Leu Leu Leu Pro Phe Arg Ser Gly Trp Asp Ala Asp
        275                 280                 285 cac gga ggc ctc ttc tac ttc cag gat gcc gat ggc ctc tgc ccc acc    912
His Gly Gly Leu Phe Tyr Phe Gln Asp Ala Asp Gly Leu Cys Pro Thr
    290                 295                 300 cag ctg gag tgg gcc atg aag ctc tgg tgg ccg cac agc gaa gcc atg    960
Gln Leu Glu Trp Ala Met Lys Leu Trp Trp Pro His Ser Glu Ala Met
305                 310                 315                 320 atc gcc ttt ctc atg ggc tac agt gag agc ggg gac cct gcc tta ctg   1008
Ile Ala Phe Leu Met Gly Tyr Ser Glu Ser Gly Asp Pro Ala Leu Leu
                325                 330                 335 cgt ctc ttc tac cag gtg gcc gag tac acg ttt cgc cag ttt cgt gat   1056
Arg Leu Phe Tyr Gln Val Ala Glu Tyr Thr Phe Arg Gln Phe Arg Asp
            340                 345                 350 ccc gag tac ggg gaa tgg ttt ggc tac ctg aac cga gag ggg aag gtt   1104
Pro Glu Tyr Gly Glu Trp Phe Gly Tyr Leu Asn Arg Glu Gly Lys Val
        355                 360                 365 gcc ctc act atc aag ggg ggt ccc ttt aaa ggc tgc ttc cac gtg ccg   1152
Ala Leu Thr Ile Lys Gly Gly Pro Phe Lys Gly Cys Phe His Val Pro
    370                 375                 380 cgg tgc ctt gcc atg tgc gaa gag atg ctg agc gcc ctg ctg agc cgc   1200
Arg Cys Leu Ala Met Cys Glu Glu Met Leu Ser Ala Leu Leu Ser Arg
385                 390                 395                 400 ctc gcc tag                                                        1209
Leu Ala

<210> SEQ ID NO 66
<211> LENGTH: 402
<212> TYPE: PRT
<213> ORGANISM: Sus scrofa

<400> SEQUENCE: 66

Met Glu Lys Glu Arg Glu Thr Leu Gln Ala Trp Lys Glu Arg Val Gly
  1               5                  10                  15

Gln Glu Leu Asp Arg Val Met Ala Phe Trp Leu Glu His Ser His Asp
                 20                  25                  30

Arg Glu His Gly Gly Phe Phe Thr Cys Leu Gly Arg Asp Gly Arg Val
             35                  40                  45

Tyr Asp Asp Leu Lys Tyr Val Trp Leu Gln Gly Arg Gln Val Trp Met
         50                  55                  60

Tyr Cys Arg Leu Tyr Arg Lys Leu Glu Arg Phe His Arg Pro Glu Leu
 65                  70                  75                  80

Leu Asp Ala Ala Lys Ala Gly Gly Glu Phe Leu Leu Arg His Ala Arg
```

```
                    85                  90                  95
Val Ala Pro Pro Glu Lys Lys Cys Ala Phe Val Leu Thr Arg Asp Gly
            100                 105                 110

Arg Pro Val Lys Val Gln Arg Ser Ile Phe Ser Glu Cys Phe Tyr Thr
        115                 120                 125

Met Ala Met Asn Glu Leu Trp Arg Val Thr Ala Glu Ala Arg Tyr Gln
    130                 135                 140

Ser Glu Ala Val Asp Met Met Asp Gln Ile Val His Trp Val Arg Glu
145                 150                 155                 160

Asp Pro Ser Gly Leu Gly Arg Pro Gln Leu Pro Gly Ala Val Ala Ser
                165                 170                 175

Glu Ser Met Ala Val Pro Met Met Leu Leu Cys Leu Val Glu Gln Leu
            180                 185                 190

Gly Glu Glu Asp Glu Glu Leu Ala Gly Arg Tyr Ala Gln Leu Gly His
        195                 200                 205

Trp Cys Ala Arg Arg Ile Leu Gln His Val Gln Arg Asp Gly Gln Ala
    210                 215                 220

Val Leu Glu Asn Val Ser Glu Asp Gly Glu Glu Leu Ser Gly Cys Leu
225                 230                 235                 240

Gly Arg His Gln Asn Pro Gly His Ala Leu Glu Ala Gly Trp Phe Leu
                245                 250                 255

Leu Arg His Ser Ser Arg Ser Gly Asp Ala Lys Leu Arg Ala His Val
            260                 265                 270

Ile Asp Thr Phe Leu Leu Leu Pro Phe Arg Ser Gly Trp Asp Ala Asp
        275                 280                 285

His Gly Gly Leu Phe Tyr Phe Gln Asp Ala Asp Gly Leu Cys Pro Thr
    290                 295                 300

Gln Leu Glu Trp Ala Met Lys Leu Trp Trp Pro His Ser Glu Ala Met
305                 310                 315                 320

Ile Ala Phe Leu Met Gly Tyr Ser Glu Ser Gly Asp Pro Ala Leu Leu
                325                 330                 335

Arg Leu Phe Tyr Gln Val Ala Glu Tyr Thr Phe Arg Gln Phe Arg Asp
            340                 345                 350

Pro Glu Tyr Gly Glu Trp Phe Gly Tyr Leu Asn Arg Glu Gly Lys Val
        355                 360                 365

Ala Leu Thr Ile Lys Gly Gly Pro Phe Lys Gly Cys Phe His Val Pro
    370                 375                 380

Arg Cys Leu Ala Met Cys Glu Glu Met Leu Ser Ala Leu Leu Ser Arg
385                 390                 395                 400

Leu Ala

<210> SEQ ID NO 67
<211> LENGTH: 894
<212> TYPE: DNA
<213> ORGANISM: Escherichia coli
<220> FEATURE:
<221> NAME/KEY: CDS
<222> LOCATION: (1)...(891)

<400> SEQUENCE: 67 atg gca acg aat tta cgt ggc gta atg gct gca ctc ctg act cct ttt    48
Met Ala Thr Asn Leu Arg Gly Val Met Ala Ala Leu Leu Thr Pro Phe
 1               5                  10                  15 gac caa caa caa gca ctg gat aaa gcg agt ctg cgt cgc ctg gtt cag    96
Asp Gln Gln Gln Ala Leu Asp Lys Ala Ser Leu Arg Arg Leu Val Gln
             20                  25                  30
```

```
ttc aat att cag cag ggc atc gac ggt tta tac gtg ggt ggt tcg acc    144
Phe Asn Ile Gln Gln Gly Ile Asp Gly Leu Tyr Val Gly Gly Ser Thr
         35                  40                  45 ggc gag gcc ttt gta caa agc ctt tcc gag cgt gaa cag gta ctg gaa    192
Gly Glu Ala Phe Val Gln Ser Leu Ser Glu Arg Glu Gln Val Leu Glu
 50                  55                  60 atc gtc gcc gaa gag ggc aaa ggt aag att aaa ctc atc gcc cac gtc    240
Ile Val Ala Glu Glu Gly Lys Gly Lys Ile Lys Leu Ile Ala His Val
 65                  70                  75                  80 ggt tgc gtc acg acc gcc gaa agc caa caa ctt gcg gca tcg gct aaa    288
Gly Cys Val Thr Thr Ala Glu Ser Gln Gln Leu Ala Ala Ser Ala Lys
                 85                  90                  95 cgt tat ggc ttc gat gcc gtc tcc gcc gtc acg ccg ttc tac tat cct    336
Arg Tyr Gly Phe Asp Ala Val Ser Ala Val Thr Pro Phe Tyr Tyr Pro
            100                 105                 110 ttc agc ttt gaa gaa cac tgc gat cac tat cgg gca att att gat tcg    384
Phe Ser Phe Glu Glu His Cys Asp His Tyr Arg Ala Ile Ile Asp Ser
        115                 120                 125 gcg gat ggt ttg ccg atg gtg gtg tac aac att cca gcc ctg agt ggg    432
Ala Asp Gly Leu Pro Met Val Val Tyr Asn Ile Pro Ala Leu Ser Gly
    130                 135                 140 gta aaa ctg acc ctg gat cag atc aac aca ctt gtt aca ttg cct ggc    480
Val Lys Leu Thr Leu Asp Gln Ile Asn Thr Leu Val Thr Leu Pro Gly
145                 150                 155                 160 gta ggt gcg ctg aaa cag acc tct ggc gat ctc tat cag atg gag cag    528
Val Gly Ala Leu Lys Gln Thr Ser Gly Asp Leu Tyr Gln Met Glu Gln
                165                 170                 175 atc cgt cgt gaa cat cct gat ctt gtg ctc tat aac ggt tac gac gaa    576
Ile Arg Arg Glu His Pro Asp Leu Val Leu Tyr Asn Gly Tyr Asp Glu
            180                 185                 190 atc ttc gcc tct ggt ctg ctg gcg ggc gct gat ggt ggt atc ggc agt    624
Ile Phe Ala Ser Gly Leu Leu Ala Gly Ala Asp Gly Gly Ile Gly Ser
        195                 200                 205 acc tac aac atc atg ggc tgg cgc tat cag ggg atc gtt aag gcg ctg    672
Thr Tyr Asn Ile Met Gly Trp Arg Tyr Gln Gly Ile Val Lys Ala Leu
    210                 215                 220 aaa gaa ggc gat atc cag acc gcg cag aaa ctg caa act gaa tgc aat    720
Lys Glu Gly Asp Ile Gln Thr Ala Gln Lys Leu Gln Thr Glu Cys Asn
225                 230                 235                 240 aaa gtc att gat tta ctg atc aaa acg ggc gta ttc cgc ggc ctg aaa    768
Lys Val Ile Asp Leu Leu Ile Lys Thr Gly Val Phe Arg Gly Leu Lys
                245                 250                 255 act gtc ctc cat tat atg gat gtc gtt tct gtg ccg ctg tgc cgc aaa    816
Thr Val Leu His Tyr Met Asp Val Val Ser Val Pro Leu Cys Arg Lys
            260                 265                 270 ccg ttt gga ccg gta gat gaa aaa tat cag cca gaa ctg aag gcg ctg    864
Pro Phe Gly Pro Val Asp Glu Lys Tyr Gln Pro Glu Leu Lys Ala Leu
        275                 280                 285 gcc cag cag ttg atg caa gag cgc ggg tga                            894
Ala Gln Gln Leu Met Gln Glu Arg Gly
    290                 295
```

<210> SEQ ID NO 68
<211> LENGTH: 297
<212> TYPE: PRT
<213> ORGANISM: Escherichia coli

<400> SEQUENCE: 68

```
Met Ala Thr Asn Leu Arg Gly Val Met Ala Ala Leu Leu Thr Pro Phe
 1               5                  10                  15
```

-continued

```
Asp Gln Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
 50                  55                  60

Ile Val Ala Glu Glu Gly Lys Gly Lys Ile Lys Leu Ile Ala His Val
 65                  70                  75                  80

Gly Cys Val Thr Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
 130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
 210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Gln Pro Glu Leu Lys Ala Leu
        275                 280                 285

Ala Gln Gln Leu Met Gln Glu Arg Gly
 290                 295
```

<210> SEQ ID NO 69
<211> LENGTH: 32
<212> TYPE: DNA
<213> ORGANISM: Artificial Sequence
<220> FEATURE:
<223> OTHER INFORMATION: Synthetic primer

<400> SEQUENCE: 69
atggagaaga acgggaacaa ccgaaagctc cg             32

<210> SEQ ID NO 70
<211> LENGTH: 30
<212> TYPE: DNA
<213> ORGANISM: Artificial Sequence
<220> FEATURE:
<223> OTHER INFORMATION: Synthetic primer

<400> SEQUENCE: 70
ctagtggatc ctgcgcgttg tgtagtccag             30

<210> SEQ ID NO 71
<211> LENGTH: 31
<212> TYPE: DNA
<213> ORGANISM: Artificial Sequence
<220> FEATURE:
<223> OTHER INFORMATION: Synthetic primer

<400> SEQUENCE: 71
atgccgctgg aactggagct gtgtcccggg c                          31

<210> SEQ ID NO 72
<211> LENGTH: 33
<212> TYPE: DNA
<213> ORGANISM: Artificial Sequence
<220> FEATURE:
<223> OTHER INFORMATION: Synthetic primer

<400> SEQUENCE: 72
ttaagccttg attttcttgc tgtgactttc cac                        33

<210> SEQ ID NO 73
<211> LENGTH: 50
<212> TYPE: DNA
<213> ORGANISM: Artificial Sequence
<220> FEATURE:
<223> OTHER INFORMATION: Synthetic primer

<400> SEQUENCE: 73
gggagaatgc ggccgccacc atggggctga gccgcgtgcg ggcggttttc      50

<210> SEQ ID NO 74
<211> LENGTH: 42
<212> TYPE: DNA
<213> ORGANISM: Artificial Sequence
<220> FEATURE:
<223> OTHER INFORMATION: Synthetic primer

<400> SEQUENCE: 74
gtatagactg caaagtcagt atgtccactt gattaattaa cc              42

<210> SEQ ID NO 75
<211> LENGTH: 30
<212> TYPE: DNA
<213> ORGANISM: Artificial Sequence
<220> FEATURE:
<223> OTHER INFORMATION: Synthetic primer

<400> SEQUENCE: 75
atggactcgg tggagaaggg ggccgccacc                            30

<210> SEQ ID NO 76
<211> LENGTH: 31
<212> TYPE: DNA
<213> ORGANISM: Artificial Sequence
<220> FEATURE:
<223> OTHER INFORMATION: Synthetic primer

<400> SEQUENCE: 76
ctatttttgg catgaattat taacttttttc                           31

<210> SEQ ID NO 77
<211> LENGTH: 52
<212> TYPE: DNA
<213> ORGANISM: Artificial Sequence
<220> FEATURE:
<223> OTHER INFORMATION: Synthetic primer

<400> SEQUENCE: 77
gggagaatgc ggccgccacc atggagaaga atggaaataa ccgaaagctg cg                52

<210> SEQ ID NO 78
<211> LENGTH: 43
<212> TYPE: DNA
<213> ORGANISM: Artificial Sequence
<220> FEATURE:
<223> OTHER INFORMATION: Synthetic primer

<400> SEQUENCE: 78
ccttaattaa ctagtagatc ctgcgtgttg tgtagtccag aac                          43

<210> SEQ ID NO 79
<211> LENGTH: 48
<212> TYPE: DNA
<213> ORGANISM: Artificial Sequence
<220> FEATURE:
<223> OTHER INFORMATION: Synthetic primer

<400> SEQUENCE: 79
gggagaatgc ggccgccacc atgccgctgg agctggagct gtgtcccg                     48

<210> SEQ ID NO 80
<211> LENGTH: 44
<212> TYPE: DNA
<213> ORGANISM: Artificial Sequence
<220> FEATURE:
<223> OTHER INFORMATION: Synthetic primer

<400> SEQUENCE: 80
ccttaattaa ttaagacttg attttttgc catgattatc tacc                          44

<210> SEQ ID NO 81
<211> LENGTH: 38
<212> TYPE: DNA
<213> ORGANISM: Artificial Sequence
<220> FEATURE:
<223> OTHER INFORMATION: Synthetic primer

<400> SEQUENCE: 81
ggctcgagat ttaaatgcgt acctcttcta cgagattc                                38

<210> SEQ ID NO 82
<211> LENGTH: 39
<212> TYPE: DNA
<213> ORGANISM: Artificial Sequence
<220> FEATURE:
<223> OTHER INFORMATION: Synthetic primer

<400> SEQUENCE: 82
ccctcgagat ttaaatccaa ccgataaggt gtacaggag                               39

<210> SEQ ID NO 83
<211> LENGTH: 49
<212> TYPE: DNA
<213> ORGANISM: Artificial Sequence
<220> FEATURE:
<223> OTHER INFORMATION: Synthetic primer

<400> SEQUENCE: 83
ggctcgagcg gccgccacca tgaatagcat acacatgaac gccaatacg                    49

<210> SEQ ID NO 84

```
<211> LENGTH: 47
<212> TYPE: DNA
<213> ORGANISM: Artificial Sequence
<220> FEATURE:
<223> OTHER INFORMATION: Synthetic primer

<400> SEQUENCE: 84
ccctcgagtt aattaactag acgcgcggca gcagcttctc ctcatcg        47

<210> SEQ ID NO 85
<211> LENGTH: 21
<212> TYPE: DNA
<213> ORGANISM: Artificial Sequence
<220> FEATURE:
<223> OTHER INFORMATION: Synthetic primer

<400> SEQUENCE: 85
atgactggtg ttcatgaagg g                                    21

<210> SEQ ID NO 86
<211> LENGTH: 21
<212> TYPE: DNA
<213> ORGANISM: Artificial Sequence
<220> FEATURE:
<223> OTHER INFORMATION: Synthetic primer

<400> SEQUENCE: 86
ttacttatat gtcttggtat g                                    21

<210> SEQ ID NO 87
<211> LENGTH: 94
<212> TYPE: DNA
<213> ORGANISM: Artificial Sequence
<220> FEATURE:
<223> OTHER INFORMATION: Synthetic primer

<400> SEQUENCE: 87
gcggccgcat gactggtgtt catgaaggga ctgtgttggt tactggcggc gctggttata   60
taggttctca tacgtgcgtt gttttgttag aaaa                              94

<210> SEQ ID NO 88
<211> LENGTH: 29
<212> TYPE: DNA
<213> ORGANISM: Artificial Sequence
<220> FEATURE:
<223> OTHER INFORMATION: Synthetic primer

<400> SEQUENCE: 88
ttaattaatt acttatatgt cttggtatg                            29

<210> SEQ ID NO 89
<211> LENGTH: 27
<212> TYPE: DNA
<213> ORGANISM: Artificial Sequence
<220> FEATURE:
<223> OTHER INFORMATION: Synthetic primer

<400> SEQUENCE: 89
gccgcgacct gagccgcctg ccccaac                              27

<210> SEQ ID NO 90
<211> LENGTH: 27
<212> TYPE: DNA
<213> ORGANISM: Artificial Sequence
<220> FEATURE:
<223> OTHER INFORMATION: Synthetic primer
```

```
<400> SEQUENCE: 90
ctagctcggt gtcccgatgt ccactgt                                     27

<210> SEQ ID NO 91
<211> LENGTH: 36
<212> TYPE: DNA
<213> ORGANISM: Artificial Sequence
<220> FEATURE:
<223> OTHER INFORMATION: Synthetic primer

<400> SEQUENCE: 91
cttaggcgcg ccggccgcga cctgagccgc ctgccc                           36

<210> SEQ ID NO 92
<211> LENGTH: 21
<212> TYPE: DNA
<213> ORGANISM: Artificial Sequence
<220> FEATURE:
<223> OTHER INFORMATION: Synthetic primer

<400> SEQUENCE: 92
ggggcatatc tgccgcccat c                                           21

<210> SEQ ID NO 93
<211> LENGTH: 21
<212> TYPE: DNA
<213> ORGANISM: Artificial Sequence
<220> FEATURE:
<223> OTHER INFORMATION: Synthetic primer

<400> SEQUENCE: 93
gatgggcggc agatatgccc c                                           21

<210> SEQ ID NO 94
<211> LENGTH: 36
<212> TYPE: DNA
<213> ORGANISM: Artificial Sequence
<220> FEATURE:
<223> OTHER INFORMATION: Synthetic primer

<400> SEQUENCE: 94
cttcttaatt aactagctcg gtgtcccgat gtccac                           36

<210> SEQ ID NO 95
<211> LENGTH: 52
<212> TYPE: DNA
<213> ORGANISM: Artificial Sequence
<220> FEATURE:
<223> OTHER INFORMATION: Synthetic primer

<400> SEQUENCE: 95
gggagaatgc ggccgccacc atggactcgg tggagaaggg ggccgccacc tc         52

<210> SEQ ID NO 96
<211> LENGTH: 45
<212> TYPE: DNA
<213> ORGANISM: Artificial Sequence
<220> FEATURE:
<223> OTHER INFORMATION: Synthetic primer

<400> SEQUENCE: 96
ccttaattaa ctattttggg catgaattat taacttttc catta                  45

<210> SEQ ID NO 97
```

<210> SEQ ID NO 97
<211> LENGTH: 38
<212> TYPE: DNA
<213> ORGANISM: Artificial Sequence
<220> FEATURE:
<223> OTHER INFORMATION: Synthetic primer

<400> SEQUENCE: 97
cggaattcca ccatggctcc ggcgagagaa aatgtcag                        38

<210> SEQ ID NO 98
<211> LENGTH: 37
<212> TYPE: DNA
<213> ORGANISM: Artificial Sequence
<220> FEATURE:
<223> OTHER INFORMATION: Synthetic primer

<400> SEQUENCE: 98
cggaattctc acacaccaat gattctctct tttgaag                         37

<210> SEQ ID NO 99
<211> LENGTH: 38
<212> TYPE: DNA
<213> ORGANISM: Artificial Sequence
<220> FEATURE:
<223> OTHER INFORMATION: Synthetic primer

<400> SEQUENCE: 99
ggctcgagat ttaaatgcgt acctcttcta cgagattc                        38

<210> SEQ ID NO 100
<211> LENGTH: 39
<212> TYPE: DNA
<213> ORGANISM: Artificial Sequence
<220> FEATURE:
<223> OTHER INFORMATION: Synthetic primer

<400> SEQUENCE: 100
ccctcgagat ttaaatccaa ccgataaggt gtacaggag                       39

<210> SEQ ID NO 101
<211> LENGTH: 37
<212> TYPE: DNA
<213> ORGANISM: Artificial Sequence
<220> FEATURE:
<223> OTHER INFORMATION: Synthetic primer

<400> SEQUENCE: 101
ggcgcgccag caagcaagac cctaaggaag acattcc                         37

<210> SEQ ID NO 102
<211> LENGTH: 41
<212> TYPE: DNA
<213> ORGANISM: Artificial Sequence
<220> FEATURE:
<223> OTHER INFORMATION: Synthetic primer

<400> SEQUENCE: 102
ccttaattaa tcaacaacga atgttccgga agccagaaag g                    41

<210> SEQ ID NO 103
<211> LENGTH: 1225
<212> TYPE: DNA
<213> ORGANISM: Homo sapiens
<220> FEATURE:
<221> NAME/KEY: CDS
<222> LOCATION: (13)...(1218)

```
<400> SEQUENCE: 103
gcggccgcca cc atg ttg ttg act aag aga ttc tcc aag ttg ttc aag ttg         51
              Met Leu Leu Thr Lys Arg Phe Ser Lys Leu Phe Lys Leu
                1               5                  10 act ttc atc gtt ttg atc ttg tgt ggt ttg ttc gtt atc act aac aag           99
Thr Phe Ile Val Leu Ile Leu Cys Gly Leu Phe Val Ile Thr Asn Lys
 15              20                  25 tac atg gac gag aat act tca ggg cgc gcc gaa ttt caa gtt ttg aag          147
Tyr Met Asp Glu Asn Thr Ser Gly Arg Ala Glu Phe Gln Val Leu Lys
 30              35                  40                   45 tcc ttg gga aag ttg gct atg ggt tct gac tct caa tct gtt tcc tcc          195
Ser Leu Gly Lys Leu Ala Met Gly Ser Asp Ser Gln Ser Val Ser Ser
                 50                  55                  60 tcc tct act caa gat cca cac aga ggt aga caa act ttg gga tct ttg          243
Ser Ser Thr Gln Asp Pro His Arg Gly Arg Gln Thr Leu Gly Ser Leu
                 65                  70                  75 aga gga ttg gct aag gct aag cca gaa gct tct ttc caa gtt tgg aac          291
Arg Gly Leu Ala Lys Ala Lys Pro Glu Ala Ser Phe Gln Val Trp Asn
         80                  85                  90 aag gac tcc tcc tcc aag aac ttg atc cca aga ttg cag aaa atc tgg          339
Lys Asp Ser Ser Ser Lys Asn Leu Ile Pro Arg Leu Gln Lys Ile Trp
 95             100                 105 aag aac tac ttg tcc atg aac aag tac aag gtt tcc tac aag ggt cca          387
Lys Asn Tyr Leu Ser Met Asn Lys Tyr Lys Val Ser Tyr Lys Gly Pro
110             115                 120                 125 ggt cca ggt att aag ttc tcc gct gag gct ttg aga tgt cac ttg aga          435
Gly Pro Gly Ile Lys Phe Ser Ala Glu Ala Leu Arg Cys His Leu Arg
                130                 135                 140 gac cac gtt aac gtt tcc atg gtt gaa gtt act gac ttc cca ttc aac          483
Asp His Val Asn Val Ser Met Val Glu Val Thr Asp Phe Pro Phe Asn
                145                 150                 155 act tcc gaa tgg gaa gga tac ttg cca aag gag tcc atc aga act aaa          531
Thr Ser Glu Trp Glu Gly Tyr Leu Pro Lys Glu Ser Ile Arg Thr Lys
            160                 165                 170 gct ggt cca tgg gga aga tgt gct gtt gtt tct tcc gct ggt tct ttg          579
Ala Gly Pro Trp Gly Arg Cys Ala Val Val Ser Ser Ala Gly Ser Leu
175                 180                 185 aag tcc tcc cag ttg ggt aga gaa att gat gac cac gac gct gtt ttg          627
Lys Ser Ser Gln Leu Gly Arg Glu Ile Asp Asp His Asp Ala Val Leu
190                 195                 200                 205 aga ttc aac ggt gct cca act gct aac ttc caa caa gat gtt ggt act          675
Arg Phe Asn Gly Ala Pro Thr Ala Asn Phe Gln Gln Asp Val Gly Thr
                210                 215                 220 aag act act atc aga ttg atg aac tcc cag ttg gtt act act gag aag          723
Lys Thr Thr Ile Arg Leu Met Asn Ser Gln Leu Val Thr Thr Glu Lys
                225                 230                 235 aga ttc ttg aag gac tcc ttg tac aac gag gga atc ttg att gtt tgg          771
Arg Phe Leu Lys Asp Ser Leu Tyr Asn Glu Gly Ile Leu Ile Val Trp
            240                 245                 250 gac cca tct gtt tac cac tcc gac atc cca aag tgg tat cag aac cca          819
Asp Pro Ser Val Tyr His Ser Asp Ile Pro Lys Trp Tyr Gln Asn Pro
255                 260                 265 gac tac aac ttc ttc aac aac tac aag act tac aga aag ttg cac cca          867
Asp Tyr Asn Phe Phe Asn Asn Tyr Lys Thr Tyr Arg Lys Leu His Pro
270                 275                 280                 285 aac cag cca ttc tac atc ttg aag cca caa atg cca tgg gaa ttg tgg          915
Asn Gln Pro Phe Tyr Ile Leu Lys Pro Gln Met Pro Trp Glu Leu Trp
                290                 295                 300 gac atc ttg caa gaa att tcc cca gag gag att caa cca aac cca cca          963
```

```
Asp Ile Leu Gln Glu Ile Ser Pro Glu Ile Gln Pro Asn Pro Pro
            305                 310                 315 tct tct gga atg ttg ggt atc atc atc atg atg act ttg tgt gac cag    1011
Ser Ser Gly Met Leu Gly Ile Ile Ile Met Met Thr Leu Cys Asp Gln
            320                 325                 330 gtt gac atc tac gaa ttt ttg cca tcc aag aga aag act gat gtt tgt    1059
Val Asp Ile Tyr Glu Phe Leu Pro Ser Lys Arg Lys Thr Asp Val Cys
        335                 340                 345 tac tac tac cag aag ttc ttc gac tcc gct tgt act atg gga gct tac    1107
Tyr Tyr Tyr Gln Lys Phe Phe Asp Ser Ala Cys Thr Met Gly Ala Tyr
350                 355                 360                 365 cac cca ttg ttg tac gag aag aac ttg gtt aag cac ttg aac caa ggt    1155
His Pro Leu Leu Tyr Glu Lys Asn Leu Val Lys His Leu Asn Gln Gly
                370                 375                 380 act gac gag gac atc tac ttg ttg gga aag gct act ttg cca ggt ttc    1203
Thr Asp Glu Asp Ile Tyr Leu Leu Gly Lys Ala Thr Leu Pro Gly Phe
            385                 390                 395 aga act atc cac tgt taattaa                                        1225
Arg Thr Ile His Cys
            400

<210> SEQ ID NO 104
<211> LENGTH: 402
<212> TYPE: PRT
<213> ORGANISM: Homo sapiens

<400> SEQUENCE: 104

Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
                20                  25                  30

Glu Asn Thr Ser Gly Arg Ala Glu Phe Gln Val Leu Lys Ser Leu Gly
            35                  40                  45

Lys Leu Ala Met Gly Ser Asp Ser Gln Ser Val Ser Ser Ser Ser Thr
50                  55                  60

Gln Asp Pro His Arg Gly Arg Gln Thr Leu Gly Ser Leu Arg Gly Leu
65                  70                  75                  80

Ala Lys Ala Lys Pro Glu Ala Ser Phe Gln Val Trp Asn Lys Asp Ser
                85                  90                  95

Ser Ser Lys Asn Leu Ile Pro Arg Leu Gln Lys Ile Trp Lys Asn Tyr
            100                 105                 110

Leu Ser Met Asn Lys Tyr Lys Val Ser Tyr Lys Gly Pro Gly Pro Gly
        115                 120                 125

Ile Lys Phe Ser Ala Glu Ala Leu Arg Cys His Leu Arg Asp His Val
130                 135                 140

Asn Val Ser Met Val Glu Val Thr Asp Phe Pro Phe Asn Thr Ser Glu
145                 150                 155                 160

Trp Glu Gly Tyr Leu Pro Lys Glu Ser Ile Arg Thr Lys Ala Gly Pro
                165                 170                 175

Trp Gly Arg Cys Ala Val Val Ser Ser Ala Gly Ser Leu Lys Ser Ser
            180                 185                 190

Gln Leu Gly Arg Glu Ile Asp Asp His Asp Ala Val Leu Arg Phe Asn
        195                 200                 205

Gly Ala Pro Thr Ala Asn Phe Gln Gln Asp Val Gly Thr Lys Thr Thr
    210                 215                 220

Ile Arg Leu Met Asn Ser Gln Leu Val Thr Thr Glu Lys Arg Phe Leu
225                 230                 235                 240
```

```
Lys Asp Ser Leu Tyr Asn Glu Gly Ile Leu Ile Val Trp Asp Pro Ser
                245                 250                 255

Val Tyr His Ser Asp Ile Pro Lys Trp Tyr Gln Asn Pro Asp Tyr Asn
            260                 265                 270

Phe Phe Asn Asn Tyr Lys Thr Tyr Arg Lys Leu His Pro Asn Gln Pro
        275                 280                 285

Phe Tyr Ile Leu Lys Pro Gln Met Pro Trp Glu Leu Trp Asp Ile Leu
    290                 295                 300

Gln Glu Ile Ser Pro Glu Ile Gln Pro Asn Pro Pro Ser Ser Gly
305                 310                 315                 320

Met Leu Gly Ile Ile Met Met Thr Leu Cys Asp Gln Val Asp Ile
                325                 330                 335

Tyr Glu Phe Leu Pro Ser Lys Arg Lys Thr Asp Val Cys Tyr Tyr Tyr
            340                 345                 350

Gln Lys Phe Phe Asp Ser Ala Cys Thr Met Gly Ala Tyr His Pro Leu
        355                 360                 365

Leu Tyr Glu Lys Asn Leu Val Lys His Leu Asn Gln Gly Thr Asp Glu
    370                 375                 380

Asp Ile Tyr Leu Leu Gly Lys Ala Thr Leu Pro Gly Phe Arg Thr Ile
385                 390                 395                 400

His Cys

<210> SEQ ID NO 105
<211> LENGTH: 1968
<212> TYPE: DNA
<213> ORGANISM: Mus musculus
<220> FEATURE:
<221> NAME/KEY: CDS
<222> LOCATION: (1)...(1965)

<400> SEQUENCE: 105 atg ccc gtg ggg ggc ctg ttg ccg ctc ttc agt agc cct ggg ggc ggc    48
Met Pro Val Gly Gly Leu Leu Pro Leu Phe Ser Ser Pro Gly Gly Gly
 1               5                  10                  15 ggc ctg ggc agt ggc ctg ggc ggg ggg ctt ggc ggc ggg agg aag ggg    96
Gly Leu Gly Ser Gly Leu Gly Gly Gly Leu Gly Gly Gly Arg Lys Gly
            20                  25                  30 tct ggc ccc gct gcc ttc cgc ctc acc gag aag ttc gtg ctg ctg ctg   144
Ser Gly Pro Ala Ala Phe Arg Leu Thr Glu Lys Phe Val Leu Leu Leu
        35                  40                  45 gtg ttc agc gcc ttc atc acg ctc tgc ttc ggg gca atc ttc ttc ctg   192
Val Phe Ser Ala Phe Ile Thr Leu Cys Phe Gly Ala Ile Phe Phe Leu
    50                  55                  60 cct gac tcc tcc aag ctg ctc agc ggg gtc ctg ttc cac tcc aac cct   240
Pro Asp Ser Ser Lys Leu Leu Ser Gly Val Leu Phe His Ser Asn Pro
65                  70                  75                  80 gcc ttg cag ccg ccg gcg gag cac aag ccc ggg ctc ggg gcg cgt gcg   288
Ala Leu Gln Pro Pro Ala Glu His Lys Pro Gly Leu Gly Ala Arg Ala
                85                  90                  95 gag gat gcc gcc gag ggg aga gtc cgg cac cgc gag gaa ggc gcg cct   336
Glu Asp Ala Ala Glu Gly Arg Val Arg His Arg Glu Glu Gly Ala Pro
            100                 105                 110 ggg gac cct gga gct gga ctg gaa gac aac tta gcc agg atc cgc gaa   384
Gly Asp Pro Gly Ala Gly Leu Glu Asp Asn Leu Ala Arg Ile Arg Glu
        115                 120                 125 aac cac gag cgg gct ctc agg gaa gcc aag gag acc ctg cag aag ctg   432
Asn His Glu Arg Ala Leu Arg Glu Ala Lys Glu Thr Leu Gln Lys Leu
    130                 135                 140
```

```
ccg gag gag atc caa aga gac att ctg ctg gag aag gaa aag gtg gcc      480
Pro Glu Glu Ile Gln Arg Asp Ile Leu Leu Glu Lys Glu Lys Val Ala
145                 150                 155                 160 cag gac cag ctg cgt gac aag gat ctg ttt agg ggc ttg ccc aag gtg      528
Gln Asp Gln Leu Arg Asp Lys Asp Leu Phe Arg Gly Leu Pro Lys Val
                165                 170                 175 gac ttc ctg ccc ccc gtc ggg gta gag aac cgg gag ccc gct gac gcc      576
Asp Phe Leu Pro Pro Val Gly Val Glu Asn Arg Glu Pro Ala Asp Ala
        180                 185                 190 acc atc cgt gag aag agg gca aag atc aaa gag atg atg acc cat gct      624
Thr Ile Arg Glu Lys Arg Ala Lys Ile Lys Glu Met Met Thr His Ala
                195                 200                 205 tgg aat aat tat aaa cgc tat gcg tgg ggc ttg aac gaa ctg aaa cct      672
Trp Asn Asn Tyr Lys Arg Tyr Ala Trp Gly Leu Asn Glu Leu Lys Pro
210                 215                 220 ata tca aaa gaa ggc cat tca agc agt ttg ttt ggc aac atc aaa gga      720
Ile Ser Lys Glu Gly His Ser Ser Ser Leu Phe Gly Asn Ile Lys Gly
225                 230                 235                 240 gct aca ata gta gat gcc ctg gat acc ctt ttc att atg ggc atg aag      768
Ala Thr Ile Val Asp Ala Leu Asp Thr Leu Phe Ile Met Gly Met Lys
                245                 250                 255 act gaa ttt caa gaa gct aaa tcg tgg att aaa aaa tat tta gat ttt      816
Thr Glu Phe Gln Glu Ala Lys Ser Trp Ile Lys Lys Tyr Leu Asp Phe
                260                 265                 270 aat gtg aat gct gaa gtt tct gtt ttt gaa gtc aac ata cgc ttc gtc      864
Asn Val Asn Ala Glu Val Ser Val Phe Glu Val Asn Ile Arg Phe Val
                275                 280                 285 ggt gga ctg ctg tca gcc tac tat ttg tcc gga gag gag ata ttt cga      912
Gly Gly Leu Leu Ser Ala Tyr Tyr Leu Ser Gly Glu Glu Ile Phe Arg
        290                 295                 300 aag aaa gca gtg gaa ctt ggg gta aaa ttg cta cct gca ttt cat act      960
Lys Lys Ala Val Glu Leu Gly Val Lys Leu Leu Pro Ala Phe His Thr
305                 310                 315                 320 ccc tct gga ata cct tgg gca ttg ctg aat atg aaa agt ggg atc ggg     1008
Pro Ser Gly Ile Pro Trp Ala Leu Leu Asn Met Lys Ser Gly Ile Gly
                325                 330                 335 cgg aac tgg ccc tgg gcc tct gga ggc agc agt atc ctg gcc gaa ttt     1056
Arg Asn Trp Pro Trp Ala Ser Gly Gly Ser Ser Ile Leu Ala Glu Phe
                340                 345                 350 gga act ctg cat tta gag ttt atg cac ttg tcc cac tta tca gga gac     1104
Gly Thr Leu His Leu Glu Phe Met His Leu Ser His Leu Ser Gly Asp
        355                 360                 365 cca gtc ttt gcc gaa aag gtt atg aaa att cga aca gtg ttg aac aaa     1152
Pro Val Phe Ala Glu Lys Val Met Lys Ile Arg Thr Val Leu Asn Lys
        370                 375                 380 ctg gac aaa cca gaa ggc ctt tat cct aac tat ctg aac ccc agt agt     1200
Leu Asp Lys Pro Glu Gly Leu Tyr Pro Asn Tyr Leu Asn Pro Ser Ser
385                 390                 395                 400 gga cag tgg ggt caa cat cat gtg tcg gtt gga gga ctt gga gac agc     1248
Gly Gln Trp Gly Gln His His Val Ser Val Gly Gly Leu Gly Asp Ser
                405                 410                 415 ttt tat gaa tat ttg ctt aag gcg tgg tta atg tct gac aag aca gat     1296
Phe Tyr Glu Tyr Leu Leu Lys Ala Trp Leu Met Ser Asp Lys Thr Asp
                420                 425                 430 ctc gaa gcc aag aag atg tat ttt gat gct gtt cag gcc atc gag act     1344
Leu Glu Ala Lys Lys Met Tyr Phe Asp Ala Val Gln Ala Ile Glu Thr
            435                 440                 445 cac ttg atc cgc aag tca agt ggg gga cta acg tac atc gca gag tgg     1392
His Leu Ile Arg Lys Ser Ser Gly Gly Leu Thr Tyr Ile Ala Glu Trp
```

```
aag ggg ggc ctc ctg gaa cac aag atg ggc cac ctg acg tgc ttt gca    1440
Lys Gly Gly Leu Leu Glu His Lys Met Gly His Leu Thr Cys Phe Ala
465             470                 475                 480 gga ggc atg ttt gca ctt ggg gca gat gga gct ccg gaa gcc cgg gcc    1488
Gly Gly Met Phe Ala Leu Gly Ala Asp Gly Ala Pro Glu Ala Arg Ala
                485                 490                 495 caa cac tac ctt gaa ctc gga gct gaa att gcc cgc act tgt cat gaa    1536
Gln His Tyr Leu Glu Leu Gly Ala Glu Ile Ala Arg Thr Cys His Glu
            500                 505                 510 tct tat aat cgt aca tat gtg aag ttg gga ccg gaa gcg ttt cga ttt    1584
Ser Tyr Asn Arg Thr Tyr Val Lys Leu Gly Pro Glu Ala Phe Arg Phe
        515                 520                 525 gat ggc ggt gtg gaa gct att gcc acg agg caa aat gaa aag tat tac    1632
Asp Gly Gly Val Glu Ala Ile Ala Thr Arg Gln Asn Glu Lys Tyr Tyr
    530                 535                 540 atc tta cgg ccc gag gtc atc gag aca tac atg tac atg tgg cga ctg    1680
Ile Leu Arg Pro Glu Val Ile Glu Thr Tyr Met Tyr Met Trp Arg Leu
545                 550                 555                 560 act cac gac ccc aag tac agg acc tgg gcc tgg gaa gcc gtg gag gct    1728
Thr His Asp Pro Lys Tyr Arg Thr Trp Ala Trp Glu Ala Val Glu Ala
                565                 570                 575 cta gaa agt cac tgc aga gtg aac gga ggc tac tca ggc tta cgg gat    1776
Leu Glu Ser His Cys Arg Val Asn Gly Gly Tyr Ser Gly Leu Arg Asp
            580                 585                 590 gtt tac att gcc cgt gag agt tat gac gat gtc cag caa agt ttc ttc    1824
Val Tyr Ile Ala Arg Glu Ser Tyr Asp Asp Val Gln Gln Ser Phe Phe
        595                 600                 605 ctg gca gag aca ctg aag tat ttg tac ttg ata ttt tcc gat gat gac    1872
Leu Ala Glu Thr Leu Lys Tyr Leu Tyr Leu Ile Phe Ser Asp Asp Asp
    610                 615                 620 ctt ctt cca cta gaa cac tgg atc ttc aac acc gag gct cat cct ttc    1920
Leu Leu Pro Leu Glu His Trp Ile Phe Asn Thr Glu Ala His Pro Phe
625                 630                 635                 640 cct ata ctc cgt gaa cag aag aag gaa att gat ggc aaa gag aaa        1965
Pro Ile Leu Arg Glu Gln Lys Lys Glu Ile Asp Gly Lys Glu Lys
                645                 650                 655 tga                                                                 1968
```

<210> SEQ ID NO 106
<211> LENGTH: 655
<212> TYPE: PRT
<213> ORGANISM: Mus musculus

<400> SEQUENCE: 106

```
Met Pro Val Gly Gly Leu Leu Pro Leu Phe Ser Ser Pro Gly Gly Gly
 1               5                  10                  15

Gly Leu Gly Ser Gly Leu Gly Gly Leu Gly Gly Arg Lys Gly
            20                  25                  30

Ser Gly Pro Ala Ala Phe Arg Leu Thr Glu Lys Phe Val Leu Leu
        35                  40                  45

Val Phe Ser Ala Phe Ile Thr Leu Cys Phe Gly Ala Ile Phe Phe Leu
    50                  55                  60

Pro Asp Ser Ser Lys Leu Leu Ser Gly Val Leu Phe His Ser Asn Pro
65                  70                  75                  80

Ala Leu Gln Pro Pro Ala Glu His Lys Pro Gly Leu Gly Ala Arg Ala
                85                  90                  95

Glu Asp Ala Ala Glu Gly Arg Val Arg His Arg Glu Glu Gly Ala Pro
```

```
            100                 105                 110
Gly Asp Pro Gly Ala Gly Leu Glu Asp Asn Leu Ala Arg Ile Arg Glu
            115                 120                 125

Asn His Glu Arg Ala Leu Arg Glu Ala Lys Glu Thr Leu Gln Lys Leu
            130                 135             140

Pro Glu Glu Ile Gln Arg Asp Ile Leu Leu Glu Lys Glu Lys Val Ala
145                 150                 155                 160

Gln Asp Gln Leu Arg Asp Lys Asp Leu Phe Arg Gly Leu Pro Lys Val
                165                 170                 175

Asp Phe Leu Pro Pro Val Gly Val Glu Asn Arg Glu Pro Ala Asp Ala
            180                 185                 190

Thr Ile Arg Glu Lys Arg Ala Lys Ile Lys Glu Met Met Thr His Ala
            195                 200                 205

Trp Asn Asn Tyr Lys Arg Tyr Ala Trp Gly Leu Asn Glu Leu Lys Pro
            210                 215                 220

Ile Ser Lys Glu Gly His Ser Ser Leu Phe Gly Asn Ile Lys Gly
225                 230                 235                 240

Ala Thr Ile Val Asp Ala Leu Asp Thr Leu Phe Ile Met Gly Met Lys
                245                 250                 255

Thr Glu Phe Gln Glu Ala Lys Ser Trp Ile Lys Lys Tyr Leu Asp Phe
                260                 265                 270

Asn Val Asn Ala Glu Val Ser Val Phe Glu Val Asn Ile Arg Phe Val
            275                 280                 285

Gly Gly Leu Leu Ser Ala Tyr Tyr Leu Ser Gly Glu Glu Ile Phe Arg
            290                 295                 300

Lys Lys Ala Val Glu Leu Gly Val Lys Leu Leu Pro Ala Phe His Thr
305                 310                 315                 320

Pro Ser Gly Ile Pro Trp Ala Leu Leu Asn Met Lys Ser Gly Ile Gly
                325                 330                 335

Arg Asn Trp Pro Trp Ala Ser Gly Gly Ser Ser Ile Leu Ala Glu Phe
                340                 345                 350

Gly Thr Leu His Leu Glu Phe Met His Leu Ser His Leu Ser Gly Asp
            355                 360                 365

Pro Val Phe Ala Glu Lys Val Met Lys Ile Arg Thr Val Leu Asn Lys
            370                 375                 380

Leu Asp Lys Pro Glu Gly Leu Tyr Pro Asn Tyr Leu Asn Pro Ser Ser
385                 390                 395                 400

Gly Gln Trp Gly Gln His His Val Ser Val Gly Gly Leu Gly Asp Ser
                405                 410                 415

Phe Tyr Glu Tyr Leu Leu Lys Ala Trp Leu Met Ser Asp Lys Thr Asp
                420                 425                 430

Leu Glu Ala Lys Lys Met Tyr Phe Asp Ala Val Gln Ala Ile Glu Thr
            435                 440                 445

His Leu Ile Arg Lys Ser Ser Gly Gly Leu Thr Tyr Ile Ala Glu Trp
            450                 455                 460

Lys Gly Gly Leu Leu Glu His Lys Met Gly His Leu Thr Cys Phe Ala
465                 470                 475                 480

Gly Gly Met Phe Ala Leu Gly Ala Asp Gly Ala Pro Glu Ala Arg Ala
                485                 490                 495

Gln His Tyr Leu Glu Leu Gly Ala Glu Ile Ala Arg Thr Cys His Glu
            500                 505                 510

Ser Tyr Asn Arg Thr Tyr Val Lys Leu Gly Pro Glu Ala Phe Arg Phe
            515                 520                 525
```

```
Asp Gly Gly Val Glu Ala Ile Ala Thr Arg Gln Asn Glu Lys Tyr Tyr
    530                 535                 540

Ile Leu Arg Pro Glu Val Ile Glu Thr Tyr Met Tyr Met Trp Arg Leu
545                 550                 555                 560

Thr His Asp Pro Lys Tyr Arg Thr Trp Ala Trp Glu Ala Val Glu Ala
                565                 570                 575

Leu Glu Ser His Cys Arg Val Asn Gly Gly Tyr Ser Gly Leu Arg Asp
            580                 585                 590

Val Tyr Ile Ala Arg Glu Ser Tyr Asp Asp Val Gln Gln Ser Phe Phe
        595                 600                 605

Leu Ala Glu Thr Leu Lys Tyr Leu Tyr Leu Ile Phe Ser Asp Asp Asp
    610                 615                 620

Leu Leu Pro Leu Glu His Trp Ile Phe Asn Thr Glu Ala His Pro Phe
625                 630                 635                 640

Pro Ile Leu Arg Glu Gln Lys Lys Glu Ile Asp Gly Lys Glu Lys
                645                 650                 655

<210> SEQ ID NO 107
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 107

His His His His His His
 1               5
```